US012084495B2

(12) United States Patent
Flies et al.

(10) Patent No.: US 12,084,495 B2
(45) Date of Patent: Sep. 10, 2024

(54) COMPOSITIONS AND METHODS FOR MODULATING LAIR SIGNAL TRANSDUCTION

(71) Applicant: NextCure, Inc., Beltsville, MD (US)

(72) Inventors: Dallas Benjamin Flies, Rockville, MD (US); Linda Liu, Clarksville, MD (US); Solomon Langermann, Baltimore, MD (US)

(73) Assignee: NEXTCURE, INC., Beltsville, MD (US)

( * ) Notice: Subject to any disclaimer, the term of this patent is extended or adjusted under 35 U.S.C. 154(b) by 404 days.

(21) Appl. No.: 16/321,726

(22) PCT Filed: Aug. 3, 2017

(86) PCT No.: PCT/US2017/045310
§ 371 (c)(1),
(2) Date: Jan. 29, 2019

(87) PCT Pub. No.: WO2018/027039
PCT Pub. Date: Feb. 8, 2018

(65) Prior Publication Data

US 2021/0363240 A1 Nov. 25, 2021

Related U.S. Application Data

(60) Provisional application No. 62/450,300, filed on Jan. 25, 2017, provisional application No. 62/370,334, filed on Aug. 3, 2016.

(51) Int. Cl.

| | |
|---|---|
| ***C07K 14/705*** | (2006.01) |
| ***A61K 38/17*** | (2006.01) |
| ***A61K 39/395*** | (2006.01) |
| ***A61K 45/06*** | (2006.01) |
| ***A61P 35/00*** | (2006.01) |
| ***C07K 16/28*** | (2006.01) |
| ***C07K 19/00*** | (2006.01) |
| *A61K 39/00* | (2006.01) |

(52) U.S. Cl.
CPC ...... *C07K 16/2803* (2013.01); *A61K 38/1774* (2013.01); *A61K 39/3955* (2013.01); *A61K 45/06* (2013.01); *A61P 35/00* (2018.01); *C07K 14/70596* (2013.01); *C07K 16/2818* (2013.01); *C07K 16/2896* (2013.01); *C07K 19/00* (2013.01); *A61K 2039/505* (2013.01); *A61K 2039/507* (2013.01); *C07K 2317/30* (2013.01); *C07K 2317/51* (2013.01); *C07K 2317/515* (2013.01); *C07K 2317/565* (2013.01); *C07K 2317/76* (2013.01); *C07K 2317/92* (2013.01); *C07K 2319/00* (2013.01)

(58) Field of Classification Search
CPC ............ A61K 38/16; A61K 39/001102; A61K 39/3955; A61K 2039/505; A61K 38/177; A61K 38/179; A61K 2300/00; A61K 31/5025; A61K 39/395; A61P 37/02; A61P 35/00; C07K 2317/32; C07K 2317/70; C07K 2319/30; C07K 14/70596; C07K 14/71; C07K 19/00; C07K 2319/00; C07K 16/2803; C07K 16/2827; C07K 16/28
See application file for complete search history.

(56) References Cited

U.S. PATENT DOCUMENTS

| | | | |
|---|---|---|---|
| 5,013,556 A | 5/1991 | Woodle et al. |
| 5,120,727 A | 6/1992 | Kao et al. |
| 5,162,333 A | 11/1992 | Failli et al. |
| 5,190,929 A | 4/1993 | Hughes et al. |
| 5,202,332 A | 4/1993 | Hughes et al. |
| 5,385,908 A | 1/1995 | Nelson et al. |

(Continued)

FOREIGN PATENT DOCUMENTS

| | | |
|---|---|---|
| AU | 2017306560 A1 | 2/2019 |
| BR | 112019002127 A2 | 9/2019 |

(Continued)

OTHER PUBLICATIONS

Meyaard et al., "Leukocyte-Associated Ig-Like Receptor-1 Functions as an Inhibitory Receptor on Cytotoxic T Cells," 1999, J Immunol, 162:5800-5804 (Year: 1999).*

(Continued)

*Primary Examiner* — Bridget E Bunner

(74) *Attorney, Agent, or Firm* — Smith, Gambrell & Russell, LLP; Judy Jarecki-Black; Sharon Ngwenya

(57) ABSTRACT

Compositions and methods of use thereof for modulating LAIR-1 are provided. For example, immunomodulatory agents are provided that reduce LAIR-1 expression, ligand binding, crosslinking, negative signaling, or a combination thereof. Such agents can be used to increase an immune response in a subject in need thereof. Exemplary agents include (i) a soluble LAIR-2 polypeptide or fusion protein, (ii) a soluble LAIR-1 polypeptide or fusion protein, (iii) a function blocking anti-LAIR-1 antibody, (iv) an antibody that depletes LAIR-1 positive cells, and (y) combinations thereof. Immunomodulatory agents are also provided that increase LAIR-1 expression, ligand binding, crosslinking, negative signaling, or a combination thereof. Such agents can be used to reduce an immune response in a subject in need thereof. Exemplary agents include: (i) a function activating anti-LAIR-1 antibody, (ii) a function blocking anti-LAIR-2 antibody, and (iii) a combination thereof.

12 Claims, 29 Drawing Sheets

Specification includes a Sequence Listing.

(56) References Cited

U.S. PATENT DOCUMENTS

| | | | | |
|---|---|---|---|---|
| 5,484,790 | A | 1/1996 | Failli et al. | |
| 5,530,006 | A | 6/1996 | Waranis et al. | |
| 5,559,112 | A | 9/1996 | Skotnicki et al. | |
| 5,567,709 | A | 10/1996 | Skotnicki et al. | |
| 5,624,821 | A | 4/1997 | Winter et al. | |
| 5,780,462 | A | 7/1998 | Lee et al. | |
| 5,989,591 | A | 11/1999 | Nagi | |
| 6,005,079 | A | 12/1999 | Casterman et al. | |
| 6,015,809 | A | 1/2000 | Zhu et al. | |
| 6,140,076 | A | 10/2000 | Adema et al. | |
| 6,194,551 | B1 | 2/2001 | Idusogie et al. | |
| 6,479,638 | B1 | 11/2002 | Adema et al. | |
| 7,052,694 | B2 | 5/2006 | Pease et al. | |
| 7,332,582 | B2 | 2/2008 | Hardy et al. | |
| 7,390,888 | B2 | 6/2008 | Pease et al. | |
| 7,411,051 | B2 | 8/2008 | Rosen et al. | |
| 7,563,869 | B2 | 7/2009 | Honjo | |
| 7,595,048 | B2 | 9/2009 | Honjo | |
| 7,943,743 | B2 | 5/2011 | Korman | |
| 7,999,078 | B2 | 8/2011 | Adema et al. | |
| 8,114,845 | B2 | 2/2012 | Langermann et al. | |
| 8,609,089 | B2 | 12/2013 | Langermann et al. | |
| 8,709,416 | B2 | 4/2014 | Langermann et al. | |
| 8,993,265 | B2 * | 3/2015 | Cload | A61K 47/60<br>536/23.53 |
| 2007/0166281 | A1 | 7/2007 | Kosak | |
| 2007/0202077 | A1 | 8/2007 | Brodsky et al. | |
| 2007/0243184 | A1 | 10/2007 | Fischkoff et al. | |
| 2009/0030468 | A1 | 12/2009 | Meyaard et al. | |
| 2009/0304686 | A1 | 12/2009 | Meyaard et al. | |
| 2010/0040614 | A1 | 2/2010 | Ahmed et al. | |
| 2011/0195068 | A1 * | 8/2011 | Langermann | C12N 15/62<br>514/19.5 |
| 2012/0156191 | A1 | 6/2012 | Goetsch et al. | |
| 2015/0315294 | A1 | 11/2015 | Escher | |
| 2018/0179274 | A1 * | 6/2018 | Lanzavecchia | C07K 16/205 |

FOREIGN PATENT DOCUMENTS

| | | | | |
|---|---|---|---|---|
| CA | 3032826 | A1 | 2/2018 | |
| CN | 109789197 | A | 5/2019 | |
| EP | 2036570 | | 3/2009 | |
| EP | 3496746 | A1 | 6/2019 | |
| JP | 2019-528311 | A | 10/2019 | |
| KR | 2019-0044070 | A | 4/2019 | |
| RU | 2019105294 | A | 9/2020 | |
| RU | 2757394 | C2 | 10/2021 | |
| WO | 199824906 | | 6/1998 | |
| WO | 2004056875 | | 7/2004 | |
| WO | 2006121168 | | 11/2006 | |
| WO | 2006133396 | | 12/2006 | |
| WO | 2007/102736 | A2 | 9/2007 | |
| WO | 2009014708 | | 1/2009 | |
| WO | 2009073533 | | 6/2009 | |
| WO | 2010/078580 | A2 | 7/2010 | |
| WO | WO-2016207402 | A1 * | 12/2016 | A61P 33/02 |
| WO | 2018/027039 | A1 | 2/2018 | |

OTHER PUBLICATIONS

Lebbink et al., "The Mouse Homologue of the Leukocyte-Associated Ig-Like Receptor-1 Is an Inhibitory Receptor That Recruits Src Homology Region 2-Containing Protein Tyrosine Phosphatase (SHP)-2, but Not SHP-1," J Immunol 2004; 172:5535-5543 (Year: 2004).*

Huang, C., "Receptor-Fc fusion therapeutics, traps, and MIMETIBODYTM technology," Current Opinion in Biotechnology 2009; 20: 692-699 (Year: 2009).*

Amino acid sequence for leukocyte-associated immunoglobulin-like receptor 2 isoform a precursor [*Homo sapiens*] NCBI accession No. NM_002279, published Oct. 23, 2000 [retrieved on Feb. 28, 2022]. Retrieved from the Internet: <URL:https://www.ncbi.nlm.nih.gov/protein/NP_002279>. (Year: 2000).*

FC Fragment of Human IGG1 [*Homo sapiens*] The Protein Data Bank 1DN2, published May 17, 2000 [retrieved on Feb. 28, 2022]. Retrieved from the Internet: <URL:https://www.rcsb.org/sequence/1DN2>. (Year: 2000).*

Lebbink et al., "The Mouse Homologue of the Leukocyte-Associated Ig-Like Receptor-1 Is an Inhibitory Receptor That Recruits Src Homology Region 2-Containing Protein Tyrosine Phosphatase (SHP)-2, but Not SHP-1," J. of Immun. 172 pp. 5535-5543. (Year: 2004).*

Lake et al., "Immunotherapy and chemotherapy—a practical partnership," Nat. Rev. Cancer, vol. 5, pp. 397-405. (Year: 2005).*

Roopenian et al., "FcRn: the neonatal Fc receptor comes of age," Nat. Rev. Immunology, vol. 7, pp. 715-725. (Year: 2007).*

Pardoll et al., "The blockade of immune checkpoints in cancer immunotherapy," Nat. Rev. Cancer, vol. 12, pp. 252-264. (Year: 2012).*

Bhattacharya et al. Impact of genetic variation on three dimensional structure and function of proteins. PLoS ONE 12(3): e0171355, 2017.*

Bork, P. Powers and pitfalls in sequence analysis: the 70% hurdle. Genome Res 10: 398-400, 2000.*

Bork, P. Go hunting in sequence databases but watch out for the traps. Trends in Genetics 12(10): 425-427, 1996.*

Brenner. S.E. Errors in genome annotation. Trends in Genetics 15:132-133, 1999.*

Doerks et al. Protein annotation: detective work for function prediction. Trends in Genetics 14:248-250, 1998.*

Fenton et al. Rheostat positions: a new classification of protein positions relevant to pharmacogenomics. Medicinal Chem Res 29: 1133-1146, 2020.*

Kang et al. The ITIM-containing receptor LAIR1 is essential for acute myeloid leukaemia development. Nat Cell Biol 17(5): 665-677, 2015 (Final version and supplemental materials).*

Kantarjian, H. Acute myeloid leukemia—major progress over four decades and glimpses into the future. Am J Hematol 91: 131-145, 2016; published online Nov. 24, 2015.*

Skolnick et al. From genes to protein structure and function: novel applications of computational approaches in the genomic era. Trends Biotechnol 18(I):34-39 2000.*

Sehgal et al. Programmed death-1 checkpoint blockade in acute myeloid leukemia. Exp Opin Biol Ther 15(8): 1191-1203, 2015.*

Smith et al. The challenges of genome sequence annotation or "the devil is in the details". Nature Biotechnol 15: 1222-1223, 1997.*

Tokuriki et al. Stability effects of mutations and protein evolvability. Curr Opin Structural Biol 19: 596-604, 2009.*

Wang et al. Establishment of leukocyte-associated immunoglobulin like-receptor 2 (CD306) eukaryotic expression vectors and purification and identification of fusion protein. J Clin Rehabilitative Tissue Eng Res 13(50): 9928-9932, 2009 (abstract only).*

Vilgelm et al. Combinatorial approach to cancer immunotherapy: strength in numbers. J Leuk Biol 100: 275-290, 2016 (published online Jun. 2, 2016).*

Ramos et al. Cancer immunotherapy by NC410, a LAIR-2 Fc protein blocking human LAIR-collagen interaction. eLife 10: e62927, 2021.*

Xu et al. Cancer immunotherapy based on blocking immune suppression mediated by an immune modulator LAIR-1. Oncoimmunol 9(1): e1740477, 2020 (9 total pages).*

Founds, et al., "LAIR2 localizes specifically to sites of extravillous trophoblast invasion", Placenta, 31(10):880-885.

Office Action received for Japanese Application No. 2019527776, mailed on Jun. 23, 2021, 8 pages (4 pages of English Translation and 4 pages of Original Document).

International Preliminary Report on Patentability received for PCT Patent Application No. PCT/US17/45310, mailed on Feb. 14, 2019, 10 pages.

International Search Report and Written Opinion received for PCT Patent Application No. PCT/US17/045310, mailed on Dec. 14, 2017, 6 pages.

Supplementary European Search Report and Search Opinion Received for EP Application No. 17837690, mailed on Jan. 13, 2020, 12 pages.

(56) References Cited

OTHER PUBLICATIONS

Angal, et al., "A single amino acid substitution abolishes the heterogeneity of chimeric mouse/human (IgG4) antibody," Mol. Immunol. 30:105-08 (1993) Abstract only.
Bass, K.K. & Mastrangelo, J.J., "Immunopotentiation with low-dose cyclophosphamide in the active specific immunotherapy of cancer," Cancer Immunol. Immunother. 47:1-12 (1998) Abstract Only.
Berger et al., "Phase I safety and pharmacokinetic study of CT-011, a humanized antibody interacting with PD-1, in patients with advanced hematologic malignancies," Clin. Cancer Res., 14:30443051 (2008).
Brode, S., & Cooke, A., "Immune-potentiating effects of the chemotherapeutic drug cyclophosphamide," Crit Rev. Immunol. 28:109-126 (2008). Abstract Only.
Brondijk Harma, T., et al., "Crystal structure and collagen-binding site of immune inhibitory receptor LAIR-1: unexpected implications for collagen binding by platelet receptor GPVI," Blood, 115:1364-1373 (2009).
Butte et al., "PD-L1 interacts specifically with B7-1 to inhibit T cell proliferation," Immunity, 27(1): 111-122 (2007).
Cao et al., 2015, "Leukocyte-associated immunoglobulin-like receptor-1 expressed in epithelial ovarian cancer cells and involved in cell proliferation and invasion," Biochem. Biophys. Res. Commun. 458:399-404.
Chen et al., "Signaling thresholds and negative B cell selection in acute lymphoblastic leukemia" Nature, 521:357-361 (2015).
Chothia and Lesk, "Canonical structures for the hypervariable regions of immunoglobulins," J. Mol. Biol. 196:901-917 (1987).
Cubillos-Ruiz et al., "Polyethylenimine-based siRNA nanocomplexes reprogram tumor-associated dendritic cells via TLR5 to elicit therapeutic antitumor immunity," J. Clin. Invest. 119(8): 2231-2244 (2009).
Erbe et al., "Small Molecule Ligands Define a Binding Site on the Immune Regulatory Protein B7.1," J. Biol. Chem., 277:7363-7368 (2002).
Freeman, "Structures of PD-1 with its ligands: Sideways and dancing cheek to cheek," Proc. Natl. Acad. Sci. U. S. A, 105:10275-10276 (2008).
Guatelli et al. "Isothermal, in vitro amplification of nucleic acids by a multienzyme reaction modeled after retroviral replication," Proc. Natl. Acad. Sci. USA 87:1874-1878 (1990).
Hengst, J.C., et al., "Importance of Timing of Cyclophosphamide Therapy of MOPC-315 Tumor-bearing Mice," Cancer Res. 40:2135-2141 (1980).
Hengst et al. "Cooperation between Cyclophosphamide Tumoricidal Activity and Host Antitumor Immunity in the Cure of Mice Bearing Large MOPC-315 Tumors," Cancer Res. 41:2163-2167 (1981).
Herias et al., "Expression sites of the collectin SP-D suggest its importance in first line host defence: power of combining in situ hybridisation, RT-PCR and immunohistochemistry" Mol. Immunol. 44:3324-3332 (2007).
Hyrup et al. "Peptide nucleic acids (PNA): synthesis, properties and potential applications," Bioorgan. Med. Chem. 4:5-23 (1996).
Jarvis, et al., "Identification of a major GpVI-binding locus in human type III collagen", Blood, 111(10):4986-4996 (2008).
Jones, P.T., et al. "Replacing the complementarity-determining regions in a human antibody with those from a mouse." Nature 321, 522-525 (1986).
Kang, Xunlei, et al., "The ITIM-containing receptor LAIR1 is essential for acute myeloid leukaemia development," Nature Cell Biology, 17:665-677 (2015).
Lebbink et al., "Mouse leukocyte-associated Ig-like receptor-1 (mLAIR-1) functions as an inhibitory collagen-binding receptor on immune cells." Int. Immunol. 19:1011-1019 (2007).
Lebbink et al., J. Immunol 180:1662-1669 (2008).
Lebbink et al., "Identification of multiple potent binding sites for human leukocyte associated Ig-like receptor LAIR on collagens II and III" Matrix Biol. 28:202-210 (2009).
Li et al., "Vascular endothelial growth factor blockade reduces intratumoral regulatory T cells and enhances the efficacy of a GM-CSF-secreting cancer immunotherapy," Clin Cancer Res., 12(22):6808-16 (2006).
Liang J, Huang M, Duan W, Yu XQ, Zhou S. Design of new oxazaphosphorine anticancer drugs. Curr Pharm Des. 13 (9):963-78 (2007).
Machiels et al. "Cyclophosphamide, doxorubicin, and paclitaxel enhance the antitumor immune response of granulocyte/macrophage-colony stimulating factor-secreting whole-cell vaccines in HER-2/neu tolerized mice," Cancer Res. 61:3689-3697 (2001).
Meyaard et al., "LAIR-1, a novel inhibitory receptor expressed on human mononuclear leukocytes." Immunity 7:283-290 (1997).
Meyaard, et al., "The inhibitory collagen receptor LAIR-1 (CD305)" J. Leukoc. Biol. 83:799-803 (2008).
Meyaard, et al., "LAIR and collagens in immune regulation" Immunol. Lett. 128:26-28 (2010).
Mirkowska et al., "Leukemia surfaceome analysis reveals new disease-associated features," Blood, 121(25):e149-59 (2013).
Molnar et al., "Crystal structure of the complex between programmed death-1 (PD-1) and its ligand PD-L2," PNAS, 105:10483-10488 (2008).
Muyldermans, et al., "Recodnigition of antigens by single-domain antibody fragments:the superfluous luxury of paried domains," Trends Biochem. Sci. 26:230 (2001).
Nuttall, et al., "Immunoglobulin VH Domains and Beyond: Design and Selection of Single-Domain Binding and Targeting Reagents," Curr. Pharm. Biotech. 1:253 (2000).
Olde Nordkamp et al., "Enhanced secretion of leukocyte-associated immunoglobulin-like receptor 2 (LAIR-2) and soluble LAIR-1 in rheumatoid arthritis: LAIR-2 is a more efficient antagonist of the LAIR-1-collagen inhibitory interaction than is soluble LAIR-1", Arthritis Rheum. 63:3749-3757 (2011).
Olde Nordkamp et al., "Leukocyte-associated Ig-like receptor-1 is a novel inhibitory receptor for surfactant protein D" J. Leukoc. Biol. 96:105-111 (2014).
Olde Nordkamp et al., "Inhibition of the Classical and Lectin Pathway of the Complement System by Recombinant LAIR-2," J. Innate Immun., 6(3):284-92 (2014).
Perbellini et al., "Clinical significance of LAIR1 (CD305) as assessed by flow cytometry in a prospective series of patients with chronic lymphocytic leukemia," Haematolagica, 99:881-887 (2014).
Poggi et al., Engagement of the leukocyte-associated Ig-like receptor-1 induces programmed cell death and prevents NF-κB nuclear translocation in human myeloid leukemias, Eur. J. Immunol. 30:2751-2758 (2000).
Poggi et al., "Lack of the leukocyte-associated Ig-like receptor-1 expression in high-risk chronic lymphocytic leukaemia results in the absence of a negative signal regulating kinase activation and cell division," Leukemia 22:980-988 (2008).
Reff, et al., "Depletion of B cells in vivo by a chimeric mouse human monoclonal antibody to CD20," Blood. 83(2):435-445 (1994).
Reichmann and Muyldermans, J. Immunol. Meth. 231:25 (1999).
Rygiel et al., "Tumor-expressed collagens can modulate immune cell function through the inhibitory collagen receptor LAIR-1," Mol. Immunol. 49:402-406 (2011).
Sammartino, et al., "Anti-GBM disease following CTLA4 blockade in a patient with metastatic melanoma," NDT Plus, 3(2):135-137 (2010).
Son et al., "C1q limits dendritic cell differentiation and activation by engaging LAIR-1," Proc. Natl. Acad. Sci. USA 109:E3160-3167 (2012).
Son and Diamond, "C1q-Mediated Repression of Human Monocytes Is Regulated by Leukocyte-Associated Ig-Like Receptor 1 (LAIR-1)," Mol. Med., 20:559-568 (2015).
Son et al., "C1q and HMGB1 reciprocally regulate human macrophage polarization," PNAS, 109(46): E3160-3167 (2016).
Sun, Shuqiu, et al., "Comparison of LAIR-1 genetic pathways in murine vs human," Gene, 552:140-145 (2014).
Taieb, J., et al., "Chemoimmunotherapy of tumors: cyclophosphamide synergizes with exosome based vaccines," J. Immunol. 176:2722-2729 (2006).

(56) References Cited

OTHER PUBLICATIONS

Tang et al., "Leukocyte-Associated Ig-like Receptor-1-Deficient Mice Have an Altered Immune Cell Phenotype," J. Immunol. 188:548-558 (2012).
Van der Most et al., "Cyclophosphamide Chemotherapy Sensitizes Tumor Cells to TRAIL-Dependent CD8 T Cell- Mediated Immune Attack Resulting in Suppression of Tumor Growth," Cancer Immunol. Immunother. 58:1219-1228 (2009).
Office Action received for Russian Patent Application No. 2019105294, mailed on Feb. 16, 2021, 7 Pages (3 pages of English Translation and 4 pages of Original Document).
Office Action received for Russian Patent Application No. 2019105294, mailed on Sep. 21, 2020, 13 pages (6 pages of English Translation and 7 pages of Original Document).
Search Report received for Russian Patent Application No. 2019105294, mailed on Sep. 21, 2020, 5 pages (2 pages of English Translation and 3 pages of Original Document).
Van der Vuurst de Vries et al., "Leukocyte-associated immunoglobulin-like receptor-1 (LAIR-1) is differentially expressed during human B cell differentiation and inhibits B cell receptor-mediated signaling", Eur J Immunol, 29:3160-3167 (1999).
Verbrugge, et al., "Differential contribution of the immunoreceptor tyrosine-based inhibitory motifs of human leukocyte-associated Ig-like receptor-1 to inhibitory function and phosphatase recruitment", Int Immunol, 15:1349-1358 (2003). Abstract Only.
Verbrugge, et al., "Leukocyte-associated Ig-like receptor-1 has SH2 domain-containing phosphatase-independent function and recruits C-terminal Src kinase", Eur J Immunol, 36:190-198 (2006).
Verbrugge et al., "Differential expression of leukocyte-associated Ig-like receptor-1 during neutrophil differentiation and activation", J Leukoc Biol, 79:828-836 (2006).
Xu, et al., "Identification and Characterization of Leukocyte-associated Ig-like Receptor-1 as a Major Anchor Protein of Tyrosine Phosphatase SHP-1 in Hematopoietic Cells," J Biol Chem, 275:17440-17446 (2000).
Zhang et al., "Inhibitory leukocyte immunoglobulin-like receptors in cancer development," Science China Life Sciences, 58(12):1216-1225 (2015).
Zhou, Long, et al., "Structural basis for collagen recognition by the immune receptor OSCAR," Blood, 127:529-537 (2015).
Zocchi et al., "Leukocyte-associated Ig-like receptor-1 prevents granulocyte-monocyte colony stimulating factor-dependent proliferation and Akt1/PKB alpha activation in primary acute myeloid leukemia cells," Eur. J. Immunol. 31:3667-3675 (2001).
"UniProt Sequence Revision History," Retrived at https://www.uniprot.org/uniprot/Q6ISS4.txt?version=102, Uploaded Jul. 6, 2016, pp. 3.
Borrok., "Chain A, Ig Gamma-1 Chain C Region," GenBank PDB_3S7G_A, NCBI, 2012, pp. 2.
Iwai, Y., "Immunotherapy Targeting the PD-1 Signaling Pathway", Japanese J. of Lung Cancer, 56(1): 61-65 (2016).
Office Action issued on Mar. 25, 2022 in CN 201780060801.9 (5 pages).
Office Action received for Japanese Application No. 2019527776, mailed on May 16, 2022, 11 pages (6 pages of English Translation and 5 pages of Original Document).
Founds, et al., "LAIR2 localizes specifically to sites of extravillous trophoblast invasion", Placenta, 31(10):880-885, 2010.
Lenting, Peter J, et al., "Efficient Inhibition of Collagen-Induced Platelet Activation and Adhesion by LAIR-2, a Soluble Ig-Like Receptor Family Member," PLOS One, 5(8): e12174 (2010).
Maasho, K., et al., "The inhibitory leukocyte-associated Ig-like receptor-1 (LAIR-1) is expressed at high levels by human naïve T cells and inhibits TCR mediated activation", Molecular Immunology, 42(12):1521-1530 (2005).
The extended European search report mailed Jan. 13, 2020 in the corresponding European application; 13 pages.
Office Action received in corresponding application KR 10-2019-7005926 on Jun. 30, 2023 (5 pages Original Document, 6 pages English Translation).
Office Action received for CA Patent Application No. 3032826, mailed on Jul. 13, 2023, 5 pages.
Office Action received for Chinese Patent Application No. 201780060801.9, mailed on May 19, 2023, 11 pages (7 pages of English Translation and 4 pages of Original Document).
Office Action received for Brazil Patent Application No. 112019002127, mailed on Sep. 26, 2022, 7 pages (2 pages of English Translation and 5 pages of Original Document).
Office Action received for Chinese Patent Application No. 201780060801, mailed on Nov. 28, 2022, 10 pages (Only English Translation).
Office Action received for European Patent Application No. 17837690, mailed on Nov. 4, 2022, 8 pages.
Office Action received for Korean Patent Application No. 10-2019-7005926, mailed on Oct. 27, 2022, 11 pages (6 pages of English Translation and 5 pages of Original Document).
Office Action received for Japanese Patent Application No. 2019-527776, mailed on Feb. 1, 2023, 7 pages (3 pages of English Translation and 4 pages of Original Document).
Office Action received for European Patent Application No. 17837690, mailed on Jan. 31, 2024, 4 pages.
Office Action received for Australian Patent Application No. 2017306560, mailed on Aug. 10, 2023, 4 pages.
Office Action received for Indian Patent Application No. 201917007864, mailed on Dec. 29, 2023, 8 pages.
Office Action received for Korean Patent Application No. 10-2019-7005926, mailed on Nov. 3, 2023, 10 pages (5 pages of English Translation and 5 pages of Original Document).
Office Action received for Japanese Patent Application No. 2023-088687, mailed on Apr. 15, 2024, 8 pages (4 pages of English Translation and 4 pages of Original Document).

* cited by examiner

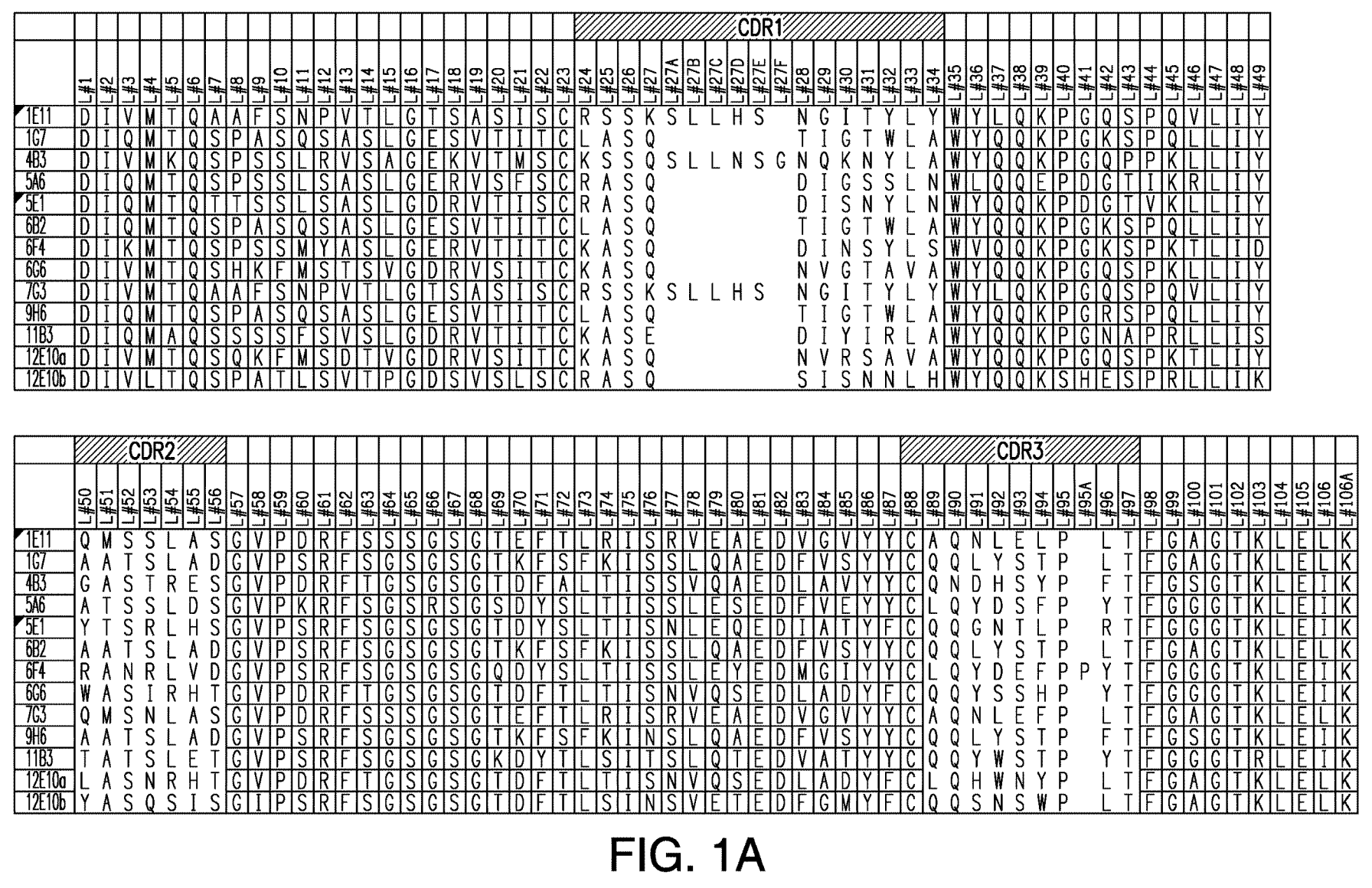

| | | | | | | | | | | | | | | | | | | | | | | | | CDR1 | | | | | | | | | |
|---|---|---|---|---|---|---|---|---|---|---|---|---|---|---|---|---|---|---|---|---|---|---|---|---|---|---|---|---|---|---|---|---|---|
| | L#1 | L#2 | L#3 | L#4 | L#5 | L#6 | L#7 | L#8 | L#9 | L#10 | L#11 | L#12 | L#13 | L#14 | L#15 | L#16 | L#17 | L#18 | L#19 | L#20 | L#21 | L#22 | L#23 | L#24 | L#25 | L#26 | L#27 | L#27A | L#27B | L#27C | L#27D | L#27E | L#27F |
| 1E11 | D | I | V | M | T | Q | A | A | F | S | N | P | V | T | L | G | T | S | A | S | I | S | C | R | S | S | K | S | L | L | H | S | |
| 1G7 | D | I | Q | M | T | Q | S | P | A | S | Q | S | A | S | L | G | E | S | V | T | I | T | C | L | A | S | Q | | | | | | |
| 4B3 | D | I | V | M | K | Q | S | P | S | S | L | R | V | S | A | G | E | K | V | T | M | S | C | K | S | S | Q | S | L | L | N | S | G |
| 5A6 | D | I | Q | M | T | Q | S | P | S | S | L | S | A | S | L | G | E | R | V | S | F | S | C | R | A | S | Q | | | | | | |
| 5E1 | D | I | Q | M | T | Q | T | T | S | S | L | S | A | S | L | G | D | R | V | T | I | S | C | R | A | S | Q | | | | | | |
| 6B2 | D | I | Q | M | T | Q | S | P | A | S | Q | S | A | S | L | G | E | S | V | T | I | T | C | L | A | S | Q | | | | | | |
| 6F4 | D | I | K | M | T | Q | S | P | S | S | M | Y | A | S | L | G | E | R | V | T | I | T | C | K | A | S | Q | | | | | | |
| 6G6 | D | I | V | M | T | Q | S | H | K | F | M | S | T | S | V | G | D | R | V | S | I | T | C | K | A | S | Q | | | | | | |
| 7G3 | D | I | V | M | T | Q | A | A | F | S | N | P | V | T | L | G | T | S | A | S | I | S | C | R | S | S | K | S | L | L | H | S | |
| 9H6 | D | I | Q | M | T | Q | S | P | A | S | Q | S | A | S | L | G | E | S | V | T | I | T | C | L | A | S | Q | | | | | | |
| 11B3 | D | I | Q | M | A | Q | S | S | S | S | F | S | V | S | L | G | D | R | V | T | I | T | C | K | A | S | E | | | | | | |
| 12E10a | D | I | V | M | T | Q | S | Q | K | F | M | S | D | T | V | G | D | R | V | S | I | T | C | K | A | S | Q | | | | | | |
| 12E10b | D | I | V | L | T | Q | S | P | A | T | L | S | V | T | P | G | D | S | V | S | L | S | C | R | A | S | Q | | | | | | |

| | CDR1 | | | | | | | | | | | | | | | | | | | | | |
|---|---|---|---|---|---|---|---|---|---|---|---|---|---|---|---|---|---|---|---|---|---|---|
| | L#28 | L#29 | L#30 | L#31 | L#32 | L#33 | L#34 | L#35 | L#36 | L#37 | L#38 | L#39 | L#40 | L#41 | L#42 | L#43 | L#44 | L#45 | L#46 | L#47 | L#48 | L#49 |
| 1E11 | N | G | I | T | Y | L | Y | W | Y | L | Q | K | P | G | Q | S | P | Q | V | L | I | Y |
| 1G7 | T | I | G | T | W | L | A | W | Y | Q | Q | K | P | G | K | S | P | Q | L | L | I | Y |
| 4B3 | N | Q | K | N | Y | L | A | W | Y | Q | Q | K | P | G | Q | P | P | K | L | L | I | Y |
| 5A6 | D | I | G | S | S | L | N | W | L | Q | Q | E | P | D | G | T | I | K | R | L | I | Y |
| 5E1 | D | I | S | N | Y | L | N | W | Y | Q | Q | K | P | D | G | T | V | K | L | L | I | Y |
| 6B2 | T | I | G | T | W | L | A | W | Y | Q | Q | K | P | G | K | S | P | Q | L | L | I | Y |
| 6F4 | D | I | N | S | Y | L | S | W | V | Q | Q | K | P | G | K | S | P | K | T | L | I | D |
| 6G6 | N | V | G | T | A | V | A | W | Y | Q | Q | K | P | G | Q | S | P | K | L | L | I | Y |
| 7G3 | N | G | I | T | Y | L | Y | W | Y | L | Q | K | P | G | Q | S | P | Q | V | L | I | Y |
| 9H6 | T | I | G | T | W | L | A | W | Y | Q | Q | K | P | G | R | S | P | Q | L | L | I | Y |
| 11B3 | D | I | Y | I | R | L | A | W | Y | Q | Q | K | P | G | N | A | P | R | L | L | I | S |
| 12E10a | N | V | R | S | A | V | A | W | Y | Q | Q | K | P | G | Q | S | P | K | T | L | I | Y |
| 12E10b | S | I | S | N | N | L | H | W | Y | Q | Q | K | S | H | E | S | P | R | L | L | I | K |

| | CDR2 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | L#50 | L#51 | L#52 | L#53 | L#54 | L#55 | L#56 | L#57 | L#58 | L#59 | L#60 | L#61 | L#62 | L#63 | L#64 | L#65 | L#66 | L#67 | L#68 | L#69 | L#70 | L#71 | L#72 | L#73 | L#74 | L#75 | L#76 | L#77 | L#78 | L#79 |
| 1E11 | Q | M | S | S | L | A | S | G | V | P | D | R | F | S | S | S | G | S | G | T | E | F | T | L | R | I | S | R | V | E |
| 1G7 | A | A | T | S | L | A | D | G | V | P | S | R | F | S | G | S | G | S | G | T | K | F | S | F | K | I | S | S | L | Q |
| 4B3 | G | A | S | T | R | E | S | G | V | P | D | R | F | T | G | S | G | S | G | T | D | F | A | L | T | I | S | S | V | Q |
| 5A6 | A | T | S | S | L | D | S | G | V | P | K | R | F | S | G | S | R | S | G | S | D | Y | S | L | T | I | S | S | L | E |
| 5E1 | Y | T | S | R | L | H | S | G | V | P | S | R | F | S | G | S | G | S | G | T | D | Y | S | L | T | I | S | N | L | E |
| 6B2 | A | A | T | S | L | A | D | G | V | P | S | R | F | S | G | S | G | S | G | T | K | F | S | F | K | I | S | S | L | Q |
| 6F4 | R | A | N | R | L | V | D | G | V | P | S | R | F | S | G | S | G | S | G | Q | D | Y | S | L | T | I | S | S | L | E |
| 6G6 | W | A | S | I | R | H | T | G | V | P | D | R | F | T | G | S | G | S | G | T | D | F | T | L | T | I | S | N | V | Q |
| 7G3 | Q | M | S | N | L | A | S | G | V | P | D | R | F | S | S | S | G | S | G | T | E | F | T | L | R | I | S | R | V | E |
| 9H6 | A | A | T | S | L | A | D | G | V | P | S | R | F | S | G | S | G | S | G | T | K | F | S | F | K | I | N | S | L | Q |
| 11B3 | T | A | T | S | L | E | T | G | V | P | S | R | F | S | G | S | G | S | G | K | D | Y | T | L | S | I | T | S | L | Q |
| 12E10a | L | A | S | N | R | H | T | G | V | P | D | R | F | T | G | S | G | S | G | T | D | F | T | L | T | I | S | N | V | Q |
| 12E10b | Y | A | S | Q | S | I | S | G | I | P | S | R | F | S | G | S | G | S | G | T | D | F | T | L | S | I | N | S | V | E |

| | | | | | | | | | | CDR3 | | | | | | | | | | | | | | | | | | |
|---|---|---|---|---|---|---|---|---|---|---|---|---|---|---|---|---|---|---|---|---|---|---|---|---|---|---|---|---|
| | L#80 | L#81 | L#82 | L#83 | L#84 | L#85 | L#86 | L#87 | L#88 | L#89 | L#90 | L#91 | L#92 | L#93 | L#94 | L#95 | L#95A | L#96 | L#97 | L#98 | L#99 | L#100 | L#101 | L#102 | L#103 | L#104 | L#105 | L#106 | L#106A |
| 1E11 | A | E | D | V | G | V | Y | Y | C | A | Q | N | L | E | L | P | | L | T | F | G | A | G | T | K | L | E | L | K |
| 1G7 | A | E | D | F | V | S | Y | Y | C | Q | Q | L | Y | S | T | P | | L | T | F | G | A | G | T | K | L | E | L | K |
| 4B3 | A | E | D | L | A | V | Y | Y | C | Q | N | D | H | S | Y | P | | F | T | F | G | S | G | T | K | L | E | I | K |
| 5A6 | S | E | D | F | V | E | Y | Y | C | L | Q | Y | D | S | F | P | | Y | T | F | G | G | G | T | K | L | E | I | K |
| 5E1 | Q | E | D | I | A | T | Y | F | C | Q | Q | G | N | T | L | P | | R | T | F | G | G | G | T | K | L | E | I | K |
| 6B2 | A | E | D | F | V | S | Y | Y | C | Q | Q | L | Y | S | T | P | | L | T | F | G | A | G | T | K | L | E | L | K |
| 6F4 | Y | E | D | M | G | I | Y | Y | C | L | Q | Y | D | E | F | P | P | Y | T | F | G | G | G | T | K | L | E | I | K |
| 6G6 | S | E | D | L | A | D | Y | F | C | Q | Q | Y | S | S | H | P | | Y | T | F | G | G | G | T | K | L | E | I | K |
| 7G3 | A | E | D | V | G | V | Y | Y | C | A | Q | N | L | E | F | P | | L | T | F | G | A | G | T | K | L | E | L | K |
| 9H6 | A | E | D | F | V | S | Y | Y | C | Q | Q | L | Y | S | T | P | | F | T | F | G | S | G | T | K | L | E | I | K |
| 11B3 | T | E | D | V | A | T | Y | Y | C | Q | Q | Y | W | S | T | P | | Y | T | F | G | G | G | T | R | L | E | I | K |
| 12E10a | S | E | D | L | A | D | Y | F | C | L | Q | H | W | N | Y | P | | L | T | F | G | A | G | T | K | L | E | L | K |
| 12E10b | T | E | D | F | G | M | Y | F | C | Q | Q | S | N | S | W | P | | L | T | F | G | A | G | T | K | L | E | L | K |

FIG. 1A

| | | | | | | | | | | | | | | | | | | | | | | | | | | | | | | | CDR1 | | | | |
|---|---|---|---|---|---|---|---|---|---|---|---|---|---|---|---|---|---|---|---|---|---|---|---|---|---|---|---|---|---|---|---|---|---|---|---|
| | H#1 | H#2 | H#3 | H#4 | H#5 | H#6 | H#7 | H#8 | H#9 | H#10 | H#11 | H#12 | H#13 | H#14 | H#15 | H#16 | H#17 | H#18 | H#19 | H#20 | H#21 | H#22 | H#23 | H#24 | H#25 | H#26 | H#27 | H#28 | H#29 | H#30 | H#31 | H#32 | H#33 | H#34 | H#35 |
| 1E11 | Q | V | Q | L | Q | Q | S | G | P | E | L | V | K | P | G | A | S | V | K | L | S | C | K | A | S | G | Y | T | F | T | S | Y | D | I | N |
| 1G7 | E | V | Q | L | V | E | S | G | G | G | L | V | Q | P | K | G | S | L | K | L | S | C | A | A | S | G | F | T | F | N | T | N | A | M | Y |
| 4B3 | Q | I | Q | L | Q | Q | S | G | A | E | L | A | R | P | G | A | S | V | K | L | P | C | K | A | S | D | Y | I | F | I | S | Y | G | L | N |
| 5A6 | Q | V | Q | L | Q | Q | S | G | A | E | L | A | R | P | G | A | S | V | K | L | S | C | K | A | S | G | Y | T | F | T | S | Y | G | I | S |
| 5E1 | E | V | Q | L | Q | Q | S | G | P | E | L | V | K | P | G | A | S | V | K | I | S | C | K | A | S | G | Y | S | F | T | G | Y | F | M | N |
| 6B2 | E | V | Q | L | V | E | S | G | G | G | L | V | Q | P | K | G | S | L | K | L | S | C | A | A | S | G | F | S | F | N | I | N | A | M | N |
| 6F4 | Q | V | Q | L | Q | Q | S | G | A | E | L | A | K | P | G | A | S | V | K | L | S | C | K | A | S | G | Y | T | F | T | S | Y | W | M | H |
| 6G6 | E | V | Q | L | Q | Q | S | G | P | E | L | V | K | P | G | A | S | V | K | I | S | C | K | A | S | G | Y | T | F | T | T | Y | Y | M | N |
| 7G3 | Q | V | Q | L | Q | Q | S | G | P | E | L | V | K | P | G | A | S | V | K | L | S | C | K | A | S | G | Y | T | F | T | T | Y | D | I | N |
| 9H6 | E | V | Q | L | V | E | S | G | G | G | L | V | Q | P | K | G | S | L | K | L | S | C | A | A | S | G | F | S | F | N | T | H | A | M | N |
| 11B3 | E | V | Q | L | V | E | S | G | G | G | L | V | Q | P | K | G | S | L | K | L | S | C | A | A | S | D | F | T | F | N | T | Y | A | M | H |
| 12E10 | Q | V | Q | L | Q | Q | S | G | A | E | L | A | R | P | G | T | S | V | K | L | S | C | K | A | S | G | Y | T | F | T | S | C | G | L | S |

| | | | | | | | | | | | | | | | CDR2 | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| | H#36 | H#37 | H#38 | H#39 | H#40 | H#41 | H#42 | H#43 | H#44 | H#45 | H#46 | H#47 | H#48 | H#49 | L#50 | L#51 | L#52 | L#52A | L#52B | L#52C | L#53 | L#54 | L#55 | L#56 | L#57 | L#58 | L#59 | L#60 | L#61 | L#62 | L#63 | L#64 | L#65 |
| 1E11 | W | V | K | Q | R | P | G | Q | G | L | E | W | I | G | W | I | Y | P | | | R | D | G | S | T | K | Y | N | E | K | L | K | G |
| 1G7 | W | V | R | Q | A | P | G | K | G | L | E | W | V | A | R | I | R | S | K | S | S | N | Y | A | T | Y | Y | A | D | S | V | K | D |
| 4B3 | W | V | R | Q | T | T | G | Q | G | L | E | W | I | G | E | I | Y | P | | | R | S | G | H | T | Y | Y | N | E | K | F | K | G |
| 5A6 | W | V | K | Q | R | T | G | Q | G | L | E | W | I | G | E | I | Y | P | | | R | R | G | N | T | Y | Y | N | E | K | F | K | G |
| 5E1 | W | V | K | Q | S | P | E | K | S | L | E | W | I | G | E | I | H | P | | | S | T | G | S | I | I | Y | N | Q | K | F | K | A |
| 6B2 | W | V | R | Q | A | P | G | K | G | L | E | W | V | A | R | I | R | S | K | S | N | N | Y | E | T | Y | Y | A | D | S | V | K | D |
| 6F4 | W | V | K | Q | R | P | G | Q | G | L | E | W | I | G | Y | I | N | P | | | F | S | G | H | T | K | Y | N | Q | K | F | K | D |
| 6G6 | W | V | K | Q | S | H | G | K | S | L | E | W | I | G | N | I | N | P | | | D | N | G | I | T | S | Y | N | Q | K | F | K | G |
| 7G3 | W | V | K | Q | R | P | G | Q | G | L | E | W | I | G | W | I | Y | P | | | R | D | G | T | T | K | Y | N | E | K | F | K | G |
| 9H6 | W | V | R | Q | A | P | G | K | G | L | E | W | V | A | R | I | R | T | K | S | N | N | Y | A | T | Y | Y | A | D | S | V | K | D |
| 11B3 | W | V | R | Q | A | P | G | K | G | L | E | W | V | A | R | I | R | T | K | S | N | N | Y | A | T | Y | Y | A | D | S | V | K | D |
| 12E10 | W | V | K | Q | R | T | G | Q | G | L | E | W | I | G | E | I | Y | P | | | S | N | G | N | S | Y | Y | S | D | K | V | K | D |

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | H#66 | H#67 | H#68 | H#69 | H#70 | H#71 | H#72 | H#73 | H#74 | H#75 | H#76 | H#77 | H#78 | H#79 | H#80 | H#81 | H#82 | H#82A | H#82B | H#82C | H#83 | H#84 | H#85 | H#86 | H#87 | H#88 | H#89 | H#90 | H#91 | H#92 | H#93 | H#94 |
| 1E11 | K | A | T | L | T | V | D | T | S | S | R | T | A | Y | M | E | L | H | S | L | T | S | E | D | S | A | V | Y | F | C | A | R |
| 1G7 | R | F | T | I | S | R | D | D | S | Q | S | M | L | Y | L | Q | M | N | N | L | K | T | E | D | T | A | R | Y | Y | C | V | R |
| 4B3 | K | A | T | L | T | A | D | K | S | S | S | T | A | Y | M | E | L | R | S | L | T | S | E | D | S | A | V | Y | F | C | A | R |
| 5A6 | K | A | T | L | T | A | D | K | S | S | S | T | A | Y | M | E | L | R | S | L | T | S | E | D | S | A | V | Y | F | C | A | R |
| 5E1 | K | A | T | L | T | I | D | K | S | S | S | T | A | Y | M | Q | L | K | S | L | T | S | E | D | S | A | V | Y | Y | C | A | R |
| 6B2 | R | F | T | I | S | R | D | D | S | E | S | M | V | Y | L | Q | M | N | N | L | K | T | E | D | T | A | M | Y | Y | C | V | R |
| 6F4 | K | A | T | L | T | A | D | K | S | S | S | T | A | Y | M | Q | L | S | S | L | T | Y | E | D | S | A | V | Y | Y | C | A | R |
| 6G6 | K | A | T | L | T | V | D | K | S | S | S | T | A | Y | M | E | L | R | S | L | T | S | E | D | S | A | V | Y | Y | C | A | R |
| 7G3 | K | A | T | L | T | V | D | T | S | S | T | T | A | Y | M | E | L | H | S | L | T | S | E | D | S | A | V | Y | F | C | A | R |
| 9H6 | R | F | I | I | S | R | D | D | S | E | N | M | V | Y | L | Q | M | N | N | L | K | T | E | D | T | A | I | Y | Y | C | V | R |
| 11B3 | R | F | T | I | S | R | D | D | S | Q | S | M | L | Y | L | Q | M | N | N | L | T | T | E | D | T | A | M | Y | Y | C | V | R |
| 12E10 | K | A | T | L | T | A | D | K | S | S | S | T | A | Y | M | E | L | R | S | L | T | S | E | D | S | A | V | Y | F | C | A | R |

| | CDR3 | | | | | | | | | | | | | | | | | | | | | | | | | |
|---|---|---|---|---|---|---|---|---|---|---|---|---|---|---|---|---|---|---|---|---|---|---|---|---|---|---|
| | H#95 | H#96 | H#97 | H#98 | H#99 | H#100 | H#100A | H#100B | H#100C | H#100D | H#100E | H#100F | H#100G | H#101 | H#102 | H#103 | H#104 | H#105 | H#106 | H#107 | H#108 | H#109 | H#110 | H#111 | H#112 | H#113 |
| 1E11 | G | G | Y | Y | D | Y | D | | | | | | | G | Y | W | G | Q | G | T | L | V | T | V | S | A |
| 1G7 | G | G | S | G | F | F | | | | | | | | A | Y | W | G | Q | G | T | L | V | T | V | S | A |
| 4B3 | R | S | V | F | Y | D | Y | D | K | N | G | F | | D | Y | W | G | Q | G | T | T | L | T | V | S | S |
| 5A6 | Q | L | F | | | | | | | | | | | A | Y | W | G | Q | G | T | L | V | T | V | S | A |
| 5E1 | F | D | Y | S | N | S | F | | | | | | | A | Y | W | G | Q | G | T | L | V | T | V | S | A |
| 6B2 | S | L | W | F | | | | | | | | | | V | Y | W | G | Q | G | T | L | V | T | V | S | A |
| 6F4 | N | F | | | | | | | | | | | | D | Q | W | G | Q | G | T | T | L | T | V | S | S |
| 6G6 | G | K | S | L | | | | | | | | | | A | Y | W | G | Q | G | T | L | V | T | V | S | A |
| 7G3 | G | G | Y | Y | D | Y | D | | | | | | | G | Y | W | G | Q | G | T | L | V | T | V | S | A |
| 9H6 | L | R | G | G | F | L | | | | | | | | D | Y | W | G | Q | G | T | T | L | T | V | S | S |
| 11B3 | D | R | Y | G | G | A | M | | | | | | | D | Y | W | G | Q | G | T | S | V | T | V | S | S |
| 12E10 | A | Y | Y | T | N | G | Y | Y | A | M | | | | D | Y | W | G | Q | G | T | S | V | T | V | S | S |

FIG. 1B

Alignment Results

| | |
|---|---|
| Data Name: | anti-Lair1 VL Tree Alignment |
| Description: | Multi-way Protein alignment, 13 sequences |
| File Name: | \\corp.nextcure.com\corpdata\Users$\...\anti-Lair1 VL Tree Alignment.am4 |
| Alignment: | Multi-way Protein alignment. |
| Parameters: | Scoring matrix: BLOSUM 62 |

Number of sequences to align: 13
Total length of aligned sequences with gaps: 114 aas Alignment Results

| | |
|---|---|
| Data Name: | anti-Lair1 VH Tree Alignment |
| Description: | Multi-way Protein alignment, 12 sequences |
| File Name: | \\corp.nextcure.com\corpdata\Users$\...\anti-Lair1 VH Tree Alignment.am4 |
| Alignment: | Multi-way Protein alignment. |
| Parameters: | Scoring matrix: BLOSUM 62 |

Number of sequences to align: 12
Total length of aligned sequences with gaps: 128 aas

- Cancer cells expressing multiple interacting inhibitory receptors may respond better to therapies disrupting these interactions
  - Cis/Trans interactions?
  - Tonic Signaling

| LAIR-1 | TM collagen (3) | LILRB4 | Anti-tumor effect |
|---|---|---|---|
| (-) | (-) | (-) | (-) |
| (+) | (-) | (-) | (+/-) |
| (+) | (+) | (-) | (+) |
| (+) | (-) | (+) | (++) |
| (+) | (+) | (+) | (+++) |

FIG. 3

| | |
|---|---|
| LAIR-1 Inhibitory Receptor | • Two ITIM-motifs-inhibits T cells, DCs, NK cells, MΦ and APC function<br>• Known ligands include collagens, C1q (complement C1 complex) and Surfactant Protein-D (SP-D)<br>• LAIR-1 expression is increased in tumor environments<br>• Maintains stemness of Acute myeloid leukemia (AML) cells |
| LAIR-2 Soluble Homolog | • Produced primarily by CD4+ T cells<br>• LAIR-1 decoy: Binds with *increased affinity* to collagen<br>• Increased levels of sLAIR-2 are associated with autoimmune diseases<br>• Not expressed in mouse |

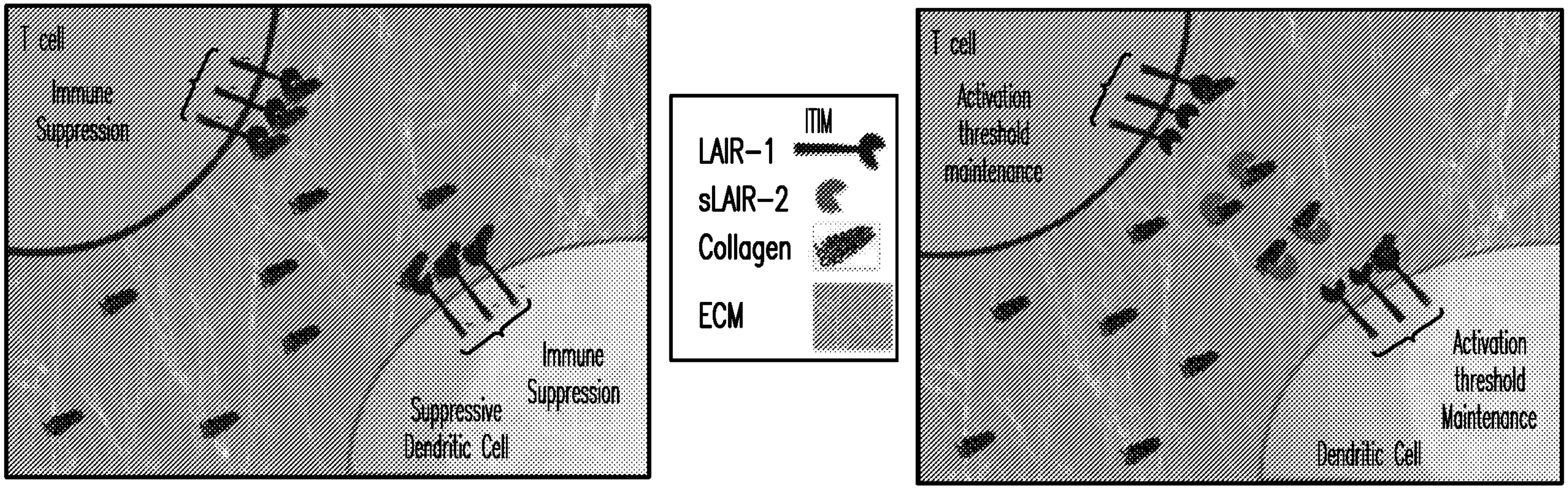

FIG. 4

2nd mAb

| 1st mAb | 4B3 | 5E1 | 6B2 | 11B3 | NKTA255 | 6F4 | 1E11 | 7G3 | 1A4 | 10G7 | 9H6 | 5A6 | DX26 | 6G6 |
|---|---|---|---|---|---|---|---|---|---|---|---|---|---|---|
| 4B3 | 0.0217 | 0.0123 | 0.0256 | 0.043 | 0.0305 | 0.3528 | −0.0098 | −0.0025 | −0.0005 | −0.0068 | 0.0005 | 0.4912 | 0.6297 | 0.687 |
| 5E1 | 0.0219 | 0.0188 | 0.0658 | 0.0731 | 0.2314 | 0.1526 | −0.0114 | −0.0063 | 0.0095 | 0.0395 | 0.036 | 0.2325 | 0.674 | 0.7905 |
| 6B2 | 0.0064 | 0.0218 | 0.0087 | 0.0198 | 0.0121 | 0.0119 | −0.006 | −0.0047 | −0.0013 | −0.0003 | 0.0111 | 0.4523 | 0.0124 | 0.6653 |
| 11B3 | 0.0052 | 0.0101 | 0.0067 | 0.0169 | 0.0087 | 0.0071 | −0.0063 | −0.0045 | −0.0055 | 0.0027 | 0.0068 | 0.4274 | −0.001 | 0.618 |
| NKTA255 | 0.0051 | 0.1018 | 0.0094 | 0.0231 | 0.0137 | 0.0153 | −0.0066 | 0.0001 | −0.0004 | 0.0061 | 0.0128 | 0.4367 | 0.0124 | 0.665 |
| 6F4 | 0.3312 | 0.3987 | 0.0105 | 0.0246 | 0.0131 | 0.0102 | 0.0375 | 0.0294 | −0.0243 | −0.0136 | −0.0057 | 0.4378 | −0.0008 | 0.6923 |
| 1E11 | 0.2729 | 0.2577 | 0.3583 | 0.4162 | 0.3416 | 0.3677 | 0.033 | 0.0316 | 0.0194 | 0.0655 | 0.1322 | 0.4807 | 0.6615 | 0.696 |
| 7G3 | 0.3035 | 0.2813 | 0.3911 | 0.4393 | 0.3802 | 0.3853 | 0.0403 | 0.0402 | 0.0376 | 0.0819 | 0.1501 | 0.5044 | 0.691 | 0.7623 |
| 1A4 | 0.5416 | 0.5306 | 0.6659 | 0.7656 | 0.6292 | 0.4269 | 0.0905 | 0.0813 | 0.0353 | 0.0939 | 0.175 | 0.5333 | 0.6867 | 0.8121 |
| 10G7 | 0.31 | 0.4089 | 0.3273 | 0.3971 | 0.3218 | 0.2802 | 0.0329 | 0.041 | 0.0246 | 0.0792 | 0.1396 | 0.5255 | 0.3399 | 0.772 |
| 9H6 | 0.1366 | 0.2045 | 0.0622 | 0.0931 | 0.072 | 0.0828 | 0.0123 | 0.0215 | 0.0176 | 0.0301 | 0.0501 | 0.5033 | 0.1383 | 0.7774 |
| 5A6 | 0.4351 | 0.1455 | 0.5596 | 0.6474 | 0.4861 | 0.3122 | 0.0263 | 0.0249 | −0.0543 | 0.0029 | 0.0798 | 0.0093 | 0.5941 | 0.0278 |
| DX26 | 0.386 | 0.4638 | 0.0018 | 0.0184 | −0.0006 | −0.0201 | 0.0773 | 0.0675 | −0.01 | −0.0128 | −0.0051 | 0.45 | 0.0178 | 0.7021 |
| 6G6 | 0.3936 | 0.4498 | 0.5605 | 0.6443 | 0.5099 | 0.3467 | 0.0188 | 0.0285 | 0.0058 | 0.0634 | 0.1378 | −0.0068 | 0.5876 | 0.0167 |

FIG. 21

| Rank | LAIR-1 chmeras | Kd(nM) | Kdis (1/s) | Kon |
|---|---|---|---|---|
| 1 | 1E11 | 1.37 | 0.00124 | 6.5-04 |
| 2 | 7G3 | 1.63 | 0.000111 | 7.8E-04 |
| 3 | 11B3 | 1.98 | 0.0017 | 8.4E-05 |
| 4 | 5E1 | 3.92 | 0.00189 | 4.8E-05 |
| 5 | 6G6 | 4.7 | 0.00322 | 8.5E-05 |
| 6 | 6B2 | 6.53 | 0.00354 | 5.1E-05 |
| 7 | 9H6 | 11.6 | 0.0104 | 8.4E-05 |
| 8 | 6F4 | 12.77 | 0.0115 | 9.1E-05 |
| 9 | 10G7 | 14.9 | 0.0154 | 9.0E-05 |
| 10 | 12E10V1 | 20.2 | 0.0127 | 6.3E-05 |
| 11 | 5A6 | 23.3 | 0.0302 | 1.3E-06 |
| 12 | 4B3 | 32.3 | 0.02 | 6.3E-05 |
| 13 | 12E10V2 | No binding | | |

COMPOSITIONS AND METHODS FOR MODULATING LAIR SIGNAL TRANSDUCTION

CROSS REFERENCE TO RELATED APPLICATIONS

This application claims benefit to and priority to U.S. Provisional Patent Application No. 62/370,334 filed on Aug. 3, 2016 and U.S. Provisional Patent Application No. 62/450,300 filed on Jan. 25, 2017, both of which are incorporated by reference in their entireties.

REFERENCE TO SEQUENCE LISTING

The instant application contains a Sequence Listing which has been submitted electronically in ASCII format and is hereby incorporated by reference in its entirety. Said ASCII copy, created on Jun. 14, 2021, is named "064467_002US_SL.txt" and is 155,786 bytes in size.

FIELD OF THE INVENTION

The invention is generally related to the field of immunomodulation, and more particularly to compositions and methods for modulating LAIR-1 signaling to increase or decrease an immune response and for the treatment of leukemias by direct regulation of leukemia cell survival and self-renewal.

BACKGROUND OF THE INVENTION

Leukocyte-associated immunoglobulin-like receptor-1 (LAIR-1) is an inhibitory cell surface receptor that is expressed on many immune cells and exerts inhibitory signaling through two cytoplasmic immunoreceptor tyrosine-based inhibitory motif (ITIM) domains (Verbrugge et al., 2006, *J. Leukoc. Biol.* 79:828-836). LAIR-1 is cross-linked by multiple collagens, complement component C1q, and surfactant protein D (SP-D) to induce negative signaling that inhibits immune cell maturation, proliferation and degranulation (Lebbink et al., 2009, *Matrix Biol.* 28:202-210; Meyaard., 2008, *J. Leukoc. Biol.* 83:799-803). The human, but not mouse, genome encodes a soluble LAIR-2 protein (Sun et al., 2014, *Gene* 552:140-145). The LAIR-2 protein binds the same ligands as LAIR-1, and thus may function as a decoy to reduce inhibitory signals through LAIR-1.

LAIR-1 inhibitory signaling may prevent autoimmune diseases such as lupus erythematosus, rheumatoid arthritis, autoimmune thyroid disease and atherosclerosis as well as contact hypersensitivity (Sun et al., 2014, *Gene* 552:140-145). Reduced expression of LAIR-1 on chronic lymphocytic leukemia cells is associated with increased disease (Poggi et al., 2008, *Leukemia* 22:980-988; Perbellini et al., 2014, *Haematolagica* 99:881-887). LAIR-1 has also been shown to be expressed on epithelial ovarian cancer cells and other human tumors, although the function of LAIR-1 expressed on solid tumors remains unclear (Meyaard et al., 1997, *Immunity* 7:283-290; Cao et al., 2015, *Biochem. Biophys. Res. Commun.* 458:399-404).

LAIR-1 expression on acute myeloid leukemia (AML) cells and potentially acute lymphoblastic leukemia (ALL) cells has been shown to be essential for their growth through a phosphatase independent LAIR-1-SHP-1-CAMK1-CREB signaling pathway that inhibits apoptosis and differentiation of leukemia stem cells to retain the self-renewal capacity or 'stemness' of these cells (Kang et al., 2015, *Nat. Cell Biol.* 17:665-677).

Together, the accumulated data on LAIR-1 indicates an important role in immune homeostasis, however, there remains a need for compositions and methods of modulating LAIR-1 for the treatment of diseases and disorders.

Thus, it is an object of the invention to provide compositions that increase LAIR-1 negative signaling and methods of use thereof for the treatment of inflammatory diseases and disorders and autoimmune diseases.

It is also an object of the invention to provide compositions that reduce LAIR-1 negative signaling and methods of use thereof for the treatment of cancer and infectious diseases.

SUMMARY OF THE INVENTION

Compositions and methods of use thereof for modulating LAIR-1 are provided. For example, immunomodulatory agents are provided that reduce LAIR-1 expression, ligand binding, crosslinking, signal transduction, or a combination thereof. LAIR-1 can be expressed by, for example, a myeloid cell, a T cell, a Natural Killer (NK) cell, or a combination thereof. The myeloid cell can be an antigen-presenting cell, for example, a monocyte, macrophage, or dendritic cell. In some embodiments, the compositions specifically target one or more of the foregoing cell types.

The disclosed agents can be used to increase an immune response in a subject in need thereof. An immune response can be, for example, a primary immune response to an antigen or an increase in effector cell function such as increasing antigen-specific proliferation of T cells, enhancing cytokine production by T cells, stimulating differentiation, or a combination thereof. Exemplary agents include (i) a soluble LAIR-2 polypeptide or fusion protein, (ii) a soluble LAIR-1 polypeptide or fusion protein, (iii) a function blocking anti-LAIR-1 antibody, (iv) an antibody that can be used to deplete LAIR-1 positive cells, and (v) combinations thereof. In some embodiments, the immunomodulatory agent is an antagonist of LAIR-1.

In particular embodiments the agent is a LAIR-2 fusion protein, for example a fusion protein that includes an extracellular domain of LAIR-2 or functional variant thereof linked to an immunoglobulin domain. An exemplary fusion protein includes the amino acid sequence of SEQ ID NO:16.

In other embodiments the agent is a LAIR-2 protein or a functional fragment or variant thereof. For example, the LAIR-2 protein or functional fragment or variant thereof can have at least 80%, 90%, 95%, or 100% sequence identity to SEQ ID NO:6.

The agent can be a LAIR-1 fusion protein, for example a fusion protein that includes an extracellular domain of LAIR-1 or functional variant thereof linked to an immunoglobulin domain. An exemplary LAIR-1 fusion protein includes the amino acid sequence of SEQ ID NO:9.

In other embodiments, the agent is a soluble LAIR-1 protein or a functional fragment or variant thereof. For example, the soluble LAIR-1 protein can consist of an extracellular domain of LAIR-1 or a functional fragment or variant thereof. An exemplary soluble protein has at least 80%, 90%, 95%, or 100% sequence identity to SEQ ID NO:2.

Methods of increasing an immune response in a subject typically include administering to a subject in need thereof an effective amount of an immunomodulatory agent that reduces LAIR-1 expression, ligand binding, crosslinking, signal transduction, or a combination thereof. The subject can have, for example, cancer or an infectious disease.

In some embodiments, the subject, the cancer, or the disease is characterized by increased expression of LAIR-1, increased expression of a LAIR-1 ligand, decreased expression of LAIR-2, or a combination thereof. In particular embodiments, the cancer is an ovarian, lung, gastrointestinal cancer, acute myeloid leukemia (AML) or acute lymphoid leukemia (ALL). The agent can be administered contemporaneously or in combination as a single composition with a vaccine or a component thereof.

Immunomodulatory agents are also provided that increase LAIR-1 expression, ligand binding, crosslinking, negative signaling, or a combination thereof. Such agents can be used to reduce an immune response in a subject in need thereof. Exemplary agents include: (i) a function activating anti-LAIR-1 antibody, (ii) a function blocking anti-LAIR-2 antibody, and (iii) a combination thereof.

One embodiment provides an anti-LAIR antibody produced by a hybridoma selected from the group consisting of 1E11, 1G7, 4B3, 5A6, 5E1, 6B2, 6F4, 6G6, 7G3, 9H6, 11B3, 12E10a, and 12E10b.

Another embodiment provides an anti-LAIR antibody having at least one light chain or at least one heavy chain of the antibody produced by one or more of the hybridomas selected from the group consisting of 1E11, 1G7, 4B3, 5A6, 5E1, 6B2, 6F4, 6G6, 7G3, 9H6, 11B3, 12E10a, and 12E10b.

Another embodiment provides an anti-LAIR antibody having a variable light chain having at least 50, 60, 70, 80, 85, 90, 95, 96, 97, 98, 99, or 100% sequence identity to a variable light chain having an amino acid sequence according to SEQ ID NO: 19, 27, 35, 43, 51, 59, 67, 75, 83, 91, 99, 107, or 115.

Another embodiment provides an anti-LAIR antibody having a variable heavy chain having at least 50, 60, 70, 80, 85, 90, 95, 96, 97, 98, 99, or 100% sequence identity to a variable heavy chain having an amino acid sequence according to SEQ ID NO: 23, 31, 39, 47, 55, 63, 71, 79, 87, 95, 103, or 111.

Another embodiment provides an anti-LAIR antibody having a variable light chain having at least 50, 60, 70, 80, 85, 90, 95, 96, 97, 98, 99, or 100% sequence identity to a variable light chain having an amino acid sequence according to SEQ ID NO: 19, 27, 35, 43, 51, 59, 67, 75, 83, 91, 99, 107, or 115, and a variable heavy chain having at least 50, 60, 70, 80, 85, 90, 95, 96, 97, 98, 99, or 100% sequence identity to an amino acid sequence according to SEQ ID NO: 23, 31, 39, 47, 55, 63, 71, 79, 87, 95, 103, or 111.

Another embodiment provides an anti-LAIR antibody having a complementarity-determining region (CDR) selected from the group of CDRs having an amino acid sequence selected from the group consisting of SEQ ID NOs: 20-22, 24-26, 28-30, 32-34, 36-38, 40-42, 44-46, 48-50, 52-54, 56-58, 60-62, 64-66, 68-70, 72-74, 76-78, 80-82, 84-86, 88-90, 92-94, 96-98, 100-102, 104-106, 108-110, 112-114, and 116-118.

Another embodiment provides an anti-LAIR antibody having a plurality of CDRs selected from the group consisting of SEQ ID NOs: 20-22, 24-26, 28-30, 32-34, 36-38, 40-42, 44-46, 48-50, 52-54, 56-58, 60-62, 64-66, 68-70, 72-74, 76-78, 80-82, 84-86, 88-90, 92-94, 96-98, 100-102, 104-106, 108-110, 112-114, and 116-117. The plurality of CDRs can be from 2-12.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:120 or SEQ ID NO:122 and/or a light chain with an amino acid sequence at least 50, 60, 70, 80, 85, 90, 95, 96, 97, 98, 99, or 100% sequence identity to the amino acid sequence set forth in SEQ ID NO:124.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:126 or SEQ ID NO:128 and/or a light chain with an amino acid sequence at least 50, 60, 70, 80, 85, 90, 95, 96, 97, 98, 99, or 100% sequence identity to the amino acid sequence set forth in SEQ ID NO:130.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:132 or SEQ ID NO:134 and/or a light chain with an amino acid sequence at least 50, 60, 70, 80, 85, 90, 95, 96, 97, 98, 99, or 100% sequence identity to the amino acid sequence set forth in SEQ ID NO:136.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:138 or SEQ ID NO:140 and/or a light chain with an amino acid sequence at least 50, 60, 70, 80, 85, 90, 95, 96, 97, 98, 99, or 100% sequence identity to the amino acid sequence set forth in SEQ ID NO:142.

Another embodiment provides a nucleic acid sequence encoding an antibody having a light chain amino acid sequence according to SEQ ID NO:124, 130, 136, or 142 and/or a heavy chain amino acid according to SEQ ID NO: 120, 122, 126, 128, 132, 134, 138 or 140.

Another embodiment provides a nucleic acid sequence encoding a variable light chain according to SEQ ID NOs 19, 27, 35, 43, 51, 59, 67, 75, 83, 91, 99, 107, or 115 and/or a variable heavy chain according to SEQ ID NOs 23, 31, 39, 47, 55, 63, 71, 79, 87, 95, 103, or 111. The nucleic acids encoding the light chain and/or heavy chain can be part of an expression vector. The nucleic acids can be expressed by cell. Expression can be inducible or constitutive.

Another embodiment provides a cell constitutively- or inducibly-expressing an antibody or antigen binding fragment thereof that specifically binds to LAIR-1, wherein the cell has a nucleic acid or nucleic acids encoding an amino acid sequence according to SEQ ID NOs: 19, 27, 35, 43, 51, 59, 67, 75, 83, 91, 99, 107, 115, 23, 31, 39, 47, 55, 63, 71, 79, 87, 95, 103, 111, or a combination thereof.

Another embodiment provides a cell constitutively- or inducibly-expressing an antibody or antigen binding fragment thereof that specifically binds to LAIR-1, wherein the cell has a nucleic acid or nucleic acids encoding an amino acid a sequence according to SEQ ID NOs: 120, 122, 124, 126, 128, 130, 132, 134, 136, 138, 140, 142, or a combination thereof.

Methods of reducing an immune response in a subject typically include administering a subject in need thereof an effective amount of an immunomodulatory agent that increases LAIR-1 expression, ligand binding, crosslinking, negative signaling, or a combination thereof. In some embodiments, the subject has inflammation, an autoimmune disorder. In a particular embodiment, the subject has rheumatoid arthritis.

In some embodiments, the subject or the disease or condition is characterized by reduced expression of LAIR-1, reduced expression of a LAIR-1 ligand, increased expression of LAIR-2, or a combination thereof.

Any of the disclosed methods can include administering to the subject an immunomodulatory agent alone or in combination with one or more additional therapeutic agents.

One embodiment provides a method for treating leukemia in a subject in need thereof by administering to the subject an effective amount of a pharmaceutical composition comprising a LAIR-1 monoclonal antibody, soluble LAIR-1 polypeptide, soluble LAIR-2 polypeptide, LAIR-1 fusion protein, LAIR-2 fusion protein, or combinations thereof to inhibit or reduce LAIR-1 signal transduction in leukemia cells and thereby inhibit leukemia cell survival or promote an anti-tumor immune response to the leukemia cells. The leukemia can be acute myeloid leukemia.

One embodiment provides a method for assessing or predicting the efficacy of a treatment using an anti-LAIR binding moiety by assaying the cells of a subject in need of treatment to determine whether the cells express LAIR, binding partners of LAIR, or both. Exemplary cells to be assayed include, but are not limited to cancer cells obtained from the subjected. Exemplar cancer cells, include but are not limited to acute myeloid leukemia (AML) cells. Cancer cells expressing multiple interacting inhibitory receptors are believed to respond better to treatments using anti-LAIR binding moieties. Exemplary LAIR binding partners include, but are not limited to transmembrane collagens (XIII, XVII and XXIII) and LILRB4. FIG. 3 shows a predicted outcome of treatment based on the presence of LAIR-1 or binding partners of LAIR-1 on cancer cells.

One embodiment provides a fusion protein according to SEQ ID NO:9, 10, 11, 12, 13, 14, 15, 16, 17, or 18.

BRIEF DESCRIPTION OF THE FIGURES

FIG. 1A is a table showing the amino acid sequence of variable light chains in anti-LAIR-1 antibodies from clones 1E11, 1G7, 4B3, 5A6, 5E1, 6B2, 6F4, 6G6, 7G3, 9H6, 11B3, 12E10a, and 12E10b. FIG. 1A discloses SEQ ID NOS 19, 27, 35, 43, 51, 27, 67, 75, 83, 91, 99, 107, and 115, respectively, in order of appearance. FIG. 1B is a table showing the amino acid sequence of variable heavy chains in anti-LAIR-1 antibodies from clones 1E11, 1G7, 4B3, 5A6, 5E1, 6B2, 6F4, 6G6, 7G3, 9H6, 11B3, and 12E10 (a and b). FIG. 1B discloses SEQ ID NOS 23, 31, 39, 47, 55, 63, 71, 79, 87, 95, 103, and 111, respectively, in order of appearance.

FIG. 3 is a table show projected treatment outcomes based on expressing of LAIR-1, LAIR-1 binding partners, or combinations thereof.

FIG. 4 is a schematic diagram illustrating LAIR regulation of immune function and homeostasis.

FIG. 10B is a bar graph of IRF (interferon regulatory factor) Induction—RLU for THP-1 cells treated with 1 μg/ml LPS and LAIR-2 Fc (right column of each pair) or control Fc (left column of each pair).

FIG. 21 is a table showing the results of LAIR-1 chimeric mAb epitope binning assay. Single underlined antibodies show no blocking. Double underlined antibodies show blocking. mAbs that bind the same epitope will be blocked from binding LAIR-1 Fc due to binding saturation, as can be observed when the same mAb is used as the first and second mAb (no underlined, stipled background).

DETAILED DESCRIPTION OF THE INVENTION

I. Definitions

Figure 2A:
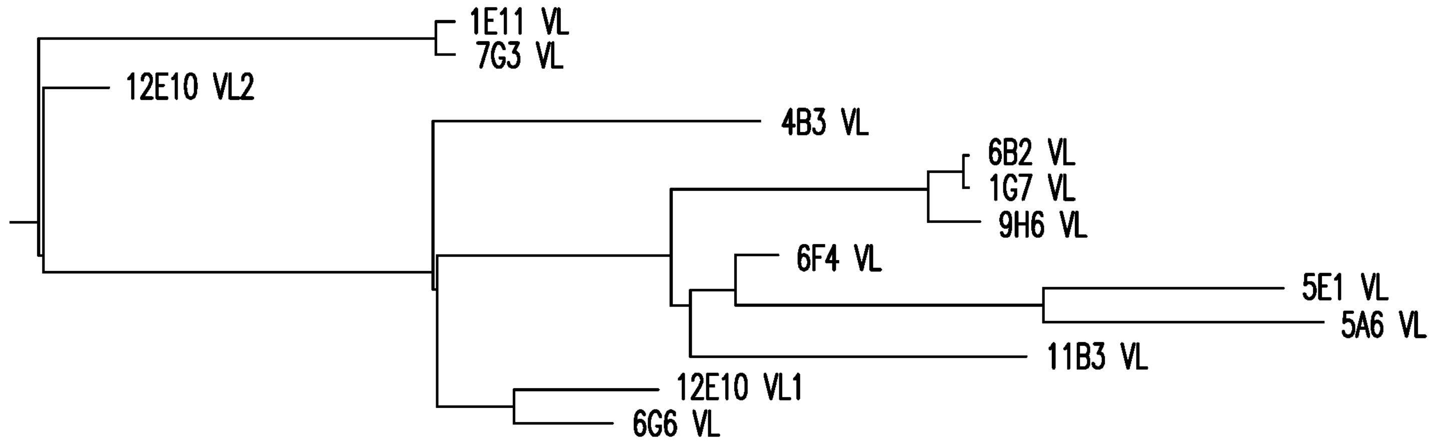
FIG. 2A is a multiple way alignment graph of variable light chains from the indicated hybridomas.
Figure 2B:
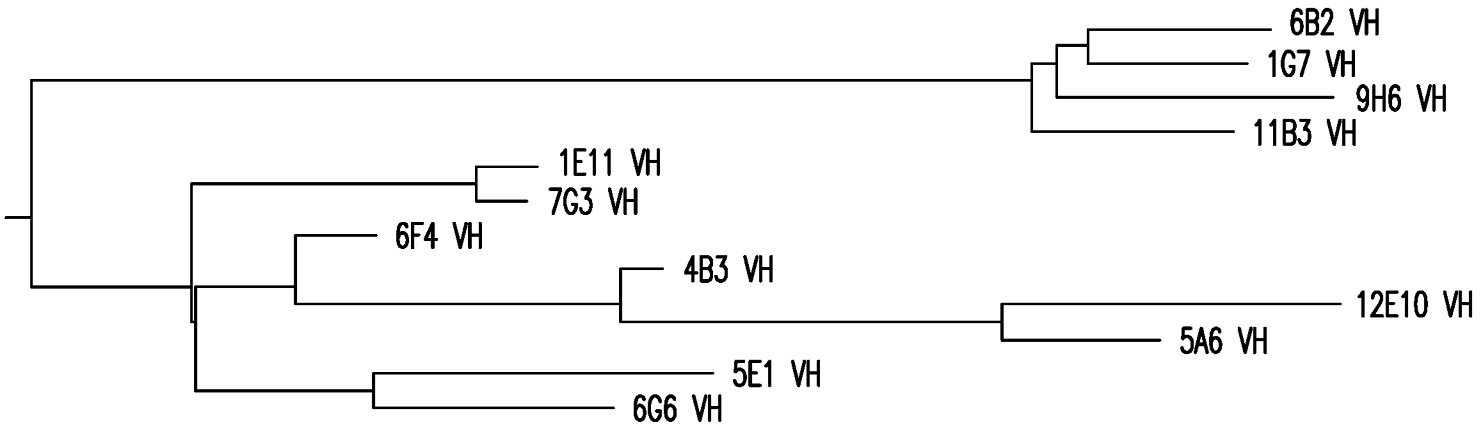
FIG. 2B is a multiple way alignment graph of variable heavy chains from the indicated hybridomas.

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. In some embodiments, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J.* Mol. Biol. 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')2, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. In some embodiments, such modulation will provide at least a 10% change in a measurable immune system activity, at least a 50% change in such activity, or at least a 2-fold, 5-fold, 10-fold, or at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "co-stimulatory" signals encompass positive co-stimulatory signals (e.g., signals that result in enhancing an activity) and negative co-stimulatory signals (e.g., signals that result in inhibiting an activity).

The term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. In some embodiments such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, or about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

The term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "inflammatory molecules" refer to molecules that result in inflammatory responses including, but not limited to, cytokines and metalloproteases such as including, but not limited to, IL-1β, TNF-α, TGF-beta, IFN-γ, IL-18, IL-17, IL-6, IL-23, IL-22, IL-21, and MMPs.

As used herein, "valency" refers to the number of binding sites available per molecule.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4+T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

As used herein, the terms "individual," "host," "subject," and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

II. Compositions

Figure 5:
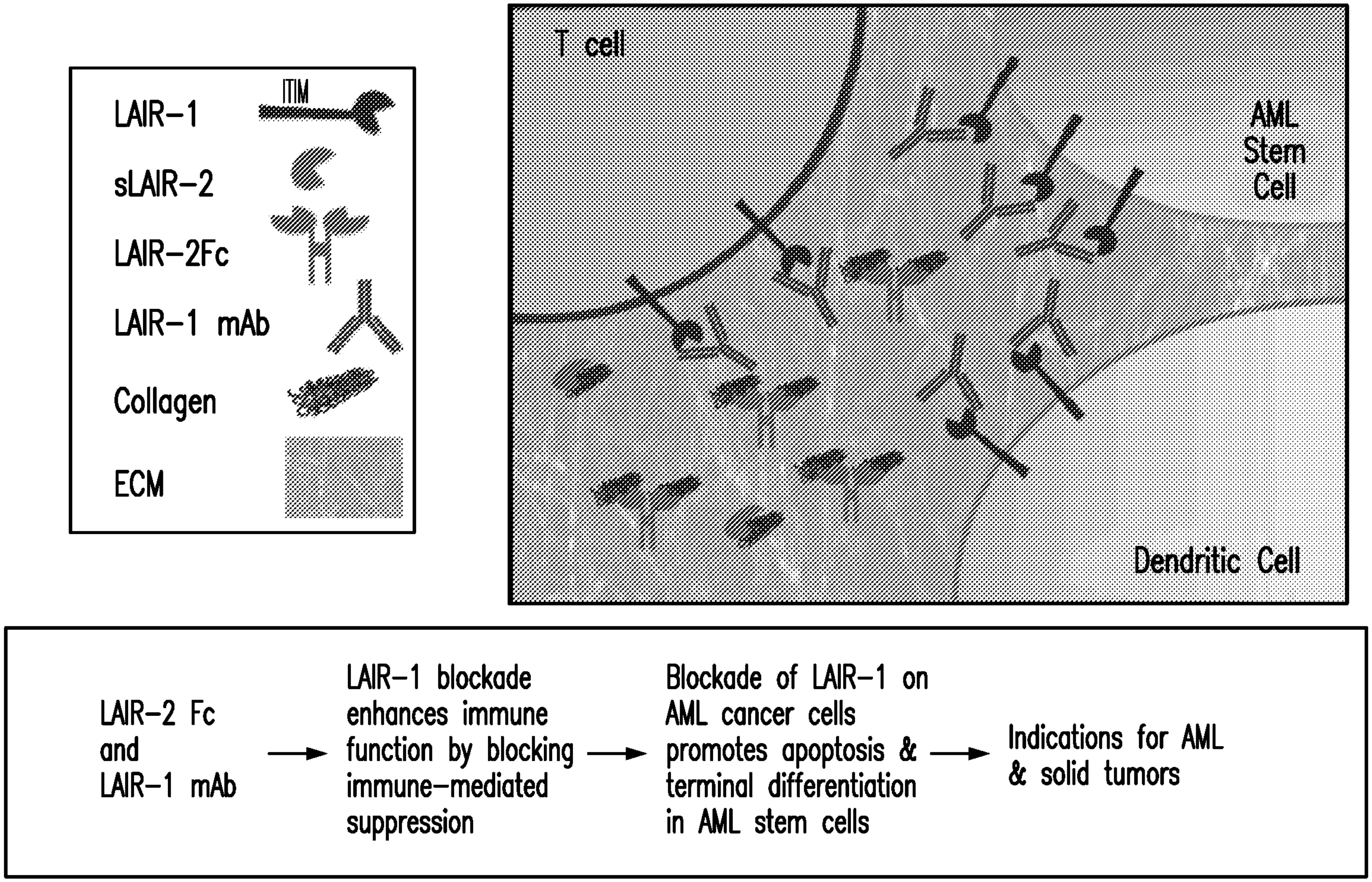
FIG. 5 is a schematic diagram of LAIR-2 Fc and LAIR-1 monoclonal antibodies (mAbs) as therapeutics.

LAIR binding moieties are provided that are useful for modulating signal transduction through LAIR proteins. FIG. 4 shows LAIR regulation of immune function and homeostasis. FIG. 5 shows how LAIR-1 mAbs and LAIR-2 Fc can be used as therapeutics.

A. LAIR Polypeptides

LAIR-1 and LAIR-2 polypeptides are disclosed. The polypeptides can include an amino acid sequence of full-length LAIR-1 or LAIR-2 proteins, or a fragment or variant thereof, or a fusion protein thereof.

LAIR-1 is an inhibitory cell surface receptor that is expressed on many immune cells and exerts inhibitory signaling through two cytoplasmic immunoreceptor tyrosine-based inhibitory motifs (ITIMs) (Verbrugge et al., 2006) (FIG. 4). Human and non-human primate, but not mouse, genomes encode a LAIR-2 gene that is a soluble homolog of LAIR-1 (Sun et al., 2014). LAIR-2 lacks transmembrane and cytoplasmic domains, but binds the same ligands as LAIR-1, and thus may function as a decoy to reduce inhibitory signals through LAIR-1 (Meyaard, 2008). LAIR-1 and LAIR-2 interact with multiple collagens, including fibrillar collagens I and III, and transmembrane collagens 13, 17 and 23, but may also bind other collagens to varying extents due to recognition of canonical Gly-Pro-Hyp hydroxyproline repeat (Meyaard, 2008). LAIR-1 and LAIR-2 also bind to complement component C1q, surfactant protein D (SP-D) and mannose binding lectin (MBL). Cross-linking of these molecules with LAIR-1 on the leukocyte plasma membrane induce negative signaling that inhibits immune cell maturation, proliferation and degranulation (Lebbink et al., 2009), Meyaard., (2008)).

LAIR-1 inhibitory signaling may prevent autoimmune diseases such as lupus erythematosus, rheumatoid arthritis, autoimmune thyroid disease and atherosclerosis as well as contact hypersensitivity (Sun et al., 2014). Meanwhile, overexpression of LAIR-2 may promote autoimmunity through decoy binding of LAIR-1 ligands. LAIR-2 binding of LAIR-1 ligands can essentially reduce the cell surface cross-linking of LAIR-1, delimiting inhibitory signaling pathways leading to over-reactive immune function. Conversely, it hypothesized that increased levels of LAIR-2 may promote anti-tumor immunity through the same mechanism.

Reduced expression of LAIR-1 on chronic lymphocytic leukemia (CLL) cells is associated with increased disease (Poggi et al., 2008; Perbellini et al., 2014). Conversely, studies suggest that increased expression of LAIR-1 on acute myeloid leukemia (AML) promotes AML survival by maintaining a stem-like state and preventing differentiation and apoptosis (Kang et al., 2015). IN support of this notion, other studies have also indicated that LAIR-1 is increased on AML and acute lymphoblastic leukemia (ALL) cancers (Mirkowska et al, Blood, 2013; Chen et al, Nature, 2015; Zhang et al., review in life.sciechina.com, 2015). LAIR-1 has also been shown to be expressed on epithelial ovarian cancer cells and other human tumors, although the function of LAIR-1 expressed on solid tumors remains unclear (Meyaard et al., 1997; Cao et al., 2015).

Tumor microenvironments are often rich in extracellular matrix proteins (ECMs), including the collagens (Rygiel et al., 2011). Therefore, LAIR-1 expressing cells localized to tumor microenvironments may be particularly suppressed through collagen cross-linking of Lair-1 and subsequent inhibitory signaling. Interestingly, both collagen and C1q have been shown to limit or alter antigen-presenting cell (monocyte/macrophage/DC) differentiation and activation through LAIR-1. Studies have indicated that cross-linking Lair-1 on NK cells that T cells can inhibit proliferation and function. However, the role LAIR-1 in the regulation anti-tumor immunity requires further study.

Together, the accumulated data on LAIR-1 indicates an important role in immune modulation. However, differential expression of LAIR-1 on murine and human cells, as well as the presence of LAIR-2 in humans, but not in mice, have suggested that mouse studies may not be indicative of the function of LAIR-1/LAIR-2 in humans. Whereas, it is hypothesized that the human system may be more easily exploited therapeutically because of the presence of LAIR-2. In other words, LAIR-2 may be utilized therapeutically to modulate LAIR-1 function in humans, which is not possible in the murine system. Therefore, LAIR-2 Fc decoy proteins or blocking (antagonist) LAIR-1 mAbs may be effective for cancer immunotherapy to enhance immune function by preventing signaling through cell surface LAIR-1 (FIG. 5). Conversely, agonist LAIR-1 mAbs, or blockade of LAIR-2 by mAbs could be utilized for treatment of autoimmune disease, as this would essentially increase signaling through LAIR-1, thus downregulating immune responses.

1. LAIR-1

Sequences for LAIR-1 are provided. In some embodiments, the leading methionine amino acid is cleaved in the post-translation form of the protein.

a. Human LAIR-1

Sequences for human LAIR-1 are known in the art. For example, a consensus sequence for LAIR-1a (isoform 1) is

```
MSPHPTALLGLVLCLAQTIHTQEEDLPRPSISAEPGTVIPLGSHVTFVC
RGPVGVQTFRLERESRSTYNDTEDVSQASPSESEARFRIDSVSEGNAGP
YRCIYYKPPKWSEQSDYLELLVKETSGGPDSPDTEPGSSAGPTQRPSDN
SHNEHAPASQGLKAEHLYILIGVSVVFLFCLLLLVLFCLHRQNQIKQGP
PRSKDEEQKPQQRPDLAVDVLERTADKATVNGLPEKDRETDTSALAAGS
SQEVTYAQLDHWALTQRTARAVSPQSTKPMAESITYAAVARH (SEQ
ID NO: 1, UniProtKB-Q6GTX8 (LAIR1_HUMAN)),
```

where amino acids 1-21 are a signal sequence, amino acids 22-165 (underlined) are an extracellular domain, amino acids 166-186 are a transmembrane domain, and amino acids 187-287 are a cytoplasmic domain. Amino acids 29-117 form an Ig-like C2-domain. Amino acids 249-254 and 279-284 form ITIM motif 1 and 2, respectively. LAIR-1b (also known as isoform 2) is missing amino acids 122-138 relative to SEQ ID NO:1. LAIR-1c (also known as isoform 3) is missing amino acids 23-23 and 122-138 relative to SEQ ID NO:1. LAIR-1d (also known as isoform 4) is missing amino acids 210-287 relative to SEQ ID NO:1.

As introduced above, an extracellular domain for human LAIR-1 can be (SEQ ID NO: 2)

QEEDLPRPSISAEPGTVIPLGSHVTFV*CRGPVGVQTFRLERESRSTYND*

*TEDVSQASPSESEARFRIDSVSEGNAGPYRC*IYYKPPKWSEQSDYLELL

VKETSGGPDSPDTEPGSSAGPTQRPSDNSHNEHAPASQGLKAEHLY, or a fragment thereof, for example, the Ig-like C2-domain IDC-68 DNA M (underlined amino acids 8-96 of SEQ ID NO:2), or the region framed by the cysteines that form the disulfide bond between amino acids 49-101 of SEQ ID NO:1 (amino acids 28-80 of SEQ ID NO:2, illustrated in italics).

Known variants and mutants of LAIR-1 include E63D, Y251F, and Y251F, relative to SEQ ID NO:1. Evidence shows that Y215F reduced tyrosine phosphorylation and loss of binding to PTPN6 and CSK as well as complete loss of inhibitory activity, as well as loss of phosphorylation and of inhibition of calcium mobilization when associated with F-281 (Xu, et al., *J. Biol. Chem.* 275:17440-17446 (2000), Verbrugge, et al., *Int. Immunol.,* 15:1349-1358 (2003), Verbrugge, et al., *Eur. J. Immunol.,* 36:190-198 (2006)). Y281F shows reduced tyrosine phosphorylation and loss of binding to PTPN6, and partial inhibition of cytotoxic activity.

Meyaard, 2008, *J. Leukoc. Biol.* 83:799-803 indicates that LAIR-1 is broadly expressed on human immune cells. An examination of actual flow cytometry expression data in research papers shows that LAIR-1 is much more highly expressed on myeloid lineage cells such as monocytes, macrophages and dendritic cells, than on T cells and NK cells (Meyaard et al., 1997, *Immunity* 7:283-290). However, B cells differentially express high levels of LAIR-1 during differentiation (van der Vuurst de Vries et al., 1999, *Eur. J. Immunol.* 29:3160-3167). LAIR-1 has also been found to be expressed on acute myeloid leukemia cells, acute lymphoblastic leukemia cells and chronic lymphocytic leukemia cells (van der Vuurst de Vries et al., 1999, *Eur. J. Immunol.* 29:3160-3167; Poggi et al., 2000, *Eur. J. Immunol.* 30:2751-2758; Zocchi et al., 2001, *Eur. J. Immunol.* 31:3667-3675; Perbellini et al., 2014, *Haematologica,* 99:881-887; (Kang et al., 2015, *Nat. Cell Biol.* 17:665-677). Finally, LAIR-1 was shown be expressed on several human tumor cell lines (Meyaard et al., 1997, *Immunity* 7:283-290; Cao et al., 2015, *Biochem. Biophys, Res. Commun.* 458:399-404; (Kang et al., 2015, *Nat. Cell Biol.* 17:665-677).

In humans and mice, LAIR-1 binds several types of collagen with high affinity (Meyaard, 2008, *J. Leukoc. Biol.* 83:799-803 and Meyaard, 2010, *Immunol. Lett.* 128:26-28). In humans, LAIR-1 has also been shown to bind the complement component C1q (Son et al., 2012, *Proc. Natl. Acad. Sci. USA* 109:E3160-3167) and the collagenous C-type lectin, surfactant protein-D (SP-D), a collagenous carbohydrate binding glycoprotein (collectin) that plays important roles in the lung's innate immune response to microbial and antigenic challenge (Olde Nordkamp et al., 2014, *J. Leukoc. Biol.* 96:105-111). The ability of murine LAIR-1 to bind C1q and SP-D has not been examined.

Systemic lupus erythematosus (SLE) is a prototypic autoimmune disease characterized by the loss of immune tolerance. An immunosuppressive role for C1q is supported by the high percentage of C1q-deficient individuals who develop SLE. Dr. Son and her Feinstein Institute collaborators Dr. Betty Diamond, Dr. Frances Santiago-Schwarz and Dr. Yousef Al-Abed have shown that C1q is a functional ligand for LAIR-1, which is known as a universal collagen receptor. They have further shown that C1q promotes tolerance by inhibition of monocyte to DC differentiation and pDC activation through engagement of LAIR-1 (Son and Diamond, *Mol. Med.,* 2015, 20:559-568; Son et al., *PNAS,* 109(46):E3160-3167). This discovery has a high impact on the lupus field, because these findings elucidate the mechanism by which the complement system regulates tolerance and prevents autoimmune diseases, such as lupus.

All collagens are composed of 3 polypeptide chains that are characterized by a repeating Gly-X-X' sequence, where X is often proline and X' frequently 4-R-hydroxyproline (Hyp, O) (Brondijk, *Blood,* 115(7):1364-1373 (2010). The GPO triplets are an almost exclusive feature of collagens and allow the formation of the characteristic triplehelical collagen structure.

The ectodomains of the known immunoglobulin superfamily collagen receptors, LAIR-1, GPVI, and OSCAR, consist of 1 or 2 immunoglobulin-like domains. Although GPVI and LAIR-1 are functionally different, they are similar in their collagen-binding properties. However, as discussed in Zhou, et al., *Blood,* 127(5):529-537 (2016), despite their structural homogeneity, the three proteins have very different collagen recognition sites. GPVI binds most strongly to the model collagen-related peptide with sequence glycine-proline-hydroxyproline (GPO)-rich tracts of collagen III $(GPO)_{10}$ and to a few Toolkit peptides (III-1, III-30, and III-40), which contain 1 or 2 GPO triplets (Jarvis, et al., *Blood,* 111(10):4986-4996 (2008)). LAIR-1 also displays high affinity for III-30 and for a subset of amino acid-rich peptides, but binds III-1 and collagen related peptide less tightly (Lebbink, et al., *Matrix Biol.,* 28(4):202-210 (2009)).

Mutagenesis and nuclear magnetic resonance titration indicated a patch of residues on the membrane-distal region of LAIR-1 that contact the model triple-helical peptide (THP), residing in a groove composed of strands C, C9, F, and the FG loop (Brondijk, *Blood,* 115(7):1364-1373 (2010), which is specifically incorporated by reference in its entirety). For example, adhesion to immobilized collagens I, III, and IV was significantly reduced in the R59A, E61A, R65A, and E111A mutants, although the magnitude of the effect depended on the type of collagen tested. In addition, adhesion was somewhat reduced for mutants R62A and N69A, which showed near wild-type collagen binding in the flow cytometric assay. Brondijk, et al., reports that LAIR-1 residues E61, S66, Y68, I102, W109, and Y115 provide Van derWaals interactions, whereas hydrogen bonds to the ligand frequently involve LAIR-1 residues R59, E63, R100, E111, and Q112, and concludes that R59, E61, and also W109 make up the core of the collagen-binding site, whereas more peripheral residues such as E111 contribute less to binding (residues with reference, for example, to SEQ ID NO:1).

b. Mouse LAIR-1

Sequences for mouse LAIR-1 (mLAIR-1) are known in the art. For example, a consensus sequence for mLAIR-1a (isoform 1) is MSLHPVILLVLVLVLGWKINTQEGSLPDITIFPNSSLMISQGTFVTVVC
SYSDKHDLYNMVRLEKDGSTFMEKSTEPYKTEDEFEIGPVNETITGHYS
CIYSKGITWSERSKTLELKVIKENVIQTPAPGPTSDTSWLKTYSIYIFT
VVSVIFLLCLSALLFCFLRHRQKKQGLPNNKRQQQRPEERLNLATNGLE
MTPDIVADDRLPEDRWTETWTPVAGDLQEVTYIQLDHHSLTQRAVGAVT
SQSTDMAESSTYAAIIRH (SEQ ID NO: 3, UniProtKB-
Q8BG84 (LAIR1_MOUSE)), where amino acids 1-21 are a signal sequence, amino acids 22-144 (underlined) are an extracellular domain, amino acids 145-165 are a transmembrane domain, and amino acids 166-263 are a cytoplasmic domain. Amino acids 27-115 form an Ig-like C2-domain. Amino acids 226-231 and 255-260 form ITIM motif 1 and 2, respectively. mLAIR-1b (also known as isoform 2) is missing amino acids 124-133 relative to SEQ ID NO:3. Isoform 3 has amino acids 25-56 [SLPDITIFPNSSLMISQGTFVTVVCSYSDKHD (SEQ ID NO:7) of SEQ ID NO:3)] replaced with ELCLWFLLYPWATLELIMCTWDAWKETLEYFL (SEQ ID NO:8) and is missing amino acids 57-263 relative to SEQ ID NO:3. mLAIR-1d (also known as isoform 5) is missing amino acids 24-172 relative to SEQ ID NO:3. mLAIR-1e (also known as isoform 6) is missing amino acids 134-172.

As introduced above, an extracellular domain for murine LAIR-1 can be (SEQ ID NO: 4)
QEGSLPDITIFPNSSLMISQGTFVTVV*CSYSDKHDLYNMVRLEKDGSTF*
*MEKSTEPYKTEDEFEIGPVNETITGHYSC*IYSKGITWSERSKTLELKVI
KENVIQTPAPGPTSDTSWLKTYSIY, or a fragment thereof, for example, the Ig-like C2-domain IDC-70 DNA M (underlined amino acids 6-94 of SEQ ID NO:4), or the region framed by the cysteines that form the disulfide bond between amino acids 49-99 of SEQ ID NO:3 (amino acids 28-78 of SEQ ID NO:4, illustrated in italics). An exemplary alignment of the human and mouse extracellular domains is shown below:

| Score | Expect | Method | Identities | Positives | Gaps |
|---|---|---|---|---|---|
| 46.6 bits (109) | 2e-12 | Compositional matrix adjust. | 35/104(34%) | 49/104(47%) | 7/104(6%) |

```
Query   1    QEEDLPRPSISAEPGTVIPLGSHVTFVCRGPVGVQTFRLERESR--STYNDTEDVSQASP    58
             QE  LP  +I       +I  G+ VT VC         + + R  +  ST+ +        P
Sbjct   1    QEGSLPDITIFPNSSLMISQGTFVTVVCSVSDKHDLYMMVRLEKDGSTFME----KSTEP    56

Query  59    SESEARFRIDSVSEGNAGPYRCIYYKPPKWSEESDYLEL-LVKE                   101
              ++E  F I  V+E   G Y CIY K    WSE+S  LEL ++KE
Sbjct  59    YKTEDEFEIGPVNETITGHYSCIYSKGITWSERSKTLELKVIKE                   100
```

Query 1 is SEQ ID NO:144 and Sbjct is SEQ ID NO:145.

Known variants and mutants of LAIR-1 include IYI→MYM at amino acid positions 143-145, V149G, L154P, and H263R relative to SEQ ID NO:3.

Meyaard (2008, *J. Leukoc. Biol.* 83:799-803) indicates broad expression of LAIR-1 on mouse immune cells, with one major difference being that LAIR-1 appears negative on B cells, as opposed to being highly expressed on subsets of human B cells. As with the human expression pattern, when examining the actual flow cytometry data of LAIR-1 expression, it is found that once again, LAIR-1 is highly expressed on monocytes, macrophages and DCs, while T cells, NK cells and Gr-1+ cells express LAIR-1 at relatively lower levels (Lebbink et al., 2007 *Int. Immunol.* 19:1011-1019; Tang et al., 2012, *J. Immunol.* 188:548-558).

Tang et al. (2012, *J. Immunol.* 188:548-558) investigated the phenotype of LAIR-1 deficient mice. KO mice are healthy and fertile, and display indications of altered immune function, but without gross autoimmunity or inflammation that is observed in CTLA-4 KO mice. LAIR-1 KO mice have increased numbers of dendritic cells, splenic B cells and regulatory T cells, as well as a higher frequency of activated and memory T cells, suggesting enhanced T cell reactivity. However, there was no difference in EAE and colitis disease models in LAIR-1 wt and KO mice. These disease models may not have been optimal for investigating LAIR-1 KO phenotype, and in vitro functional studies of LAIR-1 deficient immune cell subsets were not performed. It is also speculated that LAIR-1 KO mice may not be indicative of the role of LAIR-1 in humans due to differential expression and the presence of soluble LAIR-2 in humans. Differences between LAIR-1 genetic pathways in murine and human internal organs are discussed in Sun, et al., *Gene,* 552:14-145 (2014), and can be accounted for when designing and evaluating experiments utilizing a mouse model.

2. LAIR-2

Sequences for LAIR-2 and fusion proteins thereof are provided. In some embodiments, the leading methionine amino acid is cleaved in the post-translation form of the protein.

Sequences for human LAIR-2 are known in the art. For example, a consensus sequence for LAIR-2a (isoform 1) is MSPHLTALLGLVLCLAQTIHTQEGALPRPSISAEPGTVISPGSHVTFMC
RGPVGVQTFRLEREDRAKYKDSYNVFRLGPSESEARFHIDSVSEGNAGL -continued YRCLYYKPPGWSEHSDFLELLVKESSGGPDSPDTEPGSSAGTVPGTEAS
GFDAP (SEQ ID NO: 5, UniProtKB-Q6ISS4 (LAIR2_HUMAN)), where amino acids 1-21 are a signal sequence, amino acids 22-152 (underlined) are the Leukocyte-associated immunoglobulin-like receptor 2 domain. Amino acids 29-117 form an Ig-like C2-domain. LAIR-2b (also known as isoform 2) is missing amino acids 122-138 relative to SEQ ID NO:5.

As introduced above, a Leukocyte-associated immunoglobulin-like receptor 2 domain for human LAIR-2 can be (SEQ ID NO: 6)
QEGALPRPSISAEPGTVISPGSHVTFM*CRGPVGVQTFRLEREDRAKYKD*
*SYNVFRLGPSESEARFHIDSVSEGNAGLYRC*LYYKPPGWSEHSDFLELL
VKESSGGPDSPDTEPGSSAGTVPGTEASGFDAP, or a fragment thereof, for example, the Ig-like C2-domain (underlined amino acids 8-96 of SEQ ID NO:6), or the region framed by the cysteines that form the disulfide bond between amino acids 49-101 of SEQ ID NO:1 (amino acids 28-80 of SEQ ID NO:6, illustrated in italics).

Known variants and mutants of LAIR-2 include G78S, H87R, and F115Y, relative to SEQ ID NO:5.

LAIR-2 in humans has been shown to bind collagen and SP-D with higher affinity than LAIR-1 (Meyaard, 2008, *J. Leukoc. Biol.* 83:799-803). Dr. Linde Meyaard has demonstrated that LAIR-2 also binds C1q and mannose-binding lectin (MBL), both of which contain collagen-like domains (Olde Nordkamp et al., *J. Innate Immun.,* 2014, 6(3):284-92). This finding confirms evidence by Son et al that LAIR-2 binds C1q (Son et al., 2012, *Proc. Natl. Acad. Sci. USA* 109:E3160-3167). While collagens and C1q are ubiquitously expressed, SP-D is largely restricted to mucosal surfaces (lung alveolar surface and GI tract) where it functions as a first-line innate defense against pathogens (Herias et al., 2007, *Mol. Immunol.* 44:3324-3332).

An exemplary alignment of the human LAIR-1 and human LAIR-2 extracellular domains is shown below:

| Score | Expect | Method | Identities | Positives | Gaps |
|---|---|---|---|---|---|
| 194 bits (493) | 4e-70 | Compositional matrix adjust. | 95/118(81%) | 103/118(87%) | 0/118(0%) |

```
Query   1   QEEDLPRPSISAEPGTVIPLGSHVTFVCRGPVGVQTFRLERESRSTVNDTEDVSQASPSE   68
            QE  LPRPSISAEPGTVI  GSHVTF+CRGPVGVQTFRLERE R+ Y D+ +V +  PSE
Sbjct   1   QEGALPRPSISAEPGTVISPGSHVTFMCRGPVGVQTFRLEREDRAKYKDSYNVFRLGPSE   68

Query  61   SEARFRIDSVSEGNAGPYRCIYYKPPKWSEQSQYLELLVKETSGGPDSPDTEPGSSAG   118
            SEARF IDSVSEGNAG YRC+YYKPP WSE SD+LELLVKE+SGGPDSPDTEPGSSAG
Sbjct  61   SEARFHIDSVSEGNAGLYRCLYYKPPGWSEHSDFLELLVKESSGGPDSPDTEPGSSAG   118
```

Query is SEQ ID NO:146 and Sbjct is SEQ ID NO:147.

B. Immunomodulatory Agents

Immunomodulatory agents including agonists and antagonists of LAIR-1 and antagonists of LAIR-2 are provided. An agonist of LAIR-1 typically induces, potentiates, or activates LAIR-1 negative signaling. An antagonist of LAIR-1 typically prevents, reduces, or blocks LAIR-1 negative signaling. An antagonist of LAIR-2 typically reduces or prevents the ability of LAIR-2 to bind a ligand thereof, including ligands shared by LAIR-1 and LAIR-2. The compositions and methods can be used to modulate LAIR-1 negative signaling on, for example, myeloid cells including antigen-presenting cells (e.g., monocyte, macrophage, or dendritic cell), T cells, Natural Killer (NK) cells, or a combination thereof. In some embodiments, the compositions are specifically targeted one or more cells types. Exemplary molecules that can be an agonist or antagonist of LAIR-1 and an antagonist of LAIR-2 are discussed in more detail below.

In some embodiments, the LAIR-1 antagonists, including anti-LAIR-1 function blocking antibodies, bind to or otherwise interfere with a collagen binding domain, a C1q binding domain, a SP-D binding domain, or a combination thereof of LAIR-1. For example, in some embodiments, the LAIR-1 antagonist binds to, blocks, creates a conformations change, or otherwise 15 interferes with LAIR-1 residue R59, E61, R62, E63, R65, S66, Y68, N69, I102, R100, W109, E111, Q112, and Y115 or any combination of any of the foregoing. In some embodiments, a LAIR-1 function blocking antibody or functional fragment thereof specifically binds to an epitope including one or more of R59, E61, R62, E63, R65, S66, Y68, N69, I102, R100, W109, E111, Q112, and Y115 (e.g., relative to SEQ ID NO:1). In some embodiments, the immunomodulatory agent does not interfere with OSCAR binding or activity, GPVI binding or activity, or a combination thereof.

1. Antibodies

The immunomodulatory agent can be an antibody. Suitable antibodies are known in the art or can be prepared by one of skill in the art. Nucleic acid and polypeptide sequences for LAIR-1 and LAIR-2 are known in the art, and exemplary protein sequences are provided above. The sequences can be used, as discussed in more detail below, by one of skill in the art to prepare an antibody or antigen binding fragment thereof specific for LAIR-1 or LAIR-2. The antibody, or antigen binding fragment therefore, can be an agonist or antagonist of LAIR-1 or an antagonist of LAIR-2.

The activity (i.e., agonist or antagonist) of an antibody or antigen binding fragment thereof that is specific for LAIR-1 or LAIR-2, can be determined using functional assays that are known in the art, and include the assays discussed below. Typically the assays include determining if the antibody or antigen binding fragment thereof increases (i.e., agonist) or decreases (i.e., antagonist) signaling through LAIR-1. In some embodiments the assay includes determining if the antibody or antigen binding fragment thereof decreases (i.e., agonist) or increases (i.e., antagonist) an immune response negatively regulated by LAIR-1.

In some embodiments, the disclosed antibodies and antigen binding fragments thereof immunospecifically bind to LAIR-1 or LAIR-2 (e.g., any one of SEQ ID NO:1-6). In some embodiments, the antibody binds to an extracellular domain of LAIR-1 or LAIR-2.

For example, molecules are provided that can immunospecifically bind to LAIR-1:

(I) arrayed on the surface of a cell (especially a live cell);
(II) arrayed on the surface of a cell (especially a live cell) at an endogenous concentration;
(III) arrayed on the surface of a live cell, and modulates binding between LAIR-1 and a ligand thereof;
(IV) arrayed on the surface of a live cell, and reduces or inhibits immune suppression by LAIR-1;
(V) arrayed on the surface of a live cell, and induces or enhances immune suppression by LAIR-1;
(VI) arrayed on the surface of a live cell, wherein the cell is a myeloid cell including antigen-presenting cells (e.g., monocyte, macrophage, or dendritic cell), a T cell, a Natural Killer (NK) cell, or a combination thereof;
(VII) combinations of I-IV and VI;
(VIII) combinations of I-III and V-IV; and
(IX) arrayed on the surface of a live myeloid or lymphoid derived cancer cells (AML or ALL), and enhances apoptosis and differentiation resulting in reduced self-renewal of cancer stem cells.

Molecules are also provided that can immunospecifically bind to soluble endogenous LAIR-2. In some embodiments the molecules reduce or prevent the LAIR-2 from binding or otherwise interacting with its ligand.

In some embodiments, the molecules are capable of inducing antibody dependent cell cytotoxicity (ADCC), complement dependent cytotoxicity (CDC) or cellular apoptosis through other mechanisms, of LAIR-1 expressing cell.

To prepare an antibody or antigen binding fragment thereof that specifically binds to LAIR-1 or LAIR-2, purified proteins, polypeptides, fragments, fusions, or epitopes to LAIR-1 or LAIR-2, or polypeptides expressed from nucleic acid sequences thereof, can be used. The antibodies or antigen binding fragments thereof can be prepared using any suitable methods known in the art such as those discussed in more detail below.

a. Human and Humanized Antibodies

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', $F(ab')_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all, of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. See for example, Jones, P. T., et al. (1986). Replacing the complementarity-determining regions in a human antibody with those from a mouse. Nature 321, 522-525. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a nonhuman antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

b. Single-Chain Antibodies

Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

c. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the $F(ab')_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The $F(ab')_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

d. Hybrid Antibodies

The antibody can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

e. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, CA). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

f. Exemplary Antibodies

One embodiment provides an anti-LAIR antibody produced by a hybridoma selected from the group consisting of 1E11, 1G7, 4B3, 5A6, 5E1, 6B2, 6F4, 6G6, 7G3, 9H6, 11B3, 12E10a, and 12E10b.

Another embodiment provides an anti-LAIR antibody having at least one light chain or at least one heavy chain of the antibody produced by one or more of the hybridomas selected from the group consisting of 1E11, 1G7, 4B3, 5A6, 5E1, 6B2, 6F4, 6G6, 7G3, 9H6, 11B3, 12E10a, and 12E10b.

Another embodiment provides an anti-LAIR antibody having a variable light chain having at least 50, 60, 70, 80, 85, 90, 95, 96, 97, 98, 99, or 100% sequence identity to a variable light chain having an amino acid sequence according to SEQ ID NO: 19, 27, 35, 43, 51, 59, 67, 75, 83, 91, 99, 107, or 115.

Another embodiment provides an anti-LAIR antibody having a variable heavy chain having at least 50, 60, 70, 80, 85, 90, 95, 96, 97, 98, 99, or 100% sequence identity to a variable heavy chain having an amino acid sequence according to SEQ ID NO: 23, 31, 39, 47, 55, 63, 71, 79, 87, 95, 103, or 111.

Another embodiment provides an anti-LAIR antibody having a variable light chain having at least 50, 60, 70, 80, 85, 90, 95, 96, 97, 98, 99, or 100% sequence identity to a variable light chain having an amino acid sequence according to SEQ ID NO: 19, 27, 35, 43, 51, 59, 67, 75, 83, 91, 99, 107, or 115, and a variable heavy chain having at least 50, 60, 70, 80, 85, 90, 95, 96, 97, 98, 99, or 100% sequence identity to an amino acid sequence according to SEQ ID NO: 23, 31, 39, 47, 55, 63, 71, 79, 87, 95, 103, or 111.

Another embodiment provides an anti-LAIR antibody having a complementarity-determining region (CDR) selected from the group of CDRs having an amino acid sequence selected from the group consisting of SEQ ID NOs: 20-22, 24-26, 28-30, 32-34, 36-38, 40-42, 44-46, 48-50, 52-54, 56-58, 60-62, 64-66, 68-70, 72-74, 76-78, 80-82, 84-86, 88-90, 92-94, 96-98, 100-102, 104-106, 108-110, 112-114, and 116-118.

Another embodiment provides an anti-LAIR antibody having a plurality of CDRs selected from the group consisting of SEQ ID NOs: 20-22, 24-26, 28-30, 32-34, 36-38, 40-42, 44-46, 48-50, 52-54, 56-58, 60-62, 64-66, 68-70, 72-74, 76-78, 80-82, 84-86, 88-90, 92-94, 96-98, 100-102, 104-106, 108-110, 112-114, and 116-117. The plurality of CDRs can be from 2-12.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:120 or SEQ ID NO:122 and/or a light chain with an amino acid sequence at least 50, 60, 70, 80, 85, 90, 95, 96, 97, 98, 99, or 100% sequence identity to the amino acid sequence set forth in SEQ ID NO:124.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:126 or SEQ ID NO:128 and/or a light chain with an amino acid sequence at least 50, 60, 70, 80, 85, 90, 95, 96, 97, 98, 99, or 100% sequence identity to the amino acid sequence set forth in SEQ ID NO:130.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:132 or SEQ ID NO:134 and/or a light chain with an amino acid sequence at least 50, 60, 70, 80, 85, 90, 95, 96, 97, 98, 99, or 100% sequence identity to the amino acid sequence set forth in SEQ ID NO:136.

Another embodiment provides a chimeric antibody having a heavy chain with an amino acid sequence at least 50, 60, 70, 80, 85, 90, 95, 96, 97, 98, 99, or 100% sequence identity to the amino acid sequence set forth in SEQ ID NO:138 or SEQ ID NO:140 and/or a light chain with an amino acid sequence at least 50, 60, 70, 80, 85, 90, 95, 96, 97, 98, 99, or 100% sequence identity to the amino acid sequence set forth in SEQ ID NO:142.

Another embodiment provides a nucleic acid sequence encoding an antibody having a light chain amino acid sequence according to SEQ ID NO:124, 130, 136, or 142 and/or a heavy chain amino acid according to SEQ ID NO: 120, 122, 126, 128, 132, 134, 138 or 140.

Another embodiment provides a nucleic acid sequence encoding a variable light chain according to SEQ ID NOs 19, 27, 35, 43, 51, 59, 67, 75, 83, 91, 99, 107, or 115 and/or a variable heavy chain according to SEQ ID NOs 23, 31, 39, 47, 55, 63, 71, 79, 87, 95, 103, or 111. The nucleic acids encoding the light chain and/or heavy chain can be part of an expression vector. The nucleic acids can be expressed by cell. Expression can be inducible or constitutive.

2. Proteins and Polypeptides a. Protein and Polypeptide Compositions

The immunomodulatory agent can be a protein, polypeptide, or fusion protein. For example, the immunomodulatory agent can be an isolated or recombinant protein or polypeptide, or functional fragment, variant, or fusion protein thereof of LAIR-1 or LAIR-2.

The protein or polypeptide, or functional fragment, variant, or fusion protein thereof can be an agonist or an antagonist. For example, in some embodiments an antagonist of LAIR-1 is a LAIR-1 or LAIR-2 polypeptide or a fragment or fusion protein thereof that binds to a ligand of LAIR-1. The polypeptide can be a soluble fragment, for example the extracellular domain of LAIR-1 or LAIR-2, or a functional fragment thereof, or a fusion protein thereof. In some embodiments, a soluble ligand of LAIR-1 may serve as an agonist, increasing signal transduction through LAIR-1.

The activity (i.e., agonist or antagonist) of a protein or polypeptide of LAIR-1 or LAIR-2, or any fragment, variant or fusion protein thereof can be determined using functional assays that are known in the art, and include the assays discussed below. Typically the assays include determining if the protein, polypeptide or fragment, variant or fusion protein thereof increases (i.e., agonist) or decreases (i.e., antagonist) signaling through the LAIR-1 receptor. In some embodiments the assay includes determining if the protein, polypeptide or fragment, variant, or fusion protein thereof increases (i.e., agonist) or decreases (i.e., antagonist) the immune response (i.e., costimulatory or coinhibitory) associated with LAIR-1. Typically the assays include determining if the protein, polypeptide or fragment, variant, or fusion protein thereof increases (i.e., agonist) or decreases (i.e., antagonist) signaling through LAIR-1. In some embodiments the assay includes determining if the protein, polypeptide or fragment, variant, or fusion protein thereof decreases (i.e., agonist) or increases (i.e., antagonist) an immune response negatively regulated by LAIR-1. In some embodiments the assay includes determining if the protein, polypeptide or fragment, variant, or fusion protein thereof increases (i.e., antagonist) the apoptosis and differentiation of acute myeloid leukemia cells and acute lymphoblastic leukemia cells resulting in reduced self-renewal capacity of AML and ALL stem cells.

Nucleic acid and polypeptide sequences for LAIR-1 and LAIR-2 are known in the art and exemplary protein and peptide sequences are provided above. The sequences can be used, as discussed in more detail below, by one of skill in the art to prepare any protein or polypeptide of LAIR-1 or LAIR-2, or any fragment, variant, or fusion protein thereof. Generally, the proteins, polypeptides, fragments, variants, and fusions thereof of LAIR-1 and LAIR-2 are expressed from nucleic acids that include sequences that encode a signal sequence. The signal sequence is generally cleaved from the immature polypeptide to produce the mature polypeptide lacking the signal sequence. The signal sequence can be replaced by the signal sequence of another polypeptide using standard molecule biology techniques to affect the expression levels, secretion, solubility, or other property of the polypeptide. LAIR-1 and LAIR-2 both with and without a signal sequence are disclosed. It is understood that in some cases, the mature protein as it is known or described in the art, i.e., the protein sequence without the signal sequence, is a putative mature protein. During normal cell expression, a signal sequence can be removed by a cellular peptidase to yield a mature protein. The sequence of the mature protein can be determined or confirmed using methods that are known in the art.

i. Fragments

As used herein, a fragment of LAIR-1 or LAIR-2 refers to any subset of the polypeptide that is at least one amino acid shorter than full length protein. Useful fragments include those that retain the ability to bind to their natural ligand or ligands. A polypeptide that is a fragment of any full-length LAIR-1 or LAIR-2 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural ligand respectively as compared to the full-length protein.

Fragments of LAIR-1 and LAIR-2 include cell free fragments. Cell free polypeptide can be fragments of full-length, transmembrane, polypeptides that may be shed, secreted or otherwise extracted from the producing cells. Cell free fragments of polypeptides can include some or all of the extracellular domain of the polypeptide, and lack some or all of the intracellular and/or transmembrane domains of the full-length protein. In one embodiment, polypeptide fragments include the entire extracellular domain of the full-length protein. In other embodiments, the cell free fragments of the polypeptides include fragments of the extracellular domain that retain biological activity of full-length protein. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both. In some embodiments the extracellular domain is the only functional domain of the fragment (e.g., the ligand binding domain).

ii. Variants

Variants of LAIR-1 and LAIR-2, and fragments thereof are also provided. In some embodiments, the variant is at least 50, 60, 70, 80, 85, 90, 95, 96, 97, 98, or 99 percent identical to any one of SEQ ID NO:1-6. Useful variants include those that increase biological activity, as indicated by any of the assays described herein, or that increase half-life or stability of the protein. The protein and polypeptides of LAIR-1 or LAIR-2, and fragments, variants, and fusion proteins thereof can be engineered to increase biological activity. For example, in some embodiments, a LAIR-2 polypeptide, protein, or fragment, variant or fusion thereof has been modified with at least one amino acid substitution, deletion, or insertion that increases a function thereof.

Other variants are those that are engineered to selectively bind to one or more type of LAIR-1 and/or LAIR-2 ligands versus other LAIR-1 and/or LAIR-2 ligands. For example, the variants can be engineered to bind preferentially to one or more collagens, SP-D, C1q or MBL, or a specific combination thereof. Preferential binding refers to binding that is at least 10%, 20%, 30%, 40%, 50%, 60%, 70%, 80%, 90%, 95%, or greater for one type of ligand over another type of ligand.

Still other variants can be engineered to have reduced binding to one ligand compared to another. These variants can be used in combination with variants having stronger binding properties to modulate the immune response with a moderate impact.

In still other embodiments, the variants can be engineered to have reduced binding to one or more collagen binds sites relative others. As discussed in Brondijk, et al., *Blood,* 18(115):1364-73 (2010), mutation of residues with LAIR-1 can have differential effect on binding to different collagen ligands. For example, adhesion to immobilized collagens I, III, and IV was significantly reduced in the R59A, E61A, R65A, and E111A mutants, although the magnitude of the effect depended on the type of collagen tested. In addition, adhesion was somewhat reduced for mutants R62A and N69A. In some embodiments, the variant is mutated at one or more of R59, E61, R62, E63, R65, S66, Y68, N69, 1102, R100, W109, E111, Q112, and Y115 relative to SEQ ID NO:1. In some embodiments, the variant is mutated at one or more of R59, E61, R65, E111, R62A, and N69A. In particular embodiments, the mutation(s) is substitution with an alanine.

Finally, variant polypeptides can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art. The variants can be modified to adjust for effects of affinity for the receptor on the half-life of proteins, polypeptides, fragments, or fusions thereof at serum and endosomal pH.

iii. Fusion Proteins

Fusion polypeptides have a first fusion partner comprising all or a part of a polypeptide LAIR-1 or Liar-2 fused to a second polypeptide directly or via a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (first polypeptide or second polypeptide) of the fusion protein. Similarly, the domain that functions to dimerize or multimerize the fusion proteins can either be a separate domain, or alternatively can be contained within one of the other domains (first polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

$$N—R_1\text{-}R_2\text{-}R_3—C$$

wherein "N" represents the N-terminus of the fusion protein, "C" represents the C-terminus of the fusion protein. In some embodiments, "$R_1$" is a polypeptide or protein of LAIR-1 or Liar-2, or fragment or variant thereof, "$R_2$" is an optional peptide/polypeptide linker domain, and "$R_3$" is a second polypeptide. Alternatively, $R_3$ may be a polypeptide or protein of LAIR-1 or Liar-2, or fragment or variant thereof and $R_1$ may be a second polypeptide. In some embodiments, the LAIR-1 or Liar-2 polypeptide is the extracellular domain or a fragment thereof such as the Ig-like C2-domain, or the region framed by the cysteines that form a disulfide bond as discussed above.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

In some embodiments, the fusion protein includes the extracellular domain of LAIR-1 or LAIR-2, or a fragment or variant thereof, fused to an Ig Fc region. Recombinant Ig fusion proteins can be prepared by fusing the coding region of the extracellular domain of an extracellular domain or a fragment or variant thereof to the Fc region of human IgG1, IgG2, IgG3 or IgG4 or mouse IgG2a, or other suitable Ig domain, as described previously (Chapoval, et al., *Methods Mol. Med.,* 45:247-255 (2000)).

iv. Exemplary Fusion Proteins

Exemplary fusion proteins are provided below. The signal sequence is indicated by double underlining, the LAIR-1 or LAIR-2 extracellular domain by single underlining, and the Ig domain by italics. The signal sequence is typically removed in the mature protein. Additionally, signal peptides from other polypeptides or organisms can be used (e.g., substituted) to enhance the secretion of the fusion protein from a host during manufacture.

hLAIR1.hG1

In some embodiments, a human LAIR1-hIg fusion protein (hIgG1) (hLAIR1.hG1) has at least 80%, 85%, 90%, 95%, 99%, or 100% sequence identity to the amino acid sequence:

(SEQ ID NO: 9)
MEWSWVFLFFLSVTTGVHSQEEDLPRPSISAEPGTVIPLGSHVTFVCRG
PVGVQTFRLERESRSTYNDTEDVSQASPSESEARFRIDSVSEGNAGPYR
CIYYKPPKWSEQSDYLELLVKETSGGPDSPDTEPGSSAGPTQRPSDNSH
NEHAPASQGLKAEH*DKTHTCPPCPAPEILGGPSVFLFPPKPKDTLMISR*
*TPEVTCVVVDVSHEDPEVKFNWYVDGVEVHNAKTKPREEQYNSTYRVVS*
*VLTVLHQDWLNGKEYKCKVSNKALPAPIEKTISKAKGQPREPQVYTLPP*
*SRDELTKNQVSLTCLVKGFYPSDIAVEWESNGQPENNYKTTPPVLDSDG*
*SFFLYSKLTVDKSRWQQGNVFSCSVMHEALHNHYTQKSLSLSPG,* with or without the signal sequence.

SEQ ID NO:9 without the signal sequence is (SEQ ID NO: 10)
QEEDLPRPSISAEPGTVIPLGSHVTFVCRGPVGVQTFRLERESRSTYND
TEDVSQASPSESEARFRIDSVSEGNAGPYRCIYYKPPKWSEQSDYLELL
VKETSGGPDSPDTEPGSSAGPTQRPSDNSHNEHAPASQGLKAEH*DKTHT*
*CPPCPAPELLGGPSVFLFPPKPKDTLMISRTPEVTCVVVDVSHEDPEVK*
*FNWYVDGVEVHNAKTKPREEQYNSTYRVVSVLTVLHQDWLNGKEYKCKV*
*SNKALPAPIEKTISKAKGQPREPQVYTLPPSRDELTKNQVSLTCLVKGF*
*YPSDIAVEWESNGQPENNYKTTPPVLDSDGSFFLYSKLTVDKSRWQQGN*
*VESCSVMHEALHNHYTQKSLSLSPG.*

Human LAIR1-hIg (hIgG1) (hLAIR1.hG1) can be an antagonist for LAIR-1 signaling by serving as a decoy for LAIR-1 ligands, and can be utilized for the treatment of cancer or an infectious disease. hLAIR1.hG1 can also be a control for testing the activity of hLAIR2.hG1.

hLAIR1.mG2a

In some embodiments, human LAIR1-mIg fusion protein (mIgG2a) (hLAIR1.mG2a) has at least 80%, 85%, 90%, 95%, 99%, or 100% sequence identity to the amino acid sequence:

(SEQ ID NO: 11)
MEWSWVFLFFLSVTTGVHSQEEDLPRPSISAEPGTVIPLGSHVTFVCRG
PVGVQTFRLERESRSTYNDTEDVSQASPSESEARFRIDSVSEGNAGPYR
CIYYKPPKWSEQSDYLELLVKETSGGPDSPDTEPGSSAGPTQRPSDNSH
NEHAPASQGLKAEHEPRGPTIKPCPPCKCPAPNLLGGPSVFIFPPKIKD
VLMISLSPIVTCVVVDVSEDDPDVQISWFVNNVEVHTAQTQTHREDYNS
TLRVVSALPIQHQDWMSGKEFKCKVNNKELPAPIERTISKPKGSVRAPQ
VYVLPPPEEEMTKKQVTLTCMVTDEMPEDIYVEWTNNGKTELNYKNTEP
VLDSEGSYFMYSKLRVEKKNWVERNSYSCSVVHEGLHNHHTTKSFSRTP
G, with or without the signal sequence.

SEQ ID NO:11 without the signal sequence is (SEQ ID NO: 12)
QEEDLPRPSISAEPGTVIPLGSHVTFVCRGPVGVQTFRLERESRSTYND
TEDVSQASPSESEARFRIDSVSEGNAGPYRCIYYKPPKWSEQSDYLELL
VKETSGGPDSPDTEPGSSAGPTQRPSDNSHNEHAPASQGLKAEHEPRGP
TIKPCPPCKCPAPNLLGGPSVFIFPPKIRDVLMISLSPIVTCVVVDVSE
DDPDVQISWFVNNVEVHTAQTQTHREDYNSTLRVVSALPIQHQDWMSGR
EFKCKVNNRDLPAPIERTISKPKGSVRAPQVYVLPPPEEEMTRKQVTLT
CMVTDFMPEDIYVEWTNNGKTELNYENTEPVLDSDGSYFMYSKLRVERK
NWVERNSYSCSVVHEGLHNHHTTRSFSRTPG.

In some embodiments, human LAIR1-mIg fusion protein (mIgG2a) (hLAIR1.mG2a) is used to generate anti-hLAIR1 antibodies. The antibodies can be, for example, LAIR-1 antagonist antibodies (e.g., mAb, or fragments thereof), which can be used for the treatment of cancer, or LAIR-1 agonist antibodies (e.g., mAb, or fragments thereof), which can be used for the treatment of autoimmune diseases.

mLAIR1.mG2a

In some embodiments, mouse LAIR1-mIg fusion protein (mLAIR1.mG2a) has at least 80%, 85%, 90%, 95%, 99%, or 100% sequence identity to the amino acid sequence:

(SEQ ID NO: 13)
MEWSWVFLFFLSVTTGVHSQEGSLPDITIFPNSSLMISQGTFVTVVCSY
SDKHDLYNMVRLEKDGSTFMEKSTEPYKTEDEFEIGPVNETITGHYSCI
YSKGITWSERSKTLELKVIKENVIQTPAPGPTSDTSWLKTYSIYEPRGP
TIKPCPPCKCPAPNLLGGPSVFIFPPKIKDVLMISLSPIVTCVVVDVSE
DDPDVQISWFVNNVEVHTAQTQTHREDYNSTLRVVSALPIQHQDWMSGK
EFKCKVNNKDLPAPIERTISKPKGSVRAPQVYVLPPPEEEMTKKQVTLT

-continued

CMVTDFMPEDIYVEWTNNGKTELNYKNTEPVLDSDGSYFMYSKLRVEKK
NWVERNSYSCSVVHEGLHNHHTTKSFSRTPG, with or without the signal sequence.

SEQ ID NO:13 without the signal sequence is (SEQ ID NO: 14)
QEGSLPDITIFPNSSLMISQGTFVTVVCSYSDKHDLYNMVRLEKDGSTE
MEKSTEPYKTEDEFEIGPVNETITGHYSCIYSKGITWSERSKTLELKVI
KENVIQTPAPGPTSDTSWLKTYSIYEPRGPTIKPCPPCKCPAPNLLGGP
SVFIFPPKIKDVLMISLSPIVTCVVVDVSEDDPDVQISWFVNNVEVHTA
QTOTHREDYNSTLRVVSALPIQHQDWMSGKEFKCKVNNKDLPAPIERTI
SKPKGSVRAPQVYVLPPPEEEMTKKQVTLTCMVTDFMPEDIYVEWTNNG
KTELNYKNTEPVLDSDGSYFMYSKLRVEKKNWVERNSYSCSVVHEGLHN
HHTTKSFSRTPG.

In some embodiments, mouse LAIR1-mIg fusion protein is the mouse analog used for in vivo studies in a mouse model.

hLAIR2.hG1

In some embodiments, mouse LAIR2-mIg fusion protein (hIgG1) (hLAIR1.hG1) has at least 80%, 85%, 90%, 95%, 99%, or 100% sequence identity to the amino acid sequence:

(SEQ ID NO: 15)
MEWSWVFLFFLSVTTGVHSQEGALPRPSISAEPGTVISPGSHVTFMCRG
PVGVQTFRLEREDRAKYKDSYNVFRLGPSESEARFHIDSVSEGNAGLYR
CLYYKPPGWSEHSDFLELLVKESSGGPDSPDTEPGSSAGTVPGTEASGF
DAPDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVD
KSRWQQGNVFSCSVMHEALHNHYTQKSLSLSPG, (SEQ ID NO: 15), with or without the signal sequence.

SEQ ID NO:15 without the signal sequence is (SEQ ID NO: 16)
QEGALPRPSISAEPGTVISPGSHVTFMCRGPVGVQTFRLEREDRAKYKD
SYNVFRLGPSESEARFHIDSVSEGNAGLYRCLYYKPPGWSEHSDFLELL
VKESSGGPDSPDTEPGSSAGTVPGTEASGFDAPDKTHTCPPCPAPELLG
GPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEK
TISKAKGOPREPQVYTLPPSRDELTKNQVSLTCLVKGFYPSDIAVEWES
NGQPENNYKTTPPVLDSDGSFFLYSKLTVDKSRWQQGNVFSCSVMHEAL
HNHYTQKSLSLSPG.

Human LAIR2-hIg fusion protein (hIgG1) (hLAIR2.hG1) can be an antagonist for Liar-1 signaling by serving as a decoy for LAIR-1 ligands, and can be utilized for the treatment of cancer or an infectious disease.

LAIR2.mIg

In some embodiments, human LAIR2.mIg fusion protein (mIgG2a) has at least 80%, 85%, 90%, 95%, 99%, or 100% sequence identity to the amino acid sequence:

(SEQ ID NO: 17)

MEWSWVFLFFLSVTTGVHSQEGALPRPSISAEPGTVISPGSHVTFMCRG
PVGVQTFRLEREDRAKYKDSYNVFRLGPSESEARFHIDSVSEGNAGLYR
CLYYKPPGWSEHSDFLELLVKESSGGPDSPDTEPGSSAGTVPGTEASGF
DAP*EPRGPTIKPCPPCKCPAPNLLGGPSVFIFPPKIKDVLMISLSPIVT*
*CVVVDVSEDDPDVQISWFVNNVEVHTAQTQTHREDYNSTLRVVSALPIQ*
*HQDWMSGKEFKCKVNNKDLPAPIERTISKPKGSVRAPQVYVLPPPEEEM*
*TKKQVTLTCMVTDFMPEDIYVEWTNNGKTELNYKNTEPVLDSDGSYFMY*
*SKLRVEKKNWVERNSYSCSVVHEGLHNHHTTKSFSRTPG*, with or without the signal sequence.

SEQ ID NO:17 without the signal sequence is (SEQ ID NO: 18)

QEGALPRPSISAEPGTVISPGSHVTFMCRGPVGVQTFRLEREDRAKYKD
SYNVFRLGPSESEARFHIDSVSEGNAGLYRCLYYKPPGWSEHSDFLELL
VKESSGGPDSPDTEPGSSAGTVPGTEASGFDAP*EPRGPTIKPCPPCKCP*
*APNLLGGPSVFIFPPKIKDVLMISLSPIVTCVVVDVSEDDPDVQISWFV*
*NNVEVHTAQTQTHREDYNSTLRVVSALPIQHQDWMSGKEFKCEVNNEDL*
*PAPIERTISKPKGSVRAPQVYVLPPPEEEMTEKQVTLTCMVTDFMPEDI*
*YVEWTNNGKTELNYKNTEPVLDSDGSYFMYSKLRVEKENWVERNSYSCS*
*VVHEGLHNHHTTKSFSRTPG*.

Human LAIR2.mIg fusion protein (mIgG2a) can be used to generate antagonistic anti-LAIR2 (e.g., mAb, or fragments thereof), which can be used for the treatment of autoimmune diseases.

v. Polypeptide Modifications

The polypeptides and fusion proteins may be modified by chemical moieties that may be present in polypeptides in a normal cellular environment, for example, phosphorylation, methylation, amidation, sulfation, acylation, glycosylation, sumoylation and ubiquitylation. Fusion proteins may also be modified with a label capable of providing a detectable signal, either directly or indirectly, including, but not limited to, radioisotopes and fluorescent compounds.

The polypeptides and fusion proteins may also be modified by chemical moieties that are not normally added to polypeptides in a cellular environment. For example, the disclosed fusion proteins may also be modified by covalent attachment of polymer chains, including, but not limited to, polyethylene glycol polymer (PEG) chains (i.e., pegylation). Conjugation of macromolecules to PEG has emerged recently as an effective strategy to alter the pharmacokinetic (PK) profiles of a variety of drugs, and thereby to improve their therapeutic potential. PEG conjugation increases retention of drugs in the circulation by protecting against enzymatic digestion, slowing filtration by the kidneys and reducing the generation of neutralizing antibodies. In addition, PEG conjugates can be used to allow multimerization of the fusion proteins.

Modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R N═C═N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Fusion proteins may also include one or more D-amino acids that are substituted for one or more L-amino acids.

vi. Modified Binding Properties

Binding properties of the proteins, polypeptides, fragments, variants and fusions thereof are relevant to the dose and dose regimen to be administered. In one embodiment the disclosed the proteins, polypeptides, fragments, variants and fusions thereof have binding properties to a LAIR-1 ligand that demonstrate a higher term, or higher percentage, of occupancy of a binding site (e.g., on the ligand) relative to other receptor molecules that bind thereto. In other embodiments, the disclosed proteins, polypeptides, fragments, variants and fusions thereof have reduced binding affinity to a LAIR-1 ligand relative to wildtype protein.

In some embodiments the proteins, polypeptides, fragments, variants and fusions thereof have a relatively high affinity for LAIR-1 ligand, and may therefore have a relatively slow off rate. In other embodiments, the proteins polypeptides, fragments, variants and fusions thereof are administered intermittently over a period of days, weeks or months to dampen immune responses which are allowed to recover prior to the next administration, which may serve to alter the immune response without completely turning the immune response on or off and may avoid long term side effects.

3. Isolated Nucleic Acid Molecules

Isolated nucleic acid sequences encoding the proteins, polypeptides, fragments, variants and fusions thereof are disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding the proteins, polypeptides, fragments, variants and fusions thereof may be optimized for expression in the expression host of choice. Codons may be substituted with alternative codons encoding the same amino acid to account for differences in codon usage between the mammal from which the nucleic acid sequence is derived and the expression host. In this manner, the nucleic acids may be synthesized using expression host-preferred codons.

Nucleic acids can be in sense or antisense orientation, or can be complementary to a reference sequence encoding a polypeptide or protein of LAIR-1 or LAIR-2. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

4. Vectors and Host Cells

Vectors encoding the proteins, polypeptides, fragments, variants and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen Life Technologies (Carlsbad, CA).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, CT), maltose E binding protein and protein A. In one embodiment, a nucleic acid molecule encoding one of the disclosed polypeptides is present in a vector containing nucleic acids that encode one or more domains of an Ig heavy chain constant region, for example, having an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the proteins, polypeptides, fragments, variants and fusions thereof described herein.

The vectors described can be used to express the proteins, polypeptides, fragments, variants and fusions thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

One embodiment provides a cell constitutively- or inducibly-expressing an antibody or antigen binding fragment thereof that specifically binds to LAIR-1, wherein the cell has a nucleic acid or nucleic acids encoding an amino acid sequence according to SEQ ID NOs: 19, 27, 35, 43, 51, 59, 67, 75, 83, 91, 99, 107, 115, 23, 31, 39, 47, 55, 63, 71, 79, 87, 95, 103, 111, or a combination thereof.

5. Small Molecules

The immunomodulatory agent can be a small molecule. Small molecules agonists and antagonists LAIR-1 and antagonists of LAIR-2 are known in the art or can be identified using routine screening methods.

In some embodiments, screening assays can include random screening of large libraries of test compounds. Alternatively, the assays may be used to focus on particular classes of compounds suspected of modulating the level of LAIR-1 or LAIR-2. Assays can include determinations of LAIR-1 signaling activity, or inhibitory response mediated LAIR-1. Other assays can include determinations of nucleic acid transcription or translation, mRNA levels, mRNA stability, mRNA degradation, transcription rates, and translation rates.

C. Pharmaceutical Compositions

Pharmaceutical compositions including the disclosed immunomodulatory agents are provided. Pharmaceutical compositions containing the immunomodulatory agent can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed immunomodulatory agents, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed immunomodulatory agents, generally dosage levels of 0.001 to 20 mg/kg of body weight daily are administered to mammals. Generally, for intravenous injection or infusion, dosage may be lower.

In certain embodiments, the immunomodulatory agent is administered locally, for example by injection directly into a site to be treated. Typically, the injection causes an increased localized concentration of the immunomodulatory agent composition which is greater than that which can be achieved by systemic administration. The immunomodulatory agent compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In embodiments the compositions are formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunem, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

The disclosed immunomodulatory agents can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

4. Controlled Delivery Polymeric Matrices

The immunomodulatory agents disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Manufacture

A. Methods of Making Antibodies

The antibodies can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition).

The disclosed antibodies can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to proteins, polypeptides, or fusion proteins of LAIR-1 or LAIR-2. See, e.g., *Antibody Engineering: A Practical Approach* (Oxford University Press, 1996).

For example, suitable antibodies with the desired biologic activities can be identified using in vitro assays including but not limited to: proliferation, migration, adhesion, soft agar growth, angiogenesis, cell-cell communication, apoptosis, transport, signal transduction, and in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment.

Techniques can also be adapted for the production of single-chain antibodies specific to an antigenic peptide. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

B. Methods for Producing Proteins

The disclosed proteins, polypeptides, fragments, variants and fusions thereof can be manufactured using conventional techniques that are known in the art. Isolated fusion proteins can be obtained by, for example, chemical synthesis or by recombinant production in a host cell. To recombinantly produce a protein, polypeptide, fragment, variant or fusion thereof, a nucleic acid containing a nucleotide sequence encoding the protein, polypeptide, fragment, variant or fusion thereof can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the protein, polypeptide, fragment, variant or fusion thereof. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express fusion proteins. Viral based expression systems are well known in the art and include, but are not limited to, baculoviral, SV40, retroviral, or vaccinia based viral vectors.

Mammalian cell lines that stably express proteins, polypeptides, fragments, variants or fusions thereof, can be produced using expression vectors with appropriate control elements and a selectable marker. For example, the eukaryotic expression vectors pCR3.1 (Invitrogen Life Technologies) and p91023(B) (see Wong et al. (1985) *Science* 228: 810-815) are suitable for expression of proteins, polypeptides, fragments, variants or fusions thereof, in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a protein, polypeptide, fragment, variant or fusion thereof, can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Proteins, polypeptides, fragments, variants or fusions thereof, can be isolated using, for example, chromatographic methods such as affinity chromatography, ion exchange chromatography, hydrophobic interaction chromatography, DEAE ion exchange, gel filtration, and hydroxylapatite chromatography. In some embodiments, Proteins, polypeptides, fragments, variants or fusions thereof can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides. Fusion proteins can additionally be engineered to contain a secretory signal (if there is not a secretory signal already present) that causes the Proteins, polypeptides, fragments, variants or fusions thereof to be secreted by the cells in which it is produced. The secreted Proteins, polypeptides, fragments, variants or fusions thereof can then conveniently be isolated from the cell media.

C. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Protein-encoding nucleic acids can be mutated using standard techniques, including oligonucleotide-directed mutagenesis and/or site-directed mutagenesis through PCR. See, Short Protocols in Molecular Biology. Chapter 8, Green Publishing Associates and John Wiley & Sons, edited by Ausubel et al, 1992.

IV. Assays and Antibody Screening

Production of LAIR-2 Fc fusion protein ("LAIR-2-Fc") for cancer therapy bypasses the need for development and screening of LAIR-1 mAbs. Because LAIR-2 has greater affinity than LAIR-1, in some embodiments, LAIR-2-Fc is selected as a therapeutic treatment over a LAIR-1 Fc fusion protein ("LAIR-1-Fc"). In some embodiments, LAIR-1-Fc may be utilized in mouse pre-clinical models because LAIR-2 does not exist in the mouse.

A. Assays for LAIR-2-Fc

1. Confirmation of the ability to bind multiple forms of collagen, SP-D, C1q and MBL by ELISA.
2. Confirmation of the ability of LAIR-2-Fc to inhibit binding of multiple collagens, SP-D and C1q to LAIR-1. This can be tested by: 1) ELISA competition assays, and 2) flow cytometry using LAIR-1 transfected cells incubated in the presence of titrated amounts of LAIR-2-Fc and fluorescently labeled LAIR ligands.
3. Analysis of binding affinity of LAIR-2-Fc to ligands in comparison to LAIR-1.
4. Functional assays to confirm LAIR-2-Fc prevents signaling by LAIR-1 expressing cells. Reporter cells may be utilized for these assays, or primary LAIR-1+ cells are another option.

B. Assays and Antibody Screening for LAIR-2 Blocking mAbs

Because LAIR-2 is not present in mice, wild type mice can be utilized for the generation of high affinity mAbs against LAIR-2. Because LAIR-2 is soluble and binds to soluble ligands, screening of transfected cells is not an option for this molecule.

1. Phase I screening: mAb binding to LAIR-2, but not LAIR-1 by ELISA. These mAbs should be highly specific for LAIR-2.
2. Phase II screening: LAIR-2 specific mAbs must block the binding of LAIR-2 to multiple collagens, SP-D, C1q and MBL. It is possible that no single mAb will block binding of all three ligands, and therefore, multiple LAIR-2 mAbs may have to be used simultaneously as a formulation to block all interactions for maximal therapeutic effect.
3. Phase III screening: Functional assays to confirm that LAIR-2 mAbs or combination of mAbs increases LAIR-1 signaling in the presence of titrated amounts of soluble LAIR-2 in the presence of titrated amounts of multiple collagens, SP-D, C1q and MBL. (i.e. LAIR-2 mAbs should block ligand access to soluble LAIR-2, thus resulting in binding of ligands to LAIR-1 on cell surface and inducing negative signaling pathways).

Phase II and III assays can be used to predict the concentrations of LAIR-2 mAb(s) required to block physiological levels of ligands in vivo.

C. Assays and Antibody Screening for LAIR-1 Blocking mAbs or LAIR-1 Depleting mAbs LAIR-1 deficient ("knockout) mice or wild type mice can be utilized for the generation of high affinity mAbs against LAIR-1 using proprietary immunization techniques.

1. Phase I screening: mAb binding to LAIR-1, but not LAIR-2 by ELISA. mAb binding to cell lines transfected to express cell surface LAIR-1. Additionally, mAbs should have the capacity to bind endogenously expressed LAIR-1 on the surface of primary human cell subsets. These mAbs should be highly specific for LAIR-1.
2. Phase II screening: LAIR-1 specific mAbs should block the binding of LAIR-1 to one or more of multiple collagens, SP-D and C1q. It is possible that no single mAb will block binding of all three ligands, and therefore, multiple LAIR-1 mAbs may have to be used simultaneously as a formulation to block all interactions for maximal therapeutic effect.
3. Phase III screening: Functional assays to confirm that LAIR-1 mAbs or combination of mAbs decreases LAIR-1 signaling in the presence of titrated amounts of multiple collagens, SP-D and C1q (antagonist or blocking mAbs). These assays will utilize cell lines that express endogenous LAIR-1, such as THP-1 cells, or primary cells such as human monocytes, macrophages and dendritic cell subsets to assess function in the presence of LAIR-1 mAbs. Additionally, reporter cells lines may be used to determine if signaling pathways such as NFkB (NFkB reporter) or NFAT (NFAT reporter) are altered following culture with LAIR-1 mAbs.
4. Phase IV screening: Functional assays to determine if LAIR-1 mAbs are capable of inducing antibody dependent cell cytotoxicity (ADCC), complement dependent cytotoxicity (CDC) or cellular apoptosis through other mechanisms, of LAIR-1 expressing cell lines. In particular, LAIR-1 mAbs will be tested for the ability to deplete through one of these methods leukemia cell lines, such as THP-1, known to express LAIR-1 on the cell surface. LAIR-1 mAbs may also be engineered to deplete LAIR-1 expressing cells and tested as described later in this document through known methods.
5. Phase V screening: Functional assays to determine if LAIR-1 mAbs are capable of delivering or inducing a negative signal (agonist) via LAIR-1 into LAIR-1 expressing cells to inhibit cellular function. Cell lines such as THP-1 or U937 that endogenously express LAIR-1, or transfectants of cell lines such as K562 will be assessed for inhibition following culture with LAIR-1 mAbs. In other assays, reporter cell lines will be used to determine in LAIR-1 mAbs dampen positive signaling pathways such as NF-kB (NF-kB reporter) or other known cell signaling reporters. Induction of apoptosis in cell lines such as THP-1 and U937 will be also be evaluated.

Phase II and III assays can be used to predict the concentrations of LAIR-1 mAb(s) required to block physiological levels of ligands in vivo.

V. Method of Use

Evidence to date illustrates an inhibitory role for the LAIR-1 cell surface receptor and that LAIR-2 antagonized the function of LAIR-1 indirectly by binding identical ligands as LAIR-1, thus serving essentially as a decoy receptor. Tumor microenvironments are often rich in extracellular matrix proteins (ECMs), including the LAIR-1 ligand collagen (Rygiel et al., 2011, *Mol. Immunol.* 49:402-406). Therefore, LAIR-1 expressing cells localized to tumor microenvironments may be particularly suppressed through collagen cross-linking of LAIR-1 and subsequent inhibitory signaling. Increased LAIR-1 expression and signaling has been shown to inhibit the proliferation, differentiation and function of several immune cell subsets, and thus is believed to suppress anti-tumor immunity, particularly in tumor microenvironments with high levels of the LAIR-1 ligands collagen, C1q and SP-D.

Both collagen and C1q have been shown to limit or alter antigen-presenting cell (monocyte/macrophage/dendritic cell (DC)) differentiation and activation through LAIR-1. LAIR-1 has also been found to be expressed on NK and T cells, but at much lower levels than on APCs. Nevertheless, studies have indicated that cross-linking LAIR-1 on NK cells and T cells can inhibit proliferation and function. Thus it is believed that reducing LAIR-1 crosslinking can increase an immune response against cancer and infectious diseases. Increased levels of LAIR-2 are believed to promote anti-tumor immunity through the same mechanism. Therefore, soluble LAIR-1 and soluble LAIR-2 including LAIR-1 and LAIR-2 polypeptides and LAIR-1 and LAIR-2 fusion proteins, can be utilized for therapy of human diseases. For example, LAIR-2Fc proteins can be used for cancer immunotherapy to enhance immune function by preventing ligand binding to LAIR-1. This strategy is particularly promising because LAIR-2 binds ligands with a higher affinity than LAIR-1.

Alternately, signaling through LAIR-1 on AML cancer cells that express high levels of LAIR-1 sustain the self-renewal capacity, or 'stemness', of AML cells by inhibiting apoptosis and differentiation through a unique LAIR-1-SHP-1-CAMK1-CREB pathway (Kang et al., 2015, *Nat. Cell Biol.* 17:665-677). In these cancers, decreased LAIR-1 signaling leads to AML cell death. Therefore, blockade (i.e. antagonism) of LAIR-1 signaling on leukemias is thought to be a treatment for the eradication of leukemias. As such, blockade of LAIR-1 signaling with LAIR-1 monoclonal antibodies, or with soluble LAIR-1 and soluble LAIR-2 including LAIR-1 and LAIR-2 polypeptides and LAIR-1 and LAIR-2 fusion proteins may be utilized for the treatment of leukemias by direct 30 inhibition of cancer cell survival, as well as by promoting the anti-tumor immune response.

Conversely, decreased LAIR-1 expression or function is associated with several autoimmune manifestations, meanwhile, overexpression of LAIR-2 may promote autoimmunity through decoy binding of LAIR-1 ligands. LAIR-2 binding of LAIR-1 ligands can essentially reduce the cell surface cross-linking of LAIR-1, delimiting inhibitory signaling pathways leading to over-reactive immune function. Thus it is believed that increasing LAIR-1 crosslinking can decrease an overactive or inappropriate immune response, for example in cases of autoimmune disease or inflammation. For example, blockade of LAIR-2 by mAbs could be utilized for treatment of autoimmune disease, as this would increase ligand binding to LAIR-1, thus downregulating immune responses. Targeting LAIR-2 would be particularly effective in diseases in which there is an imbalance between the expression of cell surface LAIR-1 and soluble LAIR-2, as has been shown for rheumatoid arthritis (Lebbink et al., 2008, *J. Immunol* 180:1662-1669).

Exemplary methods are discussed in more detail below.

A. Immune Response Stimulating

1. Therapeutic Strategies

Methods of inducing or enhancing an immune response in a subject are provided. Typically, the methods include administering a subject an effective amount of immunomodulatory agent, or cells primed ex vivo with the immunomodulatory agent. The immune response can be, for example, a primary immune response to an antigen or an increase effector cell function such as increasing antigen-specific proliferation of T cells, enhancing cytokine production by T cells, stimulating differentiation, or a combination thereof. In some embodiments, the agent can increase the development of naïve T cells into Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. In some embodiments, the agent can reduce or inhibit the activity of Tregs, reduce the production of cytokines such as IL-10 from Tregs, reduce the differentiation of Tregs, reduce the number of Tregs, reduce the ratio of Tregs within an immune cell population, or reduce the survival of Tregs. The immunomodulatory agent can be administered to a subject in need thereof in an effective amount to overcome T cell exhaustion and/or T cell anergy. Overcoming T cell exhaustion or T cell anergy can be determined by measuring T cell function using known techniques.

The methods can be used in vivo or ex vivo as immune response-stimulating therapeutic applications. Thus in some embodiments, the agent, or nucleic acid encoding the agent, is administered directly to the subject. In some embodiments, the agent or nucleic acid encoding the agent, is contacted with cells (e.g., immune cells) ex vivo, and the treat cells are administered to the subject (e.g. adoptive transfer). In general, the disclosed immunomodulatory agents can be used for treating a subject having or being predisposed to any disease or disorder to which the subject's immune system mounts an immune response. The agents can enable a more robust immune response to be possible. The disclosed compositions are useful to stimulate or enhance immune responses involving T cells.

The immunomodulatory agents utilized for increasing an immune response are typically those that reduce LAIR-1 expression, ligand binding, crosslinking, negative signaling, or a combination thereof. For example, the agent can be an antagonist of LAIR-1, such as an antagonist (blocking) anti-LAIR-1 antibody or antigen binding fragment thereof. In some embodiments, the antagonist binds to a LAIR-1 collagen binding domain (see, e.g., Brondijk, et al., *Blood,* 18(115):1364-73 (2010), and Zhou, et al., *Blood,* 127(5): 529-537 (2016) and its supplemental information, which are specifically incorporated by reference in their entireties). In some embodiments, a LAIR-1 antagonist such as a function blocking antibody or functional fragment thereof specifically binds to an epitope including one or more of R59, E61, R62, E63, R65, S66, Y68, N69, 1102, R100, W109, E111, Q112, and Y115 of LAIR-1 (e.g., relative to SEQ ID NO:1). The agent can also be a LAIR-1 polypeptide, for example, a soluble polypeptide, or fusion protein thereof that can serve as a decoy receptor for one or more LAIR-1 ligands. The agent can also be LAIR-2 or a functional fragment or fusion protein thereof that can serve as a decoy receptor for one or more LAIR-1 ligands.

For example, in some embodiments an effective amount of a LAIR-2 fusion protein, for example LAIR-2-Fc, is administered to a subject with cancer or an infection. Treating patients with LAIR-2-Fc would result in decreased cross-linking of the LAIR-1 receptor, and subsequently, decreased inhibitory signaling of LAIR-1+ cells and improved immune function. Tipping the ratio towards increased levels of soluble LAIR-2 in comparison to cell surface LAIR-1, particularly in tumor microenvironments where the expression of LAIR-1/2 ligands are highly expressed, would favor enhanced anti-tumor immunity.

Tumor microenvironments with high levels of both collagens, SP-D and/or C1q, and with immune infiltrates that express high levels of LAIR-1 would be ideal for the disclosed immunotherapies, (e.g., LAIR-2-Fc immunotherapy). While ovarian cancers have high levels of collagen, it is unclear whether SP-D and C1q levels are high. Whereas, lung and GI cancers may have high levels of both collagens and SP-D, and therefore may be cancers to target with LAIR-2-Fc. In other embodiments, soluble LAIR-2, soluble LAIR-1, or a LAIR-1 fusion protein (e.g., LAIR-1-Fc) is utilized. In some embodiments, LAIR-2-based molecules may be selected because LAIR-2 binds ligands with a higher affinity than LAIR-1.

LAIR-1 blockade, for example using function blocking anti-LAIR-1 antibodies, can be an alternative agent or complementary agent to soluble LAIR-1 and LAIR-2 polypeptides and fusion proteins. For example, in some embodiments, LAIR-1 blockade and is combined with a decoy receptor such as soluble LAIR-1 or LAIR-2 or fusion protein thereof. The combined treatment (e.g., LAIR-2-Fc and LAIR-1 blockade) may be complementary.

In some embodiments, immune response stimulating therapy (e.g., in the treatment of cancer or infections) includes depletion of LAIR-1+ cells. LAIR-1 is highly expressed in mouse and human ovarian cancer ascites. The upregulation of LAIR-1 is restricted to immunoregulatory macrophages and F4/80+ DCs, both of which coexpress high levels of PD-L1. Therefore, targeting the depletion of LAIR-1 expressing cells would improve the overall condition of the tumor microenvironment by removal of immunoregulatory populations. While expression of LAIR-1 on other cell subsets in ovarian cancer have not been observed, because LAIR-1 is universally inhibitory, depletion of other LAIR-1+ cells would also have the effect of decreasing immune inhibition and improving anti-tumor immunity. LAIR-1 has also been shown to be expressed on the surface of, and is crucial for the development of acute myeloid leukemia cancers (Kang et al, Nature Cell Biology, Vol17, No 5, 2015; pp 665-679). Therefore, depletion of hematopoietic ('blood') cancers with LAIR-1 depleting mAbs would have the direct effect of reducing or eradicating LAIR-1 positive cancers.

Development and identification of LAIR-1 depleting mAbs can be carried out according to known construction and screening methods including those discussed herein. See, for example, Reff, et al, *Blood*. Vol83, No 2, 1994: pp 435-445, which describes preparation of an anti-CD20 chimeric antibody that binds to human C1q, and mediates complement-dependent cell lysis (CDCC) in the presence of human complement, and anti-body-dependent cellular cytotoxicity (ADCC) with human effector cells. Rituximab destroys B cells and is therefore used to treat diseases which are characterized by overactive, dysfunctional, or excessive numbers of B cells. Other B cell-depleting antibodies include ocrelizumab and ofatumumab. In another example, CD3 Abs can preferentially target and deplete activated effector T cells while preserving $CD4^+Foxp3^+$ Tregs. The antibodies transiently deplete T cells although they display no or little complement-dependent and antibody-dependent cellular cytotoxicity. Redirected cell lysis due to the ability to crosslink CD3 molecules expressed by two different cells (cytotoxic CD8+ T cells on one side and other target T cells on the other side) has been shown, however, T cell depletion mostly results from AICD (reviewed in You, *Front Immunol.* 2015; 6: 242).

In some embodiments, the cell-depleting antibodies reduce the number of LAIR-1 positive macrophages, F4/80+ DCs, cancer cells or a combination thereof.

2. Subjects to be Treated a. Treatment of Cancer

The disclosed compositions and methods can be used to treat cancer. Generally, the agents are used to stimulate or enhance an immune response to cancer in the subject by administering to the subject an amount of an immunomodulatory agent that reduces LAIR-1 expression, ligand binding, crosslinking, negative signaling, or a combination thereof. The method can reduce or more symptoms of the cancer.

The immune system is a proven defense against cancer initiation and growth. The regulation of immune responses are governed by cell surface interactions that direct immune cell function along specific pathways, including activation or inhibition against cancer cells. LAIR-1 is an inhibitory receptor on the surface of several immune cell (leukocyte) subsets that prevents optimal immune responses. Whereas, LAIR-2 is a soluble homolog that functions as a decoy to block LAIR-1 mediated inhibition.

In one embodiment, LAIR-2 Fc fusion protein promotes immune responses in vitro and in vivo. In another embodiment, LAIR-2 Fc reduces tumor growth and promotes survival. In still another embodiment, LAIR-2 Fc promotes anti-PD-1 immunotherapy. The date provided herein demonstrate that LAIR-1 mAbs have in vitro activity in human T cell and myeloid cell lines, showing specific agonist and antagonist activity for specific mAb clones. These findings demonstrate the potential LAIR-1 pathway modulation by LAIR-2 Fc or LAIR-1 mAbs for immunotherapeutic intervention in cancer and other diseases.

In another embodiment, LAIR-Fc increases primary human T cell responsiveness to TCR stimulation. In another embodiment, LAIR-2 Fc increases antigen specific T cell responses in vivo.

Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

The disclosed compositions and methods are particularly useful for the treatment of cancers that are associated with cells that express abnormally high levels of LAIR-1, high levels of LAIR-1 ligand, low levels of LAIR-2, or a combination thereof.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

b. Treatment of Infections

The disclosed compositions and methods can be used to treat infections and infectious diseases. Generally, the agents are used to stimulate or enhance an immune response to infection causing agent in the subject by administering to the subject an amount of an immunomodulatory agent that reduces LAIR-1 expression, ligand binding, crosslinking, negative signaling, or a combination thereof. The method can reduce one or more symptoms of the infection. In addition, because soluble LAIR-1 and/or LAIR-2 can bind complement factor C1q, subjects that express abnormally high levels of soluble LAIR-1 or LAIR-2 may have reduced complement-mediated immune clearance of infections in some cases. Therefore, subjects with abnormally high levels of LAIR-1 or LAIR-2, and found to exhibit decreased complement function, can be administered agents such as LAIR-1 and LAIR-2 mAbs that block LAIR-1 and LAIR-2 binding to complement factor C1q, respectively, in order to improve the complement cascade and thus, improve the innate immune response to infection.

The infection or disease can be caused by a bacterium, virus, protozoan, helminth, or other microbial pathogen that enters intracellularly and is attacked, i.e., by cytotoxic T lymphocytes.

The infection or disease can be acute or chronic. An acute infection is typically an infection of short duration. During an acute microbial infection, immune cells begin expressing immunomodulatory receptors. Accordingly, in some embodiments, the method includes increasing an immune stimulatory response against an acute infection.

The infection can be caused by, for example, but not limited to *Candida albicans, Listeria monocytogenes, Streptococcus pyogenes, Streptococcus pneumoniae, Neisseria meningitidis, Staphylococcus aureus, Escherichia coli, Acinetobacter baumannii, Pseudomonas aeruginosa* or *Mycobacterium.*

In some embodiments, the disclosed compositions are used to treat chronic infections, for example infections in which T cell exhaustion or T cell anergy has occurred causing the infection to remain with the host over a prolonged period of time.

Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus.

Because viral infections are cleared primarily by T cells, an increase in T-cell activity would be therapeutically useful in situations where more rapid or thorough clearance of an infective viral agent would be beneficial to an animal or human subject. Thus, the disclosed compositions can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) and other viral infections, caused by, for example, HTLV, hepatitis virus, respiratory syncytial virus, vaccinia virus, and rabies virus. The molecules can be administered topically to treat viral skin diseases such as herpes lesions or shingles, or genital warts. The molecules can also be administered systemically to treat systemic viral diseases, including, but not limited to, AIDS, influenza, the common cold, or encephalitis.

Representative infections that can be treated, include but are not limited to infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus*

A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.*

Other microorganisms that can be treated using the disclosed compositions and methods include, bacteria, such as those of *Klebsiella, Serratia, Pasteurella*; pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus *Mucorales* (*mucor, absidia, rhizophus*), *Sporothrix* (*schenkii*), *Blastomyces* (*dermatitidis*), *Paracoccidioides* (*brasiliensis*), *Coccidioides* (*immitis*) and *Histoplasma* (*capsulatuma*), *Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi,* etc.), *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia*, or *Trypanosoma*, etc.

B. Immune Response Inhibiting

1. Therapeutic Strategies

Methods of reducing or inhibiting an immune response in a subject are provided. Typically the methods include administering a subject an effective amount of immunomodulatory agent, or cells primed ex vivo with the immunomodulatory agent. The immune response can be, for example, a primary immune response to an antigen or an increase effector cell function such as increasing antigen-specific proliferation of T cells, enhancing cytokine production by T cells, stimulating differentiation, or a combination thereof. Thus in some embodiments, the agent reduces T cell proliferation, T cell cytokine production, T cell differentiation, or a combination thereof. In some embodiments, the agent can reduce the development of naïve T cells into Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. In some embodiments, the agent can increase or promote the activity of Tregs, increase the production of cytokines such as IL-10 from Tregs, increase the differentiation of Tregs, increase the number of Tregs, increase the ratio of Tregs within an immune cell population, or increase the survival of Tregs.

The methods can be used in vivo or ex vivo as immune response-inhibiting therapeutic applications. Thus in some embodiments, the agent, or nucleic acid encoding the agent, is administered directly to the subject. In some embodiments, the agent or nucleic acid encoding the agent, is contacted with cells (e.g., immune cells) ex vivo, and the treat cells are administered to the subject (e.g. adoptive transfer). In general, the disclosed immunomodulatory agents can be used for treating a subject having or being predisposed to any disease or disorder to which the subject's immune system mounts an overactive or inappropriate immune response. The agents can enable a less robust immune response to be possible. The disclosed compositions are useful to reduce or inhibit immune responses involving T cells.

The immunomodulatory agents utilized for reducing an immune response are typically those that increase LAIR-1 expression, ligand binding, crosslinking, negative signaling, or a combination thereof. For example, the agent can be an agonist of LAIR-1, such as an agonist (stimulating) anti-LAIR-1 antibody or antigen binding fragment thereof. The agent can also be an antagonist of LAIR-2, such as an antagonistic (blocking) anti-LAIR-2 antibody, that reduces the ability of LAIR-2 to serve as a decoy receptor for one or more LAIR-1 ligands.

For example, in some embodiments, an effective amount of an agent that induces LAIR-2 blockade is administered to a subject with an autoimmune disease or inflammatory disease or disorder. LAIR-1 signaling functions to delimit immune responses, which is particularly important to prevent autoimmune and immune autoreactive manifestations. Therefore, decreased LAIR-1 expression may result in increased autoimmunity. Alternately, increased levels of LAIR-2 can promote autoimmunity by preventing ligand cross-linking and inhibitory signaling by LAIR-1. Indeed, increased levels of LAIR-2 have been reported in patients with rheumatoid arthritis (Olde Nordkamp et al. 2011, Arthritis Rheum. 63:3749-3757). As such, despite increased levels of LAIR-1 in RA patients, because LAIR-2 has higher ligand affinity, the increase in LAIR-1 expression will have little effect. Therefore, blockade of LAIR-2 binding to collagens, SP-D and C1q would result in increased cross-linking of LAIR-1, with a subsequent decrease in immune inflammatory pathways. mAbs that deplete LAIR-2 or block LAIR-2 ligand binding may be particularly effective for the treatment of autoimmune diseases in which systemic or localized levels of LAIR-2 are increased. In fact, autoimmune diseases with increased expression of both LAIR-2 and LAIR-1 would have the greatest chance for success with LAIR-2 mAb immunotherapy because once LAIR-2 is neutralized, high levels of LAIR-1 would have a greater inhibitory effect than in diseases with low levels of LAIR-1 expression. Thus in some embodiments, LAIR-2 mAb immunotherapy is utilized to treat a subject with rheumatoid arthritis.

a. Inflammatory Responses

The disclosed compositions and methods can be used to treat inflammation. Generally, the agents are used to reduce or inhibit an immune response in the subject by administering to the subject an amount of an immunomodulatory agent that increases LAIR-1 expression, ligand binding, crosslinking, negative signaling, or a combination thereof. The method can reduce or more symptoms of the inflammation. In inflammation can be acute, chronic, or persistent inflammation.

In some embodiments, the immunomodulatory agents slow down the immune system. For example, agent can be used to control hyper-inflammatory response causing damage healthy tissues. Accordingly, in some embodiments, the agents are administered to a subject undergoing a hyper-inflammatory response. In such cases, controlling excessive immune responses can be beneficial to the subject.

b. Inflammatory and Autoimmune Diseases/disorders

Agents that increase LAIR-1 expression, ligand binding, crosslinking, negative signaling, or a combination thereof can also be used to treat inflammatory or autoimmune diseases and disorders. Representative inflammatory or autoimmune diseases/disorders include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In some embodiments the inflammation or autoimmune disease is caused by a pathogen, or is the result of an infection.

V. Combination Therapies

The disclosed immunomodulatory agents can be administered to a subject in need thereof alone or in combination with one or more additional therapeutic agents. In some embodiments, the immunomodulatory agent and the additional therapeutic agent are administered separately, but simultaneously. The immunomodulatory agent and the additional therapeutic agent can also be administered as part of the same composition. In other embodiments, the immunomodulatory agent and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The immunomodulatory agent can be the first or the second therapeutic agent.

The immunomodulatory agent and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the immunomodulatory agent can be co-administered with one or more additional agents that function to enhance or promote an immune response or reduce or inhibit an immune response.

A. Increasing Immune Responses

1. Antimicrobials

For example, a LAIR-1 or LAIR-2 immunomodulatory agent can be used in a preventive or prophylactic role in the treatment and prevention of disease as discussed above, and also in the context of severe trauma injuries like major burn, open bone fracture, accidental amputation or other wounds. Therefore, the LAIR-1 or LAIR-2 immunomodulatory agents can be administered to the subject in combination with an antimicrobial such as an antibiotic, an antifungal, an antiviral, an antiparasitics, or essential oil.

In some embodiments, the subject is administered the LAIR-1 or LAIR-2 immunomodulatory agent and/or the antimicrobial at time of admission to the hospital to prevent further bacterial, fungal or viral complications. The antibiotic can target pathogens and the LAIR-1 or LAIR-2 immunomodulatory agent can stimulate the immune system to provide an enhanced response to treat or prevent further infection or disease.

2. Chemotherapeutic Agents

The LAIR-1 or LAIR-2 immunomodulatory agents can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

3. Other Immunomodulators a. PD-1 Antagonists

In some embodiments, LAIR-1 or LAIR-2 immunomodulatory agents are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U. S. A,* 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following publications:

PCT/IL03/00425 (Hardy et al., WO/2003/099196)
PCT/JP2006/309606 (Korman et al., WO/2006/121168)
PCT/US2008/008925 (Li et al., WO/2009/014708)
PCT/JP03/08420 (Honjo et al., WO/2004/004771)
PCT/JP04/00549 (Honjo et al., WO/2004/072286)
PCT/IB2003/006304 (Collins et al., WO/2004/056875)
PCT/US2007/088851 (Ahmed et al., WO/2008/083174)
PCT/US2006/026046 (Korman et al., WO/2007/005874)
PCT/US2008/084923 (Terrett et al., WO/2009/073533)
Berger et al., *Clin. Cancer Res.,* 14:30443051 (2008).

A specific example of an anti-PD-1 antibody is an antibody described in Kosak, US 20070166281 (pub. 19 Jul. 2007) at par. 42), a human anti-PD-1 antibody, which in some embodiments is administered at a dose of 3 mg/kg.

Exemplary anti-B7-H1 antibodies include, but are not limited to, those described in the following publications:

PCT/US06/022423 (WO/2006/133396, pub. 14 Dec. 2006)
PCT/US07/088851 (WO/2008/083174, pub. 10 Jul. 2008)
US 2006/0110383 (pub. 25 May 2006)

A specific example of an anti-B7-H1 antibody is an antibody described (WO/2007/005874, published 11 Jan. 2007)), a human anti-B7-H1 antibody.

Additional anti-PD-1 and anti-B7-H1 antibodies are disclosed in 2014/0044738, which is specifically incorporated by reference herein in its entirety.

For anti-B7-DC antibodies see U.S. Pat. Nos. 7,411,051, 7,052,694, 7,390,888, and U.S. Published Application No. 2006/0099203.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., *PNAS,* 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., *Clinical Kidney Journal,* 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.,* 277:7363-7368 (2002). Such small organics could be administered alone or together with an anti-CTLA4 antibody to reduce inhibitory signal transduction of T cells.

4. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety. While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke *Crit Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-7 and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

The optimal dose for CTX to potentiate an anti-tumor immune response, is one that lowers overall T cell counts by lowering Treg levels below the normal range but is subtherapeutic (see Machiels et al. Cancer Res. 61:3689-3697 (2001)).

In human clinical trials where CTX has been used as an immunopotentiating agent, a dose of 300 $mg/m^2$ has usually been used. For an average male (6 ft, 170 pound (78 kg) with a body surface area of 1.98 $m^2$), 300 $mg/m^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such $mg/m^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

B. Reducing Immune Responses

1. Immunosuppressive Agents

In some embodiments, the immune response, or inflammatory/autoimmune disease/disorder is treated by administering to the subject a LAIR-1 or LAIR-2 immunomodulatory agent and a second agent that is an immune suppressant. Immunosuppressive agents include, but are not limited to antibodies against other lymphocyte surface markers (e.g., CD40, alpha-4 integrin) or against cytokines), fusion proteins (e.g., CTLA-4-Ig (Orencia®), TNFR-Ig (Enbrel®)), TNF-α blockers such as Enbrel, Remicade, Cimzia and Humira, cyclophosphamide (CTX) (i.e., Endoxan®, Cytoxan®, Neosar®, Procytox®, Revimmune™), methotrexate (MTX) (i.e., Rheumatrex®, Trexall®), belimumab (i.e., Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

The therapeutic agent can be a CTLA-4 fusion protein, such as CTLA-4-Ig (abatacept). CTLA-4-Ig fusion proteins compete with the co-stimulatory receptor, CD28, on T cells for binding to CD80/CD86 (B7-1/B7-2) on antigen presenting cells, and thus function to inhibit T cell activation. In another embodiment, the therapeutic agent is a CTLA-4-Ig fusion protein known as belatacept. Belatacept contains two amino acid substitutions (L104E and A29Y) that markedly increase its avidity to CD86 in vivo. In another embodiment, the therapeutic agent is Maxy-4.

In another embodiment, the therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. Cyclophosphamide (CTX) is the primary drug used for diffuse proliferative glomerulonephritis in patients with renal lupus.

The therapeutic agent can be administered in an effective amount to reduce the blood or serum levels of anti-double stranded DNA (anti-ds DNA) auto antibodies and/or to reduce proteinuria in a patient in need thereof.

In another embodiment, the therapeutic agent increases the amount of adenosine in the serum, see, for example, WO 08/147482. For example, the second therapeutic agent can be CD73-Ig, recombinant CD73, or another agent (e.g., a cytokine or monoclonal antibody or small molecule) that increases the expression of CD73, see for example WO 04/084933. In another embodiment the therapeutic agent is Interferon-beta.

The therapeutic agent can be a small molecule that inhibits or reduces differentiation, proliferation, activity, and/or cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-18 IL-17, IL-6, IL-23, IL-22, IL-21, and MMPs. In another embodiment, the therapeutic agent is a small molecule that interacts with Tregs, enhances Treg activity, promotes or enhances IL-10 secretion by Tregs, increases the number of Tregs, increases the suppressive capacity of Tregs, or combinations thereof.

In some embodiments, the composition increases Treg activity or production. Exemplary Treg enhancing agents include but are not limited to glucocorticoid fluticasone, salmeteroal, antibodies to IL-12, IFN-γ, and IL-4; vitamin D3, and dexamethasone, and combinations thereof.

In some embodiments, the therapeutic agent is an antibody, for example, a functions blocking antibody against a proinflammatory molecule such as IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. Nos. 6,015,809; 5,989,591; 5,567,709; 5,559,112; 5,530, 006; 5,484,790; 5,385,908; 5,202,332; 5,162,333; 5,780, 462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. In some embodiments, the language "rapamycin compound" as used herein does not include FK506-like compounds.

2. Anti-Inflammatories

Other suitable therapeutic agents include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

VI. AML Biomarkers

One embodiment provides a method for assessing or predicting the efficacy of a treatment using an anti-LAIR binding moiety by assaying the cells of a subject in need of treatment to determine whether the cells express LAIR, binding partners of LAIR, or both. Exemplary cells to be assayed include, but are not limited to cancer cells obtained from the subjected. Exemplar cancer cells, include but are not limited to acute myeloid leukemia (AML) cells. Cancer cells expressing multiple interacting inhibitory receptors are believed to respond better to treatments using anti-LAIR binding moieties. Exemplary LAIR binding partners include, but are not limited to transmembrane collagens (XIII, XVII and XXIII) and LILRB4. FIG. 3 shows a predicted outcome of treatment based on the presence of LAIR-1 or binding partners of LAIR-1 on cancer cells.

VII. Kits

The disclosed LAIR-1 and LAIR-2 immunomodulatory agents can be packaged in a hermetically sealed container, such as an ampoule or sachette, indicating the quantity. The agent can be supplied as a dry sterilized lyophilized powder or water free concentrate in a hermetically sealed container and can be reconstituted, e.g., with water or saline to the appropriate concentration for administration to a subject. For example, the agent can be supplied as a dry sterile lyophilized powder in a hermetically sealed container at a unit dosage of at least 5 mg, or at least 10 mg, at least 15 mg, at least 25 mg, at least 35 mg, at least 45 mg, at least 50 mg, or at least 75 mg. The lyophilized agent can be stored at between 2 and 8° C. in their original container and are typically administered within 12 hours, or within 6 hours, or within 5 hours, or within 3 hours, or within 1 hour after being reconstituted.

In an alternative embodiment, agent supplied in liquid form in a hermetically sealed container indicating the quantity and concentration. In some embodiments, the liquid form of the agent supplied in a hermetically sealed container including at least 1 mg/ml, or at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the agent.

Pharmaceutical packs and kits including one or more containers filled with agent are also provided. Additionally, one or more other prophylactic or therapeutic agents useful for the treatment of a disease can also be included in the pharmaceutical pack or kit. The pharmaceutical pack or kit can also include one or more containers filled with one or more of the ingredients of the disclosed pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

Kits designed for the above-described methods are also provided. Embodiments typically include one or more LAIR-1 and/or LAIR-2 immunomodulatory agents. In particular embodiments, a kit also includes one or more other prophylactic or therapeutic agents useful for the treatment of cancer, in one or more containers. In other embodiments, a kit also includes one or more anti-inflammatory agents useful for the treatment inflammatory and autoimmune diseases, in one or more containers.

EXAMPLES

Example 1: LAIR Antibodies and Heavy and Light Chains Sequences Thereof

Materials and Methods

Mouse Anti-Human LAIR-1 Monoclonal Antibodies

Mice were immunized with soluble human LAIR-1 (soluble LAIR-1 refers to the extracellular domain of LAIR-1) fused to a murine G2a Fc (SEQ ID NO:10). Mice were challenged with the same immunogen 2 weeks later. Mice received a 3rd dose of antigen two weeks later. Three days after the final boost, mouse splenocytes were harvested and resuspended in RPMI supplemented with 10% FBS and glutamine, and later fused to form hybridomas.

RACE

RACE (Rapid Amplification of cDNA Ends) identification of the heavy and light chains was performed according to the following protocol: (1) mRNA denaturing, (2) cDNA synthesis, (3) 5'RACE Reaction, (4) analyzed PCR results (on an agarose gel to visualize the amplified DNA fragment—the correct antibody variable region DNA fragments should have a size between 500-700 base pairs, (5) TOPO cloned PCR positive bands; (6) PCR-amplified TOPO clones, followed by gel electrophoresis and recovery from agarose gel, (7) sequenced 218 clones in total, (8) performed CDR analysis using sequencing data (CDR regions were defined using VBASE2 available through vbase2.org).

Results

Antibodies were cloned using RACE methods. Antibody sequence analysis identified one variable heavy chain and one variable light chain for 13 antibody hybridomas referred to herein as 1E11, 1G7, 4B3, 5A6, 5E1, 6B2, 6F4, 6G6, 7G3, 9H6, 11B3, 12E10a, and 12E10b. The sequences are provided below and above. Heavy and light chain sequences and CDRs are provided above, below, and illustrated in FIGS. 1A and 1B.

```
1E11 SEQUENCES
1E11 VL Amino Acid Sequence
                                        (SEQ ID NO: 19)
DIVMTQAAFSNPVTLGTSASISCRSSKSLLHSNGITYLYWYLQKPGQSPQ
VLIYQMSSLASGVPDRFSSSGSGTEFTLRISRVEAEDVGVYYCAQNLELP
LTFGAGTKLELK

CDR1 of 1E11 VL
The amino acid of CDR1 of 1E11 VL includes
                                        (SEQ ID NO: 20)
RSSKSLLHSNGITYLY

CDR2 of 1E11 VL
The amino acid of CDR2 of 1E11 VL includes
                                        (SEQ ID NO: 21)
QMSSLAS.

CDR3 of 1E11 VL
The amino acid of CDR3 of 1E11 VL includes
                                        (SEQ ID NO: 22)
AQNLELPLT.

1E11 VH Amino Acid Sequence
                                        (SEQ ID NO: 23)
QVQLQQSGPELVKPGASVKLSCKASGYTFTSYDINWVKQRPGQGLEWI
GWIYPRDGSTKYNEKLKGKATLTVDTSSRTAYMELHSLTSEDSAVYFC
ARGGYYDYDGYWGQGTLVTVSA

CDR1 of 1E11 VH
The amino acid of CDR1 of 1E11VH includes
                                        (SEQ ID NO: 24)
SYDIN.

CDR2 of 1E11 VH
The amino acid of CDR2 of 1E11VH includes
                                        (SEQ ID NO: 25)
WIYPRDGSTKYNEKLKG.

CDR3 if 1E11 VH
The amino acid of CDR3 of 1E11VH includes
                                        (SEQ NO: 26)
GGYYDYDGY.
```

-continued

1G7 SEQUENCES
1G7 VL Amino Acid Sequence
(SEQ ID NO: 27)
DIQMTQSPASQSASLGESVTITCLASQTIGTWLAWYQQKPGKSPQLLIYA
ATSLADGVPSRFSGSGSGTKFSFKISSLQAEDFVSYYCQQLYSTPLTFGA
GTKLELK.

CDR1 of IG7 VL
The amino acid of CDR1 of 1G7 VL includes
(SEQ ID NO: 28)
LASQTIGTWLA.

CDR2 of IG7 VL
The amino acid of CDR2 of 1G7 VL includes
(SEQ ID NO: 29)
AATSLAD.
CDR3 of IG7 VL The amino acid of CDR3 of 1G7 VL includes
(SEQ ID NO: 30)
QQLYSTPLT.

1G7 VH Amino Acid Sequence
(SEQ ID NO: 31)
EVQLVESGGGLVQPKGSLKLSCAASGFTFNTNAMYWVRQAPGKGLEW
VARIRSKSSNYATYYADSVKDRFTISRDDSQSMLYLQMNNLKTEDTAR
YYCVRGGSGFFAYWGQGTLVTVSA.

CDR1 of 1G7 VH
The amino acid of CDR1 of 1G7 VH includes
(SEQ ID NO: 32)
TNAMY.

CDR2 of 1G7 VH
The amino acid of CDR2 of 1G7 VH includes
(SEQ ID NO: 33)
RIRSKSSNYATYYADSVKD.

CDR3 of 1G7 VH
The amino acid of CDR3 of 1G7 VH includes
(SEQ ID NO: 34)
GGSGFFAY.

4B3 Sequences
4B3 VL Amino Acid Sequence
(SEQ ID NO: 35)
DIVMKQSPSSLRVSAGEKVTMSCKSSQSLLNSGNQKNYLAWYQQKPGQ
PPKLLIYGASTRESGVPDRFTGSGSGTDFALTISSVQAEDLAVYYCQNDH
SYPFTFGSGTKLEIK CDR1 of 4B3 VL
The amino acid of CDR1 of 4B3 VL includes
(SEQ ID NO: 36)
KSSQSLLNSGNQKNYLA.

CDR2 of 4B3 VL
The amino acid of CDR2 of 4B3 VL includes
(SEQ ID NO: 37)
GASTRES.

CDR3 of 4B3 VL
The amino acid of CDR3 of 4B3 VL includes
(SEQ ID NO: 38)
QNDHSYPFT.

4B3 VH Amino Acid Sequence
(SEQ ID NO: 39)
QIQLQQSGAELARPGASVKLPCKASDYIFISYGLNWVRQTTGQGLEWIG
EIYPRSGHTYYNEKFKGKATLTADKSSSTAYMELRSLTSEDSAVYFCAR
RSVFYDYDKNGFDYWGQGTTLTVSS.

CDR1 of 4B3 VH
The amino acid of CDR1 of 4B3 VH includes
(SEQ ID NO: 40)
SYGLN.

CDR2 of 4B3 VH
The amino acid of CDR2 of 4B3 VH includes
(SEQ ID NO: 41)
EIYPRSGHTYYNEKFKG.

-continued

CDR3 of 4B3 VH
The amino acid of CDR3 of 4B3 VH includes
(SEQ ID NO: 42)
RSVFYDYDKNGFDY.

5A6 Sequences
5A6 VL Amino Acid Sequence
(SEQ ID NO: 43)
DIQMTQSPSSLSASLGERVSFSCRASQDIGSSLNWLQQEPDGTIKRLIY
ATSSLDSGVPKRFSGSRSGSDYSLTISSLESEDFVEYYCLQYDSFPYTF
GGGTKLEIK.

CDR1 of 5A6 VL
The amino acid of CDR1 of 5A6 VL includes
(SEQ ID NO: 44)
RASQDIGSSLN.

CDR2 of 5A6 VL
The amino acid of CDR2 of 5A6 VL includes
(SEQ ID NO: 45)
ATSSLDS.

CDR3 of 5A6 VL
The amino acid of CDR3 of 5A6 VL includes
(SEQ ID NO: 46)
LQYDSFPYT.

5A6 VH Amino Acid Sequence
(SEQ ID NO: 47)
QVQLQQSGAELARPGASVKLSCKASGYTFTSYGISWVKQRTGQGLEWI
GEIYPRRGNTYYNEKFKGKATLTADKSSSTAYMELRSLTSEDSAVYFCA
RQLFAYWGQGTLVTVSA.

CDR1 of 5A6 VH
The amino acid of CDR1 of 5A6 VH includes
(SEQ ID NO: 48)
SYGIS.

CDR2 of 5A6 VH
The amino acid of CDR2 of 5A6 VH includes
(SEQ ID NO: 49)
EIYPRRGNTYYNEKFKG.

CDR3 of 5A6 VH
The amino acid of CDR3 of 5A6 VH includes
(SEQ ID NO: 50)
QLFAY.

5E1 Sequences
5E1 VL Amino Acid Sequence
(SEQ ID NO: 51)
DIQMTQTTSSLSASLGDRVTISCRASQDISNYLNWYQQKPDGTVKLLIYY
TSRLHSGVPSRFSGSGSGTDYSLTISNLEQEDIATYFCQQGNTLPRTFGG
GTKLEIK.

CDR1 of 5E1 VL
The amino acid sequence for CDR1 of 5E1 VL includes
(SEQ ID NO: 52)
RASQDISNYLN.

CDR2 of 5E1 VL
The amino acid sequence for CDR2 of 5E1 VL includes
(SEQ ID NO: 53)
YTSRLHS.

CDR3 of 5E1 VL
The amino acid sequence for CDR3 of 5E1 VL includes
(SEQ ID NO: 54)
QQGNTLPRT.

5E1 VH Amino Acid Sequence
(SEQ ID NO: 55)
EVQLQQSGPELVKPGASVKISCKASGYSFTGYFMNWVKQSPEKSLEWIG
EIHPSTGSIIYNQKFKAKATLTIDKSSSTAYMQLKSLTSEDSAVYYCAR
FDYSNSFAYWGQGTLVTVSA.

-continued

CDR1 for 5E1 VH
The amino acid sequence for CDR1 of 5E1 VH includes
(SEQ ID NO: 56)
GYFMN.

CDR2 for 5E1 VH
The amino acid sequence for CDR2 of 5E1 VH includes
(SEQ ID NO: 57)
EIHPSTGSIIYNQKFKA.

CDR3 for 5E1 VH
The amino acid sequence for CDR3 of 5E1 VH includes
(SEQ ID NO: 58)
FDYSNSFAY.

6B2 Sequences
6B2 VL Amino Acid Sequences
(SEQ ID NO: 59)
DIQMTQSPASQSASLGESVTITCLASQTIGTWLAWYQQKPGKSPQLLIYA
ATSLADGVPSRFSGSGSGTKFSFKISSLQAEDFVSYYCQQLYSTPLTFGA
GTKLELK.

CDR1 of 6B2 VL
The amino acid sequence of CDR1 for 6B2 VL includes
(SEQ ID NO: 60)
LASQTIGTWLA.

CDR2 of 6B2 VL
The amino acid sequence of CDR2 for 6B2 VL includes
(SEQ ID NO: 61)
AATSLAD.

CDR3 of 6B2 VL
The amino acid sequence of CDR3 for 6B2 VL includes
(SEQ ID NO: 62)
QQLYSTPLT.

6B2 VH Amino Acid Sequences
(SEQ ID NO: 63)
EVQLVESGGGLVQPKGSLKLSCAASGFSFNINAMNWVRQAPGKGLEWV
ARIRSKSNNYETYYADSVKDRFTISRDDSESMVYLQMNNLKTEDTAMY
YCVRSLWFVYWGQGTLVTVSA.

CDR1 for 6B2 VH
The amino acid sequence for CDR1 of 6B2 VH includes
(SEQ ID NO: 64)
INAMN.

CDR2 for 6B2 VH
The amino acid sequence for CDR2 of 6B2 VH includes
(SEQ ID NO: 65)
RIRSKSNNYETYYADSVKD.

CDR3 for 6B2 VH
The amino acid sequence for CDR3 of 6B2 VH includes
(SEQ ID NO: 66)
SLWFVY.

6F4 Sequences
6F4 VL Amino Acid Sequences
(SEQ ID NO: 67)
DIKMTQSPSSMYASLGERVTITCKASQDINSYLSWVQQKPGKSPKTLIDR
ANRLVDGVPSRFSGSGSGQDYSLTISSLEYEDMGIYYCLQYDEFPPYTFG
GGTKLEIK.

CDR1 of 6F4 VL
The amino acid sequence of CDR1 for 6F4 includes
(SEQ ID NO: 68)
KASQDINSYLS.

CDR2 of 6F4 VL
The amino acid sequence of CDR2 for 6F4 includes
(SEQ ID NO: 69)
RANRLVD.

CDR3 of 6F4 VL
The amino acid sequence of CDR3 for 6F4 includes
(SEQ ID NO: 70)
LQYDEFPPYT.

6F4 VH Amino Acid Sequences
(SEQ ID NO: 71)
QVQLQQSGAELAKPGASVKLSCKASGYTFTSYWMHWVKQRPGQGLE
WIGYINPFSGHTKYNQKFKDKATLTADKSSSTAYMQLSSLTYEDSAVYY
CARNFDQWGQGTTLTVSS.

CDR1 for 6F4 VH
The amino acid sequence for CDR1 of 6F4 VH includes
(SEQ ID NO: 72)
SYWMH.

CDR2 for 6F4 VH
The amino acid sequence for CDR2 of 6F4 VH includes
(SEQ ID NO: 73)
YINPFSGHTKYNQKFKD.

CDR3 for 6F4 VH
The amino acid sequence for CDR3 of 6F4 VH includes
(SEQ ID NO: 74)
NFDQ.

6G6 Sequences
6G6 VL Amino Acid Sequences
(SEQ ID NO: 75)
DIVMTQSHKFMSTSVGDRVSITCKASQNVGTAVAWYQQKPGQSPKLLI
YWASIRHTGVPDRFTGSGSGTDFTLTISNVQSEDLADYFCQQYSSHPYTF
GGGTKLEIK.

CDR1 for 6G6 VL
The amino acid sequence for CDR1 of 6G6 VL includes
(SEQ ID NO: 76)
KASQNVGTAVA.

CDR2 for 6G6 VL
The amino acid sequence for CDR2 of 6G6 VL includes
(SEQ ID NO: 77)
WASIRHT.

CDR3 for 6G6 VL
The amino acid sequence for CDR3 of 6G6 VL includes
(SEQ ID NO: 78)
QQYSSHPYT.

G6G VH Amino Acid Sequences
(SEQ ID NO: 79)
EVQLQQSGPELVKPGASVKISCKASGYTFTTYYMNWVKQSHGKSLEWI
GNINPDNGITSYNQKFKGKATLTVDKSSSTAYMELRSLTSEDSAVYYCA
RGKSLAYWGQGTLVTVSA.

CDR1 for 6G6 VH
The amino acid sequence for CDR1 of 6G6 VH includes
(SEQ ID NO: 80)
TYYMN.

CDR2 for 6G6 VH
The amino acid sequence for CDR2 of 6G6 VH includes
(SEQ ID NO: 81)
NINPDNGITSYNQKFKG.

-continued

CDR3 for 6G6 VH
The amino acid sequence for CDR3 of 6G6 VH includes (SEQ ID NO: 82)
GKSLAY.

7G3 Sequences
7G3 VL Amino Acid Sequences (SEQ ID NO: 83)
DIVMTQAAFSNPVTLGTSASISCRSSKSLLHSNGITYLYWYLQKPGQSPQ
VLIYQMSNLASGVPDRFSSSGSGTEFTLRISRVEAEDVGVYYCAQNLEFP
LTFGAGTKLELK.

CDR1 for 7G3 VL
The amino acid sequence for CDR1 of 7G3 VL includes (SEQ ID NO: 84)
RSSKSLLHSNGITYLY.

CDR2 for 7G3 VL
The amino acid sequence for CDR2 of 7G3 VL includes (SEQ ID NO: 85)
QMSNLAS.

CDR3 for 7G3 VL
The amino acid sequence for CDR3 of 7G3 VL includes (SEQ ID NO: 86)
AQNLEFPLT.

7G3 VH Amino Acid Sequences (SEQ ID NO: 87)
QVQLQQSGPELVKPGASVKLSCKASGYTFTTYDINWVKQRPGQGLEWI
GWIYPRDGTTKYNEKFKGKATLTVDTSSTTAYMELHSLTSEDSAVYFCA
RGGYYDYDGYWGQGTLVTVSA.

CDR1 for 7G3 VH
The amino acid sequence for CDR1 of 7G3 VH includes (SEQ ID NO: 88)
TYDIN.

CDR2 for 7G3 VH
The amino acid sequence for CDR2 of 7G3 VH includes (SEQ ID NO: 89)
WIYPRDGTTKYNEKFKG.

CDR3 for 7G3 VH
The amino acid sequence for CDR3 of 7G3 VH includes (SEQ ID NO: 90)
GGYYDYDGY.

9116 Sequences
9H6 VL Amino Acid Sequences (SEQ ID NO: 91)
DIQMTQSPASQSASLGESVTITCLASQTIGTWLAWYQQKPGRSPQLLIYA
ATSLADGVPSRFSGSGSGTKFSFKINSLQAEDFVSYYCQQLYSTPFTFGS
GTKLEIK.

CDR1 for 9H6 VL
The amino acid sequence for CDR1 of 9H6 VL includes (SEQ ID NO: 92)
LASQTIGTWLA.

CDR2 for 9H6 VL
The amino acid sequence for CDR2 of 9H6 VL includes (SEQ ID NO: 93)
AATSLAD.

CDR3 for 9H6 VL
The amino acid sequence for CDR3 of 9H6 VL includes (SEQ ID NO: 94)
QQLYSTPFT.

-continued

9H6 VH Amino Acid Sequences (SEQ ID NO: 95)
EVQLVESGGGLVQPKGSLKLSCAASGFSFNTHAMNWVRQAPGKGLEW
VARIRTKSNNYATYYADSVKDRFIISRDDSENMVYLQMNNLKTEDTAIY
YCVRLRGGFLDYWGQGTTLTVSS.

CDR1 of 9H6 VH
The amino acid sequence for CDR1 of 9H6 VH includes (SEQ ID NO: 96)
THAMN.

CDR2 of 9H6 VH
The amino acid sequence for CDR2 of 9H6 VH includes (SEQ ID NO: 97)
RIRTKSNNYATYYADSVKD.

CDR3 of 9H6 VH
The amino acid sequence for CDR3 of 9H6 VH includes (SEQ ID NO: 98)
LRGGFLDY.

11B3 Sequences
11B3 VL Amino Acid Sequences (SEQ ID NO: 99)
DIQMAQSSSSFSVSLGDRVTITCKASEDIYIRLAWYQQKPGNAPRLLIST
ATSLETGVPSRFSGSGSGKDYTLSITSLQTEDVATYYCQQYWSTPYTFGG
GTRLEIK.

CDR1 of 11B3 VL
The amino acid sequence for CDR1 of 11B3 VL includes (SEQ ID NO: 100)
KASEDIYIRLA.

CDR2 of 11B3 VL
The amino acid sequence for CDR2 of 11B3 VL includes (SEQ ID NO: 101)
TATSLET.

CDR3 of 11B3 VL
The amino acid sequence for CDR3 of 11B3 VL includes (SEQ ID NO: 102)
QQYWSTPYT.

11B3 VH Amino Acid Sequences (SEQ ID NO: 103)
EVQLVESGGGLVQPKGSLKLSCAASDFTFNTYAMHWVRQAPGKGLEW
VARIRTKSNNYATYYADSVKDRFTISRDDSQSMLYLQMNNLTTEDTAM
YYCVRDRYGGAMDYWGQGTSVTVSS CDR1 for 11B3 VH
The amino acid sequence for CDR1 of 11B3 VH includes (SEQ ID NO: 104)
TYAMH.

CDR2 for 11B3 VH
The amino acid sequence for CDR2 of 11B3 VH includes (SEQ ID NO: 105)
RIRTKSNNYATYYADSVKD.

CDR3 for 11B3 VH
The amino acid sequence for CDR3 of 11B3 VH includes (SEQ ID NO: 106)
DRYGGAMDY.

12E10a Sequences
Clone 12E10 was found to have two light chains (12E10a and 12E10b). mb
12E10a VL Amino Acid Sequences (SEQ ID NO: 107)
DIVMTQSQKFMSTSVGDRVSITCKASQNVRSAVAWYQQKPGQSPKTLIY
LASNRHTGVPDRFTGSGSGTDFTLTISNVQSEDLADYFCLQHWNYPLTF
GAGTKLELK.

-continued

CDR1 of 12E10a VL
The amino acid sequence of CDR1 of 12E10a VL includes (SEQ ID NO: 108)
KASQNVRSAVA.

CDR2 of 12E10a VL
The amino acid sequence of CDR2 of 12E10a VL includes (SEQ ID NO: 109)
LASNRHT.

CDR3 of 12E10a VL
The amino acid sequence of CDR3 of 12E10a VL includes (SEQ ID NO: 110)
LQHWNYPLT.

12E10(a and b) VH Amino Acid Sequences (SEQ ID NO: 111)
QVQLQQSGAELARPGTSVKLSCKASGYTFTSCGLSWVKQRTGQGLEWI
GEIYPSNGNSYYSDKVKDKATLTADKSSSTAYMELRSLTSEDSAVYFCA
RAYYTNGYYAMDYWGQGTSVTVSS.

CDR1 of 12E10 VH
The amino acid sequence of CDR1 for 12E10 VH includes (SEQ ID NO: 112)
SCGLS.

CDR2 of 12E10 VH
The amino acid sequence of CDR2 for 12E10 VH includes (SEQ ID NO: 113)
EIYPSNGNSYYSDKVKD.

CDR3 of 12E10 VH
The amino acid sequence of CDR3 for 12E10 VH includes (SEQ ID NO: 114)
AYYTNGYYAMDY.

12E10b VL Amino Acid Sequences (SEQ ID NO: 115)
DIVLTQSPATLSVTPGDSVSLSCRASQSISNNLHWYQQKSHESPRLLIKY
ASQSISGIPSRFSGSGSGTDFTLSINSVETEDFGMYFCQQSNSWPLTFGA
GTKLELK.

CDR1 for 12E10b VL
The amino acid sequence for CDR1 of 12E10b VL includes (SEQ ID NO: 116)
RASQSISNNLH.

CDR2 for 12E10b VL
The amino acid sequence for CDR2 of 12E 10b VL includes (SEQ ID NO: 117)
YASQSIS.

CDR3 for 12E10b VL
The amino acid sequence for CDR3 of 12E 10b VL includes (SEQ ID NO: 118)
QQSNSWPLT.

Example 2: Purification of LAIR-2 Fc

Methods and Materials

Figure 6B:
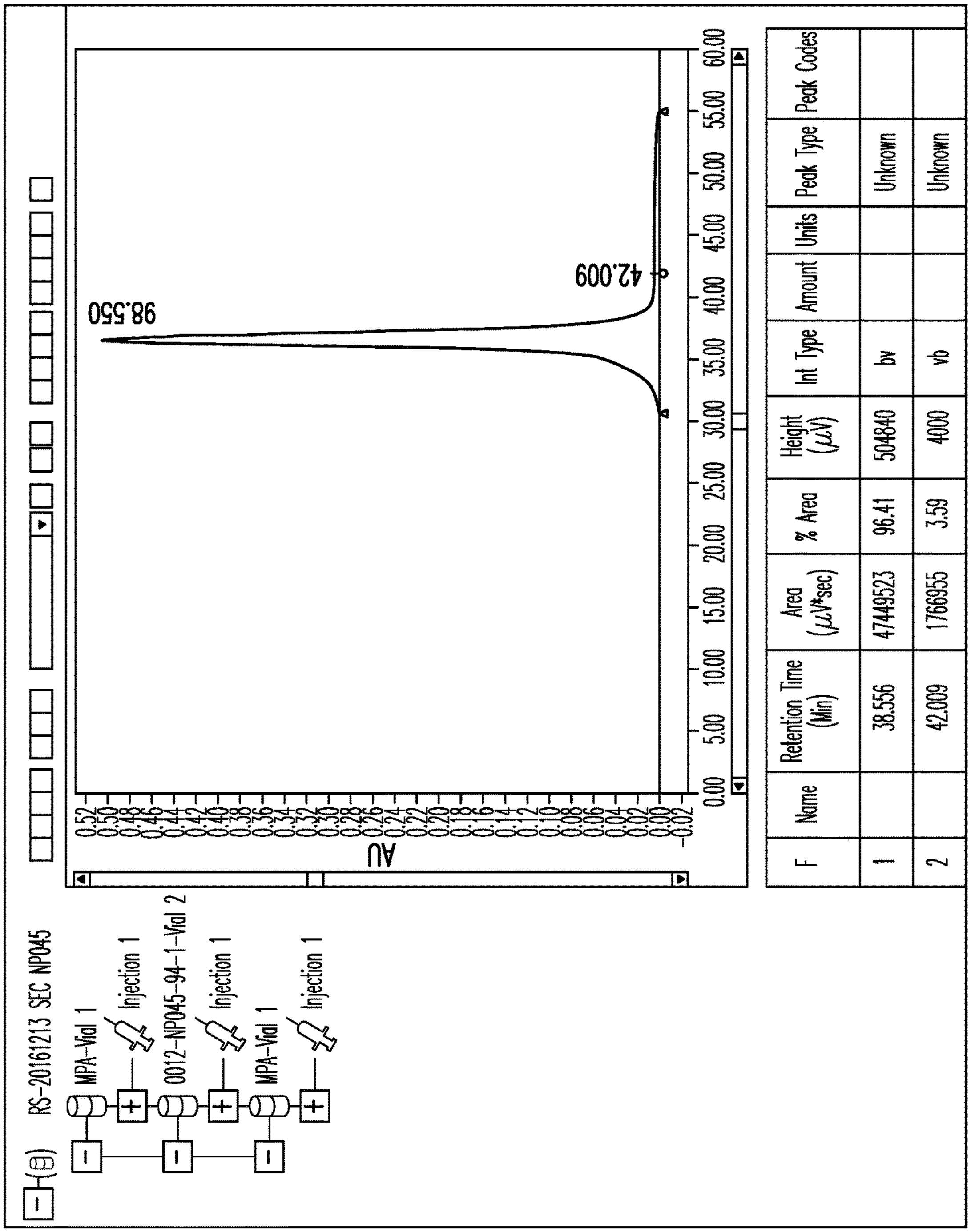
FIG. 6B shows a size exclusion chromatogram of LAIR-2 Fc.

LAIR-2 hIgG1 (hereafter termed LAIR-2 Fc) was generated by using CHOK1SV KO parent lines transfected with the Lonza G S Vector. This cell line was used to express both the lead candidate, LAIR-2 hIgG1 (native IgG1), and a mutated Fc versions LAIR2-hIgG1 Fc (L145A/L146A). LAIR-2 Fc was purified by protein A chromatography and assessed by SDS-PAGE (FIG. 6A) and Size-Exclusion chromatogram for purity (FIG. 6B). LAIR-1 Fc was prepared similarly as a control LAIR-2 Fc was purified by size-exclusion chromatography and visualized using SDS PAGE.

Results

Figure 6A:
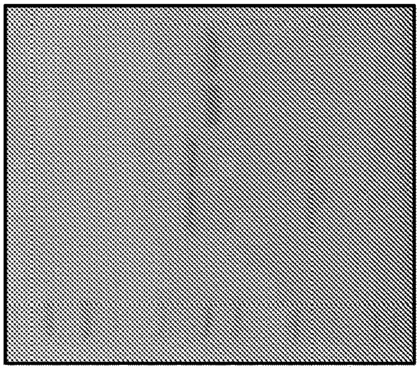
FIG. 6A shows an SDS PAGE gel of LAIR-2 Fc.

FIG. 6A is an SDS-PAGE gel showing LAIR-2 Fc under reducing and non-reducing conditions. FIG. 6B is a chromatogram showing a single, major peak at 38.550 minutes. The data confirm the expected size of LAIR-2 Fc, and the high level of purity of the LAIR-2 Fc protein used in studies described here.

Example 3: LAIR-2Fc Binds to Collagen

Materials and Methods

K562 AML cell line with stable expression of collagen 17 or controls lacking collagen 17 were stained with 1 ug of LAIR-2 Fc and LAIR-1 Fc, incubated for 30 minutes on ice, followed by washing of cells in FACS buffer (PBS+1% FBS), then stained with 0.05 ug anti-hIgG-PE for 30 minutes on ice. Cells were washed, resuspended in FACS fixing buffer (3% paraformaldehyde in PBS) and assessed by flow cytometry.

Results

Figure 7A:
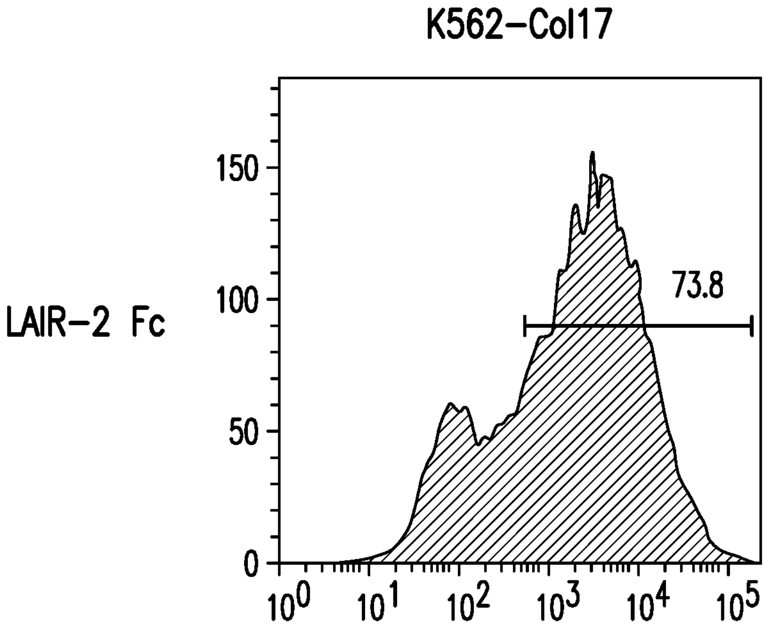
FIG. 7A is a fluorescence-activated cell sorting (FACS) histogram of K562-Col17 cells stained with LAIR-2 Fc followed by staining with anti-hIg-PE.
Figure 7B:
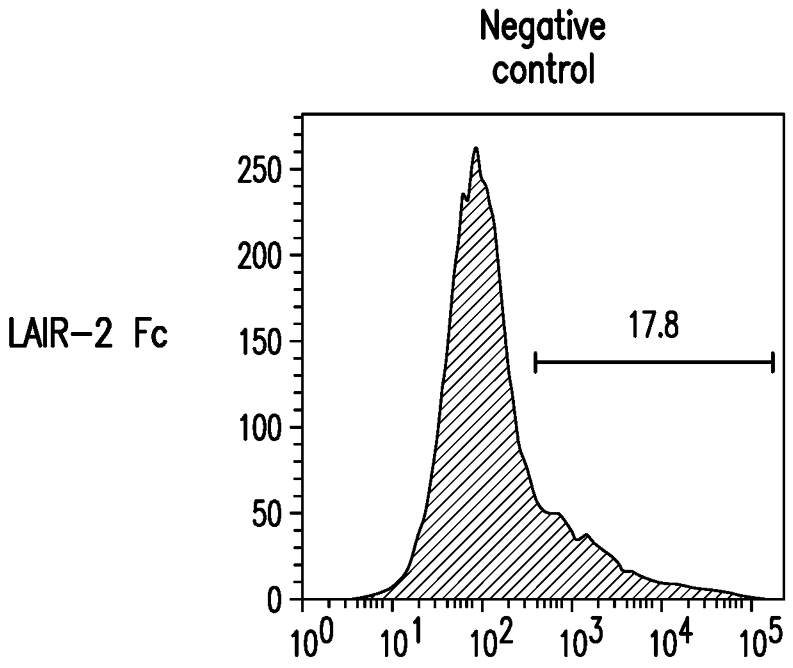
FIG. 7B is a FACS histogram of control cells stained with LAIR-2 Fc followed by staining with anti-hIg-PE.
Figure 7C:
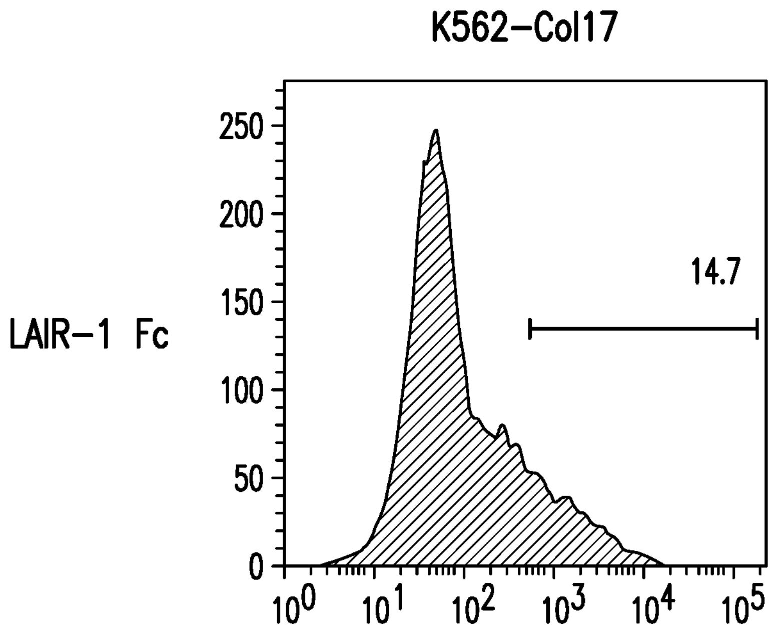
FIG. 7C is a FACS histogram of control cells stained with LAIR-1 Fc followed by staining with anti-hIg-PE.
Figure 7D:
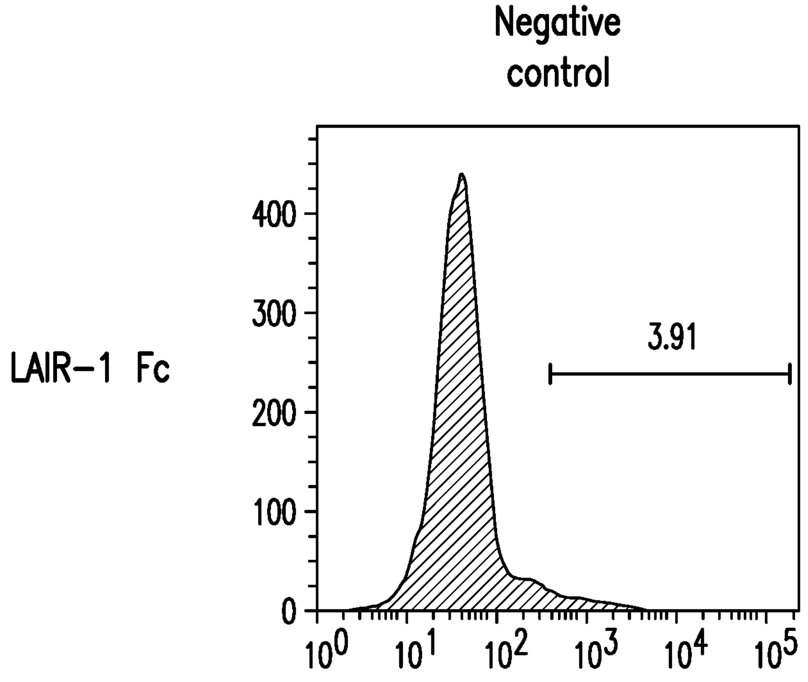
FIG. 7D is a FACS histogram of control cells stained with LAIR-1 Fc followed by staining with anti-hIg-PE.
Figure 7E:
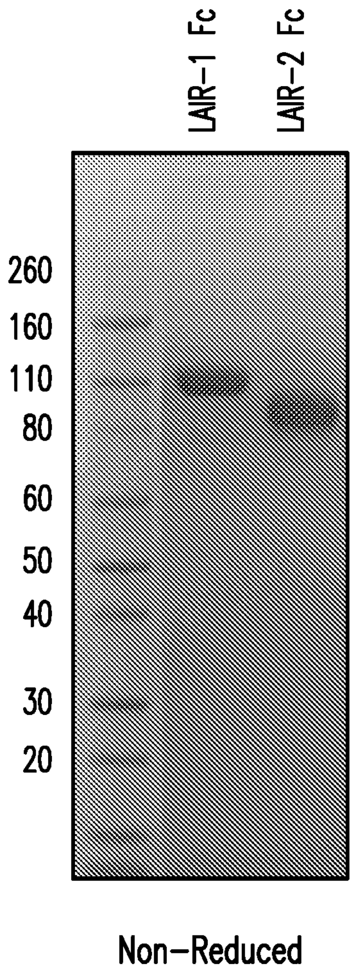
FIG. 7E is a non-reducing SDS-PAGE gel of LAIR-1 Fc and LAIR-2 Fc.
Figure 7F:
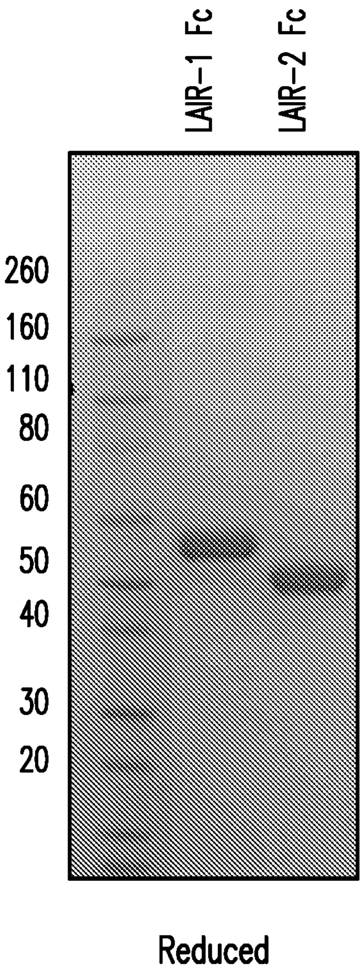
FIG. 7F is a reducing SDS-PAGE gel LAIR-1 Fc and LAIR-2 Fc.

LAIR-2 Fc (FIGS. 7A and 7B) and LAIR-1 Fc (FIGS. 7C and 7D) functionality was assessed by ability to bind endogenous transmembrane ligand collagen 17 expressed on the surface of K562 cells. SDS-PAGE analysis of LAIR-2 Fc and LAIR-1 Fc was used to assess purity of proteins used in this and following studies (FIGS. 7E and 7F). Greater than 95% purity of LAIR-2 Fc and LAIR-1 Fc was standard for all data shown here.

Example 4: LAIR-1 Expression on AML Cell Lines and LAIR-1 Fc and LAIR-2 Fc Binding Methods and Materials Jurkat T cells, K562 Col 17 cells, and THP-1 cells were stained with 10 mg/mL anti-LAIR-1-PE (eBioscience, NKTA255) or with 10 mg/mL Biotinylated LAIR-1 Fc or LAIR-2 Fc following blockade of Fc receptors with TruStain FcX (Biolegend) and hIgG (Innovative Research). After 30 minutes incubation, cells were washed with FACS buffer and stained with 0.4 ug/mL Streptadivin-PE. Expression was assessed by flow cytometry.

Results

LAIR-1 is confirmed to be highly expressed on specific AML cells lines. LAIR-2 Fc binds to unknown molecules on the surface of specific AML cell lines, whereas LAIR-1 Fc binding was not observed.

In order to assess cell lines useful for in vitro assays, hematopoietic-derived AML cell lines were assessed for LAIR-1 expression, as well as potential binding by LAIR-2 Fc and LAIR-1 Fc binding (FIGS. 8A-8I).

Figure 8A:
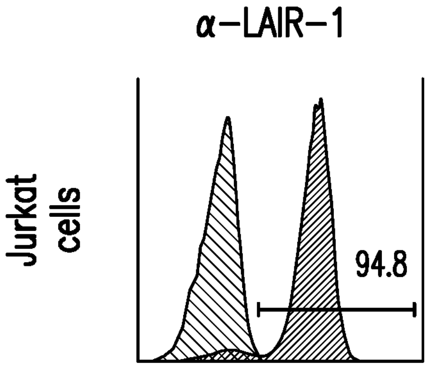
FIG. 8A is a FACS histogram of Jurkat T cells stained with α-LAIR-1.
Figure 8B:
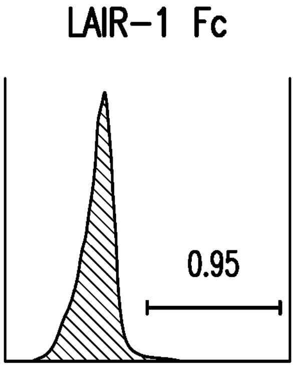
FIG. 8B is a FACS histogram of Jurkat T cells stained with LAIR-1 Fc.
Figure 8C:
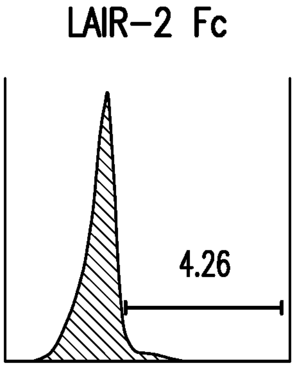
FIG. 8C is a FACS histogram of Jurkat T cells stained with LAIR-2 Fc.

FIGS. 8A-8I are histograms of flow cytometry of the indicated cell line treated with anti-LAIR-1, LAIR-1 Fc, or LAIR-2 Fc. FIGS. 8A-8C show Jurkat cells treated with anti-LAIR-1, LAIR-1 Fc, and LAIR-2 Fc, respectively.

Figure 8D:
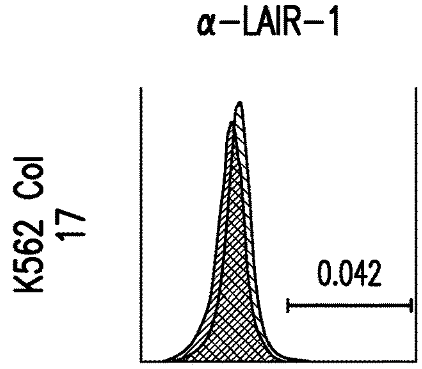
FIG. 8D is a FACS histogram of K562 Col 17 cells stained with α-LAIR-1.
Figure 8E:
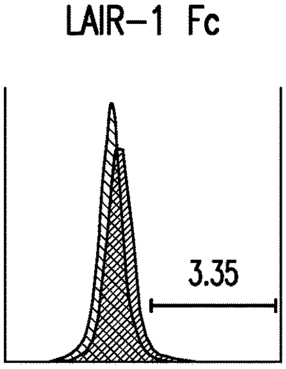
FIG. 8E is a FACS histogram of K562 Col 17 cells stained with LAIR-1 Fc.
Figure 8F:
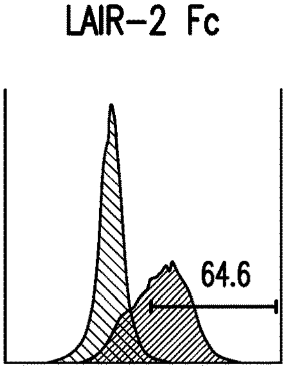
FIG. 8F is a FACS histogram of K562 Col 17 cells stained with LAIR-2 Fc.

FIGS. 8D-8F show K562 Col 17 cells treated with anti-LAIR-1, LAIR-1 Fc, and LAIR-2 Fc, respectively.

Figure 8G:
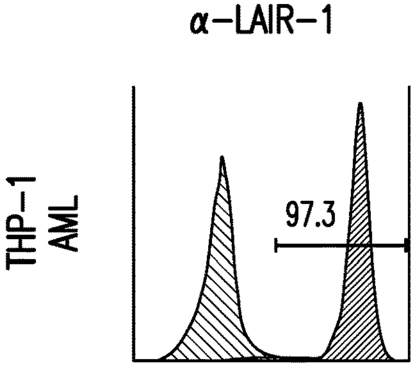
FIG. 8G is a FACS histogram of THP-1 AML cells stained with α-LAIR-1.
Figure 8H:
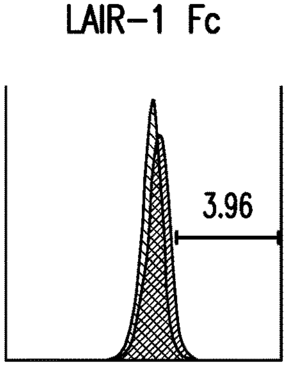
FIG. 8H is a FACS histogram of K562 Col 17 cells stained with LAIR-1 Fc.
Figure 8I:
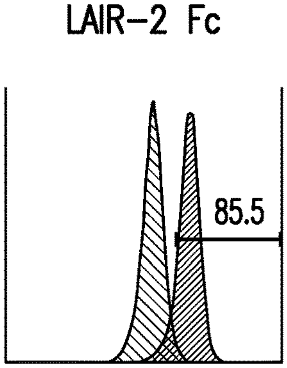
FIG. 8I is a FACS histogram of K562 Col 17 cells stained with LAIR-2Fc.

FIGS. 8G-8I show THP-1 cells treated with anti-LAIR-1, LAIR-1 Fc, and LAIR-2 Fc, respectively.

As indicated, Jurkat T cells, a T cell leukemia, and THP-1 cells, a monocytic leukemia, both expressed high levels of LAIR-1, whereas K562 cells do not. Furthermore, LAIR-2 Fc bound to THP-1 cells, as well as the positive control K562-collagen 17 expressing cells, but not Jurkat T cells.

From these results Jurkat T cells and THP-1 cells transduced with signaling pathway reporters were selected for in vitro studies.

Example 5: LAIR-2 Fe Induces NF-kB and NFAT Signaling in Jurkat T Cells

Materials and Methods 96-well flat-bottom plates were coated with titrated amounts of anti-CD3 (OKT3) overnight followed by aspiration prior to addition of cells. Jurkat T cells with NF-kB-GFP pathway reporter were plated at 50,000 cells/well/200 ul RPMI-C in the presence of 10 ug/ml LAIR-2 Fc, control Fc or without proteins. Cells were cultured 1 day. Cell were harvested from plates and assessed for GFP expression by flow cytometry.

Jurkat T cells with an NFAT pathway reporter were cultured in the presence of 0.5 ug/mL coated anti-CD3 and titrated amounts of soluble LAIR-2 Fc or control Fc. At approximately 24 hours, supernatants were assessed for secreted Lucia levels according to protocol (Invivogen). Readings were recorded with a Perkin-Elmer Envision plate reader.

Supernatants from Jurkat-NFAT-Lucia T cells treated with 10 ug/ml LAIR-2 Fc or control Fc were assessed for IL-2 and TNF levels by MSD cytokine analysis.

Results

Figure 9A:
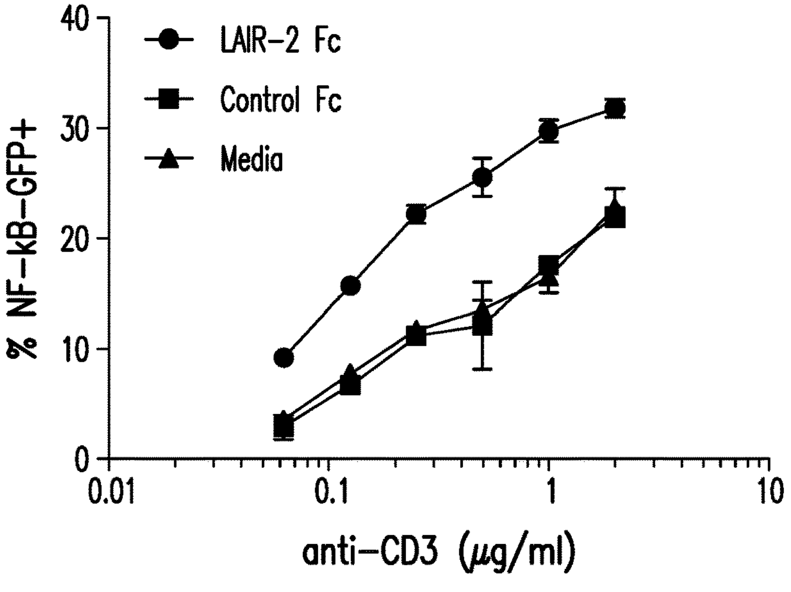
FIG. 9A is a line graph of % NF-kB-GFP+ versus anti-CD3 (μg/ml). LAIR-2 Fc (●), Control Fc (■), and Media (♦).

In vitro assays indicate that LAIR-2 Fc is capable of inducing activity in hematopoietic derived leukemia cell lines. Jurkat T cells with an NF-kB-GFP pathway reporter were cultured with titrated concentrations of coated anti-CD3 in the presence of 10 ug/ml of LAIR-2 Fc, control Fc, or media control and assessed for NF-kB induction by analysis of percent GFP+ cells by flow cytometry (FIG. 9A). This assay shows that LAIR-2 Fc promotes the induction of NF-kB signaling in Jurkat T cells. This effect occurs without appreciable binding of LAIR-2 Fc to Jurkat T cells, thus indicating that LAIR-2 Fc acts as a decoy for ligand binding to LAIR-1 expressed on the plasma membrane of Jurkat T cells.

Figure 9B:
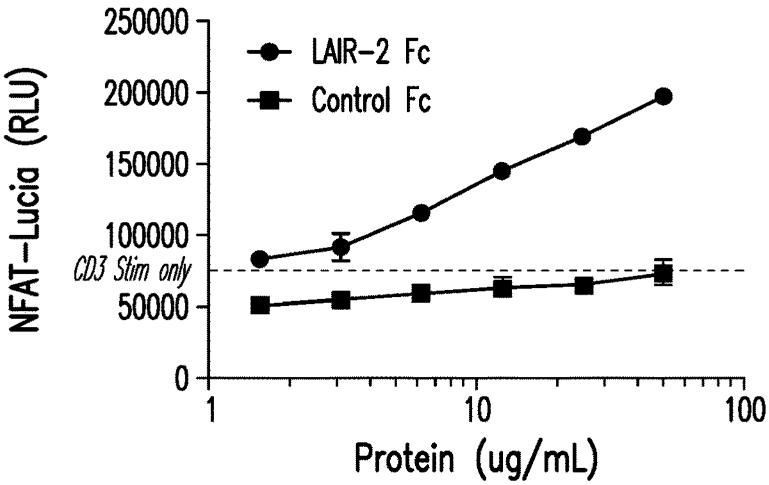
FIG. 9B is a line graph of NFAT-Lucia (RLU) versus protein (pg/ml). LAIR-2 Fc (●), and Control Fc (■).

Using a second Jurkat T cell line with an NFAT-Lucia pathway reporter, it was demonstrated that NFAT was induced in a LAIR-2 Fc dose dependent manner in the presence of a set concentration of anti-CD3 (FIG. 9B)

Figure 9C:
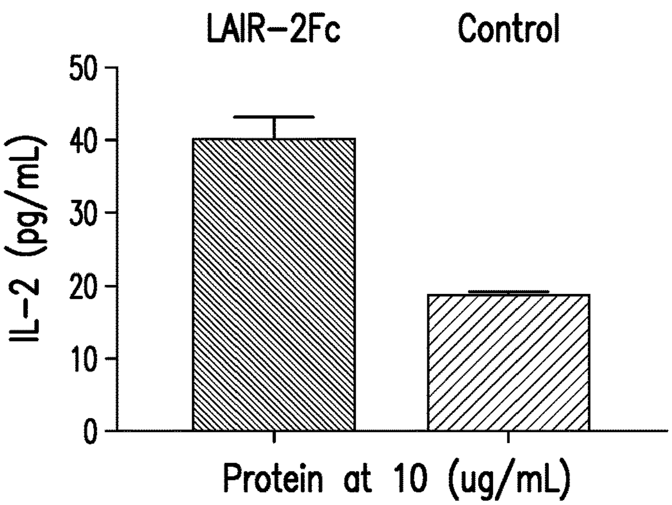
FIG. 9C is a bar graph of IL-2 (pg/ml) versus protein at 10 μg/m; for LAIR-2 Fc on the left and control Fc on the right.
Figure 9D:
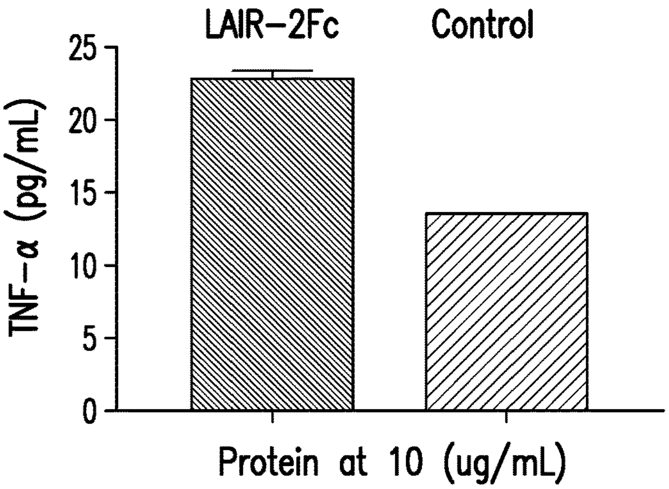
FIG. 9D is a bar graph of TNF-α (pg/ml) versus protein at 10 μg/m; for LAIR-2 Fc on the left and control Fc on the right.

Supernatants from Jurkat T cells in the NFAT reporter assay in the presence of 10 ug/ml of LAIR-2 Fc or control Fc were tested for IL-2 and TNF cytokine levels (FIGS. 9C and 9D). LAIR-2 Fc cultured Jurkat T cells displayed higher levels of both cytokines, consistent with pathway reporter induction. Because LAIR-2 Fc was not shown to bind directly to Jurkat T cells, it is posited that LAIR-2 Fc is disrupting LAIR-1 interactions with a soluble factor, or disruption of LAIR-1 inhibitory signaling through other mechanisms in order to enhance Jurkat reporter activity.

Example 6: LAIR-2 Fc Binds to THP-1 Cells and Induces Reporter Activity

Materials and Methods 0.1 ug/ml of biotinylated LAIR-2 Fc were added to THP-1 cells on ice following Fc receptor blockade with Trustain FcX (Biolegend) and hIgG (Innovative Research). Cells were subsequently washed with FACS buffer, and stained with 0.4 ug/mL Streptadivin-PE secondary (Biolegend) for 30 minutes on ice. Cells were washed, fixed and analyzed by flow cytometry.

THP-1 cells were added to 96-well flat bottom plates at 50,000 cells/well. 1 ug/ml final concentration of LPS, or RPMI-complete media, was added followed by 10 ug/ml final concentration of LAIR-2 Fc or control Fc. All wells contained a final volume of 200 ul. Cells were incubated for indicated number of days followed by analysis of supernatant for secreted Lucia according to protocol (Invivogen). Readings were performed using a Perkin-Elmer Envision plate reader.

Results

Figure 10A:
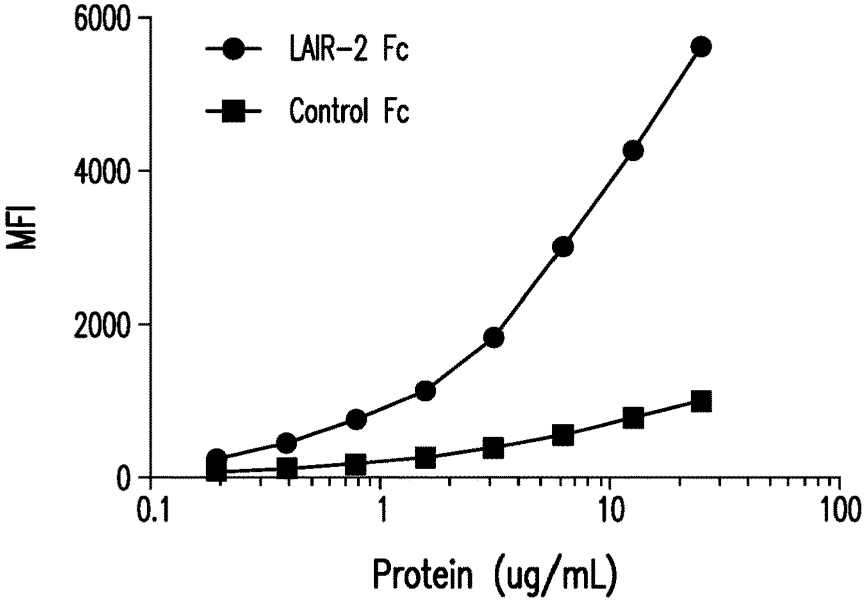
FIG. 10A is a line graph of MFI versus protein (μg/ml) showing that LAIR-2 Fc (●) binds to THP-1 cells in a dose dependent manner compared to control Fc (■).
Figure 10B:
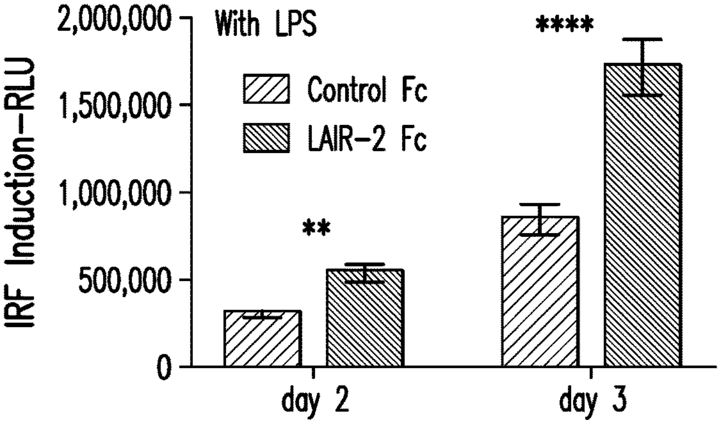
FIG. 10B is a bar graph.
Figure 10C:
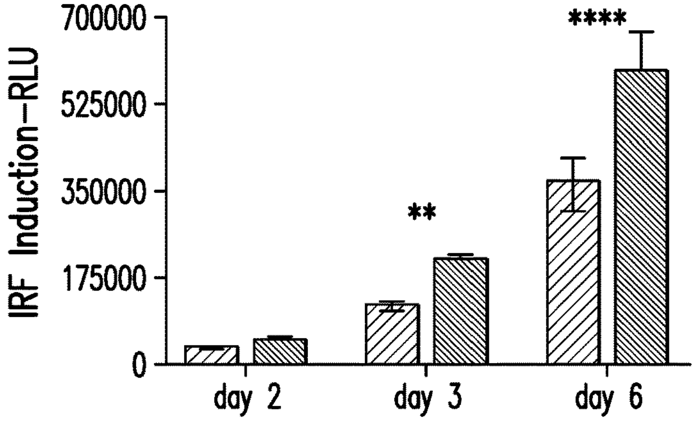
FIG. 10C is a bar graph of IRF Induction—RLU for THP-1 cells treated with RPMI media and LAIR-2 Fc (right column of each pair) or control Fc (left column of each pair).

THP-1 pathway reporter cells also assessed for response in the presence of LAIR-2 Fc or control Fc. Interestingly, it was found that in addition to LAIR-1 expression, LAIR-2 Fc binds to THP-1 cells in a dose dependent fashion (FIG. 10A). This is likely because THP-1 cells express transmembrane collagens (data not shown) that are known LAIR-2 ligands. THP-1 cells were culture with or without a Toll-Like Receptor ligand, LPS, that is known to induce the Interferon pathway in THP-1 cells. In the presence of LPS and LAIR-2 Fc, Interferon Regulatory Factor (IRF) induction was significantly increased in comparison to LPS with control Fc (FIG. 10B). Moreover, LAIR-2 Fc was capable of inducing interferon signaling induction even in the absence of LPS, showing a direct effect on THP-1 cells without the need for cosignaling (FIG. 10C). The mechanism of action is likely blockade of LAIR-1 binding to transmembrane collagens, as it remains unlikely that LAIR-2 Fc can induce signaling through transmembrane collagens.

Example 7: LAIR-2 Fc Enhances Primary T Cell Proliferation

Materials and Methods

Pan T cells including CD4+ and CD8+ T cells were isolated from healthy donor PBMCs. CD4+ T cells and CD8+ T cells were isolated from total PBMCs by MACS magnetic bead enrichment (Miltenyi), labeled with 1 uM CFSE (LifeTechnologies) and added to 96-well plates pre-coated with titrated amounts of anti-CD3 (OKT3) overnight at 4 degrees. LAIR-2 Fc or control Fc was added at 10 ug/ml and cells were culture for 72 hours followed by analysis by flow cytometry. For flow cytometric analysis of specific T cell subsets, cells were stained with anti-CD4 and anti-CD8 mAbs. CD4 and CD8 T cell subsets were thus gated and assessed for CFSE dilution as a measure of proliferation.

Results

Figure 11A:
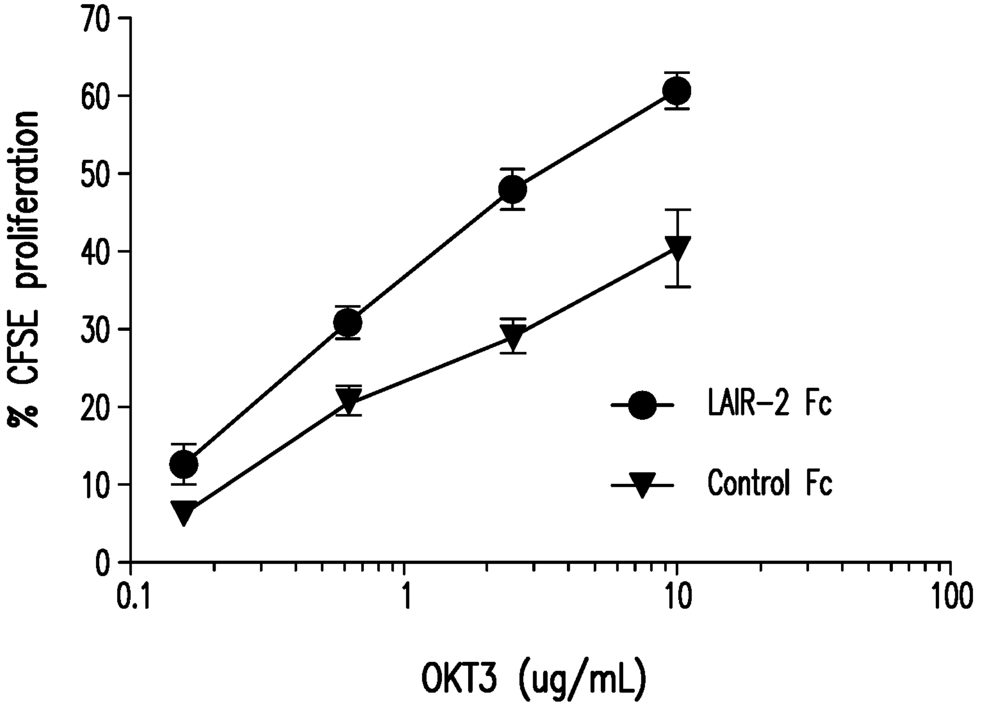
FIG. 11A is a line graph of % T cell proliferation measured by CFSE diluted cell population versus OKT3 (μg/ml) for CD4+ T cells treated with LAIR-2 Fc (●) or control Fc (◇).
Figure 11B:
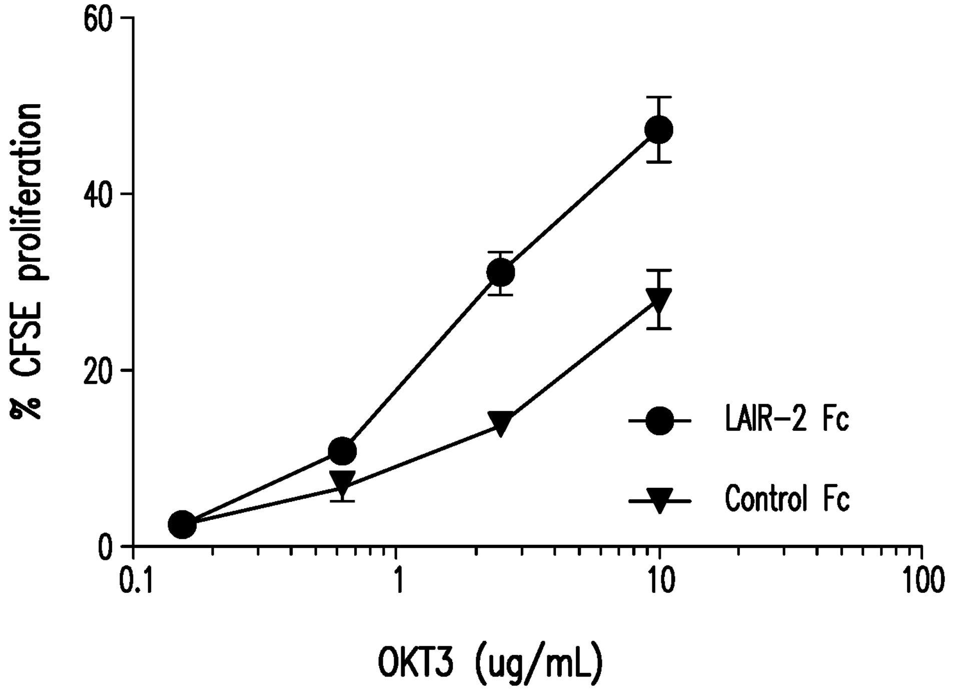
FIG. 11B is a line graph of % T cell proliferation CFSE proliferation versus OKT3 (μg/ml) for CD8+ cells treated with LAIR-Fc (●) or control Fc (◇).
Figure 12A:
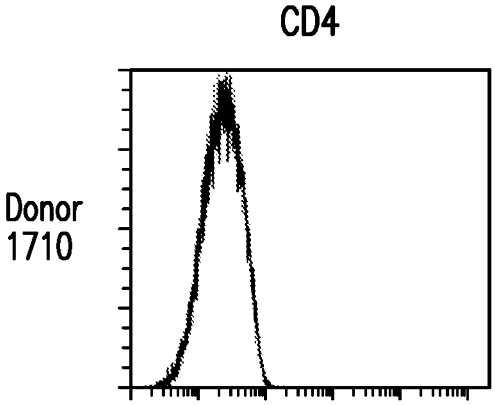
FIG. 12A is a histogram of Donor 1710 CD3+CD4+ T cells isolated from peripheral blood mononuclear cells (PBMCs) treated with LAIR-2 Fc.
Figure 12B:
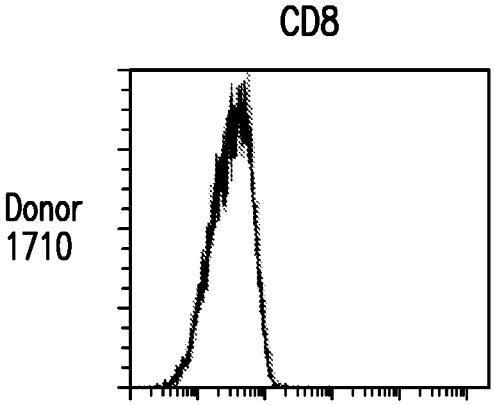
FIG. 12B is a histogram of Donor 1710 CD3+CD8+ T cells isolated from peripheral blood mononuclear cells (PBMCs) treated with LAIR-2 Fc.
Figure 12C:
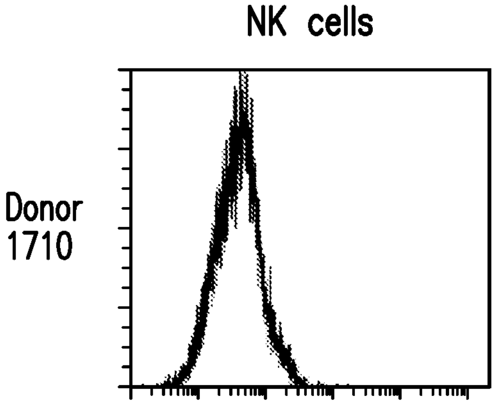
FIG. 12C is a histogram of Donor 1710 CD3-CD16+CD56+ NKC cells isolated from peripheral blood mononuclear cells (PBMCs) treated with LAIR-2 Fc.
Figure 12D:
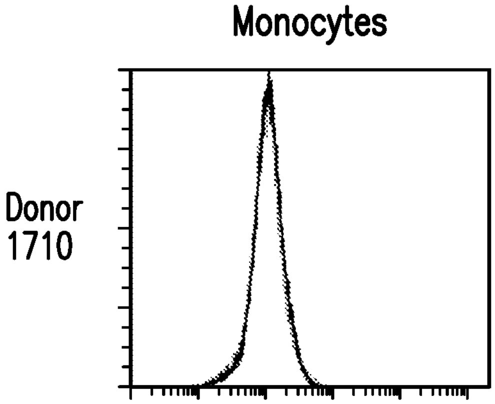
FIG. 12D is a histogram of Donor 1710 CD14+ monocytes isolated from peripheral blood mononuclear cells (PBMCs) treated with LAIR-2 Fc.
Figure 12E:
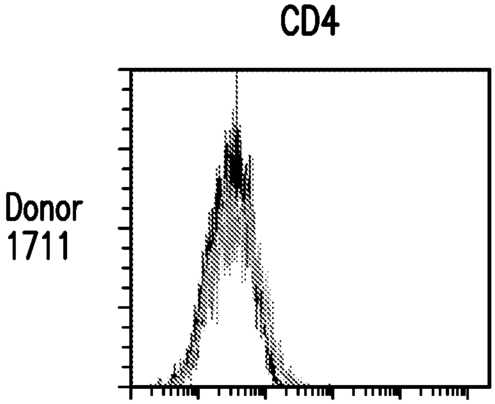
FIG. 12E is a histogram of Donor 1711 CD3+CD4+ T cells isolated from peripheral blood mononuclear cells (PBMCs) treated with LAIR-2 Fc.
Figure 12F:
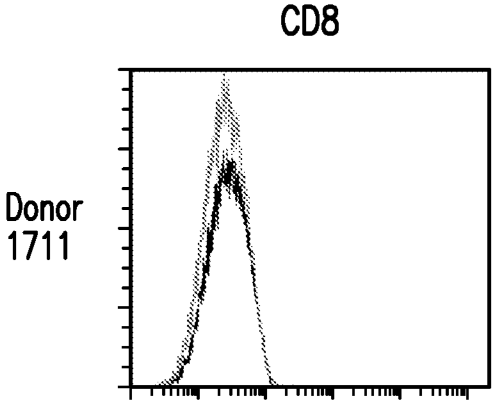
FIG. 12F is a histogram of Donor 1711 CD3+CD8+ T cells isolated from peripheral blood mononuclear cells (PBMCs) treated with LAIR-2 Fc.
Figure 12G:
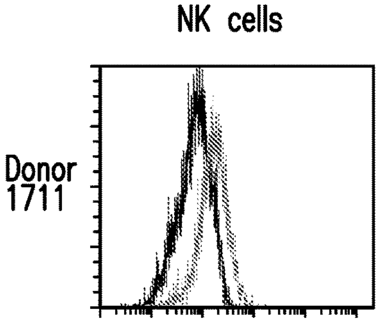
FIG. 12G is a histogram of Donor 1711 CD3-CD16+CD56+ NKC cells isolated from peripheral blood mononuclear cells (PBMCs) treated with LAIR-2 Fc.
Figure 12H:
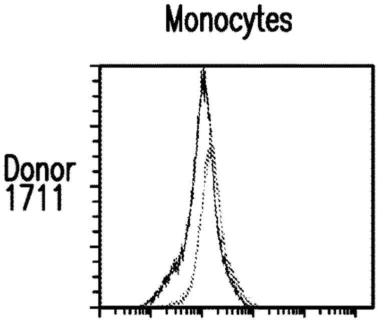
FIG. 12H is a histogram of Donor 1711 CD14+ monocytes isolated from peripheral blood mononuclear cells (PBMCs) treated with LAIR-2 Fc.
Figure 12I:
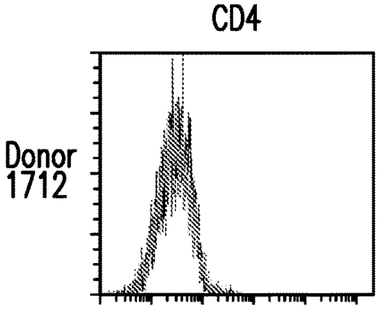
FIG. 12I is a histogram of Donor 1712 CD3+CD4+ T cells isolated from peripheral blood mononuclear cells (PBMCs) treated with LAIR-2 Fc.
Figure 12J:
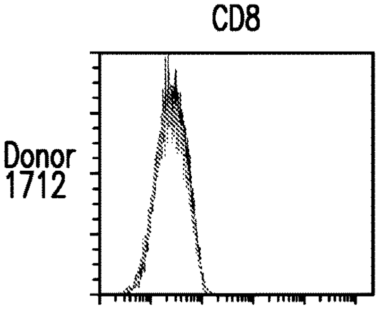
FIG. 12J is a histogram of Donor 1712 CD3+CD8+ T cells isolated from peripheral blood mononuclear cells (PBMCs) treated with LAIR-2 Fc.
Figure 12K:
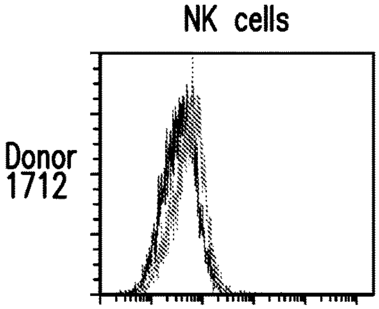
FIG. 12K is a histogram of Donor 1712 CD3-CD16+CD56+ NKC cells isolated from peripheral blood mononuclear cells (PBMCs) treated with LAIR-2 Fc.
Figure 12L:
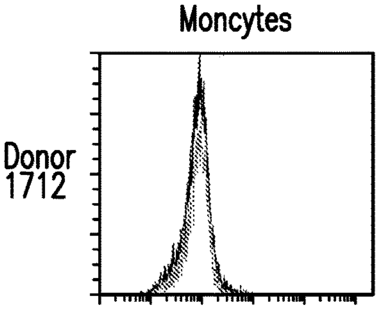
FIG. 12L is a histogram of Donor 1712 CD14+ monocytes isolated from peripheral blood mononuclear cells (PBMCs) treated with LAIR-2 Fc.

LAIR-2 Fc was next assessed for effects on primary human T cells. Results indicate increased proliferation by both CD4+ T cells and CD8+ T cells in the presence of LAIR-2 Fc (FIGS. 11A and 11B).

Example 8: LAIR-2 Fc does not Bind Directly to Human PBMC Cell Subsets

Material and Methods

Fresh human PBMCs from three normal healthy donor were stained with CD3+CD4+ T cells, CD3+CD8+ T cells, CD3-CD16+CD56+NK cells, and CD14+ monocytes, and analyzed with flow cytometry.

Results

In order to determine if this effect was due to direct binding of LAIR-2 Fc to T cells, healthy donor PBMCs were stained with LAIR-2 Fc. FIGS. 12A-12D show CD4, CD8, NK cells, and monocytes respectively form Donor 1710 treated with LAIR-2 Fc. FIGS. 12E-12H show CD4, CD8, NK cells, and monocytes respectively form Donor 1711 treated with LAIR-2 Fc. FIGS. 12I-12L show CD4, CD8, NK cells, and monocytes respectively form Donor 1712 treated with LAIR-2 Fc.

The data show that LAIR-2 Fc did not bind directly to human T cells. Moreover, LAIR-2 Fc does not appear to bind any PBMC cell subsets at substantial levels. As such, it is likely that LAIR-2 Fc is disrupting LAIR-1 interaction with LAIR ligands present or expressed in this culture system. These findings also suggest that LAIR-2 Fc should not have any effect on hematopoietic cell depletion in vivo, while cells expression transmembrane LAIR ligands could potentially be depleted or directly affected in other ways yet to be investigated.

Example 9: LAIR-2 Fc Promotes Antigen-Specific CD8+ T Cell Expansion in Vivo

Materials and Methods

CD8+ T cells that are specific for a model antigen, chicken egg ovalbumin (OVA), in the context of murine C57BL/6 MHC class I (H-2Kb) were used. The CD8+OT-I T cells recognize the OVA peptide SIINFEKL(SEQ ID NO:119) when bound to H-2Kb. In the presence of adjuvant, OT-I T cells undergo an expansion phase, followed by a contraction phase. OVA and polyL:C adjuvant were used to determine if OT-I expansion was increased and/or whether contraction was delayed.

Figure 13A:
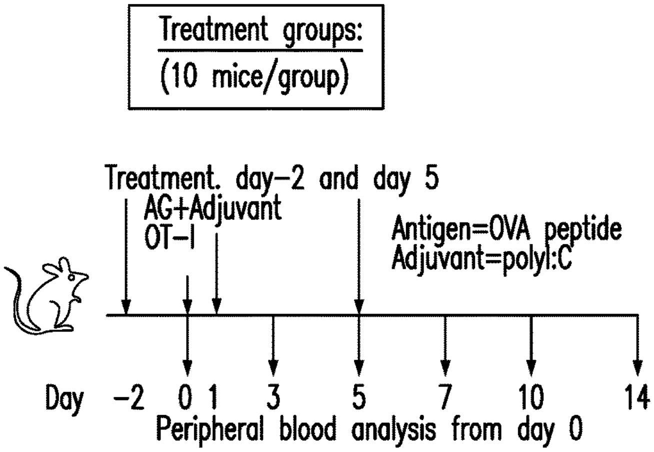
FIG. 13A is a diagram of a treatment for OT-1 T cell expansion in vivo.

The experimental design is illustrated in FIG. 13A. Ten mice/group were treated on day −2 and 5 with 500 ug of control Fc or LAIR-2 Fc. On day 0, CD8+ T cells were isolated from OT-IxLy5.1 F1 mice by MACS separation (Miltenyi) and 2e5 cells were injected ip. On day 1, 100 ug of SIINFEKL (SEQ ID NO:119) peptide (Peptides International) and 150 ug of polyL:C adjuvant (Invivogen) were injected ip in a total volume of 300 ul/mouse. Mice were bled on day 0 prior to immunization, and on days 1, 3, 5, 7, 10 and 14 and OT-I T cells in blood were analyzed by flow cytometry by gating on TCR Vbeta2+CD8+ T cells and Ly5.1 (CD45.1).

Results

Figure 13B:
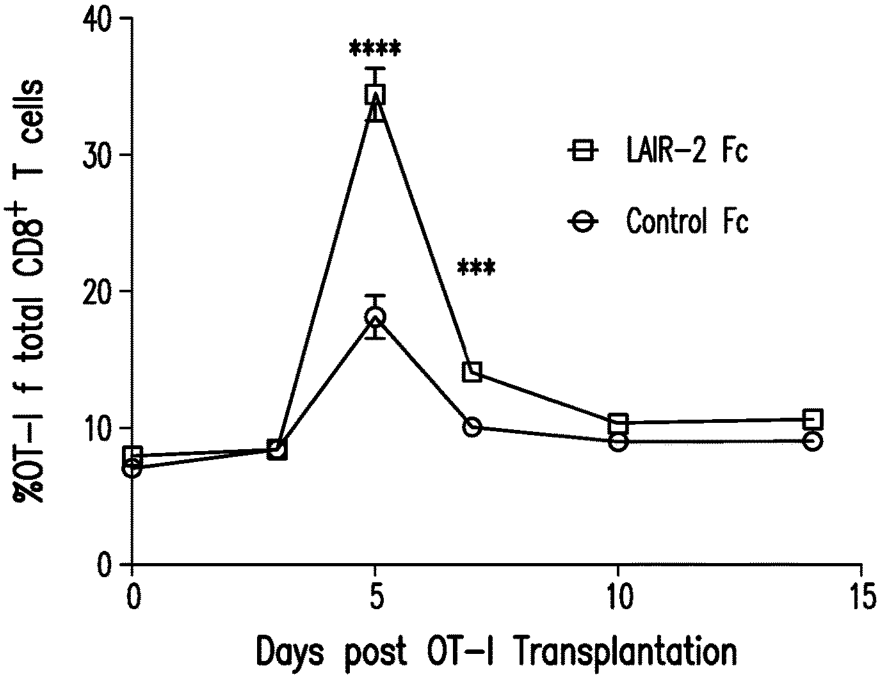
FIG. 13B is a line graph of % OT-1 (donor) of total CD8+ T cells versus days of OT-1 transplantation for cells treated with LAIR-2 Fc (Q) or control Fc (o).

LAIR-2 Fc was next tested in vivo to determine whether LAIR-2 Fc would enhance antigen-specific T cell responses. FIG. 13B shows that the percentage of OT-I of total CD8+ T cells increases significantly by day 5 relative to control Fc. Results indicate that OT-I T cells undergo significantly enhanced expansion in the presence of LAIR-2 Fc in comparison to mice treated with control Fc (FIG. 13B). These results are directly relevant to OVA expressing tumor models to assess tumor antigen specific T cell responses.

Example 10: LAIR-2 Fc Treated Mice have Significantly Improved Antigen-Specific Recall Response

Materials and Methods

At ~10 weeks after initial expansion, mice were challenged with equal numbers (1e6 each) of CD45.1 splenocytes either loaded with OVA peptide (CFSE hi) or without peptide (CFSElo). 48 hours later, mice were euthanized and splenocytes were assessed by flow cytometry for ratio of unloaded vs OVA loaded splenocytes as a measure of OT-I mediated antigen-specific memory CTL killing activity.

Results

Mice from the OT-I expansion experiment (Example 9) were rested for ~10 weeks and then assessed for antigen-specific memory CTL recall responses to determine if LAIR-2 Fc enhanced expansion translated into an enhanced functional recall response illustrated by CTL killing of antigen loaded splenocytes.

Figure 14A:
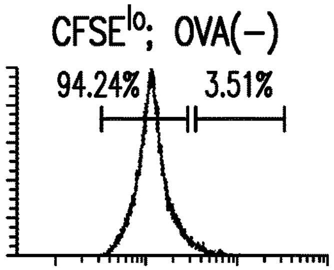
FIG. 14A is a flow cytometry histogram showing the pre-injection assessment of CFSE levels and ratio in mice challenged with CD45.1 splenocytes without ovalbumin (OVA) peptide.
Figure 14B:
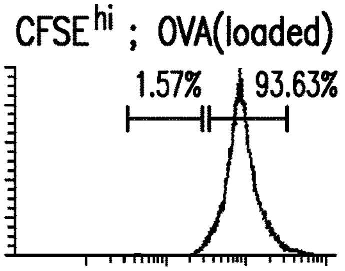
FIG. 14B is a flow cytometry histogram showing the pre-injection assessment of CFSE levels and ratio in mice challenged with CD45.1 splenocytes loaded with OVA peptide (CFSE hi).
Figure 14C:
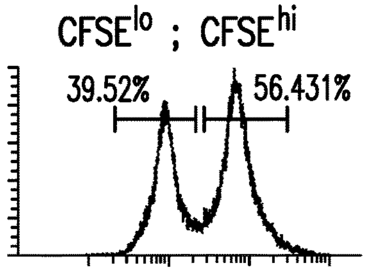
FIG. 14C is a cytometry histogram showing the pre-injection assessment of CFSE levels and ratio in mice challenged with CD45.1 splenocytes loaded without OVA peptide (CFSE lo) and with OVA peptide (CFSE hi).
Figure 14D:
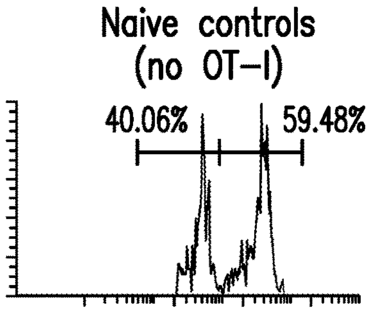
FIG. 14D is a cytometry histogram 48 hours after splenocyte transfer: assessment of labeled cells in the spleen (gated on CD45.1+ cells) (host cells are CD45.2) with naïve controls (no OT-1).
Figure 14E:
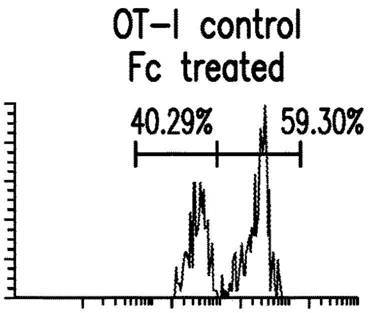
FIG. 14E is a cytometry histogram 48 hours after splenocyte transfer: assessment of labeled cells in the spleen (gated on CD45.1+ cells) (host cells are CD45.2) treated with OT-1 control Fc.
Figure 14F:
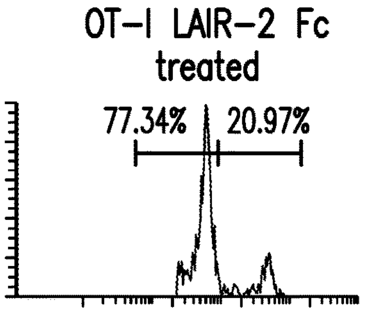
FIG. 14F is a cytometry histogram 48 hours after splenocyte transfer: assessment of labeled cells in the spleen (gated on CD45.1+ cells) (host cells are CD45.2) treated with OT-1 LAIR-2 Fc.
Figure 14G:
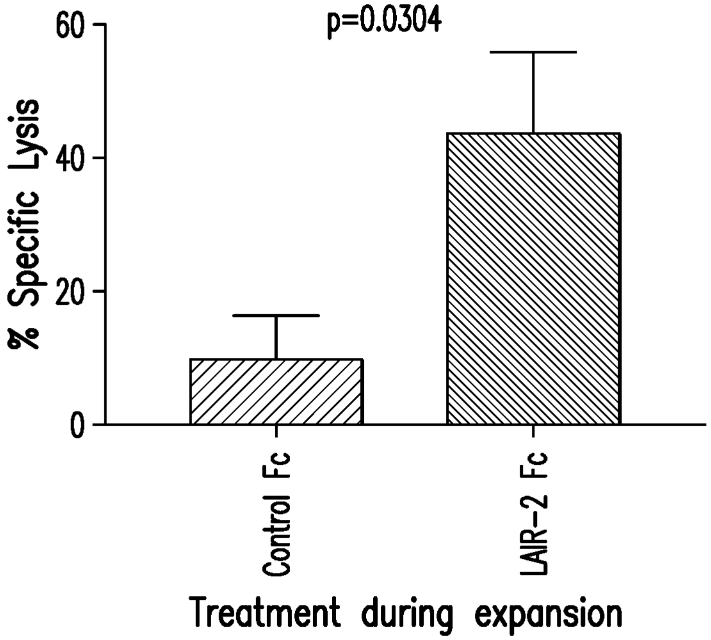
FIG. 14G is a bar graph of % specific lysis calculated as % specific lysis=[1−(no OT-I control ratio)/experimental ratio)]×100 for mice treated with Fc (left column) and mice treated with LAIR-2 Fc (right column).

Non-injected controls were assessed for CFSE peak gating and starting ratio (Figure FIGS. 14A to 14C). Representative examples of CFSE hi to lo ratios in each group are shown in FIGS. 14D to 14F. Results show that mice treated with LAIR-2 Fc during initial expansion of OT-I T cells (note that no treatment was administered during recall response) have a significantly better recall response calculated as specific lysis of OVA loaded splenocytes (FIG. 14C).

Example 11: LAIR-2 Fc Controls 1D8-OVA Ovarian Cancer Growth and Prolongs Survival

Materials and Methods

Figure 15A:
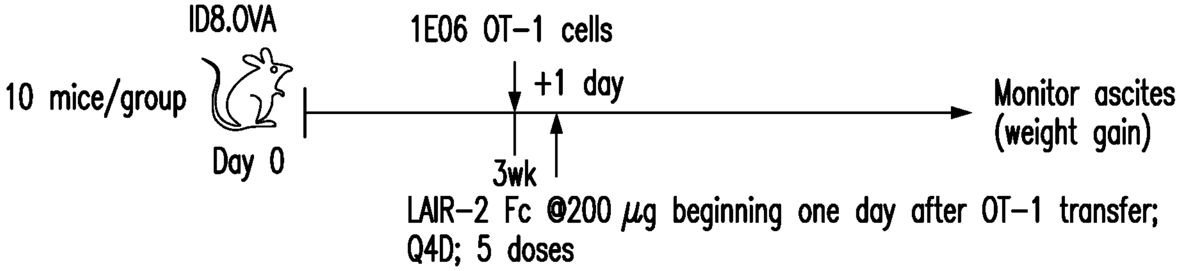
FIG. 15A is a diagram of a treatment model with 5e6 ID8-OVA tumor cells intraperitoneal injection (ip) injected on day 0. OT-I T cells were injected ip 3 weeks after tumor. Treatment with 200 ug of LAIR-2 Fc or control Fc began one day after T cell transfer and every 4 days for a total of 5 doses.

C57BL/6 mice were injected ip with 5e6 ID8-OVA cells, followed by ip injection 3 weeks later with 1e6 CD8+OT-I T cells. Mice were then treated with LAIR-2 Fc or control Fc starting one day after OT-I transfer and every four days for a total of 5 treatments. Weight gain was monitored every 2-3 days. To assess survivability, mice were euthanized when ascites production was observed and mice had a 50% increased from starting weight. FIG. 15A is a diagram of an exemplary treatment regimen 5e6 ID8-OVA tumor cells were ip injection on day 0.

Results

Whether an improved antigen-specific T cell response mediated by LAIR-2 Fc treatment translated into an improved anti-tumor immunity using an OVA-expressing tumor model and OT-I T cells was investigated. It was previously determined that OT-I T cells transferred 3 weeks after tumor inoculation are not protective and that OT-I T cells develop a dysfunctional, or exhausted phenotype. Therefore, this is a useful model to determine immunotherapeutics can promote antigen-specific T cell responses and/or reverse/prevent exhaustion from occurring.

Figure 15B:
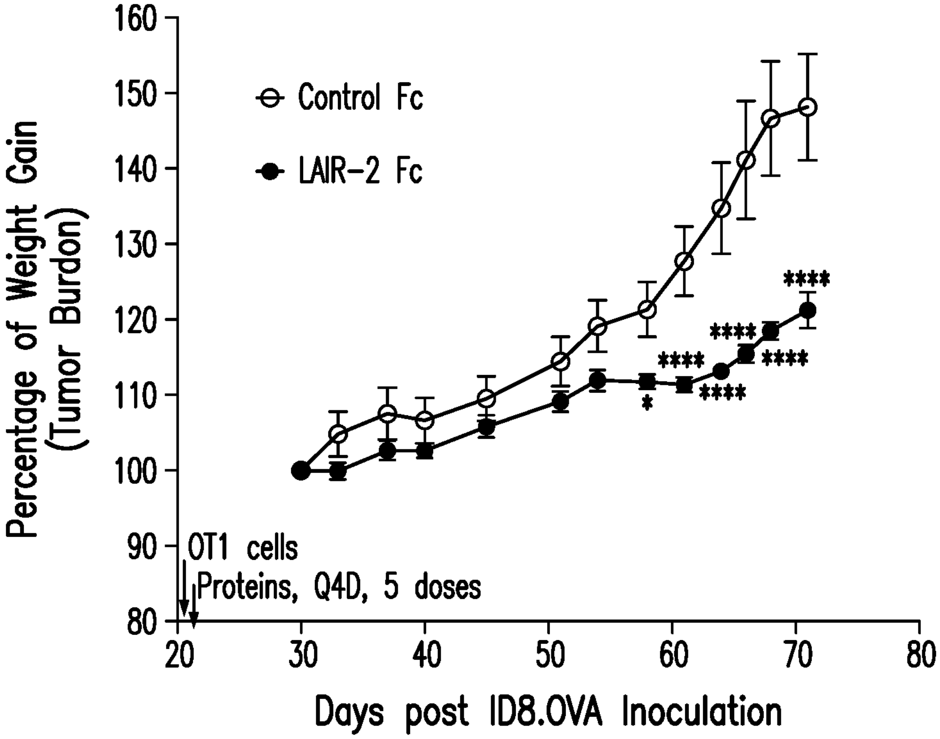
FIG. 15B is a line graph of percentage of weight gain (tumor burden) versus days post ID8.OVA inoculation. control (○); LAIR-2 Fc (●).
Figure 15C:
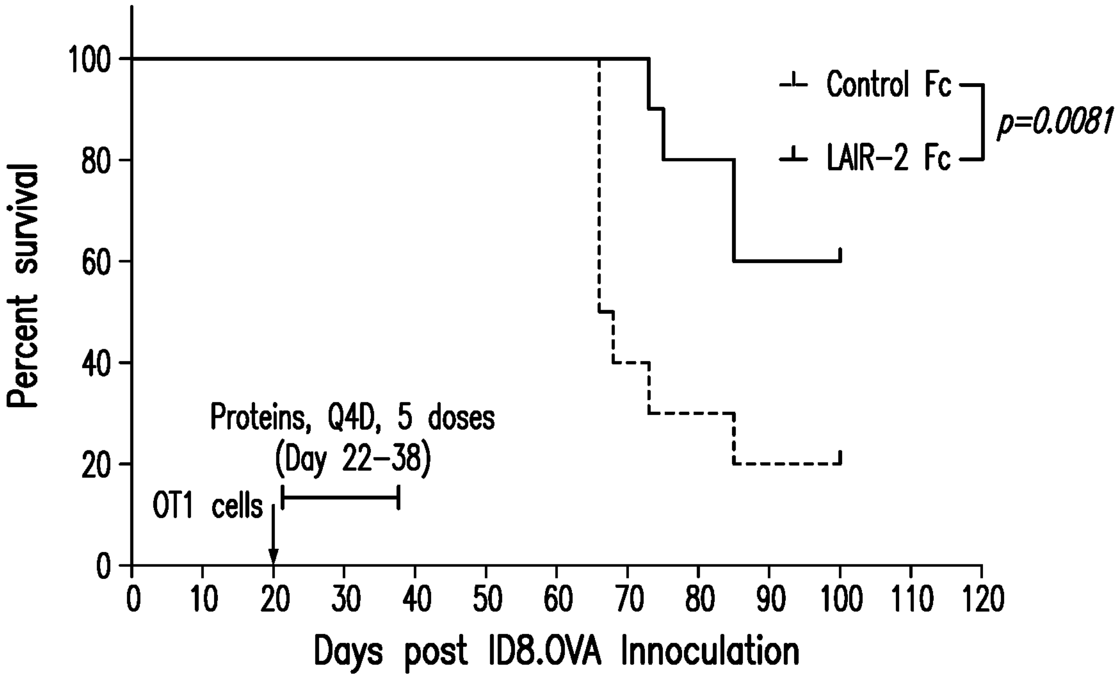
FIG. 15C is a line graph of percent survival versus days post ID8.OVA inoculation. control (broken line), LAIR-2 Fc (solid line).

Results showed significantly delayed weight gain and significantly increase in long-term survival (FIGS. 15B and 15C). 60% of mice survived long-term in comparison to 20% of controls suggestion a significant overall cure with LAIR-2 Fc (FIG. 15C).

Example 12: LAIR-2 Fc with Anti-PD-1 is an Effective Combination Immunotherapy in Ovarian Cancer

Materials and Methods

Mice were treated as in FIG. 15A except that more (6e6) ID8-OVA tumor cells were ip injected on day 0, and fewer OT-I T cells (5e5) were adoptively transferred at 3 weeks. Treatment of 200 ug of LAIR-2 Fc or control Fc began one day after T cell transfer and every 4 days for a total of 5 doses. Mice weight was monitored every 2-3 days, and mice were euthanized when ascites production was observed and mice had a 50% increased from starting weight.

Results

Figure 16:
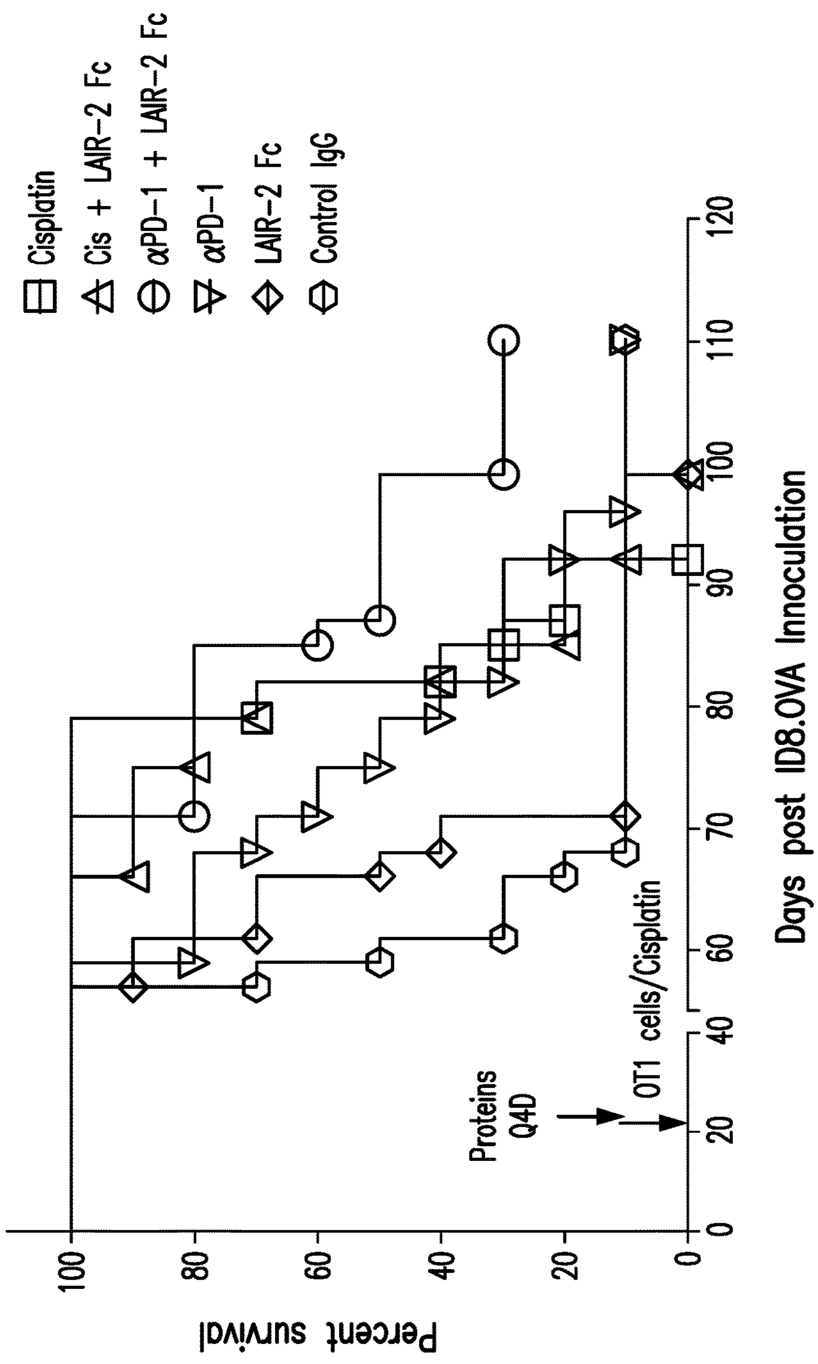
FIG. 16 is a line graph of survival versus days post ID8.OVA inoculation in mice injected with ID8-OVA tumor cells and treated with 200 ug of LAIR-2 Fc or control Fc began one day after T cell transfer and every 4 days for a total of 5 doses or with the indicate treatment. The data show LAIR-2 Fc with anti-PD-1 is an effective combination immunotherapy in ovarian cancer. (■) cisplatin, (Δ) cisplatin+LAIR-2 Fc, (○) anti-PD-1+LAIR-2 Fc, (∇) anti-PD-1, (♦) LAIR-2 Fc, (hexagon) control IgG.

LAIR-2 Fc alone in comparison to anti-PD-1 immunotherapy and Cisplatin chemotherapy, as well as in combination with PD-1 and Cisplatin was investigated to examine synergistic effects (FIG. 16). Results show a modest effect with LAIR-2 Fc alone in this model. However, the best response observed was with a combination of LAIR-2 Fc and anti-PD-1, with 50% of mice surviving past day 13 weeks. No mice in other single or combo therapies survived to 13 weeks.

Example 13: LAIR-2 Fc Delays Tumor Growth and Increases Survival in a Subcutaneous Lymphoma Model

Materials and Methods

Figure 17A:
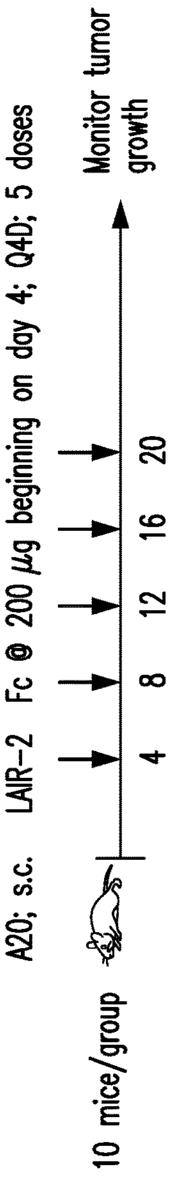
FIG. 17A is a diagram of an exemplary lymphoma treatment regime with LAIR-2 Fc.

4e5 A20 tumor cells were implanted subcutaneous (sc) on day 0. 200 ug of LAIR-2 Fc or control Fc was administered ip beginning on day 4 and every 4 days for 5 treatments. Tumor growth was monitored and measure 2-3 times/week and mice were sacrificed when average tumor diameter reached 15 mm or 2000 $mm^3$. FIG. 17A is an exemplary treatment regimen using the A20 tumor model.

Results

Figure 17B:
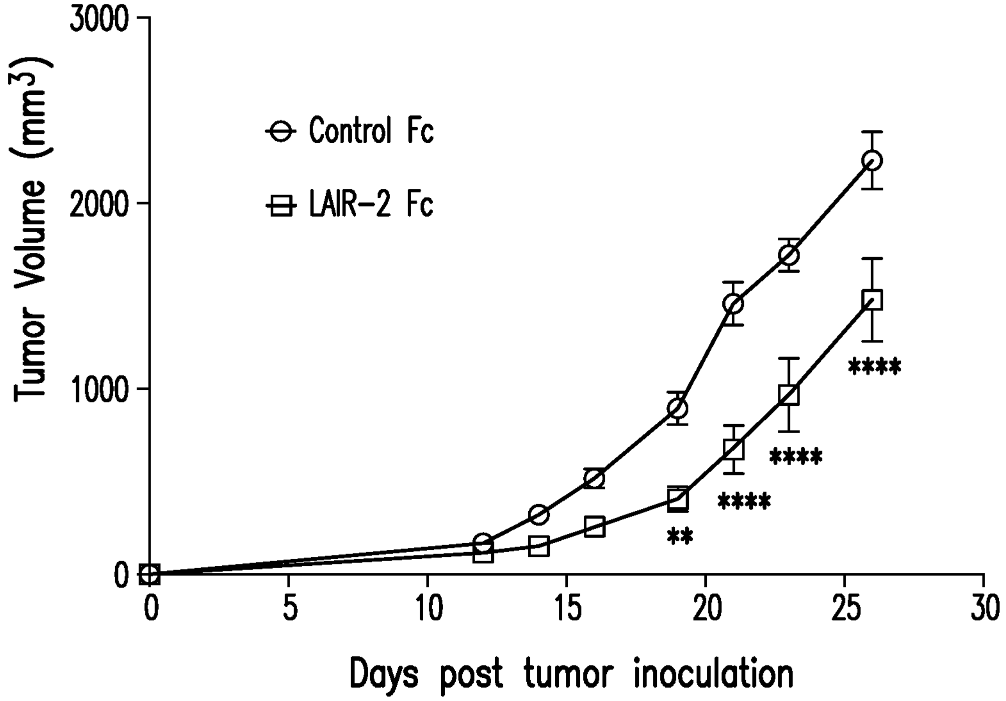
FIG. 17B is a line graph of tumor volume versus days post tumor inoculation in mice treated with control Fc (o) or LAIR-2 Fc (Q).
Figure 17C:
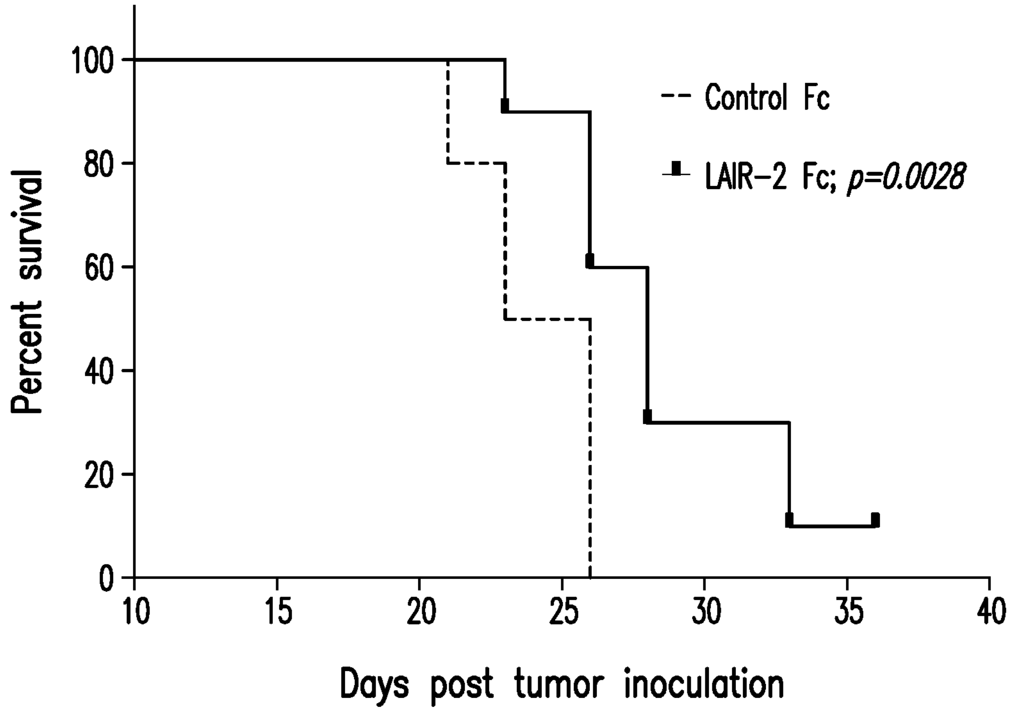
FIG. 17C is a line graph of percent survival versus days post tumor inoculation in mice treated with control Fc (broken line) or LAIR-2 Fc (solid line).

Results show that tumor growth was significantly delayed (FIG. 17B). Additionally, there was a significant extension of survival, with one animal remaining tumor free long-term (FIG. 17C).

Example 14. Generation, Selection and Characterization of LAIR-1 mAbs

Materials and Methods

Immunization, Fusion and cloning of anti-human LAIR-1 mAbs was performed with service from Precision Antibody CRO. NextCure produced human LAIR-1 mG2a Fc fusion protein for immunization and boosting of five SJL strain mice at Precision Antibody. Electrofusion was performed with splenocytes and lymph nodes from two mice with high titer. Approximately 1200 hybridoma clones were screened by ELISA for binding to human LAIR-1 hG1 Fc fusion protein, and by flow cytometry for binding to AML tumor cells lines that express endogenous LAIR-1 (Jurkat, HL-60).

Anti-human LAIR-1 hybridoma clone supernatants were incubated with cell lines known to express LAIR-1 (HL-60, MV-4-11), A cell line negative for LAIR-1 that was transfected for LAIR-1 (K562-LAIR-1) to test for specificity, and a cell line known to be negative for LAIR-1 expression (U266B1). Briefly, 50 ul of supernatant was incubated with 1e5 cells in 96-well round bottom plates for 30 minutes. Cells were washes with FACS buffer (PBS+1% FBS), and stained with 0.05 ug anti-mouse IgG-PE secondary antibody (Ab) for 30 minutes. Cells were washed and fixed in 100 ul 3% paraformaldehyde in PBS for flow cytometry analysis. Data shown is the percentage of cells staining above background media+secondary staining control (last column).

Results

Figure 18:
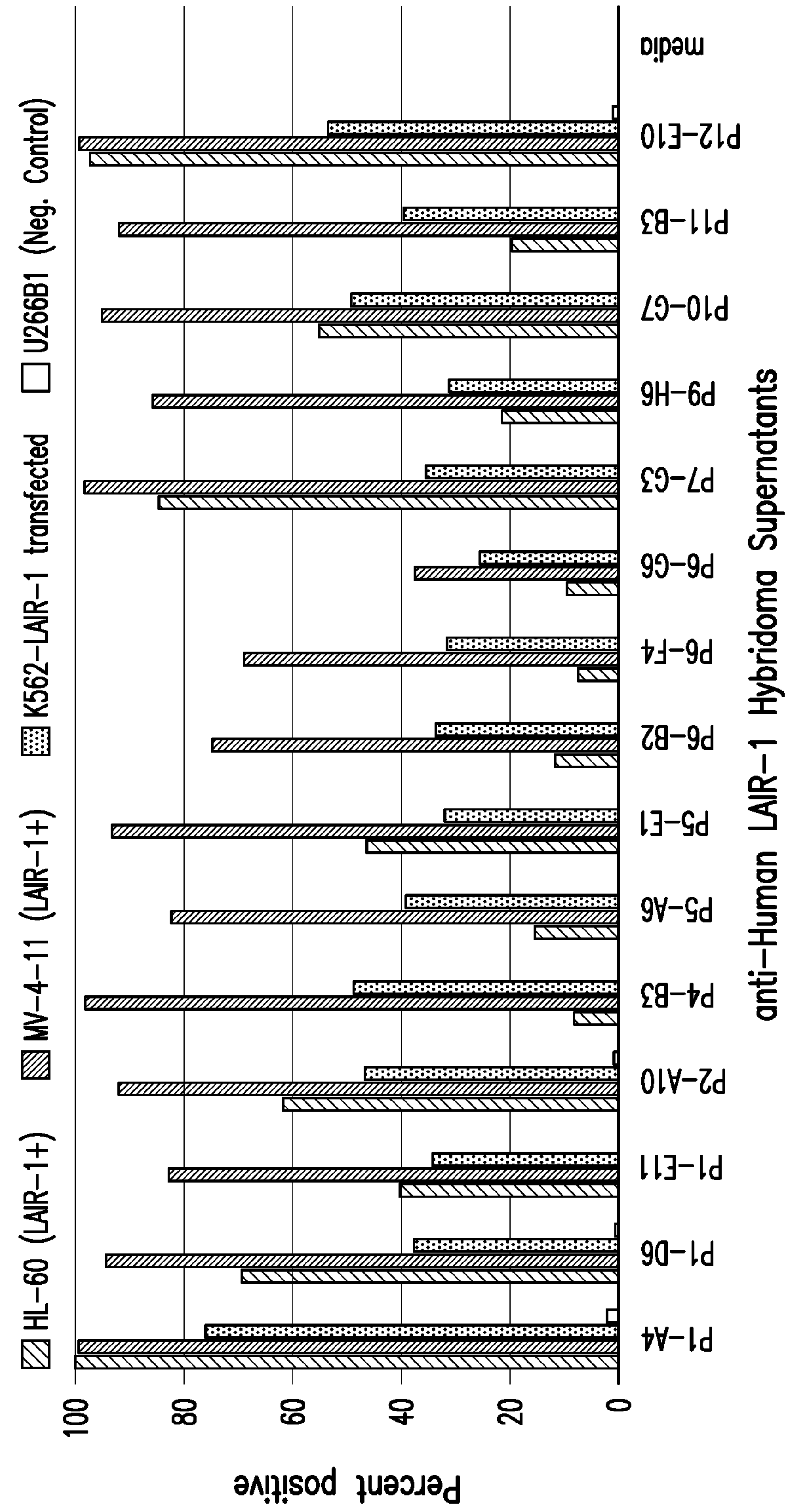
FIG. 18 is a bar graph of percent positive for binding of the indicated (monoclonal antibody) mAb to, from left to right for each group the following cell lines: HL-60 (LAIR-1+), MV-4-11 (LAIR-1+) K562-LAIR-1 transfected), and U266B1(Negative Control).

Results are shown for the final 15 selected clones (FIG. 18). Supernatants from hybridomas have differential levels of binding to specific cell types. This may be due to varying levels of mAbs in cell supernatant, or varying strength (avidity) of binding to LAIR-1 on the plasma membrane. However, because some supernatants bound at higher levels to LAIR-1 on certain cell types, it remains possible that LAIR-1 mAb clones are binding to specific glycoforms or otherwise modified forms of LAIR-1 on tumor cell lines.

In the following sequences, bold and underlined text represents the leader sequence. In some embodiments, the leader sequence is removed.

Sequences for Chimeric 1E11:

hG1 HC

The amino acid sequence for hG1 heavy chain is (SEQ ID NO: 120)

<u>MEWSWVFLFFLSVTTGVHS</u>QVQLQQSGPELVKPGASVKLSCKASGYTFT
SYDINWVKQRPGQGLEWIGWIYPRDGSTKYNEKLKGKATLTVDTSSRTA
YMELHSLTSEDSAVYECARGGYYDYDGYWGQGTLVTVSAASTKGPSVFP
LAPSSKSTSGGTAALGCLVKDYFPEPVTVSWNSGALTSGVHTEPAVLQS
SGLYSLSSVVTVPSSSLGTQTYICNVNHKPSNTKVDKKVEPKSCDKTHT
CPPCPAPELLGGPSVELEPPKPKDTLMISRTPEVTCVVVDVSHEDPEVK
ENWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGE
YPSDIAVEWESNGQPENNYKTTPPVLDSDGSFELYSKLTVDKSRWQQGN
VESCSVMHEALHNHYTQKSLSLSPG*

The nucleic acid sequence for hG1 heavy chain is (SEQ ID NO: 121)

<u>atggaatggtcctgggtgttcctgttcttcctgtctgtgaccaccggcg</u>
<u>tgcactctcaggtt</u>cagttgcagcagtctggccctgagcttgtgaaacc
tggcgcctctgtgaagctgtcttgcaaggcctctggctacaccttcacc
agctacgacatcaactgggtcaagcagaggcctggacagggactcgagt
ggatcggctggatctaccctagagatggctccaccaagtacaacgagaa
gctgaagggcaaagctaccctgaccgtggacacctcctctcggaccgct
tacatggaactgcactccctgacctctgaggactccgccgtgtactttt
gtgccagaggcggctactacgactacgatggctattggggacagggcac
cctggtcacagtgtctgctgcttctaccaaggggccctccgtgttccct
ctggccccttccagcaagtctacctctggcggcacagccgctctgggct
gcctcgtgaaggactacttccccgagcctgtgaccgtgtcctggaactc
tggcgctctgacatccggcgtgcacaccttccctgctgtgctgcagtcc
tccggcctgtactccctgtcctccgtcgtgaccgtgccttccagctctc
tgggcacccagacctacatctgcaacgtgaaccacaagccctccaacac
caaggtggacaagaaggtggaacccaagtcctgcgacaagacccacacc
tgtccccccttgtcctgccccctgaactgctgggcggacccagcgtgttcc
tgttcccccccaaagcccaaggacaccctgatgatctcccggacccccga
agtgacctgcgtggtggtggatgtgtcccacgaggaccctgaagtgaag
ttcaattggtacgtggacggcgtggaagtgcacaacgccaagaccaagc
ctagagaggaacagtacaactccacctaccgggtggtgtccgtgctgac
cgtgctgcaccaggattggctgaacggcaaagagtacaagtgcaaggtg
tccaacaaggccctgcctgcccccatcgaaaagaccatctccaaggcca
agggccagccccgggaaccccaggtgtacacactgcccccctagcaggga
cgagctgaccaagaaccaggtgtccctgacctgtctcgtgaaaggcttc
taccctccgatatcgccgtggaatgggagtccaacggccagcctgaga -continued acaactacaagaccacccccccctgtgctggactccgacggctcattctt cctgtacagcaagctgacagtggacaagtcccggtggcagcagggcaac gtgttctcctgctccgtgatgcacgaggccctgcacaaccactacaccc agaagtccctgtccctgagccccggctga hG4P HC The amino acid sequence for hG4P heavy chain is:

(SEQ ID NO: 122)

MEWSWVELFELSVTTGVHSQVQLQQSGPELVKPGASVKLSCKASGYTFTS

YDINWVKQRPGQGLEWIGWIYPRDGSTKYNEKLKGKATLTVDTSSRTAYM

ELHSLTSEDSAVYFCARGGYYDYDGYWGQGTLVTVSAASTKGPSVFPLAP

CSRSTSESTAALGCLVKDYFPEPVTVSWNSGALTSGVHTFPAVLQSSGLY

SLSSVVTVPSSSLGTKTYTCNVDHKPSNTKVDKRVESKYGPPCPPCPAPE

FLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIE

KTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALH

NHYTQKSLSLSLG*

The nucleic acid sequence for hG4P is:

(SEQ ID NO: 123)

atggaatggtcctgggtgttcctgttcttcctgtctgtgaccaccggcgt gcactctcaggttcagttgcagcagtctggccctgagcttgtgaaacctg gcgcctctgtgaagctgtcttgcaaggcctctggctacaccttcaccagc tacgacatcaactgggtcaagcagaggcctggacagggactcgagtggat cggctggatctaccctagagatggctccaccaagtacaacgagaagctga agggcaaagctaccctgaccgtggacacctcctctcggaccgcttacatg gaactgcactccctgacctctgaggactccgccgtgtacttttgtgccag aggcggctactacgactacgatggctattggggacagggcaccctggtca cagtgtctgctgcttctaccaagggggccctccgtgttccctctggcccct tgctccagatccacctccgagtctaccgccgctctgggctgcctcgtgaa ggactacttccccgagcctgtgaccgtgtcctggaactctggcgctctga cctctggcgtgcacaccttccctgctgtgctgcagtcctccggcctgtac tccctgtcctccgtcgtgaccgtgccttccagctctctgggcaccaagac ctacacctgtaacgtggaccacaagccctccaacaccaaggtggacaagc gggtggaatctaagtacggccctccctgccctccttgcccagcccctgaa tttctgggcggacccagcgtgttcctgttcccccccaaagcccaaggacac cctgatgatctcccggacccccgaagtgacctgcgtggtggtggatgtgt cccaggaagatcccgaggtgcagttcaattggtacgtggacggcgtggaa gtgcacaacgccaagaccaagcctagagaggaacagttcaactccaccta ccgggtggtgtccgtgctgaccgtgctgcaccaggattggctgaacggca aagagtacaagtgcaaggtgtccaacaagggcctgcccagctccatcgaa aagaccatctccaaggccaagggccagccccgggaaccccaggtgtacac -continued actgcctccaagccaggaagagatgaccaagaaccaggtgtccctgacct gtctcgtgaaaggcttctacccctccgatatcgccgtggaatgggagtcc aacggccagcctgagaacaactacaagaccacccccccctgtgctggactc cgacggctccttcttcctgtactctcgcctgaccgtggacaagtcccggt ggcaggaaggcaacgtgttctcctgctccgtgatgcacgaggccctgcac aaccactacacccagaagtccctgtccctgtctctgggatga Light Chain The amino acid sequence for the light chain for chimeric 1E11 is:

(SEQ ID NO: 124)

MSVPTQVLGLLLLWLTDARCDIVMTQAAFSNPVTLGTSASISCRSSKSLL

HSNGITYLYWYLQKPGQSPQVLIYQMSSLASGVPDRFSSSGSGTEFTLRI

SRVEAEDVGVYYCAQNLELPLTFGAGTKLELKRTVAAPSVFIFPPSDEQL

KSGTASVVCLLNNFYPREAKVQWKVDNALQSGNSQESVTEQDSKDSTYSL

SSTLTLSKADYEKHKVYACEVTHQGLSSPVTKSENRGEC*

The nucleic acid sequence for light chain for chimeric 1E11 is:

(SEQ ID NO: 125)

atgtccgtgcctacacaggttctgggactgctgctgctgtggctgaccga cgctagatgcgatatcgtgatgacccaggccgccttcagcaatcctgtga cactgggaacctccgcctccatctcctgcagatcctctaagtccctgctg cactccaacggcatcacctacctgtactggtatctgcagaagcccggcca gtctcctcaggtgctgatctaccagatgtcctctctggcctctggcgtgc ccgacagattctcttcttctggctctggcaccgagttcaccctgcggatc tctagagtggaagctgaggacgtgggcgtgtactactgcgcccagaatct ggaactgcctctgacctttggcgctggcaccaagctggaactgaagcgta cggtggccgctccctccgtgttcatcttcccaccttccgacgagcagctg aagtccggcaccgcttctgtcgtgtgcctgctgaacaacttctaccccg cgaggccaaggtgcagtggaaggtggacaacgccctgcagtccggcaact cccaggaatccgtgaccgagcaggactccaaggacagcacctactccctg tcctccaccctgaccctgtccaaggccgactacgagaagcacaaggtgta cgcctgcgaagtgacccaccagggcctgtctagccccgtgaccaagtctt tcaaccggggcgagtgctga Sequences for Chimeric 5E1 hG1 HC

The amino acid sequence for hG1 heavy chain is:

(SEQ ID NO: 126)

MEWSWVELFELSVTTGVHSEVQLQQSGPELVKPGASVKISCKASGYSETG

YEMNWVKQSPEKSLEWIGEIHPSTGSITYNQKFKAKATLTIDKSSSTAYM

QLKSLTSEDSAVYYCAREDYSNSFAYWGQGTLVTVSAASTKGPSVFPLAP

SSKSTSGGTAALGCLVKDYFPEPVTVSWNSGALTSGVHTEPAVLQSSGLY

-continued

SLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPG*

The nucleic acid sequence for hG1 heavy chain is:

(SEQ ID NO: 127)

atggaatggtcctgggtgttcctgttcttcctgtctgtgaccaccggcgt gcactctgaagttcagttgcagcagtctggccccgagcttgtgaaacctg gcgcctctgtgaagatctcctgcaaggcctctggctactccttcaccggc tacttcatgaactgggtcaagcagtcccctgagaagtccctggaatggat cggcgagatccatccttccaccggcagcatcatctacaaccagaagttca aggccaaggctaccctgaccatcgacaagtcctcttccaccgcctacatg cagctgaagtctctgacctctgaggactccgccgtgtactactgcgccag attcgactactccaactccttcgcttattggggccagggcaccctggtta ccgtgtctgctgcttctaccaagggcccctccgtgttccctctggcccct tccagcaagtctacctctggcggcacagccgctctgggctgcctcgtgaa ggactacttccccgagcctgtgaccgtgtcctggaactctggcgctctga catccggcgtgcacaccttccctgctgtgctgcagtcctccggcctgtac tccctgtcctccgtcgtgaccgtgccttccagctctctgggcacccagac ctacatctgcaacgtgaaccacaagccctccaacaccaaggtggacaaga aggtggaacccaagtcctgcgacaagacccacacctgtcccccttgtcct gcccctgaactgctgggcggacccagcgtgttcctgttcccccccaaagcc caaggacaccctgatgatctcccggacccccgaagtgacctgcgtggtgg tggatgtgtcccacgaggaccctgaagtgaagttcaattggtacgtggac ggcgtggaagtgcacaacgccaagaccaagcctagagaggaacagtacaa ctccacctaccgggtggtgtccgtgctgaccgtgctgcaccaggattggc tgaacggcaaagagtacaagtgcaaggtgtccaacaaggccctgcctgcc cccatcgaaaagaccatctccaaggccaagggccagccccgggaaccccca ggtgtacacactgcccccctagcagggacgagctgaccaagaaccaggtgt ccctgacctgtctcgtgaaaggcttctacccctccgatatcgccgtggaa tgggagtccaacggccagcctgagaacaactacaagaccaccccccctgt gctggactccgacggctcattcttcctgtacagcaagctgacagtggaca agtcccggtggcagcagggcaacgtgttctcctgctccgtgatgcacgag gccctgcacaaccactacacccagaagtccctgtccctgagccccggctg a hG4P HC The amino acid sequence for hG4P heavy chain is:

(SEQ ID NO: 128)

MEWSWVFLFFLSVTTGVHSEVQLQQSGPELVKPGASVKISCKASGYSFTG

YFMNWVKQSPEKSLEWIGEIHPSTGSIIYNQKFKAKATLTIDKSSSTAYM

QLKSLTSEDSAVYYCAREDYSNSFAYWGQGTLVTVSAASTKGPSVFPLAP

CSRSTSESTAALGCLVKDYFPEPVTVSWNSGALTSGVHTFPAVLQSSGLY

SLSSVVTVPSSSLGTKTYTCNVDHKPSNTKVDKRVESKYGPPCPPCPAPE

FLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIE

KTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALH

NHYTQKSLSLSLG*

The nucleic acid sequence for hG4P heavy chain is:

(SEQ ID NO: 129)

atggaatggtcctgggtgttcctgttcttcctgtctgtgaccaccggcgt gcactctgaagttcagttgcagcagtctggccccgagcttgtgaaacctg gcgcctctgtgaagatctcctgcaaggcctctggctactccttcaccggc tacttcatgaactgggtcaagcagtcccctgagaagtccctggaatggat cggcgagatccatccttccaccggcagcatcatctacaaccagaagttca aggccaaggctaccctgaccatcgacaagtcctcttccaccgcctacatg cagctgaagtctctgacctctgaggactccgccgtgtactactgcgccag attcgactactccaactccttcgcttattggggccagggcaccctggtta ccgtgtctgctgcttctaccaagggcccctccgtgttccctctggcccct tgctccagatccacctccgagtctaccgccgctctgggctgcctcgtgaa ggactacttccccgagcctgtgaccgtgtcctggaactctggcgctctga cctctggcgtgcacaccttccctgctgtgctgcagtcctccggcctgtac tccctgtcctccgtcgtgaccgtgccttccagctctctgggcaccaagac ctacacctgtaacgtggaccacaagccctccaacaccaaggtggacaagc gggtggaatctaagtacggccctccctgccctccttgcccagcccctgaa tttctgggcggacccagcgtgttcctgttcccccccaaagcccaaggacac cctgatgatctcccggacccccgaagtgacctgcgtggtggtggatgtgt cccaggaagatcccgaggtgcagttcaattggtacgtggacggcgtggaa gtgcacaacgccaagaccaagcctagagaggaacagttcaactccaccta ccgggtggtgtccgtgctgaccgtgctgcaccaggattggctgaacggca aagagtacaagtgcaaggtgtccaacaagggcctgcccagctccatcgaa aagaccatctccaaggccaagggccagccccgggaaccccaggtgtacac actgcctccaagccaggaagagatgaccaagaaccaggtgtccctgacct gtctcgtgaaaggcttctacccctccgatatcgccgtggaatgggagtcc aacggccagcctgagaacaactacaagaccaccccccctgtgctggactc cgacggctccttcttcctgtactctcgcctgaccgtggacaagtcccggt -continued ggcaggaaggcaacgtgttctcctgctccgtgatgcacgaggccctgcac aaccactacacccagaagtccctgtccctgtctctgggatga Light Chain The amino acid sequence for the light chain for chimeric 5E1 is:

(SEQ ID NO: 130)

MSVPTQVLGLLLLWLTDARCDIQMTQTTSSLSASLGDRVTISCRASQDIS

NYLNWYQQKPDGTVKLLIYYTSRLHSGVPSRFSGSGSGTDYSLTISNLEQ

EDIATYFCQQGNTLPRTFGGGTKLEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSENRGEC*

The nucleic acid sequence for the light chain for chimeric 1E5 is:

(SEQ ID NO: 131)

atgtccgtgcctacacaggttctgggactgctgctgctgtggctgaccga cgctagatgcgatatccagatgacccagaccacctccagcctgtctgctt ctctgggcgacagagtgaccatctcctgcagagcctctcaggacatctcc aactacctgaactggtatcagcagaaacccgacggcaccgtgaagctgct gatctactacacctccagactgcactccggcgtgccctctagattttctg gctctggatctggcaccgactactccctgaccatcagcaacctggaacaa gaggatatcgctacctacttctgccagcaaggcaacaccctgcctagaac ctttggcggaggcaccaagctggaaatcaagcgtacggtggccgctccct ccgtgttcatcttcccaccttccgacgagcagctgaagtccggcaccgct tctgtcgtgtgcctgctgaacaacttctacccccgcgaggccaaggtgca gtggaaggtggacaacgccctgcagtccggcaactcccaggaatccgtga ccgagcaggactccaaggacagcacctactccctgtcctccaccctgacc ctgtccaaggccgactacgagaagcacaaggtgtacgcctgcgaagtgac ccaccagggcctgtctagccccgtgaccaagtctttcaaccggggcgagt gctga Sequences for Chimeric 6G6 hG1 heavy chain

The amino acid sequence for the hG1 heavy chain is:

(SEQ ID NO: 132)

MEWSWVELFELSVTTGVHSEVQLQQSGPELVKPGASVKISCKASGYTFTT

YYMNWVKQSHGKSLEWIGNINPDNGITSYNQKFKGKATLTVDKSSSTAYM

ELRSLTSEDSAVYYCARGKSLAYWGQGTLVTVSAASTKGPSVFPLAPSSK

STSGGTAALGCLVKDYFPEPVTVSWNSGALTSGVHTEPAVLQSSGLYSLS

SVVTVPSSSLGTQTYICNVNHKPSNTKVDKKVEPKSCDKTHTCPPCPAPE

LLGGPSVELEPPKPKDTLMISRTPEVTCVVVDVSHEDPEVKENWYVDGVE

VHNAKTKPREEQYNSTYRVVSVLTVLHQDWLNGKEYKCKVSNKALPAPIE

-continued

KTISKAKGQPREPQVYTLPPSRDELTKNQVSLTCLVKGEYPSDIAVEWES

NGQPENNYKTTPPVLDSDGSFELYSKLTVDKSRWQQGNVESCSVMHEALH

NHYTQKSLSLSPG*

The nucleic acid sequence for the hG1 heavy chain is:

(SEQ ID NO: 133)

atggaatggtcctgggtgttcctgttcttcctgtctgtgaccaccggcgt gcactctgaagttcagttgcagcagtctggccccgagcttgtgaaacctg gcgcctctgtgaagatctcctgcaaggcctctggctacaccttcaccacc tactacatgaactgggtcaagcagtcccacggcaagtccctggaatggat cggcaacatcaaccccgacaacggcatcacctcctacaaccagaagttca agggcaaagctaccctgaccgtggacaagtcctcctccaccgcctacatg gaactgagatccctgacctctgaggactccgccgtgtactactgtgccag aggcaagtctctggcttattggggccagggcacactggtcacagtgtctg ctgcttccaccaaggggccctccgtgttccctctggccccttccagcaag tctacctctggcggcacagccgctctgggctgcctcgtgaaggactactt ccccgagcctgtgaccgtgtcctggaactctggcgctctgacatccggcg tgcacaccttccctgctgtgctgcagtcctccggcctgtactccctgtcc tccgtcgtgaccgtgccttccagctctctgggcacccagacctacatctg caacgtgaaccacaagccctccaacaccaaggtggacaagaaggtggaac ccaagtcctgcgacaagacccacacctgtccccctgtcctgcccctgaa ctgctgggcggacccagcgtgttcctgttccccccaaagcccaaggacac cctgatgatctcccggacccccgaagtgacctgcgtggtggtggatgtgt cccacgaggaccctgaagtgaagttcaattggtacgtggacggcgtggaa gtgcacaacgccaagaccaagcctagagaggaacagtacaactccaccta ccgggtggtgtccgtgctgaccgtgctgcaccaggattggctgaacggca aagagtacaagtgcaaggtgtccaacaaggccctgcctgcccccatcgaa aagaccatctccaaggccaagggccagccccgggaaccccaggtgtacac actgcccccctagcagggacgagctgaccaagaaccaggtgtccctgacct gtctcgtgaaaggcttctacccctccgatatcgccgtggaatgggagtcc aacggccagcctgagaacaactacaagaccaccccccctgtgctggactc cgacggctcattcttcctgtacagcaagctgacagtggacaagtcccggt ggcagcagggcaacgtgttctcctgctccgtgatgcacgaggccctgcac aaccactacacccagaagtccctgtccctgagccccggctga The amino acid sequence for hG4P heavy chain is:

(SEQ ID NO: 134)

MEWSWVELFELSVTTGVHSEVQLQQSGPELVKPGASVKISCKASGYTFTT

YYMNWVKQSHGKSLEWIGNINPDNGITSYNQKFKGKATLTVDKSSSTAYM

ELRSLTSEDSAVYYCARGKSLAYWGQGTLVTVSAASTKGPSVFPLAPCSR

STSESTAALGCLVKDYFPEPVTVSWNSGALTSGVHTFPAVLQSSGLYSLS

SVVTVPSSSLGTKTYTCNVDHKPSNTKVDKRVESKYGPPCPPCPAPEFLG

-continued

GPSVFLEPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTI
SKAKGQPREPQVYTLPPSQEEMTKNQVSLTCLVKGFYPSDIAVEWESNGQ
PENNYKTTPPVLDSDGSFELYSRLTVDKSRWQEGNVFSCSVMHEALHNHY
TQKSLSLSLG*

The nucleic acid sequence for hG4P heavy chain is:

(SEQ ID NO: 135)
atggaatggtcctgggtgttcctgttcttcctgtctgtgaccaccggcgt
gcactctgaagttcagttgcagcagtctggccccgagcttgtgaaacctg
gcgcctctgtgaagatctcctgcaaggcctctggctacaccttcaccacc
tactacatgaactgggtcaagcagtcccacggcaagtccctggaatggat
cggcaacatcaaccccgacaacggcatcacctcctacaaccagaagttca
agggcaaagctaccctgaccgtggacaagtcctcctccaccgcctacatg
gaactgagatccctgacctctgaggactccgccgtgtactactgtgccag
aggcaagtctctggcttattggggccagggcacactggtcacagtgtctg
ctgcttccaccaaggggccctccgtgttccctctggccccttgctccaga
tccacctccgagtctaccgccgctctgggctgcctcgtgaaggactactt
ccccgagcctgtgaccgtgtcctggaactctggcgctctgacctctggcg
tgcacaccttccctgctgtgctgcagtcctccggcctgtactccctgtcc
tccgtcgtgaccgtgccttccagctctctgggcaccaagacctacacctg
taacgtggaccacaagccctccaacaccaaggtggacaagcgggtggaat
ctaagtacggccctccctgccctccttgcccagcccctgaatttctgggc
ggacccagcgtgttcctgttccccccaaagcccaaggacaccctgatgat
ctcccggacccccgaagtgacctgcgtggtggtggatgtgtcccaggaag
atcccgaggtgcagttcaattggtacgtggacggcgtggaagtgcacaac
gccaagaccaagcctagagaggaacagttcaactccacctaccgggtggt
gtccgtgctgaccgtgctgcaccaggattggctgaacggcaaagagtaca
agtgcaaggtgtccaacaagggcctgcccagctccatcgaaaagaccatc
tccaaggccaagggccagccccgggaaccccaggtgtacacactgcctcc
aagccaggaagagatgaccaagaaccaggtgtccctgacctgtctcgtga
aaggcttctacccctccgatatcgccgtggaatgggagtccaacggccag
cctgagaacaactacaagaccaccccccctgtgctggactccgacggctc
cttcttcctgtactctcgcctgaccgtggacaagtcccggtggcaggaag
gcaacgtgttctcctgctccgtgatgcacgaggccctgcacaaccactac
acccagaagtccctgtccctgtctctgggatga The amino acid for the light chain is:

(SEQ ID NO: 136)
MSVPTQVLGLLLLWLTDARCDIVMTQSHKFMSTSVGDRVSITCKASQNVG
TAVAWYQQKPGQSPKLLIYWASIRHTGVPDRFTGSGSGTDFTLTISNVQS
EDLADYFCQQYSSHPYTEGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSENRGEC*

The nucleic acid sequence for the light chain is:

(SEQ ID NO: 137)
atgtccgtgcctacacaggttctgggactgctgctgctgtggctgaccg
acgctagatgcgacatcgtgatgacccagagccacaagttcatgtccac
ctccgtgggcgacagagtgtccatcacatgcaaggcctctcagaatgtg
ggcaccgccgttgcctggtatcagcagaaacctggccagtctcctaagc
tgctgatctactgggcctccatcagacacaccggcgtgccagatagatt
caccggctctggctctggcaccgacttcaccctgaccatctctaacgtg
cagtctgaggacctggccgactacttctgccagcagtacagctctcacc
cctacacctttggcggaggcaccaagctggaaatcaagcgtacggtggc
cgctccctccgtgttcatcttcccaccttccgacgagcagctgaagtcc
ggcaccgcttctgtcgtgtgcctgctgaacaacttctacccccgcgagg
ccaaggtgcagtggaaggtggacaacgccctgcagtccggcaactccca
ggaatccgtgaccgagcaggactccaaggacagcacctactccctgtcc
tccaccctgaccctgtccaaggccgactacgagaagcacaaggtgtacg
cctgcgaagtgacccaccagggcctgtctagccccgtgaccaagtcttt
caaccggggcgagtgctga Sequences for Chimeric 11B3 hG1 HC

The amino acid sequence for hG1 heavy chain is:

(SEQ ID NO: 138)
MEWSWVFLFFLSVTTGVHSEVQLVESGGGLVQPKGSLKLSCAASDFTFN
TYAMHWVRQAPGKGLEWVARIRTKSNNYATYYADSVKDRFTISRDDSQS
MLYLQMNNLTTEDTAMYYCVRDRYGGAMDYWGQGTSVTVSSASTKGPSV
FPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVK
GFYPSDIAVEWESNGQPENNYKTTPPVLDSDGSFELYSKLTVDKSRWQQ
GNVESCSVMHEALHNHYTQKSLSLSPG*

The nucleic acid sequence for hG1 heavy chain is:

(SEQ ID NO: 139)
atggaatggtcctgggtgttcctgttcttcctgtctgtgaccaccggcg
tgcactctgaagtgcagttggttgaatctggcggcggactggtgcagcc
taagggatctctgaagctgtcttgcgccgcctccgacttcaccttcaat
acctacgccatgcactgggtccgacaggcccctggaaaaggactggaat
gggtcgccagaatccggaccaagtccaacaactacgccacctactacgc -continued cgactccgtgaaggacagattcaccatctctcgggacgactcccagtcc atgctgtacctgcagatgaacaacctgaccaccgaggacaccgccatgt actactgcgtgcgggatagatatggcggcgctatggattattggggcca gggcacatctgtgaccgtgtcctctgcttccaccaaggggccctccgtg ttccctctggccccttccagcaagtctacctctggcggcacagccgctc tgggctgcctcgtgaaggactacttccccgagcctgtgaccgtgtcctg gaactctggcgctctgacatccggcgtgcacaccttccctgctgtgctg cagtcctccggcctgtactccctgtcctccgtcgtgaccgtgccttcca gctctctgggcacccagacctacatctgcaacgtgaaccacaagccctc caacaccaaggtggacaagaaggtggaacccaagtcctgcgacaagacc cacacctgtccccccttgtcctgccccctgaactgctgggcggacccagcg tgttcctgttcccccccaaagcccaaggacaccctgatgatctcccggac ccccgaagtgacctgcgtggtggtggatgtgtcccacgaggaccctgaa gtgaagttcaattggtacgtggacggcgtggaagtgcacaacgccaaga ccaagcctagagaggaacagtacaactccacctaccgggtggtgtccgt gctgaccgtgctgcaccaggattggctgaacggcaaagagtacaagtgc aaggtgtccaacaaggccctgcctgcccccatcgaaaagaccatctcca aggccaagggccagccccgggaaccccaggtgtacacactgccccctag cagggacgagctgaccaagaaccaggtgtccctgacctgtctcgtgaaa ggcttctacccctccgatatcgccgtggaatgggagtccaacggccagc ctgagaacaactacaagaccaccccccctgtgctggactccgacggctc attcttcctgtacagcaagctgacagtggacaagtcccggtggcagcag ggcaacgtgttctcctgctccgtgatgcacgaggccctgcacaaccact acacccagaagtccctgtccctgagccccggctga hG4P HC The amino acid sequence for hG4P heavy chain is:

(SEQ ID NO: 140)

MEWSWVFLFFLSVTTGVHSEVQLVESGGGLVQPKGSLKLSCAASDFTFN

TYAMHWVRQAPGKGLEWVARIRTKSNNYATYYADSVKDRFTISRDDSQS

MLYLQMNNLTTEDTAMYYCVRDRYGGAMDYWGQGTSVTVSSASTKGPSV

FPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPC

PPCPAPEELGGPSVELEPPKPKDTLMISRTPEVTCVVVDVSQEDPEVQF

NWYVDGVEVHNAKTKPREEQENSTYRVVSVLTVLHQDWLNGKEYKCKVS

NKGLPSSIEKTISKAKGQPREPQVYTLPPSQEEMTKNQVSLTCLVKGEY

PSDIAVEWESNGQPENNYKTTPPVLDSDGSFELYSRLTVDKSRWQEGNV

ESCSVMHEALHNHYTQKSLSLSLG*

The nucleic acid sequence for hG4P heavy chain is:

(SEQ ID NO: 141)

atggaatggtcctgggtgttcctgttcttcctgtctgtgaccaccggcg tgcactctgaagtgcagttggttgaatctggcggcggactggtgcagcc

-continued taagggatctctgaagctgtcttgcgccgcctccgacttcaccttcaat acctacgccatgcactgggtccgacaggcccctggaaaaggactggaat gggtcgccagaatccggaccaagtccaacaactacgccacctactacgc cgactccgtgaaggacagattcaccatctctcgggacgactcccagtcc atgctgtacctgcagatgaacaacctgaccaccgaggacaccgccatgt actactgcgtgcgggatagatatggcggcgctatggattattggggcca gggcacatctgtgaccgtgtcctctgcttccaccaaggggccctccgtg ttccctctggccccttgctccagatccacctccgagtctaccgccgctc tgggctgcctcgtgaaggactacttccccgagcctgtgaccgtgtcctg gaactctggcgctctgacctctggcgtgcacaccttccctgctgtgctg cagtcctccggcctgtactccctgtcctccgtcgtgaccgtgccttcca gctctctgggcaccaagacctacacctgtaacgtggaccacaagccctc caacaccaaggtggacaagcgggtggaatctaagtacggccctccctgc cctccttgcccagcccctgaatttctgggcggacccagcgtgttcctgt tcccccccaaagcccaaggacaccctgatgatctcccggacccccgaagt gacctgcgtggtggtggatgtgtcccaggaagatcccgaggtgcagttc aattggtacgtggacggcgtggaagtgcacaacgccaagaccaagccta gagaggaacagttcaactccacctaccgggtggtgtccgtgctgaccgt gctgcaccaggattggctgaacggcaaagagtacaagtgcaaggtgtcc aacaagggcctgcccagctccatcgaaaagaccatctccaaggccaagg gccagccccgggaaccccaggtgtacacactgcctccaagccaggaaga gatgaccaagaaccaggtgtccctgacctgtctcgtgaaaggcttctac ccctccgatatcgccgtggaatgggagtccaacggccagcctgagaaca actacaagaccaccccccctgtgctggactccgacggctccttcttcct gtactctcgcctgaccgtggacaagtcccggtggcaggaaggcaacgtg ttctcctgctccgtgatgcacgaggccctgcacaaccactacacccaga agtccctgtccctgtctctgggatga Light Chain The amino acid sequence for the light chain is:

(SEQ ID NO: 142)

MSVPTQVLGLLLLWLTDARCDIQMAQSSSSFSVSLGDRVTITCKASEDI

YIRLAWYQQKPGNAPRLLISTATSLETGVPSRFSGSGSGKDYTLSITSL

QTEDVATYYCQQYWSTPYTEGGGTRLEIKRTVAAPSVFIFPPSDEQLKS

GTASVVCLLNNFYPREAKVQWKVDNALQSGNSQESVTEQDSKDSTYSLS

STLTLSKADYEKHKVYACEVTHQGLSSPVTKSENRGEC*

The nucleic acid sequence for the light chain is:

(SEQ ID NO: 143)

atgtccgtgcctacacaggttctgggactgctgctgctgtggctgaccg acgctagatgtgatatccagatggcccagtcctcctccagcttctctgt gtctctgggcgacagagtgaccatcacatgcaaggcctccgaggacatc -continued

```
tacatccggctggcctggtatcagcagaagcctggaaacgcccctcggc

tgctgatctctaccgctacatctctggaaaccggcgtgccctctagatt

ctctggctctggatctggcaaggactacaccctgtctatcaccagcctg

cagaccgaggatgtggccacctactactgccagcagtactggtctaccc

cttacacctttggcggcggaacccggctggaaatcaaacgtacggtggc

cgctccctccgtgttcatcttcccaccttccgacgagcagctgaagtcc

ggcaccgcttctgtcgtgtgcctgctgaacaacttctacccccgcgagg

ccaaggtgcagtggaaggtggacaacgccctgcagtccggcaactccca

ggaatccgtgaccgagcaggactccaaggacagcacctactccctgtcc

tccaccctgaccctgtccaaggccgactacgagaagcacaaggtgtacg

cctgcgaagtgacccaccagggcctgtctagccccgtgaccaagtcttt

caaccggggcgagtgctga
```

The chimeric antibodies are produced by combining the light chain with one of the disclosed heavy chains.

Example 15: Screening of LAIR-1 Hybridoma Supernatants for Blockade or Enhancement of LAIR-1 Fc Binding to Collagen I and III

Materials and Methods 1 ug/ml of collagen I or collagen III (Millipore) was coated (in separate plates for separate screens) overnight in PBS. Plates were washed, blocked with ELISA blocking buffer (5% BSA in PBS). After washing, 50 ul of LAIR-1 hybridoma supernatant was added to plates, followed by addition of 50 ul of 2 ug/ml human LAIR-1Fc-biotin. Plates were washed and SA-HRP was added (eBio) at 1:10000 dilution. Following 30 minute incubation and was, TMB was added followed by stop solution. Absorbance was determined with PerkinElmer Envision analyzer.

Results

Figure 19:
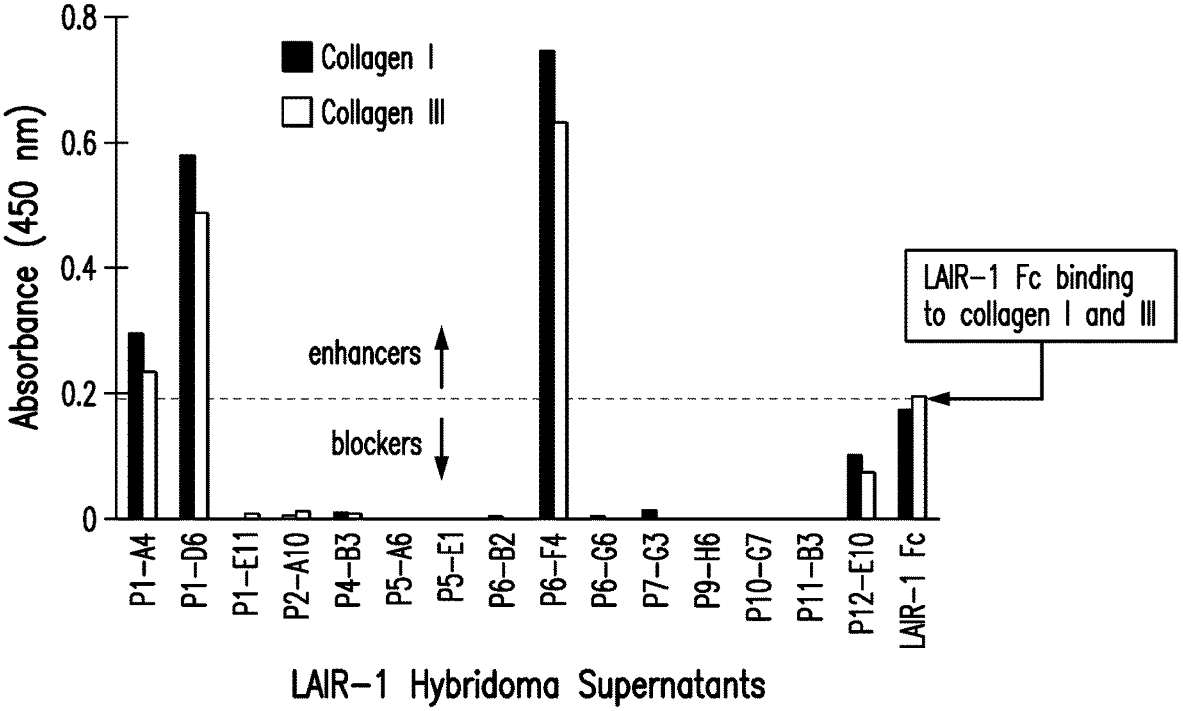
FIG. 19 is a bar graph of absorbance (450 nm) for the indicated mAb showing blockade or enhancement of LAIR-1 Fc binding to collagen I and III. Collagen I is the left column and collagen III is the right column for each mAb.

FIG. 19 shows the results of the LAIR-1 hybridoma screening. Clones P1-A4, P1-D6, and P6-F4 were identified as enhancers of binding of LAIR-1 Fc binding to collagen I and III. Clones P1-E11, P2-A10, P4-B3, P5-A6, P5-E1, P6-B2, P6-G6, P7-G3, P9-H6, P10-G7, P11-B3 and P12-E10 were found to be blockers of LAIR-1 Fc binding to collagen I and III.

Example 16: Screening of LAIR-1 Hybridoma Supernatants for Blockade or Enhancement of LAIR-1 Fc Binding to C1q and SP-D

Materials and Methods 1 ug/ml of C1q (Sigma) or SP-D (R&D Systems) were coated (in separate plates for separate screens) overnight in PBS. Plates were washed, blocked with ELISA blocking buffer (5% BSA in PBS). After washing, 50 ul of LAIR-1 hybridoma supernatant was added to plates, followed by addition of 50 ul of 2 ug/ml human LAIR-1Fc-biotin. Plates were washed and SA-HRP was added (eBio) at 1:10000 dilution. Following 30 minute incubation, TMB was added followed by stop solution. Absorbance was determined with PerkinElmer Envision analyzer.

Results

Figure 20:
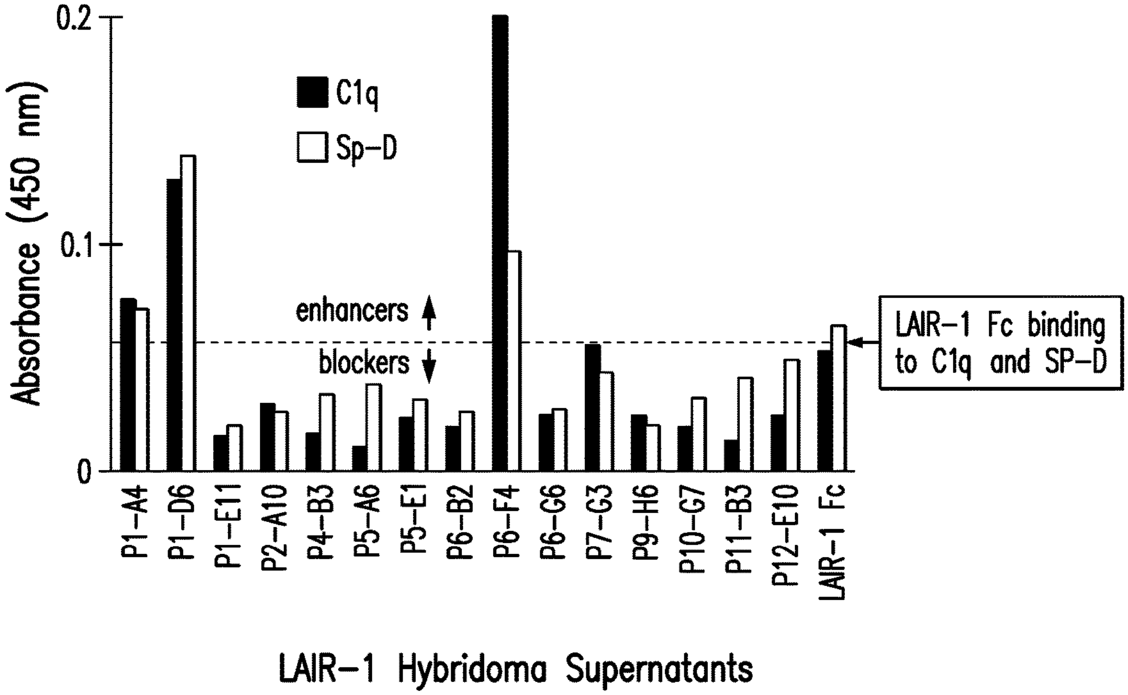
FIG. 20 is a bar graph of absorbance (450 nm) of the indicated mAbs for binding to C1q and SP-D. The left column for each set is C1q and the right column is SP-D.

FIG. 20 shows the results of the screening assay. Clones P1-A4, P1-D6, and P6-F4 were found to enhance LAIR-1 Fc binding to C1q and SP-D. Clones P1-E11, P2-A10, P4-B3, P5-A6, P5-E1, P6-B2, P6-G6, P7-G3, P9-H6, P10-G7, P11-B3, and P12-E10 were found to be blockers of LAIR-1 Fc binding to C1q and SP-D.

Example 17: LAIR-1 Chimeric mAb Binning

Methods and Materials

An Octet RED96 instrument (ForteBio) was used for binning assays. LAIR-1 Fc (hIgG1) was bound to anti-human IgG sensor. After confirming stability of LAIR-1 Fc on sensor, the sensor was dipped in a well with the first mAb listed on the left side column. Binding of first mAb was saturated by binding excess mAb to LAIR-1 Fc. Next, the sensor was placed in a well containing the 2nd mAb, as shown across the top row. mAbs that bind the same epitope will be blocked from binding LAIR-1 Fc due to binding saturation, as can be observed when the same mAb is used as the first and second mAb (FIG. 21, no underlining and stippled cells). No blockade indicated distant epitopes, as well as lack of steric hindrance. Partial blockade is likely due to slightly overlapping epitopes or steric hindrance of binding due to proximity of mAb binding sites. Based on very weak binding (low avidity), three of the clones were removed from further study, leaving 12 clones. Two commercial anti-human LAIR-1 clones, DX26 and NKTA were included for comparison purposes.

Results

FIG. 21 shows the results of LAIR-1 chimeric Ab binning. No blocking is indicated by single underline. Blocking is indicated by double underline. The data allowed for the identification of mAbs that bind to similar, overlapping or distinct sites (epitopes) on the extracellular domain (ECD) of LAIR-1, and allowed for the construction of a epitope map of LAIR-1 mAb binding.

Figure 22:
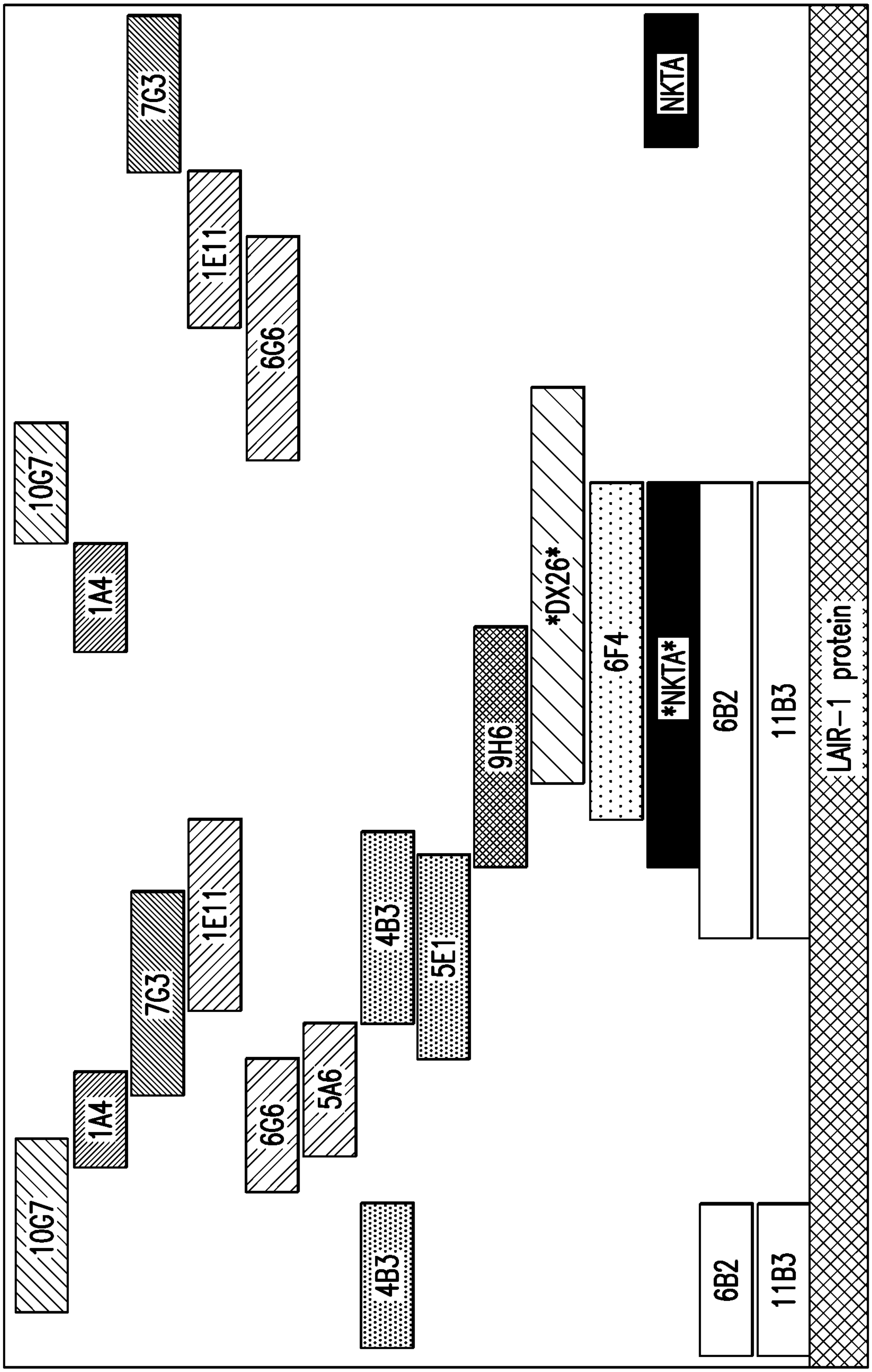
FIG. 22 is a diagram of LAIR-1 chimeric mAb binning map. This map demonstrates that there is significant overlap of mAbs, while many occupy distinct sites on the LAIR-1 molecule.

From the binning results, it was determined that four primary bins of mAbs existed within this set of 12 clones (FIG. 22). These are: bin 1: 11B3, 6B2, 6F4; bin 2: 5E1 and 4B3; bin 3: 5A6 and 6G6; bin 4: 1E11, 7G3, 1A4, and 10G7.

Example 18: LAIR-1 Chimeric mAb Binning Map

Materials and Methods

Using the binning data generated in FIG. 21, a map of binding sites was constructed in 2D format for visualization of relative binding sites.

Results

Using the binning data generated in Example 17, a map of binding sites was constructed in 2D format for visualization of relative binding sites (FIG. 22). This map demonstrates that there is significant overlap of mAbs. Simultaneously, many mAbs occupy distinct sites on the LAIR-1 molecule. The mAbs with the greatest overlap and blockade of binding to LAIR-1 are considered a bin. Together, this data suggests the mAb panel covers a major portion of the LAIR-1 protein.

Example 19: Optimized Affinity Assessments were Performed Using an Octet RED96 Instrument (ForteBio)

Materials and Methods

Anti-human IgG capture sensors were used to bind to chimeric LAIR-1 mAbs at a density to ensure 1:1 binding to monomeric LAIR-1-His (R&D Systems) in solution at various concentrations. Assay buffer was PBS with 0.05%

Tween-20 and regeneration buffer was 10 mM glycine pH 1.5. First, chimeric LAIR-1 mAbs were loaded to sensor. This was followed by association step with LAIR-1-His, and a dissociation step in a separate LAIR-1-His free well. Data was processed using ForteBio data analysis software 9.0. A global fit was used following subtraction of reference wells. The reported average KD values are from at least three independent Octet runs with high confidence of accuracy based on X2 and R2 values. Note the two chimeric versions of 12E10 were tested. Both had relatively low affinity, while the 12E10V2 mAb was removed from usage due to very low affinity.

Results

Figures 23, 24A:
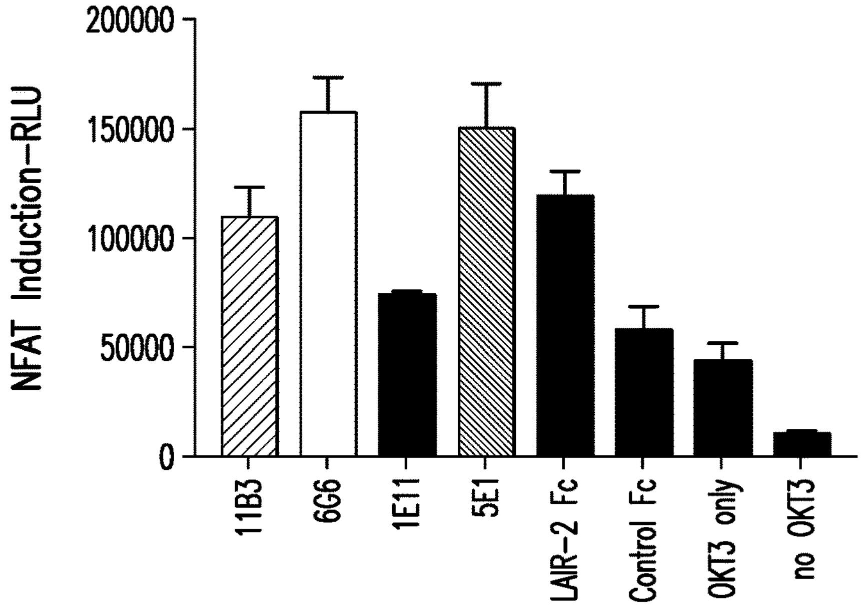
FIG. 23 is a table showing optimized affinity assessments for the indicated LAIR-1 mAb performed using an Octet RED96 instrument (ForteBio).
FIG. 24A is a bar graph of IRF induction—RLU for indicated LAIR-1 mAbs showing differential induction of interferon reporter activity in THP-1 cells when the mAbs are coated to the plate.

FIG. 23 shows the results of the affinity assessments. The dissociation constant (Kd) is shown in nM values in the third column based on the dissociation (Kdis) and association (Kon) rates. Most mAbs had very strong association rates, but also relatively fast dissociation rates. 1E11, 7G3 and 11B3, 5E1 and 6G6 all had Kd values of <5 nM, indicating very strong affinity to LAIR-1.

Example 20: LAIR-1 mAbs Demonstrate Differential Induction of Interferon Reporter Activity in THP-1 Cells

Materials and Methods

Figure 24B:
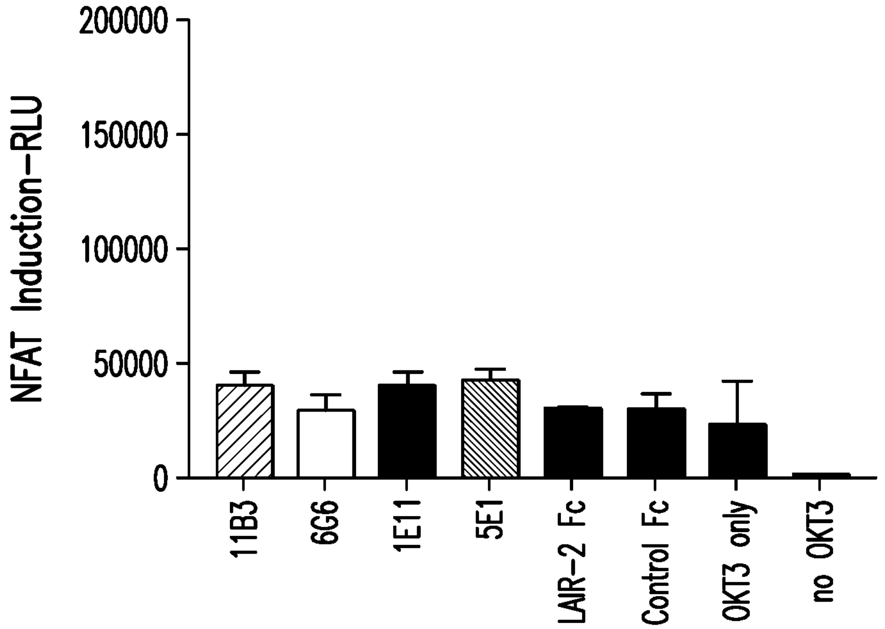
FIG. 24B is a bar graph of IRF induction—RLU for indicated LAIR-1 mAbs showing differential induction of interferon reporter activity in THP-1 cells when the mAbs are added as soluble proteins.

THP-1-Dual cells (Invivogen) with an interferon regulatory factor (IRF) reporter were plated at 25,000 cells/well of a 96-well plate to either plates that had been pre-coated with LAIR-1 mAbs (10 ug/ml) (FIG. 24A) or left uncoated (FIG. 24B). For FIG. 24B LAIR-1 mAbs were added as soluble proteins at 10 ug/ml. LAIR-2 Fc or control Fc was also coated (FIG. 24A) or added as soluble proteins (FIG. 24B) as positive and negative controls.

LPS was added as 1 ug/ml for low level IRF induction in order to test whether LAIR-1 mAbs enhanced or inhibited IRF pathway induction. At 72 hours, 10 ul of supernatant was removed from assay plates and transferred to a separate plate for analysis. Quanti-luc (Invivogen) was added according to protocol and luminescence was measured with a PerkinElmer Envision Results Plate bound LAIR-1 mAbs indicated that three mAbs, 11B3, 6G6 and 5E1 may enhance IRF signaling, whereas two mAbs, 1E11 and 7G3 had little effect or may actually inhibit IRF induction (FIG. 24A). The mAbs had a similar effect in soluble form (FIG. 24B). Interestingly, 1E11 and 7G3, which fall into the same bin, appear to have similar function. Conversely, 11B3, 6G6 and 5E1 fall into separate bins, but appear to have similar function, which contrasts with clones 1E11 and 7G3.

Example 21: LAIR-1 mAbs Screening for Induction of Jurkat T Cell Reporter Activity

Figure 25A:
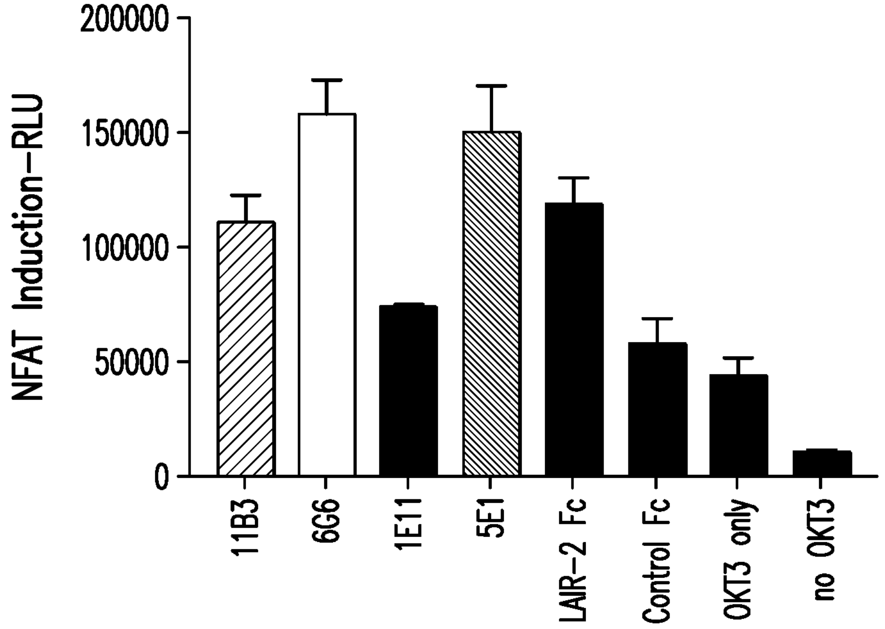
FIG. 25A is a bar graph of NFAT induction—RLU for the indicated mAbs showing induction of Jurkat T cell reporter activity when plates are coated with anti-CD3 (OKT3 at 0.5 μg/ml. Following aspiration of OKT3, LAIR-1 mAbs or LAIR-2 Fc and control Fc were coated for 24 hours at 10 ug/ml. Prior to adding Jurkat T cell NFAT-Lucia pathway reporter cells (Invivogen), unbound proteins were aspirated. Jurkat T cells were plated at 50,000 cells/well in 200 ul total volume. At 48 hours, 10 ul of supernatant was removed and transferred to a separate plate. Quanti-Luc (Inivivogen) was added according to protocol. Luminescence was assessed using a Perkin Elmer Envision plate reader.

Materials and Methods 96-well plates were coated overnight at 4 degrees C. with anti-CD3 (OKT3) at 0.5 ug/ml. Unbound CD3 was removed by aspiration. Following aspiration of OKT3, LAIR-1 mAbs or LAIR-2 Fc and control Fc were coated for 24 hours at 10 ug/ml (FIG. 25A). Prior to adding Jurkat T cell NFAT-Lucia pathway reporter cells (Invivogen), unbound proteins were aspirated. Jurkat T cells were plated at 50,000 cells/well in 200 ul total volume. At 48 hours, 10 ul of supernatant was removed and transferred to a separate plate. Quanti-Luc (Inivivogen) was added according to protocol. Luminescence was assessed using a Perkin Elmer Envision plate reader. For FIG. 25B was performed the same as FIG. 25A, but proteins were added in soluble form rather than coating on the plate.

Results

Figure 25B:
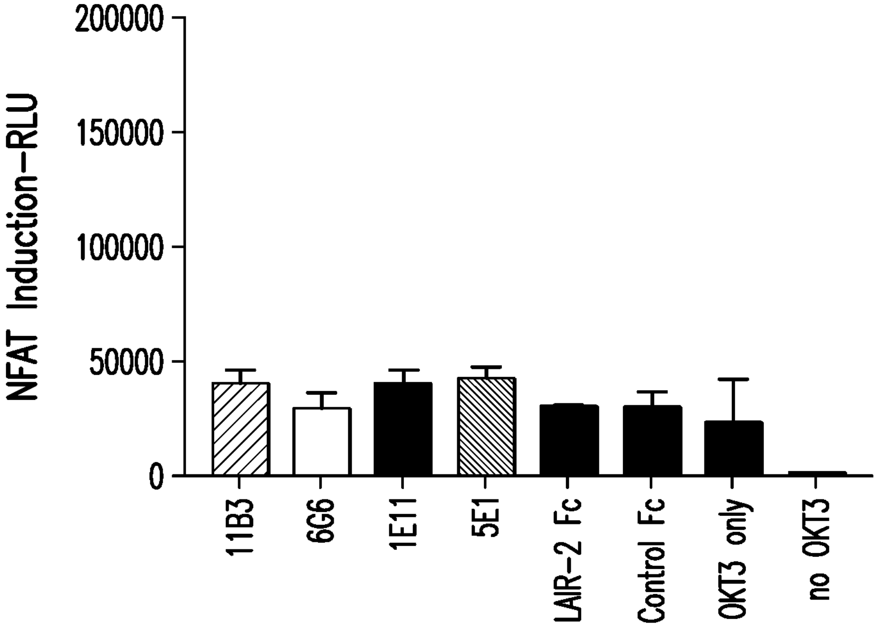
FIG. 25B is a bar graph of NFAT induction—RLU for the indicated mAbs showing induction of Jurkat T cell reporter activity as in FIG. 25*a* when LAIR-1 mAbs, LAIR-2 Fc, and control Fc are added in soluble form.

Results showed that 1E11 had little or no effect on NFAT reporter induction, whereas 11B3, 6G6 and 5E1 induced NFAT induction (FIG. 25A). In a similar assay, LAIR-1 mAbs or LAIR-2 Fc and control Fc were added as soluble proteins (FIG. 25B). In this assay little effect was observed with any of the treatments. Note that 7G3 was only tested in the THP-1 assay, but not in the Jurkat assay.

Collectively, the data in the Examples show specific functionality of LAIR-1 mAbs in cell line pathway reporter-based assays.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising a combination of:

a fusion protein comprising the amino acid sequence of SEQ ID NO:16, and an anti-PD-1 immunotherapy, wherein the fusion protein has LAIR-1 antagonistic activity, and wherein the combination synergistically enhances the efficacy of the anti-PD-1 immunotherapy.

2. The pharmaceutical composition of claim 1, wherein a vector encodes the fusion protein.

3. The pharmaceutical composition of claim 2, wherein the vector is an expression vector.

4. The pharmaceutical composition of claim 1, wherein a cell expresses the fusion protein of claim 1.

5. The pharmaceutical composition of claim 4, wherein the cell is a Chinese hamster ovary cell.

6. The pharmaceutical composition of claim 1, wherein the composition is formulated for parenteral administration.

7. The pharmaceutical composition of claim 1, wherein the anti-PD-1 immunotherapeutic is an anti-PD-1 antibody.

8. A method for promoting primary T cell proliferation comprising administering the pharmaceutical composition of claim 1 to a subject in need thereof in an amount effective to promote primary T cell proliferation.

9. A method for promoting antigen-specific CD8+ T cell expansion comprising administering the pharmaceutical composition of claim 1 to a subject in need thereof in an amount effective to promote antigen-specific CD8+ T cell expansion.

10. A method for reducing tumor burden in a subject in need thereof comprising administering the pharmaceutical composition of claim 1 to the subject in an amount effective to reduce tumor burden.

11. The method of claim 10, wherein the tumor is an ovarian tumor.

12. The method of claim 10, wherein the tumor is lymphoma.

* * * * *

SEQUENCE LISTING

```
<160> NUMBER OF SEQ ID NOS: 147

<210> SEQ ID NO 1
<211> LENGTH: 287
<212> TYPE: PRT
<213> ORGANISM: Homo sapiens

<400> SEQUENCE: 1

Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
            20                  25                  30

Ala Glu Pro Gly Thr Val Ile Pro Leu Gly Ser His Val Thr Phe Val
        35                  40                  45
```

```
Cys Arg Gly Pro Val Gly Val Gln Thr Phe Arg Leu Glu Arg Glu Ser
    50                  55                  60

Arg Ser Thr Tyr Asn Asp Thr Glu Asp Val Ser Gln Ala Ser Pro Ser
65                  70                  75                  80

Glu Ser Glu Ala Arg Phe Arg Ile Asp Ser Val Ser Glu Gly Asn Ala
                85                  90                  95

Gly Pro Tyr Arg Cys Ile Tyr Tyr Lys Pro Pro Lys Trp Ser Glu Gln
            100                 105                 110

Ser Asp Tyr Leu Glu Leu Leu Val Lys Glu Thr Ser Gly Gly Pro Asp
        115                 120                 125

Ser Pro Asp Thr Glu Pro Gly Ser Ser Ala Gly Pro Thr Gln Arg Pro
    130                 135                 140

Ser Asp Asn Ser His Asn Glu His Ala Pro Ala Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
            180                 185                 190

Lys Gln Gly Pro Pro Arg Ser Lys Asp Glu Glu Gln Lys Pro Gln Gln
        195                 200                 205

Arg Pro Asp Leu Ala Val Asp Val Leu Glu Arg Thr Ala Asp Lys Ala
    210                 215                 220

Thr Val Asn Gly Leu Pro Glu Lys Asp Arg Glu Thr Asp Thr Ser Ala
225                 230                 235                 240

Leu Ala Ala Gly Ser Ser Gln Glu Val Thr Tyr Ala Gln Leu Asp His
                245                 250                 255

Trp Ala Leu Thr Gln Arg Thr Ala Arg Ala Val Ser Pro Gln Ser Thr
            260                 265                 270

Lys Pro Met Ala Glu Ser Ile Thr Tyr Ala Ala Val Ala Arg His
        275                 280                 285


<210> SEQ ID NO 2
<211> LENGTH: 144
<212> TYPE: PRT
<213> ORGANISM: Homo sapiens

<400> SEQUENCE: 2

Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95

Leu Leu Val Lys Glu Thr Ser Gly Gly Pro Asp Ser Pro Asp Thr Glu
            100                 105                 110

Pro Gly Ser Ser Ala Gly Pro Thr Gln Arg Pro Ser Asp Asn Ser His
        115                 120                 125

Asn Glu His Ala Pro Ala Ser Gln Gly Leu Lys Ala Glu His Leu Tyr
    130                 135                 140
```

-continued

<210> SEQ ID NO 3
<211> LENGTH: 263
<212> TYPE: PRT
<213> ORGANISM: Mus musculus

<400> SEQUENCE: 3

```
Met Ser Leu His Pro Val Ile Leu Leu Val Leu Val Leu Cys Leu Gly
1               5                   10                  15

Trp Lys Ile Asn Thr Gln Glu Gly Ser Leu Pro Asp Ile Thr Ile Phe
            20                  25                  30

Pro Asn Ser Ser Leu Met Ile Ser Gln Gly Thr Phe Val Thr Val Val
        35                  40                  45

Cys Ser Tyr Ser Asp Lys His Asp Leu Tyr Asn Met Val Arg Leu Glu
    50                  55                  60

Lys Asp Gly Ser Thr Phe Met Glu Lys Ser Thr Glu Pro Tyr Lys Thr
65                  70                  75                  80

Glu Asp Glu Phe Glu Ile Gly Pro Val Asn Glu Thr Ile Thr Gly His
                85                  90                  95

Tyr Ser Cys Ile Tyr Ser Lys Gly Ile Thr Trp Ser Glu Arg Ser Lys
            100                 105                 110

Thr Leu Glu Leu Lys Val Ile Lys Glu Asn Val Ile Gln Thr Pro Ala
        115                 120                 125

Pro Gly Pro Thr Ser Asp Thr Ser Trp Leu Lys Thr Tyr Ser Ile Tyr
    130                 135                 140

Ile Phe Thr Val Val Ser Val Ile Phe Leu Leu Cys Leu Ser Ala Leu
145                 150                 155                 160

Leu Phe Cys Phe Leu Arg His Arg Gln Lys Lys Gln Gly Leu Pro Asn
                165                 170                 175

Asn Lys Arg Gln Gln Gln Arg Pro Glu Glu Arg Leu Asn Leu Ala Thr
            180                 185                 190

Asn Gly Leu Glu Met Thr Pro Asp Ile Val Ala Asp Asp Arg Leu Pro
        195                 200                 205

Glu Asp Arg Trp Thr Glu Thr Trp Thr Pro Val Ala Gly Asp Leu Gln
    210                 215                 220

Glu Val Thr Tyr Ile Gln Leu Asp His His Ser Leu Thr Gln Arg Ala
225                 230                 235                 240

Val Gly Ala Val Thr Ser Gln Ser Thr Asp Met Ala Glu Ser Ser Thr
                245                 250                 255

Tyr Ala Ala Ile Ile Arg His
            260
```

<210> SEQ ID NO 4
<211> LENGTH: 123
<212> TYPE: PRT
<213> ORGANISM: Mus musculus

<400> SEQUENCE: 4

```
Gln Glu Gly Ser Leu Pro Asp Ile Thr Ile Phe Pro Asn Ser Ser Leu
1               5                   10                  15

Met Ile Ser Gln Gly Thr Phe Val Thr Val Val Cys Ser Tyr Ser Asp
            20                  25                  30

Lys His Asp Leu Tyr Asn Met Val Arg Leu Glu Lys Asp Gly Ser Thr
        35                  40                  45

Phe Met Glu Lys Ser Thr Glu Pro Tyr Lys Thr Glu Asp Glu Phe Glu
    50                  55                  60
```

```
Ile Gly Pro Val Asn Glu Thr Ile Thr Gly His Tyr Ser Cys Ile Tyr
65                  70                  75                  80

Ser Lys Gly Ile Thr Trp Ser Glu Arg Ser Lys Thr Leu Glu Leu Lys
                85                  90                  95

Val Ile Lys Glu Asn Val Ile Gln Thr Pro Ala Pro Gly Pro Thr Ser
            100                 105                 110

Asp Thr Ser Trp Leu Lys Thr Tyr Ser Ile Tyr
        115                 120


<210> SEQ ID NO 5
<211> LENGTH: 152
<212> TYPE: PRT
<213> ORGANISM: Homo sapiens

<400> SEQUENCE: 5

Met Ser Pro His Leu Thr Ala Leu Leu Gly Leu Val Leu Cys Leu Ala
1               5                   10                  15

Gln Thr Ile His Thr Gln Glu Gly Ala Leu Pro Arg Pro Ser Ile Ser
            20                  25                  30

Ala Glu Pro Gly Thr Val Ile Ser Pro Gly Ser His Val Thr Phe Met
        35                  40                  45

Cys Arg Gly Pro Val Gly Val Gln Thr Phe Arg Leu Glu Arg Glu Asp
    50                  55                  60

Arg Ala Lys Tyr Lys Asp Ser Tyr Asn Val Phe Arg Leu Gly Pro Ser
65                  70                  75                  80

Glu Ser Glu Ala Arg Phe His Ile Asp Ser Val Ser Glu Gly Asn Ala
                85                  90                  95

Gly Leu Tyr Arg Cys Leu Tyr Tyr Lys Pro Pro Gly Trp Ser Glu His
            100                 105                 110

Ser Asp Phe Leu Glu Leu Leu Val Lys Glu Ser Ser Gly Gly Pro Asp
        115                 120                 125

Ser Pro Asp Thr Glu Pro Gly Ser Ser Ala Gly Thr Val Pro Gly Thr
    130                 135                 140

Glu Ala Ser Gly Phe Asp Ala Pro
145                 150


<210> SEQ ID NO 6
<211> LENGTH: 131
<212> TYPE: PRT
<213> ORGANISM: Homo sapiens

<400> SEQUENCE: 6

Gln Glu Gly Ala Leu Pro Arg Pro Ser Ile Ser Ala Glu Pro Gly Thr
1               5                   10                  15

Val Ile Ser Pro Gly Ser His Val Thr Phe Met Cys Arg Gly Pro Val
            20                  25                  30

Gly Val Gln Thr Phe Arg Leu Glu Arg Glu Asp Arg Ala Lys Tyr Lys
        35                  40                  45

Asp Ser Tyr Asn Val Phe Arg Leu Gly Pro Ser Glu Ser Glu Ala Arg
    50                  55                  60

Phe His Ile Asp Ser Val Ser Glu Gly Asn Ala Gly Leu Tyr Arg Cys
65                  70                  75                  80

Leu Tyr Tyr Lys Pro Pro Gly Trp Ser Glu His Ser Asp Phe Leu Glu
                85                  90                  95

Leu Leu Val Lys Glu Ser Ser Gly Gly Pro Asp Ser Pro Asp Thr Glu
            100                 105                 110
```

```
Pro Gly Ser Ser Ala Gly Thr Val Pro Gly Thr Glu Ala Ser Gly Phe
        115                 120                 125

Asp Ala Pro
    130


<210> SEQ ID NO 7
<211> LENGTH: 32
<212> TYPE: PRT
<213> ORGANISM: Mus musculus

<400> SEQUENCE: 7

Ser Leu Pro Asp Ile Thr Ile Phe Pro Asn Ser Ser Leu Met Ile Ser
1               5                   10                  15

Gln Gly Thr Phe Val Thr Val Val Cys Ser Tyr Ser Asp Lys His Asp
            20                  25                  30


<210> SEQ ID NO 8
<211> LENGTH: 32
<212> TYPE: PRT
<213> ORGANISM: Mus musculus

<400> SEQUENCE: 8

Glu Leu Cys Leu Trp Phe Leu Leu Tyr Pro Trp Ala Thr Leu Glu Leu
1               5                   10                  15

Ile Met Cys Thr Trp Asp Ala Trp Lys Glu Thr Leu Glu Tyr Phe Leu
            20                  25                  30


<210> SEQ ID NO 9
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Trp Ser Trp Val Phe Leu Phe Phe Leu Ser Val Thr Thr Gly
1               5                   10                  15

Val His Ser Gln Glu Glu Asp Leu Pro Arg Pro Ser Ile Ser Ala Glu
            20                  25                  30

Pro Gly Thr Val Ile Pro Leu Gly Ser His Val Thr Phe Val Cys Arg
        35                  40                  45

Gly Pro Val Gly Val Gln Thr Phe Arg Leu Glu Arg Glu Ser Arg Ser
    50                  55                  60

Thr Tyr Asn Asp Thr Glu Asp Val Ser Gln Ala Ser Pro Ser Glu Ser
65                  70                  75                  80

Glu Ala Arg Phe Arg Ile Asp Ser Val Ser Glu Gly Asn Ala Gly Pro
                85                  90                  95

Tyr Arg Cys Ile Tyr Tyr Lys Pro Pro Lys Trp Ser Glu Gln Ser Asp
            100                 105                 110

Tyr Leu Glu Leu Leu Val Lys Glu Thr Ser Gly Gly Pro Asp Ser Pro
        115                 120                 125

Asp Thr Glu Pro Gly Ser Ser Ala Gly Pro Thr Gln Arg Pro Ser Asp
    130                 135                 140

Asn Ser His Asn Glu His Ala Pro Ala Ser Gln Gly Leu Lys Ala Glu
145                 150                 155                 160

His Asp Lys Thr His Thr Cys Pro Pro Cys Pro Ala Pro Glu Leu Leu
                165                 170                 175
```

```
Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Asp Glu Leu Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly
385
```

<210> SEQ ID NO 10
<211> LENGTH: 368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95

Leu Leu Val Lys Glu Thr Ser Gly Gly Pro Asp Ser Pro Asp Thr Glu
            100                 105                 110

Pro Gly Ser Ser Ala Gly Pro Thr Gln Arg Pro Ser Asp Asn Ser His
        115                 120                 125

Asn Glu His Ala Pro Ala Ser Gln Gly Leu Lys Ala Glu His Asp Lys
    130                 135                 140
```

```
Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365


<210> SEQ ID NO 11
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Trp Ser Trp Val Phe Leu Phe Phe Leu Ser Val Thr Thr Gly
1               5                   10                  15

Val His Ser Gln Glu Glu Asp Leu Pro Arg Pro Ser Ile Ser Ala Glu
            20                  25                  30

Pro Gly Thr Val Ile Pro Leu Gly Ser His Val Thr Phe Val Cys Arg
        35                  40                  45

Gly Pro Val Gly Val Gln Thr Phe Arg Leu Glu Arg Glu Ser Arg Ser
    50                  55                  60

Thr Tyr Asn Asp Thr Glu Asp Val Ser Gln Ala Ser Pro Ser Glu Ser
65                  70                  75                  80

Glu Ala Arg Phe Arg Ile Asp Ser Val Ser Glu Gly Asn Ala Gly Pro
                85                  90                  95

Tyr Arg Cys Ile Tyr Tyr Lys Pro Pro Lys Trp Ser Glu Gln Ser Asp
            100                 105                 110

Tyr Leu Glu Leu Leu Val Lys Glu Thr Ser Gly Gly Pro Asp Ser Pro
        115                 120                 125

Asp Thr Glu Pro Gly Ser Ser Ala Gly Pro Thr Gln Arg Pro Ser Asp
```

```
    130                 135                 140

Asn Ser His Asn Glu His Ala Pro Ala Ser Gln Gly Leu Lys Ala Glu
145                 150                 155                 160

His Glu Pro Arg Gly Pro Thr Ile Lys Pro Cys Pro Pro Cys Lys Cys
                165                 170                 175

Pro Ala Pro Asn Leu Leu Gly Gly Pro Ser Val Phe Ile Phe Pro Pro
            180                 185                 190

Lys Ile Lys Asp Val Leu Met Ile Ser Leu Ser Pro Ile Val Thr Cys
        195                 200                 205

Val Val Val Asp Val Ser Glu Asp Asp Pro Asp Val Gln Ile Ser Trp
    210                 215                 220

Phe Val Asn Asn Val Glu Val His Thr Ala Gln Thr Gln Thr His Arg
225                 230                 235                 240

Glu Asp Tyr Asn Ser Thr Leu Arg Val Val Ser Ala Leu Pro Ile Gln
                245                 250                 255

His Gln Asp Trp Met Ser Gly Lys Glu Phe Lys Cys Lys Val Asn Asn
            260                 265                 270

Lys Asp Leu Pro Ala Pro Ile Glu Arg Thr Ile Ser Lys Pro Lys Gly
        275                 280                 285

Ser Val Arg Ala Pro Gln Val Tyr Val Leu Pro Pro Pro Glu Glu Glu
    290                 295                 300

Met Thr Lys Lys Gln Val Thr Leu Thr Cys Met Val Thr Asp Phe Met
305                 310                 315                 320

Pro Glu Asp Ile Tyr Val Glu Trp Thr Asn Asn Gly Lys Thr Glu Leu
                325                 330                 335

Asn Tyr Lys Asn Thr Glu Pro Val Leu Asp Ser Asp Gly Ser Tyr Phe
            340                 345                 350

Met Tyr Ser Lys Leu Arg Val Glu Lys Lys Asn Trp Val Glu Arg Asn
        355                 360                 365

Ser Tyr Ser Cys Ser Val Val His Glu Gly Leu His Asn His His Thr
    370                 375                 380

Thr Lys Ser Phe Ser Arg Thr Pro Gly
385                 390


<210> SEQ ID NO 12
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95
```

-continued

```
Leu Leu Val Lys Glu Thr Ser Gly Gly Pro Asp Ser Pro Asp Thr Glu
            100                 105                 110

Pro Gly Ser Ser Ala Gly Pro Thr Gln Arg Pro Ser Asp Asn Ser His
        115                 120                 125

Asn Glu His Ala Pro Ala Ser Gln Gly Leu Lys Ala Glu His Glu Pro
    130                 135                 140

Arg Gly Pro Thr Ile Lys Pro Cys Pro Pro Cys Lys Cys Pro Ala Pro
145                 150                 155                 160

Asn Leu Leu Gly Gly Pro Ser Val Phe Ile Phe Pro Pro Lys Ile Lys
                165                 170                 175

Asp Val Leu Met Ile Ser Leu Ser Pro Ile Val Thr Cys Val Val Val
            180                 185                 190

Asp Val Ser Glu Asp Asp Pro Asp Val Gln Ile Ser Trp Phe Val Asn
        195                 200                 205

Asn Val Glu Val His Thr Ala Gln Thr Gln Thr His Arg Glu Asp Tyr
    210                 215                 220

Asn Ser Thr Leu Arg Val Val Ser Ala Leu Pro Ile Gln His Gln Asp
225                 230                 235                 240

Trp Met Ser Gly Lys Glu Phe Lys Cys Lys Val Asn Asn Lys Asp Leu
                245                 250                 255

Pro Ala Pro Ile Glu Arg Thr Ile Ser Lys Pro Lys Gly Ser Val Arg
            260                 265                 270

Ala Pro Gln Val Tyr Val Leu Pro Pro Pro Glu Glu Glu Met Thr Lys
        275                 280                 285

Lys Gln Val Thr Leu Thr Cys Met Val Thr Asp Phe Met Pro Glu Asp
    290                 295                 300

Ile Tyr Val Glu Trp Thr Asn Asn Gly Lys Thr Glu Leu Asn Tyr Lys
305                 310                 315                 320

Asn Thr Glu Pro Val Leu Asp Ser Asp Gly Ser Tyr Phe Met Tyr Ser
                325                 330                 335

Lys Leu Arg Val Glu Lys Lys Asn Trp Val Glu Arg Asn Ser Tyr Ser
            340                 345                 350

Cys Ser Val Val His Glu Gly Leu His Asn His His Thr Thr Lys Ser
        355                 360                 365

Phe Ser Arg Thr Pro Gly
    370


<210> SEQ ID NO 13
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Trp Ser Trp Val Phe Leu Phe Phe Leu Ser Val Thr Thr Gly
1               5                   10                  15

Val His Ser Gln Glu Gly Ser Leu Pro Asp Ile Thr Ile Phe Pro Asn
            20                  25                  30

Ser Ser Leu Met Ile Ser Gln Gly Thr Phe Val Thr Val Val Cys Ser
        35                  40                  45

Tyr Ser Asp Lys His Asp Leu Tyr Asn Met Val Arg Leu Glu Lys Asp
    50                  55                  60

Gly Ser Thr Phe Met Glu Lys Ser Thr Glu Pro Tyr Lys Thr Glu Asp
65                  70                  75                  80
```

```
Glu Phe Glu Ile Gly Pro Val Asn Glu Thr Ile Thr Gly His Tyr Ser
                85                  90                  95

Cys Ile Tyr Ser Lys Gly Ile Thr Trp Ser Glu Arg Ser Lys Thr Leu
            100                 105                 110

Glu Leu Lys Val Ile Lys Glu Asn Val Ile Gln Thr Pro Ala Pro Gly
        115                 120                 125

Pro Thr Ser Asp Thr Ser Trp Leu Lys Thr Tyr Ser Ile Tyr Glu Pro
    130                 135                 140

Arg Gly Pro Thr Ile Lys Pro Cys Pro Pro Cys Lys Cys Pro Ala Pro
145                 150                 155                 160

Asn Leu Leu Gly Gly Pro Ser Val Phe Ile Phe Pro Pro Lys Ile Lys
                165                 170                 175

Asp Val Leu Met Ile Ser Leu Ser Pro Ile Val Thr Cys Val Val Val
            180                 185                 190

Asp Val Ser Glu Asp Asp Pro Asp Val Gln Ile Ser Trp Phe Val Asn
        195                 200                 205

Asn Val Glu Val His Thr Ala Gln Thr Gln Thr His Arg Glu Asp Tyr
    210                 215                 220

Asn Ser Thr Leu Arg Val Val Ser Ala Leu Pro Ile Gln His Gln Asp
225                 230                 235                 240

Trp Met Ser Gly Lys Glu Phe Lys Cys Lys Val Asn Asn Lys Asp Leu
                245                 250                 255

Pro Ala Pro Ile Glu Arg Thr Ile Ser Lys Pro Lys Gly Ser Val Arg
            260                 265                 270

Ala Pro Gln Val Tyr Val Leu Pro Pro Pro Glu Glu Glu Met Thr Lys
        275                 280                 285

Lys Gln Val Thr Leu Thr Cys Met Val Thr Asp Phe Met Pro Glu Asp
    290                 295                 300

Ile Tyr Val Glu Trp Thr Asn Asn Gly Lys Thr Glu Leu Asn Tyr Lys
305                 310                 315                 320

Asn Thr Glu Pro Val Leu Asp Ser Asp Gly Ser Tyr Phe Met Tyr Ser
                325                 330                 335

Lys Leu Arg Val Glu Lys Lys Asn Trp Val Glu Arg Asn Ser Tyr Ser
            340                 345                 350

Cys Ser Val Val His Glu Gly Leu His Asn His His Thr Thr Lys Ser
        355                 360                 365

Phe Ser Arg Thr Pro Gly
    370
```

```
<210> SEQ ID NO 14
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Glu Gly Ser Leu Pro Asp Ile Thr Ile Phe Pro Asn Ser Ser Leu
1               5                   10                  15

Met Ile Ser Gln Gly Thr Phe Val Thr Val Val Cys Ser Tyr Ser Asp
            20                  25                  30

Lys His Asp Leu Tyr Asn Met Val Arg Leu Glu Lys Asp Gly Ser Thr
        35                  40                  45

Phe Met Glu Lys Ser Thr Glu Pro Tyr Lys Thr Glu Asp Glu Phe Glu
```

```
    50                  55                  60

Ile Gly Pro Val Asn Glu Thr Ile Thr Gly His Tyr Ser Cys Ile Tyr
65                  70                  75                  80

Ser Lys Gly Ile Thr Trp Ser Glu Arg Ser Lys Thr Leu Glu Leu Lys
                85                  90                  95

Val Ile Lys Glu Asn Val Ile Gln Thr Pro Ala Pro Gly Pro Thr Ser
            100                 105                 110

Asp Thr Ser Trp Leu Lys Thr Tyr Ser Ile Tyr Glu Pro Arg Gly Pro
        115                 120                 125

Thr Ile Lys Pro Cys Pro Pro Cys Lys Cys Pro Ala Pro Asn Leu Leu
    130                 135                 140

Gly Gly Pro Ser Val Phe Ile Phe Pro Pro Lys Ile Lys Asp Val Leu
145                 150                 155                 160

Met Ile Ser Leu Ser Pro Ile Val Thr Cys Val Val Val Asp Val Ser
                165                 170                 175

Glu Asp Asp Pro Asp Val Gln Ile Ser Trp Phe Val Asn Asn Val Glu
            180                 185                 190

Val His Thr Ala Gln Thr Gln Thr His Arg Glu Asp Tyr Asn Ser Thr
        195                 200                 205

Leu Arg Val Val Ser Ala Leu Pro Ile Gln His Gln Asp Trp Met Ser
    210                 215                 220

Gly Lys Glu Phe Lys Cys Lys Val Asn Asn Lys Asp Leu Pro Ala Pro
225                 230                 235                 240

Ile Glu Arg Thr Ile Ser Lys Pro Lys Gly Ser Val Arg Ala Pro Gln
                245                 250                 255

Val Tyr Val Leu Pro Pro Pro Glu Glu Glu Met Thr Lys Lys Gln Val
            260                 265                 270

Thr Leu Thr Cys Met Val Thr Asp Phe Met Pro Glu Asp Ile Tyr Val
        275                 280                 285

Glu Trp Thr Asn Asn Gly Lys Thr Glu Leu Asn Tyr Lys Asn Thr Glu
    290                 295                 300

Pro Val Leu Asp Ser Asp Gly Ser Tyr Phe Met Tyr Ser Lys Leu Arg
305                 310                 315                 320

Val Glu Lys Lys Asn Trp Val Glu Arg Asn Ser Tyr Ser Cys Ser Val
                325                 330                 335

Val His Glu Gly Leu His Asn His His Thr Thr Lys Ser Phe Ser Arg
            340                 345                 350

Thr Pro Gly
        355


<210> SEQ ID NO 15
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Glu Trp Ser Trp Val Phe Leu Phe Phe Leu Ser Val Thr Thr Gly
1               5                   10                  15

Val His Ser Gln Glu Gly Ala Leu Pro Arg Pro Ser Ile Ser Ala Glu
            20                  25                  30

Pro Gly Thr Val Ile Ser Pro Gly Ser His Val Thr Phe Met Cys Arg
        35                  40                  45
```

Gly Pro Val Gly Val Gln Thr Phe Arg Leu Glu Arg Glu Asp Arg Ala
50 55 60

Lys Tyr Lys Asp Ser Tyr Asn Val Phe Arg Leu Gly Pro Ser Glu Ser
65 70 75 80

Glu Ala Arg Phe His Ile Asp Ser Val Ser Glu Gly Asn Ala Gly Leu
85 90 95

Tyr Arg Cys Leu Tyr Tyr Lys Pro Pro Gly Trp Ser Glu His Ser Asp
100 105 110

Phe Leu Glu Leu Leu Val Lys Glu Ser Ser Gly Gly Pro Asp Ser Pro
115 120 125

Asp Thr Glu Pro Gly Ser Ser Ala Gly Thr Val Pro Gly Thr Glu Ala
130 135 140

Ser Gly Phe Asp Ala Pro Asp Lys Thr His Thr Cys Pro Pro Cys Pro
145 150 155 160

Ala Pro Glu Leu Leu Gly Gly Pro Ser Val Phe Leu Phe Pro Pro Lys
165 170 175

Pro Lys Asp Thr Leu Met Ile Ser Arg Thr Pro Glu Val Thr Cys Val
180 185 190

Val Val Asp Val Ser His Glu Asp Pro Glu Val Lys Phe Asn Trp Tyr
195 200 205

Val Asp Gly Val Glu Val His Asn Ala Lys Thr Lys Pro Arg Glu Glu
210 215 220

Gln Tyr Asn Ser Thr Tyr Arg Val Val Ser Val Leu Thr Val Leu His
225 230 235 240

Gln Asp Trp Leu Asn Gly Lys Glu Tyr Lys Cys Lys Val Ser Asn Lys
245 250 255

Ala Leu Pro Ala Pro Ile Glu Lys Thr Ile Ser Lys Ala Lys Gly Gln
260 265 270

Pro Arg Glu Pro Gln Val Tyr Thr Leu Pro Pro Ser Arg Asp Glu Leu
275 280 285

Thr Lys Asn Gln Val Ser Leu Thr Cys Leu Val Lys Gly Phe Tyr Pro
290 295 300

Ser Asp Ile Ala Val Glu Trp Glu Ser Asn Gly Gln Pro Glu Asn Asn
305 310 315 320

Tyr Lys Thr Thr Pro Pro Val Leu Asp Ser Asp Gly Ser Phe Phe Leu
325 330 335

Tyr Ser Lys Leu Thr Val Asp Lys Ser Arg Trp Gln Gln Gly Asn Val
340 345 350

Phe Ser Cys Ser Val Met His Glu Ala Leu His Asn His Tyr Thr Gln
355 360 365

Lys Ser Leu Ser Leu Ser Pro Gly
370 375

<210> SEQ ID NO 16
<211> LENGTH: 357
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

Gln Glu Gly Ala Leu Pro Arg Pro Ser Ile Ser Ala Glu Pro Gly Thr
1 5 10 15

Val Ile Ser Pro Gly Ser His Val Thr Phe Met Cys Arg Gly Pro Val
20 25 30

```
Gly Val Gln Thr Phe Arg Leu Glu Arg Glu Asp Arg Ala Lys Tyr Lys
        35                  40                  45

Asp Ser Tyr Asn Val Phe Arg Leu Gly Pro Ser Glu Ser Glu Ala Arg
    50                  55                  60

Phe His Ile Asp Ser Val Ser Glu Gly Asn Ala Gly Leu Tyr Arg Cys
65                  70                  75                  80

Leu Tyr Tyr Lys Pro Pro Gly Trp Ser Glu His Ser Asp Phe Leu Glu
                85                  90                  95

Leu Leu Val Lys Glu Ser Ser Gly Gly Pro Asp Ser Pro Asp Thr Glu
            100                 105                 110

Pro Gly Ser Ser Ala Gly Thr Val Pro Gly Thr Glu Ala Ser Gly Phe
        115                 120                 125

Asp Ala Pro Asp Lys Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly
        355
```

<210> SEQ ID NO 17
<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Met Glu Trp Ser Trp Val Phe Leu Phe Phe Leu Ser Val Thr Thr Gly
1               5                   10                  15

Val His Ser Gln Glu Gly Ala Leu Pro Arg Pro Ser Ile Ser Ala Glu
```

```
            20                  25                  30

Pro Gly Thr Val Ile Ser Pro Gly Ser His Val Thr Phe Met Cys Arg
        35                  40                  45

Gly Pro Val Gly Val Gln Thr Phe Arg Leu Glu Arg Glu Asp Arg Ala
    50                  55                  60

Lys Tyr Lys Asp Ser Tyr Asn Val Phe Arg Leu Gly Pro Ser Glu Ser
65                  70                  75                  80

Glu Ala Arg Phe His Ile Asp Ser Val Ser Glu Gly Asn Ala Gly Leu
                85                  90                  95

Tyr Arg Cys Leu Tyr Tyr Lys Pro Pro Gly Trp Ser Glu His Ser Asp
            100                 105                 110

Phe Leu Glu Leu Leu Val Lys Glu Ser Ser Gly Gly Pro Asp Ser Pro
        115                 120                 125

Asp Thr Glu Pro Gly Ser Ser Ala Gly Thr Val Pro Gly Thr Glu Ala
    130                 135                 140

Ser Gly Phe Asp Ala Pro Glu Pro Arg Gly Pro Thr Ile Lys Pro Cys
145                 150                 155                 160

Pro Pro Cys Lys Cys Pro Ala Pro Asn Leu Leu Gly Gly Pro Ser Val
                165                 170                 175

Phe Ile Phe Pro Pro Lys Ile Lys Asp Val Leu Met Ile Ser Leu Ser
            180                 185                 190

Pro Ile Val Thr Cys Val Val Val Asp Val Ser Glu Asp Asp Pro Asp
        195                 200                 205

Val Gln Ile Ser Trp Phe Val Asn Asn Val Glu Val His Thr Ala Gln
    210                 215                 220

Thr Gln Thr His Arg Glu Asp Tyr Asn Ser Thr Leu Arg Val Val Ser
225                 230                 235                 240

Ala Leu Pro Ile Gln His Gln Asp Trp Met Ser Gly Lys Glu Phe Lys
                245                 250                 255

Cys Lys Val Asn Asn Lys Asp Leu Pro Ala Pro Ile Glu Arg Thr Ile
            260                 265                 270

Ser Lys Pro Lys Gly Ser Val Arg Ala Pro Gln Val Tyr Val Leu Pro
        275                 280                 285

Pro Pro Glu Glu Glu Met Thr Lys Lys Gln Val Thr Leu Thr Cys Met
    290                 295                 300

Val Thr Asp Phe Met Pro Glu Asp Ile Tyr Val Glu Trp Thr Asn Asn
305                 310                 315                 320

Gly Lys Thr Glu Leu Asn Tyr Lys Asn Thr Glu Pro Val Leu Asp Ser
                325                 330                 335

Asp Gly Ser Tyr Phe Met Tyr Ser Lys Leu Arg Val Glu Lys Lys Asn
            340                 345                 350

Trp Val Glu Arg Asn Ser Tyr Ser Cys Ser Val Val His Glu Gly Leu
        355                 360                 365

His Asn His His Thr Thr Lys Ser Phe Ser Arg Thr Pro Gly
    370                 375                 380


<210> SEQ ID NO 18
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

```
Gln Glu Gly Ala Leu Pro Arg Pro Ser Ile Ser Ala Glu Pro Gly Thr
1               5                   10                  15

Val Ile Ser Pro Gly Ser His Val Thr Phe Met Cys Arg Gly Pro Val
            20                  25                  30

Gly Val Gln Thr Phe Arg Leu Glu Arg Glu Asp Arg Ala Lys Tyr Lys
        35                  40                  45

Asp Ser Tyr Asn Val Phe Arg Leu Gly Pro Ser Glu Ser Glu Ala Arg
    50                  55                  60

Phe His Ile Asp Ser Val Ser Glu Gly Asn Ala Gly Leu Tyr Arg Cys
65                  70                  75                  80

Leu Tyr Tyr Lys Pro Pro Gly Trp Ser Glu His Ser Asp Phe Leu Glu
                85                  90                  95

Leu Leu Val Lys Glu Ser Ser Gly Gly Pro Asp Ser Pro Asp Thr Glu
            100                 105                 110

Pro Gly Ser Ser Ala Gly Thr Val Pro Gly Thr Glu Ala Ser Gly Phe
        115                 120                 125

Asp Ala Pro Glu Pro Arg Gly Pro Thr Ile Lys Pro Cys Pro Pro Cys
    130                 135                 140

Lys Cys Pro Ala Pro Asn Leu Leu Gly Gly Pro Ser Val Phe Ile Phe
145                 150                 155                 160

Pro Pro Lys Ile Lys Asp Val Leu Met Ile Ser Leu Ser Pro Ile Val
                165                 170                 175

Thr Cys Val Val Val Asp Val Ser Glu Asp Asp Pro Asp Val Gln Ile
            180                 185                 190

Ser Trp Phe Val Asn Asn Val Glu Val His Thr Ala Gln Thr Gln Thr
        195                 200                 205

His Arg Glu Asp Tyr Asn Ser Thr Leu Arg Val Val Ser Ala Leu Pro
    210                 215                 220

Ile Gln His Gln Asp Trp Met Ser Gly Lys Glu Phe Lys Cys Lys Val
225                 230                 235                 240

Asn Asn Lys Asp Leu Pro Ala Pro Ile Glu Arg Thr Ile Ser Lys Pro
                245                 250                 255

Lys Gly Ser Val Arg Ala Pro Gln Val Tyr Val Leu Pro Pro Pro Glu
            260                 265                 270

Glu Glu Met Thr Lys Lys Gln Val Thr Leu Thr Cys Met Val Thr Asp
        275                 280                 285

Phe Met Pro Glu Asp Ile Tyr Val Glu Trp Thr Asn Asn Gly Lys Thr
    290                 295                 300

Glu Leu Asn Tyr Lys Asn Thr Glu Pro Val Leu Asp Ser Asp Gly Ser
305                 310                 315                 320

Tyr Phe Met Tyr Ser Lys Leu Arg Val Glu Lys Lys Asn Trp Val Glu
                325                 330                 335

Arg Asn Ser Tyr Ser Cys Ser Val Val His Glu Gly Leu His Asn His
            340                 345                 350

His Thr Thr Lys Ser Phe Ser Arg Thr Pro Gly
        355                 360


<210> SEQ ID NO 19
<211> LENGTH: 112
<212> TYPE: PRT
<213> ORGANISM: Mus musculus

<400> SEQUENCE: 19

Asp Ile Val Met Thr Gln Ala Ala Phe Ser Asn Pro Val Thr Leu Gly
1               5                   10                  15
```

Thr Ser Ala Ser Ile Ser Cys Arg Ser Ser Lys Ser Leu Leu His Ser
20 25 30

Asn Gly Ile Thr Tyr Leu Tyr Trp Tyr Leu Gln Lys Pro Gly Gln Ser
35 40 45

Pro Gln Val Leu Ile Tyr Gln Met Ser Ser Leu Ala Ser Gly Val Pro
50 55 60

Asp Arg Phe Ser Ser Ser Gly Ser Gly Thr Glu Phe Thr Leu Arg Ile
65 70 75 80

Ser Arg Val Glu Ala Glu Asp Val Gly Val Tyr Tyr Cys Ala Gln Asn
85 90 95

Leu Glu Leu Pro Leu Thr Phe Gly Ala Gly Thr Lys Leu Glu Leu Lys
100 105 110

<210> SEQ ID NO 20
<211> LENGTH: 16
<212> TYPE: PRT
<213> ORGANISM: Mus musculus

<400> SEQUENCE: 20

Arg Ser Ser Lys Ser Leu Leu His Ser Asn Gly Ile Thr Tyr Leu Tyr
1 5 10 15

<210> SEQ ID NO 21
<211> LENGTH: 7
<212> TYPE: PRT
<213> ORGANISM: Mus musculus

<400> SEQUENCE: 21

Gln Met Ser Ser Leu Ala Ser
1 5

<210> SEQ ID NO 22
<211> LENGTH: 9
<212> TYPE: PRT
<213> ORGANISM: Mus musculus

<400> SEQUENCE: 22

Ala Gln Asn Leu Glu Leu Pro Leu Thr
1 5

<210> SEQ ID NO 23
<211> LENGTH: 118
<212> TYPE: PRT
<213> ORGANISM: Mus musculus

<400> SEQUENCE: 23

Gln Val Gln Leu Gln Gln Ser Gly Pro Glu Leu Val Lys Pro Gly Ala
1 5 10 15

Ser Val Lys Leu Ser Cys Lys Ala Ser Gly Tyr Thr Phe Thr Ser Tyr
20 25 30

Asp Ile Asn Trp Val Lys Gln Arg Pro Gly Gln Gly Leu Glu Trp Ile
35 40 45

Gly Trp Ile Tyr Pro Arg Asp Gly Ser Thr Lys Tyr Asn Glu Lys Leu
50 55 60

Lys Gly Lys Ala Thr Leu Thr Val Asp Thr Ser Ser Arg Thr Ala Tyr
65 70 75 80

Met Glu Leu His Ser Leu Thr Ser Glu Asp Ser Ala Val Tyr Phe Cys
85 90 95

Ala Arg Gly Gly Tyr Tyr Asp Tyr Asp Gly Tyr Trp Gly Gln Gly Thr

```
            100                 105                 110

Leu Val Thr Val Ser Ala
        115


<210> SEQ ID NO 24
<211> LENGTH: 5
<212> TYPE: PRT
<213> ORGANISM: Mus musculus

<400> SEQUENCE: 24

Ser Tyr Asp Ile Asn
1               5


<210> SEQ ID NO 25
<211> LENGTH: 17
<212> TYPE: PRT
<213> ORGANISM: Mus musculus

<400> SEQUENCE: 25

Trp Ile Tyr Pro Arg Asp Gly Ser Thr Lys Tyr Asn Glu Lys Leu Lys
1               5                   10                  15

Gly


<210> SEQ ID NO 26
<211> LENGTH: 9
<212> TYPE: PRT
<213> ORGANISM: Mus musculus

<400> SEQUENCE: 26

Gly Gly Tyr Tyr Asp Tyr Asp Gly Tyr
1               5


<210> SEQ ID NO 27
<211> LENGTH: 107
<212> TYPE: PRT
<213> ORGANISM: Mus musculus

<400> SEQUENCE: 27

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Leu
                85                  90                  95

Thr Phe Gly Ala Gly Thr Lys Leu Glu Leu Lys
            100                 105


<210> SEQ ID NO 28
<211> LENGTH: 11
<212> TYPE: PRT
<213> ORGANISM: Mus musculus

<400> SEQUENCE: 28

Leu Ala Ser Gln Thr Ile Gly Thr Trp Leu Ala
1               5                   10
```

<210> SEQ ID NO 29
<211> LENGTH: 7
<212> TYPE: PRT
<213> ORGANISM: Mus musculus

<400> SEQUENCE: 29

Ala Ala Thr Ser Leu Ala Asp
1               5

<210> SEQ ID NO 30
<211> LENGTH: 9
<212> TYPE: PRT
<213> ORGANISM: Mus musculus

<400> SEQUENCE: 30

Gln Gln Leu Tyr Ser Thr Pro Leu Thr
1               5

<210> SEQ ID NO 31
<211> LENGTH: 119
<212> TYPE: PRT
<213> ORGANISM: Mus musculus

<400> SEQUENCE: 31

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Tyr Trp Val Arg Gln Ala Pro Gly Lys Gly Leu Glu Trp Val
        35                  40                  45

Ala Arg Ile Arg Ser Lys Ser Ser Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Arg Tyr
                85                  90                  95

Tyr Cys Val Arg Gly Gly Ser Gly Phe Phe Ala Tyr Trp Gly Gln Gly
            100                 105                 110

Thr Leu Val Thr Val Ser Ala
        115

<210> SEQ ID NO 32
<211> LENGTH: 5
<212> TYPE: PRT
<213> ORGANISM: Mus musculus

<400> SEQUENCE: 32

Thr Asn Ala Met Tyr
1               5

<210> SEQ ID NO 33
<211> LENGTH: 19
<212> TYPE: PRT
<213> ORGANISM: Mus musculus

<400> SEQUENCE: 33

Arg Ile Arg Ser Lys Ser Ser Asn Tyr Ala Thr Tyr Tyr Ala Asp Ser
1               5                   10                  15

Val Lys Asp

<210> SEQ ID NO 34
<211> LENGTH: 8
<212> TYPE: PRT
<213> ORGANISM: Mus musculus

<400> SEQUENCE: 34

Gly Gly Ser Gly Phe Phe Ala Tyr
1               5

<210> SEQ ID NO 35
<211> LENGTH: 113
<212> TYPE: PRT
<213> ORGANISM: Mus musculus

<400> SEQUENCE: 35

Asp Ile Val Met Lys Gln Ser Pro Ser Ser Leu Arg Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Ala Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Leu Glu Ile
            100                 105                 110

Lys

<210> SEQ ID NO 36
<211> LENGTH: 17
<212> TYPE: PRT
<213> ORGANISM: Mus musculus

<400> SEQUENCE: 36

Lys Ser Ser Gln Ser Leu Leu Asn Ser Gly Asn Gln Lys Asn Tyr Leu
1               5                   10                  15

Ala

<210> SEQ ID NO 37
<211> LENGTH: 7
<212> TYPE: PRT
<213> ORGANISM: Mus musculus

<400> SEQUENCE: 37

Gly Ala Ser Thr Arg Glu Ser
1               5

<210> SEQ ID NO 38
<211> LENGTH: 9
<212> TYPE: PRT
<213> ORGANISM: Mus musculus

<400> SEQUENCE: 38

Gln Asn Asp His Ser Tyr Pro Phe Thr
1               5

<210> SEQ ID NO 39

<211> LENGTH: 123
<212> TYPE: PRT
<213> ORGANISM: Mus musculus

<400> SEQUENCE: 39

Gln Ile Gln Leu Gln Gln Ser Gly Ala Glu Leu Ala Arg Pro Gly Ala
1               5                   10                  15

Ser Val Lys Leu Pro Cys Lys Ala Ser Asp Tyr Ile Phe Ile Ser Tyr
            20                  25                  30

Gly Leu Asn Trp Val Arg Gln Thr Thr Gly Gln Gly Leu Glu Trp Ile
        35                  40                  45

Gly Glu Ile Tyr Pro Arg Ser Gly His Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Arg Ser Val Phe Tyr Asp Tyr Asp Lys Asn Gly Phe Asp Tyr
            100                 105                 110

Trp Gly Gln Gly Thr Thr Leu Thr Val Ser Ser
        115                 120

<210> SEQ ID NO 40
<211> LENGTH: 5
<212> TYPE: PRT
<213> ORGANISM: Mus musculus

<400> SEQUENCE: 40

Ser Tyr Gly Leu Asn
1               5

<210> SEQ ID NO 41
<211> LENGTH: 17
<212> TYPE: PRT
<213> ORGANISM: Mus musculus

<400> SEQUENCE: 41

Glu Ile Tyr Pro Arg Ser Gly His Thr Tyr Tyr Asn Glu Lys Phe Lys
1               5                   10                  15

Gly

<210> SEQ ID NO 42
<211> LENGTH: 14
<212> TYPE: PRT
<213> ORGANISM: Mus musculus

<400> SEQUENCE: 42

Arg Ser Val Phe Tyr Asp Tyr Asp Lys Asn Gly Phe Asp Tyr
1               5                   10

<210> SEQ ID NO 43
<211> LENGTH: 107
<212> TYPE: PRT
<213> ORGANISM: Mus musculus

<400> SEQUENCE: 43

Asp Ile Gln Met Thr Gln Ser Pro Ser Ser Leu Ser Ala Ser Leu Gly
1               5                   10                  15

Glu Arg Val Ser Phe Ser Cys Arg Ala Ser Gln Asp Ile Gly Ser Ser
            20                  25                  30

-continued

```
Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Glu Tyr Tyr Cys Leu Gln Tyr Asp Ser Phe Pro Tyr
                85                  90                  95

Thr Phe Gly Gly Gly Thr Lys Leu Glu Ile Lys
            100                 105


<210> SEQ ID NO 44
<211> LENGTH: 11
<212> TYPE: PRT
<213> ORGANISM: Mus musculus

<400> SEQUENCE: 44

Arg Ala Ser Gln Asp Ile Gly Ser Ser Leu Asn
1               5                   10


<210> SEQ ID NO 45
<211> LENGTH: 7
<212> TYPE: PRT
<213> ORGANISM: Mus musculus

<400> SEQUENCE: 45

Ala Thr Ser Ser Leu Asp Ser
1               5


<210> SEQ ID NO 46
<211> LENGTH: 9
<212> TYPE: PRT
<213> ORGANISM: Mus musculus

<400> SEQUENCE: 46

Leu Gln Tyr Asp Ser Phe Pro Tyr Thr
1               5


<210> SEQ ID NO 47
<211> LENGTH: 114
<212> TYPE: PRT
<213> ORGANISM: Mus musculus

<400> SEQUENCE: 47

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Arg Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gln Leu Phe Ala Tyr Trp Gly Gln Gly Thr Leu Val Thr Val
            100                 105                 110

Ser Ala
```

<210> SEQ ID NO 48
<211> LENGTH: 5
<212> TYPE: PRT
<213> ORGANISM: Mus musculus

<400> SEQUENCE: 48

Ser Tyr Gly Ile Ser
1               5

<210> SEQ ID NO 49
<211> LENGTH: 17
<212> TYPE: PRT
<213> ORGANISM: Mus musculus

<400> SEQUENCE: 49

Glu Ile Tyr Pro Arg Arg Gly Asn Thr Tyr Tyr Asn Glu Lys Phe Lys
1               5                   10                  15

Gly

<210> SEQ ID NO 50
<211> LENGTH: 5
<212> TYPE: PRT
<213> ORGANISM: Mus musculus

<400> SEQUENCE: 50

Gln Leu Phe Ala Tyr
1               5

<210> SEQ ID NO 51
<211> LENGTH: 107
<212> TYPE: PRT
<213> ORGANISM: Mus musculus

<400> SEQUENCE: 51

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Glu Ile Lys
            100                 105

<210> SEQ ID NO 52
<211> LENGTH: 11
<212> TYPE: PRT
<213> ORGANISM: Mus musculus

<400> SEQUENCE: 52

Arg Ala Ser Gln Asp Ile Ser Asn Tyr Leu Asn
1               5                   10

<210> SEQ ID NO 53
<211> LENGTH: 7
<212> TYPE: PRT

<213> ORGANISM: Mus musculus

<400> SEQUENCE: 53

Tyr Thr Ser Arg Leu His Ser
1 5

<210> SEQ ID NO 54
<211> LENGTH: 9
<212> TYPE: PRT
<213> ORGANISM: Mus musculus

<400> SEQUENCE: 54

Gln Gln Gly Asn Thr Leu Pro Arg Thr
1 5

<210> SEQ ID NO 55
<211> LENGTH: 118
<212> TYPE: PRT
<213> ORGANISM: Mus musculus

<400> SEQUENCE: 55

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Ser Phe Thr Gly Tyr
20 25 30

Phe Met Asn Trp Val Lys Gln Ser Pro Glu Lys Ser Leu Glu Trp Ile
35 40 45

Gly Glu Ile His Pro Ser Thr Gly Ser Ile Ile Tyr Asn Gln Lys Phe
50 55 60

Lys Ala Lys Ala Thr Leu Thr Ile Asp Lys Ser Ser Ser Thr Ala Tyr
65 70 75 80

Met Gln Leu Lys Ser Leu Thr Ser Glu Asp Ser Ala Val Tyr Tyr Cys
85 90 95

Ala Arg Phe Asp Tyr Ser Asn Ser Phe Ala Tyr Trp Gly Gln Gly Thr
100 105 110

Leu Val Thr Val Ser Ala
115

<210> SEQ ID NO 56
<211> LENGTH: 5
<212> TYPE: PRT
<213> ORGANISM: Mus musculus

<400> SEQUENCE: 56

Gly Tyr Phe Met Asn
1 5

<210> SEQ ID NO 57
<211> LENGTH: 17
<212> TYPE: PRT
<213> ORGANISM: Mus musculus

<400> SEQUENCE: 57

Glu Ile His Pro Ser Thr Gly Ser Ile Ile Tyr Asn Gln Lys Phe Lys
1 5 10 15

Ala

<210> SEQ ID NO 58
<211> LENGTH: 9
<212> TYPE: PRT
<213> ORGANISM: Mus musculus

<400> SEQUENCE: 58

Phe Asp Tyr Ser Asn Ser Phe Ala Tyr
1 5

<210> SEQ ID NO 59
<211> LENGTH: 107
<212> TYPE: PRT
<213> ORGANISM: Mus musculus

<400> SEQUENCE: 59

Asp Ile Gln Met Thr Gln Ser Pro Ala Ser Gln Ser Ala Ser Leu Gly
1 5 10 15

Glu Ser Val Thr Ile Thr Cys Leu Ala Ser Gln Thr Ile Gly Thr Trp
20 25 30

Leu Ala Trp Tyr Gln Gln Lys Pro Gly Lys Ser Pro Gln Leu Leu Ile
35 40 45

Tyr Ala Ala Thr Ser Leu Ala Asp Gly Val Pro Ser Arg Phe Ser Gly
50 55 60

Ser Gly Ser Gly Thr Lys Phe Ser Phe Lys Ile Ser Ser Leu Gln Ala
65 70 75 80

Glu Asp Phe Val Ser Tyr Tyr Cys Gln Gln Leu Tyr Ser Thr Pro Leu
85 90 95

Thr Phe Gly Ala Gly Thr Lys Leu Glu Leu Lys
100 105

<210> SEQ ID NO 60
<211> LENGTH: 11
<212> TYPE: PRT
<213> ORGANISM: Mus musculus

<400> SEQUENCE: 60

Leu Ala Ser Gln Thr Ile Gly Thr Trp Leu Ala
1 5 10

<210> SEQ ID NO 61
<211> LENGTH: 7
<212> TYPE: PRT
<213> ORGANISM: Mus musculus

<400> SEQUENCE: 61

Ala Ala Thr Ser Leu Ala Asp
1 5

<210> SEQ ID NO 62
<211> LENGTH: 9
<212> TYPE: PRT
<213> ORGANISM: Mus musculus

<400> SEQUENCE: 62

Gln Gln Leu Tyr Ser Thr Pro Leu Thr
1 5

<210> SEQ ID NO 63
<211> LENGTH: 117
<212> TYPE: PRT
<213> ORGANISM: Mus musculus

<400> SEQUENCE: 63

Glu Val Gln Leu Val Glu Ser Gly Gly Gly Leu Val Gln Pro Lys Gly
1 5 10 15

```
Ser Leu Lys Leu Ser Cys Ala Ala Ser Gly Phe Ser Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Glu Thr Tyr Tyr Ala Asp
    50                  55                  60

Ser Val Lys Asp Arg Phe Thr Ile Ser Arg Asp Asp Ser Glu Ser Met
65                  70                  75                  80

Val Tyr Leu Gln Met Asn Asn Leu Lys Thr Glu Asp Thr Ala Met Tyr
                85                  90                  95

Tyr Cys Val Arg Ser Leu Trp Phe Val Tyr Trp Gly Gln Gly Thr Leu
            100                 105                 110

Val Thr Val Ser Ala
        115


<210> SEQ ID NO 64
<211> LENGTH: 5
<212> TYPE: PRT
<213> ORGANISM: Mus musculus

<400> SEQUENCE: 64

Ile Asn Ala Met Asn
1               5


<210> SEQ ID NO 65
<211> LENGTH: 19
<212> TYPE: PRT
<213> ORGANISM: Mus musculus

<400> SEQUENCE: 65

Arg Ile Arg Ser Lys Ser Asn Asn Tyr Glu Thr Tyr Tyr Ala Asp Ser
1               5                   10                  15

Val Lys Asp


<210> SEQ ID NO 66
<211> LENGTH: 6
<212> TYPE: PRT
<213> ORGANISM: Mus musculus

<400> SEQUENCE: 66

Ser Leu Trp Phe Val Tyr
1               5


<210> SEQ ID NO 67
<211> LENGTH: 108
<212> TYPE: PRT
<213> ORGANISM: Mus musculus

<400> SEQUENCE: 67

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Val Gln Gln Lys Pro Gly Lys Ser Pro Lys Thr Leu Ile
        35                  40                  45

Asp Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80
```

```
Glu Asp Met Gly Ile Tyr Tyr Cys Leu Gln Tyr Asp Glu Phe Pro Pro
                85                  90                  95

Tyr Thr Phe Gly Gly Gly Thr Lys Leu Glu Ile Lys
            100                 105


<210> SEQ ID NO 68
<211> LENGTH: 11
<212> TYPE: PRT
<213> ORGANISM: Mus musculus

<400> SEQUENCE: 68

Lys Ala Ser Gln Asp Ile Asn Ser Tyr Leu Ser
1               5                   10


<210> SEQ ID NO 69
<211> LENGTH: 7
<212> TYPE: PRT
<213> ORGANISM: Mus musculus

<400> SEQUENCE: 69

Arg Ala Asn Arg Leu Val Asp
1               5


<210> SEQ ID NO 70
<211> LENGTH: 10
<212> TYPE: PRT
<213> ORGANISM: Mus musculus

<400> SEQUENCE: 70

Leu Gln Tyr Asp Glu Phe Pro Pro Tyr Thr
1               5                   10


<210> SEQ ID NO 71
<211> LENGTH: 113
<212> TYPE: PRT
<213> ORGANISM: Mus musculus

<400> SEQUENCE: 71

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Phe Ser Gly His Thr Lys Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Tyr Glu Asp Ser Ala Val Tyr Tyr Cys
                85                  90                  95

Ala Arg Asn Phe Asp Gln Trp Gly Gln Gly Thr Thr Leu Thr Val Ser
            100                 105                 110

Ser


<210> SEQ ID NO 72
<211> LENGTH: 5
<212> TYPE: PRT
<213> ORGANISM: Mus musculus

<400> SEQUENCE: 72

Ser Tyr Trp Met His
```

1 5

<210> SEQ ID NO 73
<211> LENGTH: 17
<212> TYPE: PRT
<213> ORGANISM: Mus musculus

<400> SEQUENCE: 73

Tyr Ile Asn Pro Phe Ser Gly His Thr Lys Tyr Asn Gln Lys Phe Lys
1 5 10 15

Asp

<210> SEQ ID NO 74
<211> LENGTH: 4
<212> TYPE: PRT
<213> ORGANISM: Mus musculus

<400> SEQUENCE: 74

Asn Phe Asp Gln
1

<210> SEQ ID NO 75
<211> LENGTH: 107
<212> TYPE: PRT
<213> ORGANISM: Mus musculus

<400> SEQUENCE: 75

Asp Ile Val Met Thr Gln Ser His Lys Phe Met Ser Thr Ser Val Gly
1 5 10 15

Asp Arg Val Ser Ile Thr Cys Lys Ala Ser Gln Asn Val Gly Thr Ala
20 25 30

Val Ala Trp Tyr Gln Gln Lys Pro Gly Gln Ser Pro Lys Leu Leu Ile
35 40 45

Tyr Trp Ala Ser Ile Arg His Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Asp Tyr Phe Cys Gln Gln Tyr Ser Ser His Pro Tyr
85 90 95

Thr Phe Gly Gly Gly Thr Lys Leu Glu Ile Lys
100 105

<210> SEQ ID NO 76
<211> LENGTH: 11
<212> TYPE: PRT
<213> ORGANISM: Mus musculus

<400> SEQUENCE: 76

Lys Ala Ser Gln Asn Val Gly Thr Ala Val Ala
1 5 10

<210> SEQ ID NO 77
<211> LENGTH: 7
<212> TYPE: PRT
<213> ORGANISM: Mus musculus

<400> SEQUENCE: 77

Trp Ala Ser Ile Arg His Thr
1 5

<210> SEQ ID NO 78

<211> LENGTH: 9
<212> TYPE: PRT
<213> ORGANISM: Mus musculus

<400> SEQUENCE: 78

Gln Gln Tyr Ser Ser His Pro Tyr Thr
1 5

<210> SEQ ID NO 79
<211> LENGTH: 115
<212> TYPE: PRT
<213> ORGANISM: Mus musculus

<400> SEQUENCE: 79

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr Thr Tyr
20 25 30

Tyr Met Asn Trp Val Lys Gln Ser His Gly Lys Ser Leu Glu Trp Ile
35 40 45

Gly Asn Ile Asn Pro Asp Asn Gly Ile Thr Ser Tyr Asn Gln Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Ala Arg Gly Lys Ser Leu Ala Tyr Trp Gly Gln Gly Thr Leu Val Thr
100 105 110

Val Ser Ala
115

<210> SEQ ID NO 80
<211> LENGTH: 5
<212> TYPE: PRT
<213> ORGANISM: Mus musculus

<400> SEQUENCE: 80

Thr Tyr Tyr Met Asn
1 5

<210> SEQ ID NO 81
<211> LENGTH: 17
<212> TYPE: PRT
<213> ORGANISM: Mus musculus

<400> SEQUENCE: 81

Asn Ile Asn Pro Asp Asn Gly Ile Thr Ser Tyr Asn Gln Lys Phe Lys
1 5 10 15

Gly

<210> SEQ ID NO 82
<211> LENGTH: 6
<212> TYPE: PRT
<213> ORGANISM: Mus musculus

<400> SEQUENCE: 82

Gly Lys Ser Leu Ala Tyr
1 5

<210> SEQ ID NO 83
<211> LENGTH: 112

<212> TYPE: PRT
<213> ORGANISM: Mus musculus

<400> SEQUENCE: 83

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Val Leu Ile Tyr Gln Met Ser Asn Leu Ala Ser Gly Val Pro
    50                  55                  60

Asp Arg Phe Ser Ser Ser Gly Ser Gly Thr Glu Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Phe Pro Leu Thr Phe Gly Ala Gly Thr Lys Leu Glu Leu Lys
            100                 105                 110
```

<210> SEQ ID NO 84
<211> LENGTH: 16
<212> TYPE: PRT
<213> ORGANISM: Mus musculus

<400> SEQUENCE: 84

```
Arg Ser Ser Lys Ser Leu Leu His Ser Asn Gly Ile Thr Tyr Leu Tyr
1               5                   10                  15
```

<210> SEQ ID NO 85
<211> LENGTH: 7
<212> TYPE: PRT
<213> ORGANISM: Mus musculus

<400> SEQUENCE: 85

```
Gln Met Ser Asn Leu Ala Ser
1               5
```

<210> SEQ ID NO 86
<211> LENGTH: 9
<212> TYPE: PRT
<213> ORGANISM: Mus musculus

<400> SEQUENCE: 86

```
Ala Gln Asn Leu Glu Phe Pro Leu Thr
1               5
```

<210> SEQ ID NO 87
<211> LENGTH: 118
<212> TYPE: PRT
<213> ORGANISM: Mus musculus

<400> SEQUENCE: 87

```
Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Asp Ile Asn Trp Val Lys Gln Arg Pro Gly Gln Gly Leu Glu Trp Ile
        35                  40                  45

Gly Trp Ile Tyr Pro Arg Asp Gly Thr Thr Lys Tyr Asn Glu Lys Phe
    50                  55                  60
```

-continued

```
Lys Gly Lys Ala Thr Leu Thr Val Asp Thr Ser Ser Thr Thr Ala Tyr
65                  70                  75                  80

Met Glu Leu His Ser Leu Thr Ser Glu Asp Ser Ala Val Tyr Phe Cys
                85                  90                  95

Ala Arg Gly Gly Tyr Tyr Asp Tyr Asp Gly Tyr Trp Gly Gln Gly Thr
            100                 105                 110

Leu Val Thr Val Ser Ala
        115


<210> SEQ ID NO 88
<211> LENGTH: 5
<212> TYPE: PRT
<213> ORGANISM: Mus musculus

<400> SEQUENCE: 88

Thr Tyr Asp Ile Asn
1               5


<210> SEQ ID NO 89
<211> LENGTH: 17
<212> TYPE: PRT
<213> ORGANISM: Mus musculus

<400> SEQUENCE: 89

Trp Ile Tyr Pro Arg Asp Gly Thr Thr Lys Tyr Asn Glu Lys Phe Lys
1               5                   10                  15

Gly


<210> SEQ ID NO 90
<211> LENGTH: 9
<212> TYPE: PRT
<213> ORGANISM: Mus musculus

<400> SEQUENCE: 90

Gly Gly Tyr Tyr Asp Tyr Asp Gly Tyr
1               5


<210> SEQ ID NO 91
<211> LENGTH: 107
<212> TYPE: PRT
<213> ORGANISM: Mus musculus

<400> SEQUENCE: 91

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Arg Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Asn Ser Leu Gln Ala
65                  70                  75                  80

Glu Asp Phe Val Ser Tyr Tyr Cys Gln Gln Leu Tyr Ser Thr Pro Phe
                85                  90                  95

Thr Phe Gly Ser Gly Thr Lys Leu Glu Ile Lys
            100                 105


<210> SEQ ID NO 92
<211> LENGTH: 11
```

<212> TYPE: PRT
<213> ORGANISM: Mus musculus

<400> SEQUENCE: 92

Leu Ala Ser Gln Thr Ile Gly Thr Trp Leu Ala
1 5 10

<210> SEQ ID NO 93
<211> LENGTH: 7
<212> TYPE: PRT
<213> ORGANISM: Mus musculus

<400> SEQUENCE: 93

Ala Ala Thr Ser Leu Ala Asp
1 5

<210> SEQ ID NO 94
<211> LENGTH: 9
<212> TYPE: PRT
<213> ORGANISM: Mus musculus

<400> SEQUENCE: 94

Gln Gln Leu Tyr Ser Thr Pro Phe Thr
1 5

<210> SEQ ID NO 95
<211> LENGTH: 119
<212> TYPE: PRT
<213> ORGANISM: Mus musculus

<400> SEQUENCE: 95

Glu Val Gln Leu Val Glu Ser Gly Gly Gly Leu Val Gln Pro Lys Gly
1 5 10 15

Ser Leu Lys Leu Ser Cys Ala Ala Ser Gly Phe Ser Phe Asn Thr His
20 25 30

Ala Met Asn Trp Val Arg Gln Ala Pro Gly Lys Gly Leu Glu Trp Val
35 40 45

Ala Arg Ile Arg Thr Lys Ser Asn Asn Tyr Ala Thr Tyr Tyr Ala Asp
50 55 60

Ser Val Lys Asp Arg Phe Ile Ile Ser Arg Asp Asp Ser Glu Asn Met
65 70 75 80

Val Tyr Leu Gln Met Asn Asn Leu Lys Thr Glu Asp Thr Ala Ile Tyr
85 90 95

Tyr Cys Val Arg Leu Arg Gly Gly Phe Leu Asp Tyr Trp Gly Gln Gly
100 105 110

Thr Thr Leu Thr Val Ser Ser
115

<210> SEQ ID NO 96
<211> LENGTH: 5
<212> TYPE: PRT
<213> ORGANISM: Mus musculus

<400> SEQUENCE: 96

Thr His Ala Met Asn
1 5

<210> SEQ ID NO 97
<211> LENGTH: 19
<212> TYPE: PRT
<213> ORGANISM: Mus musculus

<400> SEQUENCE: 97

Arg Ile Arg Thr Lys Ser Asn Asn Tyr Ala Thr Tyr Tyr Ala Asp Ser
1               5                   10                  15

Val Lys Asp

<210> SEQ ID NO 98
<211> LENGTH: 8
<212> TYPE: PRT
<213> ORGANISM: Mus musculus

<400> SEQUENCE: 98

Leu Arg Gly Gly Phe Leu Asp Tyr
1               5

<210> SEQ ID NO 99
<211> LENGTH: 107
<212> TYPE: PRT
<213> ORGANISM: Mus musculus

<400> SEQUENCE: 99

Asp Ile Gln Met Ala Gln Ser Ser Ser Ser Phe Ser Val Ser Leu Gly
1               5                   10                  15

Asp Arg Val Thr Ile Thr Cys Lys Ala Ser Glu Asp Ile Tyr Ile Arg
            20                  25                  30

Leu Ala Trp Tyr Gln Gln Lys Pro Gly Asn Ala Pro Arg Leu Leu Ile
        35                  40                  45

Ser Thr Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
            85                  90                  95

Thr Phe Gly Gly Gly Thr Arg Leu Glu Ile Lys
            100                 105

<210> SEQ ID NO 100
<211> LENGTH: 11
<212> TYPE: PRT
<213> ORGANISM: Mus musculus

<400> SEQUENCE: 100

Lys Ala Ser Glu Asp Ile Tyr Ile Arg Leu Ala
1               5                   10

<210> SEQ ID NO 101
<211> LENGTH: 7
<212> TYPE: PRT
<213> ORGANISM: Mus musculus

<400> SEQUENCE: 101

Thr Ala Thr Ser Leu Glu Thr
1               5

<210> SEQ ID NO 102
<211> LENGTH: 9
<212> TYPE: PRT
<213> ORGANISM: Mus musculus

<400> SEQUENCE: 102

Gln Gln Tyr Trp Ser Thr Pro Tyr Thr
1               5

<210> SEQ ID NO 103
<211> LENGTH: 120
<212> TYPE: PRT
<213> ORGANISM: Mus musculus

<400> SEQUENCE: 103

Glu Val Gln Leu Val Glu Ser Gly Gly Gly Leu Val Gln Pro Lys Gly
1 5 10 15

Ser Leu Lys Leu Ser Cys Ala Ala Ser Asp Phe Thr Phe Asn Thr Tyr
20 25 30

Ala Met His Trp Val Arg Gln Ala Pro Gly Lys Gly Leu Glu Trp Val
35 40 45

Ala Arg Ile Arg Thr Lys Ser Asn Asn Tyr Ala Thr Tyr Tyr Ala Asp
50 55 60

Ser Val Lys Asp Arg Phe Thr Ile Ser Arg Asp Asp Ser Gln Ser Met
65 70 75 80

Leu Tyr Leu Gln Met Asn Asn Leu Thr Thr Glu Asp Thr Ala Met Tyr
85 90 95

Tyr Cys Val Arg Asp Arg Tyr Gly Gly Ala Met Asp Tyr Trp Gly Gln
100 105 110

Gly Thr Ser Val Thr Val Ser Ser
115 120

<210> SEQ ID NO 104
<211> LENGTH: 5
<212> TYPE: PRT
<213> ORGANISM: Mus musculus

<400> SEQUENCE: 104

Thr Tyr Ala Met His
1 5

<210> SEQ ID NO 105
<211> LENGTH: 19
<212> TYPE: PRT
<213> ORGANISM: Mus musculus

<400> SEQUENCE: 105

Arg Ile Arg Thr Lys Ser Asn Asn Tyr Ala Thr Tyr Tyr Ala Asp Ser
1 5 10 15

Val Lys Asp

<210> SEQ ID NO 106
<211> LENGTH: 9
<212> TYPE: PRT
<213> ORGANISM: Mus musculus

<400> SEQUENCE: 106

Asp Arg Tyr Gly Gly Ala Met Asp Tyr
1 5

<210> SEQ ID NO 107
<211> LENGTH: 107
<212> TYPE: PRT
<213> ORGANISM: Mus musculus

<400> SEQUENCE: 107

Asp Ile Val Met Thr Gln Ser Gln Lys Phe Met Ser Thr Ser Val Gly
1 5 10 15

-continued

```
Asp Arg Val Ser Ile Thr Cys Lys Ala Ser Gln Asn Val Arg Ser Ala
            20                  25                  30

Val Ala Trp Tyr Gln Gln Lys Pro Gly Gln Ser Pro Lys Thr Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ala Gly Thr Lys Leu Glu Leu Lys
            100                 105


<210> SEQ ID NO 108
<211> LENGTH: 11
<212> TYPE: PRT
<213> ORGANISM: Mus musculus

<400> SEQUENCE: 108

Lys Ala Ser Gln Asn Val Arg Ser Ala Val Ala
1               5                   10


<210> SEQ ID NO 109
<211> LENGTH: 7
<212> TYPE: PRT
<213> ORGANISM: Mus musculus

<400> SEQUENCE: 109

Leu Ala Ser Asn Arg His Thr
1               5


<210> SEQ ID NO 110
<211> LENGTH: 9
<212> TYPE: PRT
<213> ORGANISM: Mus musculus

<400> SEQUENCE: 110

Leu Gln His Trp Asn Tyr Pro Leu Thr
1               5


<210> SEQ ID NO 111
<211> LENGTH: 121
<212> TYPE: PRT
<213> ORGANISM: Mus musculus

<400> SEQUENCE: 111

Gln Val Gln Leu Gln Gln Ser Gly Ala Glu Leu Ala Arg Pro Gly Thr
1               5                   10                  15

Ser Val Lys Leu Ser Cys Lys Ala Ser Gly Tyr Thr Phe Thr Ser Cys
            20                  25                  30

Gly Leu Ser Trp Val Lys Gln Arg Thr Gly Gln Gly Leu Glu Trp Ile
        35                  40                  45

Gly Glu Ile Tyr Pro Ser Asn Gly Asn Ser Tyr Tyr Ser Asp Lys Val
    50                  55                  60

Lys Asp Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Ala Tyr Tyr Thr Asn Gly Tyr Tyr Ala Met Asp Tyr Trp Gly
            100                 105                 110
```

```
Gln Gly Thr Ser Val Thr Val Ser Ser
        115                 120


<210> SEQ ID NO 112
<211> LENGTH: 5
<212> TYPE: PRT
<213> ORGANISM: Mus musculus

<400> SEQUENCE: 112

Ser Cys Gly Leu Ser
1               5


<210> SEQ ID NO 113
<211> LENGTH: 17
<212> TYPE: PRT
<213> ORGANISM: Mus musculus

<400> SEQUENCE: 113

Glu Ile Tyr Pro Ser Asn Gly Asn Ser Tyr Tyr Ser Asp Lys Val Lys
1               5                   10                  15

Asp


<210> SEQ ID NO 114
<211> LENGTH: 12
<212> TYPE: PRT
<213> ORGANISM: Mus musculus

<400> SEQUENCE: 114

Ala Tyr Tyr Thr Asn Gly Tyr Tyr Ala Met Asp Tyr
1               5                   10


<210> SEQ ID NO 115
<211> LENGTH: 107
<212> TYPE: PRT
<213> ORGANISM: Mus musculus

<400> SEQUENCE: 115

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys
            100                 105


<210> SEQ ID NO 116
<211> LENGTH: 11
<212> TYPE: PRT
<213> ORGANISM: Mus musculus

<400> SEQUENCE: 116

Arg Ala Ser Gln Ser Ile Ser Asn Asn Leu His
1               5                   10
```

<210> SEQ ID NO 117
<211> LENGTH: 7
<212> TYPE: PRT
<213> ORGANISM: Mus musculus

<400> SEQUENCE: 117

Tyr Ala Ser Gln Ser Ile Ser
1               5

<210> SEQ ID NO 118
<211> LENGTH: 9
<212> TYPE: PRT
<213> ORGANISM: Mus musculus

<400> SEQUENCE: 118

Gln Gln Ser Asn Ser Trp Pro Leu Thr
1               5

<210> SEQ ID NO 119
<211> LENGTH: 8
<212> TYPE: PRT
<213> ORGANISM: Gallus gallus

<400> SEQUENCE: 119

Ser Ile Ile Asn Phe Glu Lys Leu
1               5

<210> SEQ ID NO 120
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Glu Trp Ser Trp Val Phe Leu Phe Phe Leu Ser Val Thr Thr Gly
1               5                   10                  15

Val His Ser Gln Val Gln Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Asp Ile Asn Trp Val Lys Gln Arg Pro Gly Gln Gly Leu
    50                  55                  60

Glu Trp Ile Gly Trp Ile Tyr Pro Arg Asp Gly Ser Thr Lys Tyr Asn
65                  70                  75                  80

Glu Lys Leu Lys Gly Lys Ala Thr Leu Thr Val Asp Thr Ser Ser Arg
                85                  90                  95

Thr Ala Tyr Met Glu Leu His Ser Leu Thr Ser Glu Asp Ser Ala Val
            100                 105                 110

Tyr Phe Cys Ala Arg Gly Gly Tyr Tyr Asp Tyr Asp Gly Tyr Trp Gly
        115                 120                 125

Gln Gly Thr Leu Val Thr Val Ser Ala Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
195 200 205

Pro Ser Ser Ser Leu Gly Thr Gln Thr Tyr Ile Cys Asn Val Asn His
210 215 220

Lys Pro Ser Asn Thr Lys Val Asp Lys Lys Val Glu Pro Lys Ser Cys
225 230 235 240

Asp Lys Thr His Thr Cys Pro Pro Cys Pro Ala Pro Glu Leu Leu Gly
245 250 255

Gly Pro Ser Val Phe Leu Phe Pro Pro Lys Pro Lys Asp Thr Leu Met
260 265 270

Ile Ser Arg Thr Pro Glu Val Thr Cys Val Val Val Asp Val Ser His
275 280 285

Glu Asp Pro Glu Val Lys Phe Asn Trp Tyr Val Asp Gly Val Glu Val
290 295 300

His Asn Ala Lys Thr Lys Pro Arg Glu Glu Gln Tyr Asn Ser Thr Tyr
305 310 315 320

Arg Val Val Ser Val Leu Thr Val Leu His Gln Asp Trp Leu Asn Gly
325 330 335

Lys Glu Tyr Lys Cys Lys Val Ser Asn Lys Ala Leu Pro Ala Pro Ile
340 345 350

Glu Lys Thr Ile Ser Lys Ala Lys Gly Gln Pro Arg Glu Pro Gln Val
355 360 365

Tyr Thr Leu Pro Pro Ser Arg Asp Glu Leu Thr Lys Asn Gln Val Ser
370 375 380

Leu Thr Cys Leu Val Lys Gly Phe Tyr Pro Ser Asp Ile Ala Val Glu
385 390 395 400

Trp Glu Ser Asn Gly Gln Pro Glu Asn Asn Tyr Lys Thr Thr Pro Pro
405 410 415

Val Leu Asp Ser Asp Gly Ser Phe Phe Leu Tyr Ser Lys Leu Thr Val
420 425 430

Asp Lys Ser Arg Trp Gln Gln Gly Asn Val Phe Ser Cys Ser Val Met
435 440 445

His Glu Ala Leu His Asn His Tyr Thr Gln Lys Ser Leu Ser Leu Ser
450 455 460

Pro Gly
465

<210> SEQ ID NO 121
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121
atggaatggt cctgggtgtt cctgttcttc ctgtctgtga ccaccggcgt gcactctcag 60
gttcagttgc agcagtctgg ccctgagctt gtgaaacctg gcgcctctgt gaagctgtct 120
tgcaaggcct ctggctacac cttcaccagc tacgacatca actgggtcaa gcagaggcct 180
ggacagggac tcgagtggat cggctggatc taccctagag atggctccac caagtacaac 240
gagaagctga agggcaaagc taccctgacc gtggacacct cctctcggac cgcttacatg 300
gaactgcact ccctgacctc tgaggactcc gccgtgtact tttgtgccag aggcggctac 360
tacgactacg atggctattg gggacagggc accctggtca cagtgtctgc tgcttctacc 420

```
aaggggccct ccgtgttccc tctggcccct tccagcaagt ctacctctgg cggcacagcc    480

gctctgggct gcctcgtgaa ggactacttc cccgagcctg tgaccgtgtc ctggaactct    540

ggcgctctga catccggcgt gcacaccttc cctgctgtgc tgcagtcctc cggcctgtac    600

tccctgtcct ccgtcgtgac cgtgccttcc agctctctgg gcacccagac ctacatctgc    660

aacgtgaacc acaagccctc caacaccaag gtggacaaga aggtggaacc caagtcctgc    720

gacaagaccc acacctgtcc cccttgtcct gcccctgaac tgctgggcgg acccagcgtg    780

ttcctgttcc ccccaaagcc caaggacacc ctgatgatct cccggacccc cgaagtgacc    840

tgcgtggtgg tggatgtgtc ccacgaggac cctgaagtga agttcaattg gtacgtggac    900

ggcgtggaag tgcacaacgc caagaccaag cctagagagg aacagtacaa ctccacctac    960

cgggtggtgt ccgtgctgac cgtgctgcac caggattggc tgaacggcaa agagtacaag   1020

tgcaaggtgt ccaacaaggc cctgcctgcc cccatcgaaa agaccatctc caaggccaag   1080

ggccagcccc gggaacccca ggtgtacaca ctgcccccta gcagggacga gctgaccaag   1140

aaccaggtgt ccctgacctg tctcgtgaaa ggcttctacc cctccgatat cgccgtggaa   1200

tgggagtcca acggccagcc tgagaacaac tacaagacca cccccctgt gctggactcc    1260

gacggctcat tcttcctgta cagcaagctg acagtggaca agtcccggtg gcagcagggc   1320

aacgtgttct cctgctccgt gatgcacgag gccctgcaca accactacac ccagaagtcc   1380

ctgtccctga gccccggctg a                                              1401
```

```
<210> SEQ ID NO 122
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Glu Trp Ser Trp Val Phe Leu Phe Phe Leu Ser Val Thr Thr Gly
1               5                   10                  15

Val His Ser Gln Val Gln Leu Gln Gln Ser Gly Pro Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Asp Ile Asn Trp Val Lys Gln Arg Pro Gly Gln Gly Leu
    50                  55                  60

Glu Trp Ile Gly Trp Ile Tyr Pro Arg Asp Gly Ser Thr Lys Tyr Asn
65                  70                  75                  80

Glu Lys Leu Lys Gly Lys Ala Thr Leu Thr Val Asp Thr Ser Ser Arg
                85                  90                  95

Thr Ala Tyr Met Glu Leu His Ser Leu Thr Ser Glu Asp Ser Ala Val
            100                 105                 110

Tyr Phe Cys Ala Arg Gly Gly Tyr Tyr Asp Tyr Asp Gly Tyr Trp Gly
        115                 120                 125

Gln Gly Thr Leu Val Thr Val Ser Ala Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175
```

-continued

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly
    450                 455                 460
```

<210> SEQ ID NO 123
<211> LENGTH: 1392
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
atggaatggt cctgggtgtt cctgttcttc ctgtctgtga ccaccggcgt gcactctcag      60

gttcagttgc agcagtctgg ccctgagctt gtgaaacctg gcgcctctgt gaagctgtct     120

tgcaaggcct ctggctacac cttcaccagc tacgacatca actgggtcaa gcagaggcct     180

ggacagggac tcgagtggat cggctggatc taccctagag atggctccac caagtacaac     240

gagaagctga agggcaaagc taccctgacc gtggacacct cctctcggac cgcttacatg     300

gaactgcact ccctgacctc tgaggactcc gccgtgtact tttgtgccag aggcggctac     360

tacgactacg atggctattg gggacagggc accctggtca cagtgtctgc tgcttctacc     420
```

```
aaggggccct ccgtgttccc tctggcccct tgctccagat ccacctccga gtctaccgcc    480

gctctgggct gcctcgtgaa ggactacttc cccgagcctg tgaccgtgtc ctggaactct    540

ggcgctctga cctctggcgt gcacaccttc cctgctgtgc tgcagtcctc cggcctgtac    600

tccctgtcct ccgtcgtgac cgtgccttcc agctctctgg gcaccaagac ctacacctgt    660

aacgtggacc acaagccctc caacaccaag gtggacaagc gggtggaatc taagtacggc    720

cctccctgcc ctccttgccc agcccctgaa tttctgggcg gacccagcgt gttcctgttc    780

cccccaaagc ccaaggacac cctgatgatc tcccggaccc ccgaagtgac ctgcgtggtg    840

gtggatgtgt cccaggaaga tcccgaggtg cagttcaatt ggtacgtgga cggcgtggaa    900

gtgcacaacg ccaagaccaa gcctagagag gaacagttca actccaccta ccgggtggtg    960

tccgtgctga ccgtgctgca ccaggattgg ctgaacggca aagagtacaa gtgcaaggtg   1020

tccaacaagg gcctgcccag ctccatcgaa aagaccatct ccaaggccaa gggccagccc   1080

cgggaacccc aggtgtacac actgcctcca agccaggaag agatgaccaa gaaccaggtg   1140

tccctgacct gtctcgtgaa aggcttctac ccctccgata tcgccgtgga atgggagtcc   1200

aacggccagc ctgagaacaa ctacaagacc acccccccctg tgctggactc cgacggctcc   1260

ttcttcctgt actctcgcct gaccgtggac aagtcccggt ggcaggaagg caacgtgttc   1320

tcctgctccg tgatgcacga ggccctgcac aaccactaca cccagaagtc cctgtccctg   1380

tctctgggat ga                                                       1392
```

```
<210> SEQ ID NO 124
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Ser Val Pro Thr Gln Val Leu Gly Leu Leu Leu Leu Trp Leu Thr
1               5                   10                  15

Asp Ala Arg Cys Asp Ile Val Met Thr Gln Ala Ala Phe Ser Asn Pro
            20                  25                  30

Val Thr Leu Gly Thr Ser Ala Ser Ile Ser Cys Arg Ser Ser Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Val Leu Ile Tyr Gln Met Ser Ser Leu Ala
65                  70                  75                  80

Ser Gly Val Pro Asp Arg Phe Ser Ser Ser Gly Ser Gly Thr Glu Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Leu Thr Phe Gly Ala Gly Thr Lys
        115                 120                 125

Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
```

-continued

```
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 125
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

atgtccgtgc ctacacaggt tctgggactg ctgctgctgt ggctgaccga cgctagatgc     60

gatatcgtga tgacccaggc cgccttcagc aatcctgtga cactgggaac ctccgcctcc    120

atctcctgca gatcctctaa gtccctgctg cactccaacg gcatcaccta cctgtactgg    180

tatctgcaga agcccggcca gtctcctcag gtgctgatct accagatgtc ctctctggcc    240

tctggcgtgc ccgacagatt ctcttcttct ggctctggca ccgagttcac cctgcggatc    300

tctagagtgg aagctgagga cgtgggcgtg tactactgcg cccagaatct ggaactgcct    360

ctgacctttg gcgctggcac caagctggaa ctgaagcgta cggtggccgc tccctccgtg    420

ttcatcttcc caccttccga cgagcagctg aagtccggca ccgcttctgt cgtgtgcctg    480

ctgaacaact tctacccccg cgaggccaag gtgcagtgga aggtggacaa cgccctgcag    540

tccggcaact cccaggaatc cgtgaccgag caggactcca aggacagcac ctactccctg    600

tcctccaccc tgaccctgtc caaggccgac tacgagaagc acaaggtgta cgcctgcgaa    660

gtgacccacc agggcctgtc tagccccgtg accaagtctt tcaaccgggg cgagtgctga    720


<210> SEQ ID NO 126
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Glu Trp Ser Trp Val Phe Leu Phe Phe Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Phe Met Asn Trp Val Lys Gln Ser Pro Glu Lys Ser Leu
    50                  55                  60

Glu Trp Ile Gly Glu Ile His Pro Ser Thr Gly Ser Ile Ile Tyr Asn
65                  70                  75                  80

Gln Lys Phe Lys Ala Lys Ala Thr Leu Thr Ile Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Phe Asp Tyr Ser Asn Ser Phe Ala Tyr Trp Gly
```

```
        115                 120                 125

Gln Gly Thr Leu Val Thr Val Ser Ala Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly
465


<210> SEQ ID NO 127
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
```

-continued

```
atggaatggt cctgggtgtt cctgttcttc ctgtctgtga ccaccggcgt gcactctgaa     60

gttcagttgc agcagtctgg ccccgagctt gtgaaacctg gcgcctctgt gaagatctcc    120

tgcaaggcct ctggctactc cttcaccggc tacttcatga actgggtcaa gcagtcccct    180

gagaagtccc tggaatggat cggcgagatc catccttcca ccggcagcat catctacaac    240

cagaagttca aggccaaggc taccctgacc atcgacaagt cctcttccac cgcctacatg    300

cagctgaagt ctctgacctc tgaggactcc gccgtgtact actgcgccag attcgactac    360

tccaactcct tcgcttattg gggccagggc accctggtta ccgtgtctgc tgcttctacc    420

aaggggccct ccgtgttccc tctggcccct tccagcaagt ctacctctgg cggcacagcc    480

gctctgggct gcctcgtgaa ggactacttc cccgagcctg tgaccgtgtc ctggaactct    540

ggcgctctga catccggcgt gcacaccttc cctgctgtgc tgcagtcctc cggcctgtac    600

tccctgtcct ccgtcgtgac cgtgccttcc agctctctgg gcacccagac ctacatctgc    660

aacgtgaacc acaagccctc caacaccaag gtggacaaga aggtggaacc caagtcctgc    720

gacaagaccc acacctgtcc cccttgtcct gcccctgaac tgctgggcgg acccagcgtg    780

ttcctgttcc ccccaaagcc caaggacacc ctgatgatct cccggacccc cgaagtgacc    840

tgcgtggtgg tggatgtgtc ccacgaggac cctgaagtga agttcaattg gtacgtggac    900

ggcgtggaag tgcacaacgc caagaccaag cctagagagg aacagtacaa ctccacctac    960

cgggtggtgt ccgtgctgac cgtgctgcac caggattggc tgaacggcaa agagtacaag   1020

tgcaaggtgt ccaacaaggc cctgcctgcc cccatcgaaa agaccatctc caaggccaag   1080

ggccagcccc gggaacccca ggtgtacaca ctgcccccta gcagggacga gctgaccaag   1140

aaccaggtgt ccctgacctg tctcgtgaaa ggcttctacc cctccgatat cgccgtggaa   1200

tgggagtcca acggccagcc tgagaacaac tacaagacca ccccccctgt gctggactcc   1260

gacggctcat tcttcctgta cagcaagctg acagtggaca agtcccggtg gcagcagggc   1320

aacgtgttct cctgctccgt gatgcacgag gccctgcaca accactacac ccagaagtcc   1380

ctgtccctga gccccggctg a                                             1401
```

<210> SEQ ID NO 128
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Met Glu Trp Ser Trp Val Phe Leu Phe Phe Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Phe Met Asn Trp Val Lys Gln Ser Pro Glu Lys Ser Leu
    50                  55                  60

Glu Trp Ile Gly Glu Ile His Pro Ser Thr Gly Ser Ile Ile Tyr Asn
65                  70                  75                  80

Gln Lys Phe Lys Ala Lys Ala Thr Leu Thr Ile Asp Lys Ser Ser Ser
                85                  90                  95

Thr Ala Tyr Met Gln Leu Lys Ser Leu Thr Ser Glu Asp Ser Ala Val
            100                 105                 110
```

```
Tyr Tyr Cys Ala Arg Phe Asp Tyr Ser Asn Ser Phe Ala Tyr Trp Gly
        115                 120                 125

Gln Gly Thr Leu Val Thr Val Ser Ala Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly
    450                 455                 460
```

<210> SEQ ID NO 129
<211> LENGTH: 1392
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
atggaatggt cctgggtgtt cctgttcttc ctgtctgtga ccaccggcgt gcactctgaa     60
```

```
gttcagttgc agcagtctgg ccccgagctt gtgaaacctg gcgcctctgt gaagatctcc    120

tgcaaggcct ctggctactc cttcaccggc tacttcatga actgggtcaa gcagtcccct    180

gagaagtccc tggaatggat cggcgagatc catccttcca ccggcagcat catctacaac    240

cagaagttca aggccaaggc taccctgacc atcgacaagt cctcttccac cgcctacatg    300

cagctgaagt ctctgacctc tgaggactcc gccgtgtact actgcgccag attcgactac    360

tccaactcct tcgcttattg gggccagggc accctggtta ccgtgtctgc tgcttctacc    420

aaggggccct ccgtgttccc tctggcccct tgctccagat ccacctccga gtctaccgcc    480

gctctgggct gcctcgtgaa ggactacttc cccgagcctg tgaccgtgtc ctggaactct    540

ggcgctctga cctctggcgt gcacaccttc cctgctgtgc tgcagtcctc cggcctgtac    600

tccctgtcct ccgtcgtgac cgtgccttcc agctctctgg gcaccaagac ctacacctgt    660

aacgtggacc acaagccctc caacaccaag gtggacaagc gggtggaatc taagtacggc    720

cctccctgcc ctccttgccc agcccctgaa tttctgggcg gacccagcgt gttcctgttc    780

cccccaaagc ccaaggacac cctgatgatc tcccggaccc ccgaagtgac ctgcgtggtg    840

gtggatgtgt cccaggaaga tcccgaggtg cagttcaatt ggtacgtgga cggcgtggaa    900

gtgcacaacg ccaagaccaa gcctagagag gaacagttca actccaccta ccgggtggtg    960

tccgtgctga ccgtgctgca ccaggattgg ctgaacggca aagagtacaa gtgcaaggtg   1020

tccaacaagg gcctgcccag ctccatcgaa aagaccatct ccaaggccaa gggccagccc   1080

cgggaacccc aggtgtacac actgcctcca agccaggaag agatgaccaa gaaccaggtg   1140

tccctgacct gtctcgtgaa aggcttctac ccctccgata tcgccgtgga atgggagtcc   1200

aacggccagc ctgagaacaa ctacaagacc acccccccctg tgctggactc cgacggctcc   1260

ttcttcctgt actctcgcct gaccgtggac aagtcccggt ggcaggaagg caacgtgttc   1320

tcctgctccg tgatgcacga ggccctgcac aaccactaca cccagaagtc cctgtccctg   1380

tctctgggat ga                                                        1392
```

```
<210> SEQ ID NO 130
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Ser Val Pro Thr Gln Val Leu Gly Leu Leu Leu Leu Trp Leu Thr
1               5                   10                  15

Asp Ala Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110
```

-continued

```
Thr Leu Pro Arg Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 131
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
atgtccgtgc ctacacaggt tctgggactg ctgctgctgt ggctgaccga cgctagatgc     60

gatatccaga tgacccagac cacctccagc ctgtctgctt ctctgggcga cagagtgacc    120

atctcctgca gagcctctca ggacatctcc aactacctga actggtatca gcagaaaccc    180

gacggcaccg tgaagctgct gatctactac acctccagac tgcactccgg cgtgccctct    240

agattttctg gctctggatc tggcaccgac tactccctga ccatcagcaa cctggaacaa    300

gaggatatcg ctacctactt ctgccagcaa ggcaacaccc tgcctagaac ctttggcgga    360

ggcaccaagc tggaaatcaa gcgtacggtg gccgctccct ccgtgttcat cttcccacct    420

tccgacgagc agctgaagtc cggcaccgct tctgtcgtgt gcctgctgaa caacttctac    480

ccccgcgagg ccaaggtgca gtggaaggtg gacaacgccc tgcagtccgg caactcccag    540

gaatccgtga ccgagcagga ctccaaggac agcacctact ccctgtcctc caccctgacc    600

ctgtccaagg ccgactacga gaagcacaag gtgtacgcct gcgaagtgac ccaccagggc    660

ctgtctagcc ccgtgaccaa gtctttcaac cggggcgagt gctga                    705
```

<210> SEQ ID NO 132
<211> LENGTH: 463
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

```
Met Glu Trp Ser Trp Val Phe Leu Phe Phe Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45
```

-continued

```
Thr Thr Tyr Tyr Met Asn Trp Val Lys Gln Ser His Gly Lys Ser Leu
    50                  55                  60

Glu Trp Ile Gly Asn Ile Asn Pro Asp Asn Gly Ile Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Gly Lys Ser Leu Ala Tyr Trp Gly Gln Gly Thr
        115                 120                 125

Leu Val Thr Val Ser Ala Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly
    450                 455                 460
```

<210> SEQ ID NO 133
<211> LENGTH: 1392
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133
atggaatggt cctgggtgtt cctgttcttc ctgtctgtga ccaccggcgt gcactctgaa 60
gttcagttgc agcagtctgg ccccgagctt gtgaaacctg gcgcctctgt gaagatctcc 120
tgcaaggcct ctggctacac cttcaccacc tactacatga actgggtcaa gcagtcccac 180
ggcaagtccc tggaatggat cggcaacatc aaccccgaca acggcatcac ctcctacaac 240
cagaagttca agggcaaagc taccctgacc gtggacaagt cctcctccac cgcctacatg 300
gaactgagat ccctgacctc tgaggactcc gccgtgtact actgtgccag aggcaagtct 360
ctggcttatt ggggccaggg cacactggtc acagtgtctg ctgcttccac caaggggccc 420
tccgtgttcc ctctggcccc ttccagcaag tctacctctg gcggcacagc cgctctgggc 480
tgcctcgtga aggactactt ccccgagcct gtgaccgtgt cctggaactc tggcgctctg 540
acatccggcg tgcacacctt ccctgctgtg ctgcagtcct ccggcctgta ctccctgtcc 600
tccgtcgtga ccgtgccttc cagctctctg ggcacccaga cctacatctg caacgtgaac 660
cacaagccct ccaacaccaa ggtggacaag aaggtggaac ccaagtcctg cgacaagacc 720
cacacctgtc cccccttgtcc tgcccctgaa ctgctgggcg gacccagcgt gttcctgttc 780
cccccaaagc ccaaggacac cctgatgatc tcccggaccc ccgaagtgac ctgcgtggtg 840
gtggatgtgt cccacgagga ccctgaagtg aagttcaatt ggtacgtgga cggcgtggaa 900
gtgcacaacg ccaagaccaa gcctagagag gaacagtaca actccaccta ccgggtggtg 960
tccgtgctga ccgtgctgca ccaggattgg ctgaacggca aagagtacaa gtgcaaggtg 1020
tccaacaagg ccctgcctgc ccccatcgaa aagaccatct ccaaggccaa gggccagccc 1080
cgggaacccc aggtgtacac actgcccccct agcagggacg agctgaccaa gaaccaggtg 1140
tccctgacct gtctcgtgaa aggcttctac ccctccgata tcgccgtgga atgggagtcc 1200
aacggccagc ctgagaacaa ctacaagacc acccccccctg tgctggactc cgacggctca 1260
ttcttcctgt acagcaagct gacagtggac aagtcccggt ggcagcaggg caacgtgttc 1320
tcctgctccg tgatgcacga ggccctgcac aaccactaca cccagaagtc cctgtccctg 1380
agccccggct ga 1392

<210> SEQ ID NO 134
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Met Glu Trp Ser Trp Val Phe Leu Phe Phe Leu Ser Val Thr Thr Gly
1 5 10 15

Val His Ser Glu Val Gln Leu Gln Gln Ser Gly Pro Glu Leu Val Lys
20 25 30

Pro Gly Ala Ser Val Lys Ile Ser Cys Lys Ala Ser Gly Tyr Thr Phe
35 40 45

Thr Thr Tyr Tyr Met Asn Trp Val Lys Gln Ser His Gly Lys Ser Leu

```
    50                  55                  60

Glu Trp Ile Gly Asn Ile Asn Pro Asp Asn Gly Ile Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Gly Lys Ser Leu Ala Tyr Trp Gly Gln Gly Thr
        115                 120                 125

Leu Val Thr Val Ser Ala Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
            420                 425                 430

Glu Gly Asn Val Phe Ser Cys Ser Val Met His Glu Ala Leu His Asn
        435                 440                 445

His Tyr Thr Gln Lys Ser Leu Ser Leu Ser Leu Gly
    450                 455                 460

<210> SEQ ID NO 135
```

<211> LENGTH: 1383
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 135
atggaatggt cctgggtgtt cctgttcttc ctgtctgtga ccaccggcgt gcactctgaa 60
gttcagttgc agcagtctgg ccccgagctt gtgaaacctg gcgcctctgt gaagatctcc 120
tgcaaggcct ctggctacac cttcaccacc tactacatga actgggtcaa gcagtcccac 180
ggcaagtccc tggaatggat cggcaacatc aaccccgaca acggcatcac ctcctacaac 240
cagaagttca agggcaaagc taccctgacc gtggacaagt cctcctccac cgcctacatg 300
gaactgagat ccctgacctc tgaggactcc gccgtgtact actgtgccag aggcaagtct 360
ctggcttatt ggggccaggg cacactggtc acagtgtctg ctgcttccac caaggggccc 420
tccgtgttcc ctctggcccc ttgctccaga tccacctccg agtctaccgc cgctctgggc 480
tgcctcgtga aggactactt ccccgagcct gtgaccgtgt cctggaactc tggcgctctg 540
acctctggcg tgcacacctt ccctgctgtg ctgcagtcct ccggcctgta ctccctgtcc 600
tccgtcgtga ccgtgccttc cagctctctg ggcaccaaga cctacacctg taacgtggac 660
cacaagccct ccaacaccaa ggtggacaag cgggtggaat ctaagtacgg ccctccctgc 720
cctccttgcc cagcccctga atttctgggc ggacccagcg tgttcctgtt cccccccaaag 780 cccaaggaca ccctgatgat ctcccggacc cccgaagtga cctgcgtggt ggtggatgtg 840
tcccaggaag atcccgaggt gcagttcaat tggtacgtgg acggcgtgga agtgcacaac 900
gccaagacca agcctagaga ggaacagttc aactccacct accgggtggt gtccgtgctg 960
accgtgctgc accaggattg gctgaacggc aaagagtaca agtgcaaggt gtccaacaag 1020
ggcctgccca gctccatcga aaagaccatc tccaaggcca agggccagcc ccgggaaccc 1080
caggtgtaca cactgcctcc aagccaggaa gagatgacca agaaccaggt gtccctgacc 1140
tgtctcgtga aaggcttcta cccctccgat atcgccgtgg aatgggagtc caacggccag 1200
cctgagaaca actacaagac cacccccccct gtgctggact ccgacggctc cttcttcctg 1260
tactctcgcc tgaccgtgga caagtcccgg tggcaggaag gcaacgtgtt ctcctgctcc 1320
gtgatgcacg aggccctgca caaccactac acccagaagt ccctgtccct gtctctggga 1380
tga 1383

<210> SEQ ID NO 136
<211> LENGTH: 234
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 136

Met Ser Val Pro Thr Gln Val Leu Gly Leu Leu Leu Leu Trp Leu Thr
1 5 10 15

Asp Ala Arg Cys Asp Ile Val Met Thr Gln Ser His Lys Phe Met Ser
20 25 30

Thr Ser Val Gly Asp Arg Val Ser Ile Thr Cys Lys Ala Ser Gln Asn
35 40 45

Val Gly Thr Ala Val Ala Trp Tyr Gln Gln Lys Pro Gly Gln Ser Pro
50 55 60

```
Lys Leu Leu Ile Tyr Trp Ala Ser Ile Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser His Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 137
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137

```
atgtccgtgc ctacacaggt tctgggactg ctgctgctgt ggctgaccga cgctagatgc     60

gacatcgtga tgacccagag ccacaagttc atgtccacct ccgtgggcga cagagtgtcc    120

atcacatgca aggcctctca gaatgtgggc accgccgttg cctggtatca gcagaaacct    180

ggccagtctc ctaagctgct gatctactgg gcctccatca gacacaccgg cgtgccagat    240

agattcaccg gctctggctc tggcaccgac ttcaccctga ccatctctaa cgtgcagtct    300

gaggacctgg ccgactactt ctgccagcag tacagctctc acccctacac ctttggcgga    360

ggcaccaagc tggaaatcaa gcgtacggtg gccgctccct ccgtgttcat cttcccacct    420

tccgacgagc agctgaagtc cggcaccgct tctgtcgtgt gcctgctgaa caacttctac    480

ccccgcgagg ccaaggtgca gtggaaggtg gacaacgccc tgcagtccgg caactcccag    540

gaatccgtga ccgagcagga ctccaaggac agcacctact ccctgtcctc caccctgacc    600

ctgtccaagg ccgactacga gaagcacaag gtgtacgcct gcgaagtgac ccaccagggc    660

ctgtctagcc ccgtgaccaa gtctttcaac cggggcgagt gctga                    705
```

<210> SEQ ID NO 138
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

```
Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Lys Gly Ser Leu Lys Leu Ser Cys Ala Ala Ser Asp Phe Thr Phe
        35                  40                  45

Asn Thr Tyr Ala Met His Trp Val Arg Gln Ala Pro Gly Lys Gly Leu
    50                  55                  60

Glu Trp Val Ala Arg Ile Arg Thr Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Thr Thr Glu Asp Thr
            100                 105                 110

Ala Met Tyr Tyr Cys Val Arg Asp Arg Tyr Gly Gly Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415
```

```
Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465


<210> SEQ ID NO 139
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

atggaatggt cctgggtgtt cctgttcttc ctgtctgtga ccaccggcgt gcactctgaa     60

gtgcagttgg ttgaatctgg cggcggactg gtgcagccta agggatctct gaagctgtct    120

tgcgccgcct ccgacttcac cttcaatacc tacgccatgc actgggtccg acaggcccct    180

ggaaaaggac tggaatgggt cgccagaatc cggaccaagt ccaacaacta cgccacctac    240

tacgccgact ccgtgaagga cagattcacc atctctcggg acgactccca gtccatgctg    300

tacctgcaga tgaacaacct gaccaccgag gacaccgcca tgtactactg cgtgcgggat    360

agatatggcg gcgctatgga ttattggggc cagggcacat ctgtgaccgt gtcctctgct    420

tccaccaagg gcccctccgt gttccctctg gccccttcca gcaagtctac ctctggcggc    480

acagccgctc tgggctgcct cgtgaaggac tacttccccg agcctgtgac cgtgtcctgg    540

aactctggcg ctctgacatc cggcgtgcac accttccctg ctgtgctgca gtcctccggc    600

ctgtactccc tgtcctccgt cgtgaccgtg ccttccagct ctctgggcac ccagacctac    660

atctgcaacg tgaaccacaa gccctccaac accaaggtgg acaagaaggt ggaacccaag    720

tcctgcgaca agacccacac ctgtcccccct tgtcctgccc ctgaactgct gggcggaccc    780

agcgtgttcc tgttcccccc aaagcccaag gacaccctga tgatctcccg gacccccgaa    840

gtgacctgcg tggtggtgga tgtgtcccac gaggaccctg aagtgaagtt caattggtac    900

gtggacggcg tggaagtgca caacgccaag accaagccta gagaggaaca gtacaactcc    960

acctaccggg tggtgtccgt gctgaccgtg ctgcaccagg attggctgaa cggcaaagag   1020

tacaagtgca aggtgtccaa caaggccctg cctgccccca tcgaaaagac catctccaag   1080

gccaagggcc agccccggga accccaggtg tacacactgc cccctagcag ggacgagctg   1140

accaagaacc aggtgtccct gacctgtctc gtgaaaggct tctacccctc cgatatcgcc   1200

gtggaatggg agtccaacgg ccagcctgag aacaactaca agaccacccc ccctgtgctg   1260

gactccgacg gctcattctt cctgtacagc aagctgacag tggacaagtc ccggtggcag   1320

cagggcaacg tgttctcctg ctccgtgatg cacgaggccc tgcacaacca ctacacccag   1380

aagtccctgt ccctgagccc cggctga                                       1407


<210> SEQ ID NO 140
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 140

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Lys Gly Ser Leu Lys Leu Ser Cys Ala Ala Ser Asp Phe Thr Phe
        35                  40                  45

Asn Thr Tyr Ala Met His Trp Val Arg Gln Ala Pro Gly Lys Gly Leu
    50                  55                  60

Glu Trp Val Ala Arg Ile Arg Thr Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Thr Thr Glu Asp Thr
            100                 105                 110

Ala Met Tyr Tyr Cys Val Arg Asp Arg Tyr Gly Gly Ala Met Asp Tyr
        115                 120                 125

Trp Gly Gln Gly Thr Ser Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val

```
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly
465


<210> SEQ ID NO 141
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141

atggaatggt cctgggtgtt cctgttcttc ctgtctgtga ccaccggcgt gcactctgaa     60

gtgcagttgg ttgaatctgg cggcggactg gtgcagccta agggatctct gaagctgtct    120

tgcgccgcct ccgacttcac cttcaatacc tacgccatgc actgggtccg acaggcccct    180

ggaaaaggac tggaatgggt cgccagaatc cggaccaagt ccaacaacta cgccacctac    240

tacgccgact ccgtgaagga cagattcacc atctctcggg acgactccca gtccatgctg    300

tacctgcaga tgaacaacct gaccaccgag gacaccgcca tgtactactg cgtgcgggat    360

agatatggcg gcgctatgga ttattggggc cagggcacat ctgtgaccgt gtcctctgct    420

tccaccaagg gcccctccgt gttccctctg gccccttgct ccagatccac ctccgagtct    480

accgccgctc tgggctgcct cgtgaaggac tacttccccg agcctgtgac cgtgtcctgg    540

aactctggcg ctctgacctc tggcgtgcac accttccctg ctgtgctgca gtcctccggc    600

ctgtactccc tgtcctccgt cgtgaccgtg ccttccagct ctctgggcac caagacctac    660

acctgtaacg tggaccacaa gccctccaac accaaggtgg acaagcgggt ggaatctaag    720

tacggccctc cctgccctcc ttgcccagcc cctgaatttc tgggcggacc cagcgtgttc    780

ctgttccccc caaagcccaa ggacaccctg atgatctccc ggacccccga agtgacctgc    840

gtggtggtgg atgtgtccca ggaagatccc gaggtgcagt tcaattggta cgtggacggc    900

gtggaagtgc acaacgccaa gaccaagcct agagaggaac agttcaactc cacctaccgg    960

gtggtgtccg tgctgaccgt gctgcaccag gattggctga acggcaaaga gtacaagtgc   1020

aaggtgtcca acaagggcct gcccagctcc atcgaaaaga ccatctccaa ggccaagggc   1080

cagccccggg aaccccaggt gtacacactg cctccaagcc aggaagagat gaccaagaac   1140

caggtgtccc tgacctgtct cgtgaaaggc ttctacccct ccgatatcgc cgtggaatgg   1200

gagtccaacg gccagcctga gaacaactac aagaccaccc cccctgtgct ggactccgac   1260

ggctccttct tcctgtactc tcgcctgacc gtggacaagt cccggtggca ggaaggcaac   1320

gtgttctcct gctccgtgat gcacgaggcc ctgcacaacc actacaccca gaagtccctg   1380

tccctgtctc tgggatga                                                 1398


<210> SEQ ID NO 142
<211> LENGTH: 234
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 142

Met Ser Val Pro Thr Gln Val Leu Gly Leu Leu Leu Leu Trp Leu Thr
1 5 10 15

Asp Ala Arg Cys Asp Ile Gln Met Ala Gln Ser Ser Ser Ser Phe Ser
20 25 30

Val Ser Leu Gly Asp Arg Val Thr Ile Thr Cys Lys Ala Ser Glu Asp
35 40 45

Ile Tyr Ile Arg Leu Ala Trp Tyr Gln Gln Lys Pro Gly Asn Ala Pro
50 55 60

Arg Leu Leu Ile Ser Thr Ala Thr Ser Leu Glu Thr Gly Val Pro Ser
65 70 75 80

Arg Phe Ser Gly Ser Gly Ser Gly Lys Asp Tyr Thr Leu Ser Ile Thr
85 90 95

Ser Leu Gln Thr Glu Asp Val Ala Thr Tyr Tyr Cys Gln Gln Tyr Trp
100 105 110

Ser Thr Pro Tyr Thr Phe Gly Gly Gly Thr Arg Leu Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 143
<211> LENGTH: 705
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 143
atgtccgtgc ctacacaggt tctgggactg ctgctgctgt ggctgaccga cgctagatgt 60
gatatccaga tggcccagtc ctcctccagc ttctctgtgt ctctgggcga cagagtgacc 120
atcacatgca aggcctccga ggacatctac atccggctgg cctggtatca gcagaagcct 180
ggaaacgccc ctcggctgct gatctctacc gctacatctc tggaaaccgg cgtgccctct 240
agattctctg gctctggatc tggcaaggac tacaccctgt ctatcaccag cctgcagacc 300
gaggatgtgg ccacctacta ctgccagcag tactggtcta ccccttacac ctttggcggc 360
ggaacccggc tggaaatcaa acgtacggtg gccgctccct ccgtgttcat cttcccacct 420
tccgacgagc agctgaagtc cggcaccgct tctgtcgtgt gcctgctgaa caacttctac 480
ccccgcgagg ccaaggtgca gtggaaggtg gacaacgccc tgcagtccgg caactcccag 540

-continued

```
gaatccgtga ccgagcagga ctccaaggac agcacctact ccctgtcctc caccctgacc    600

ctgtccaagg ccgactacga gaagcacaag gtgtacgcct gcgaagtgac ccaccagggc    660

ctgtctagcc ccgtgaccaa gtctttcaac cggggcgagt gctga                    705


<210> SEQ ID NO 144
<211> LENGTH: 101
<212> TYPE: PRT
<213> ORGANISM: Homo sapiens

<400> SEQUENCE: 144

Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95

Leu Leu Val Lys Glu
            100


<210> SEQ ID NO 145
<211> LENGTH: 100
<212> TYPE: PRT
<213> ORGANISM: Mus musculus

<400> SEQUENCE: 145

Gln Glu Gly Ser Leu Pro Asp Ile Thr Ile Phe Pro Asn Ser Ser Leu
1               5                   10                  15

Met Ile Ser Gln Gly Thr Phe Val Thr Val Val Cys Ser Tyr Ser Asp
            20                  25                  30

Lys His Asp Leu Tyr Asn Met Val Arg Leu Glu Lys Asp Gly Ser Thr
        35                  40                  45

Phe Met Glu Lys Ser Thr Glu Pro Tyr Lys Thr Glu Asp Glu Phe Glu
    50                  55                  60

Ile Gly Pro Val Asn Glu Thr Ile Thr Gly His Tyr Ser Cys Ile Tyr
65                  70                  75                  80

Ser Lys Gly Ile Thr Trp Ser Glu Arg Ser Lys Thr Leu Glu Leu Lys
                85                  90                  95

Val Ile Lys Glu
            100


<210> SEQ ID NO 146
<211> LENGTH: 118
<212> TYPE: PRT
<213> ORGANISM: Homo sapiens

<400> SEQUENCE: 146

Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
```

-continued

```
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95

Leu Leu Val Lys Glu Thr Ser Gly Gly Pro Asp Ser Pro Asp Thr Glu
            100                 105                 110

Pro Gly Ser Ser Ala Gly
        115


<210> SEQ ID NO 147
<211> LENGTH: 118
<212> TYPE: PRT
<213> ORGANISM: Homo sapiens

<400> SEQUENCE: 147

Gln Glu Gly Ala Leu Pro Arg Pro Ser Ile Ser Ala Glu Pro Gly Thr
1               5                   10                  15

Val Ile Ser Pro Gly Ser His Val Thr Phe Met Cys Arg Gly Pro Val
            20                  25                  30

Gly Val Gln Thr Phe Arg Leu Glu Arg Glu Asp Arg Ala Lys Tyr Lys
        35                  40                  45

Asp Ser Tyr Asn Val Phe Arg Leu Gly Pro Ser Glu Ser Glu Ala Arg
    50                  55                  60

Phe His Ile Asp Ser Val Ser Glu Gly Asn Ala Gly Leu Tyr Arg Cys
65                  70                  75                  80

Leu Tyr Tyr Lys Pro Pro Gly Trp Ser Glu His Ser Asp Phe Leu Glu
                85                  90                  95

Leu Leu Val Lys Glu Ser Ser Gly Gly Pro Asp Ser Pro Asp Thr Glu
            100                 105                 110

Pro Gly Ser Ser Ala Gly
        115
```